(12) United States Patent
Nelms et al.

(10) Patent No.: US 11,787,783 B2
(45) Date of Patent: Oct. 17, 2023

(54) HEPARANASE INHIBITORS AND USE THEREOF

(71) Applicant: Beta Therapeutics Pty Ltd, Canberra (AU)

(72) Inventors: Keats Nelms, Canberra (AU); Brett Schwartz, Canberra (AU); Colin Jackson, Canberra (AU); Martin Banwell, Canberra (AU); Edward Hammond, Canberra (AU)

(73) Assignee: Beta Therapeutics Pty Ltd, Canberra (AU)

( * ) Notice: Subject to any disclaimer, the term of this patent is extended or adjusted under 35 U.S.C. 154(b) by 1035 days.

(21) Appl. No.: 16/475,669

(22) PCT Filed: Dec. 13, 2017

(86) PCT No.: PCT/AU2017/000271
§ 371 (c)(1),
(2) Date: Oct. 3, 2019

(87) PCT Pub. No.: WO2018/107201
PCT Pub. Date: Jun. 21, 2018

(65) Prior Publication Data
US 2019/0345143 A1    Nov. 14, 2019

Related U.S. Application Data

(60) Provisional application No. 62/433,639, filed on Dec. 13, 2016.

(51) Int. Cl.
| | | |
|---|---|---|
| C07D 403/14 | (2006.01) | |
| C07D 413/12 | (2006.01) | |
| C07D 413/06 | (2006.01) | |
| C07D 413/14 | (2006.01) | |
| C07D 403/04 | (2006.01) | |
| C07D 405/06 | (2006.01) | |
| C07D 403/06 | (2006.01) | |
| C07D 239/95 | (2006.01) | |
| C07D 403/12 | (2006.01) | |
| A61K 31/498 | (2006.01) | |
| A61P 3/00 | (2006.01) | |
| A61P 27/02 | (2006.01) | |
| A61P 35/00 | (2006.01) | |
| A61P 3/10 | (2006.01) | |

(52) U.S. Cl.
CPC .............. *C07D 403/14* (2013.01); *A61P 3/10* (2018.01); *C07D 239/95* (2013.01); *C07D 403/06* (2013.01); *C07D 403/12* (2013.01); *C07D 413/12* (2013.01); *C07D 413/14* (2013.01)

(58) Field of Classification Search
CPC .. C07D 403/14; C07D 413/12; C07D 413/06; C07D 413/14; C07D 403/04; C07D 405/06; C07D 403/06; C07D 223/95; C07D 403/12; C07D 239/95; A61K 31/498; A61P 3/00; A61P 27/02; A61P 35/00
See application file for complete search history.

(56) References Cited

U.S. PATENT DOCUMENTS

| | | |
|---|---|---|
| 4,341,893 A | 7/1982 | Manoury et al. |
| 4,668,787 A | 5/1987 | Bandurco et al. |
| 4,717,373 A | 1/1988 | Catchman et al. |
| 5,288,704 A | 2/1994 | Ungheri |
| 5,439,895 A | 8/1995 | Lee et al. |
| 5,514,667 A | 5/1996 | Cullis-Hill |
| 5,980,865 A | 11/1999 | Ahmed |
| 8,377,948 B2 | 2/2013 | Chen et al. |
| 2005/0074497 A1 | 4/2005 | Schultz |
| 2007/0270354 A1 | 11/2007 | Petitou et al. |
| 2011/0066101 A1 | 3/2011 | Miller et al. |
| 2011/0189174 A1 | 8/2011 | Shafiee |
| 2013/0143840 A1 | 6/2013 | Parish et al. |
| 2014/0005140 A1 | 1/2014 | Piron et al. |

FOREIGN PATENT DOCUMENTS

| | | |
|---|---|---|
| DE | 2720545 A1 | 11/1977 |
| EP | 0594877 A1 | 5/1994 |
| EP | 2484359 A1 | 8/2012 |
| JP | 2011074024 A | 4/2011 |
| JP | 2011074027 A | 4/2011 |
| WO | WO 1990/012580 A | 11/1990 |
| WO | WO 1995/005182 A1 | 2/1995 |
| WO | WO 1995/009637 A1 | 4/1995 |
| WO | WO 1996/009828 A1 | 4/1996 |
| WO | WO 1996/033726 A1 | 10/1996 |
| WO | WO 1996/035700 A1 | 11/1996 |
| WO | WO 2000/025817 A1 | 5/2000 |
| WO | WO 2000/031082 A1 | 6/2000 |
| WO | WO 2001/055221 A1 | 8/2001 |
| WO | WO 2002/024667 A1 | 3/2002 |
| WO | WO 2002/060373 A2 | 8/2002 |

(Continued)

OTHER PUBLICATIONS

U.S. Appl. No. 16/468,419, filed Jun. 11, 2019.
U.S. Appl. No. 16/475,671, filed Jul. 2, 2019.
Abu El-Asrar et al, "Upregulated expression of heparanase in the vitreous of patients with proliferative diabetic retinopathy originates from activated endothelial cells and leukocytes", Investigative Ophthalmology & Visual Science (2015), vol. 56, No. 13, pp. 8239-8247.
Abu El-Asrar et al, "Coexpression of heparanase activity, cathepsin L, tissue factor, tissue factor pathway inhibitor, and MMP-9 in proliferative diabetic retinopathy", Molecular Vision (2016), vol. 22, pp. 424-435, Published Apr. 30, 2016.

(Continued)

*Primary Examiner* — Bruck Kifle
(74) *Attorney, Agent, or Firm* — Morgan, Lewis & Bockius LLP

(57) ABSTRACT

The invention relates to functionalized dihydro- and tetrahydro-quinazoline compounds, pharmaceutical compositions comprising such compounds, and the use of such compounds as heparanase inhibitors for the treatment of diseases or conditions related to heparanase.

22 Claims, 6 Drawing Sheets

(56) References Cited

FOREIGN PATENT DOCUMENTS

| | | |
|---|---|---|
| WO | WO 2002/060374 A2 | 8/2002 |
| WO | WO 2002/060375 A2 | 8/2002 |
| WO | WO 2002/060867 A2 | 8/2002 |
| WO | WO 2002/076976 A2 | 10/2002 |
| WO | WO 2003/004454 A1 | 1/2003 |
| WO | WO 2003/022291 A1 | 3/2003 |
| WO | WO 2003/030989 A1 | 4/2003 |
| WO | WO 2003/043689 A1 | 5/2003 |
| WO | WO 2003/078427 A1 | 9/2003 |
| WO | WO 2003/097025 A2 | 11/2003 |
| WO | WO 2004/030672 A1 | 4/2004 |
| WO | WO 2004/043989 A1 | 5/2004 |
| WO | WO 2004/046122 A1 | 6/2004 |
| WO | WO 2004/070008 A2 | 8/2004 |
| WO | WO 2004/108065 A2 | 12/2004 |
| WO | WO 2005/085264 A1 | 9/2005 |
| WO | WO 2006/047788 A2 | 5/2006 |
| WO | WO 2007/050645 A2 | 5/2007 |
| WO | WO 2007/081750 A2 | 7/2007 |
| WO | WO 2007/099406 A2 | 9/2007 |
| WO | WO 2008/013913 A2 | 1/2008 |
| WO | WO 2008/046162 A2 | 4/2008 |
| WO | WO 2008/134430 A1 | 11/2008 |
| WO | WO 2009/049370 A1 | 4/2009 |
| WO | WO 2010/006982 A1 | 1/2010 |
| WO | WO 2010/009087 A1 | 1/2010 |
| WO | WO 2010/038060 A1 | 4/2010 |
| WO | WO 2010/078246 A1 | 7/2010 |
| WO | WO 2010/104851 A1 | 9/2010 |
| WO | WO 2011/082337 A1 | 7/2011 |
| WO | WO 2012/101544 A1 | 8/2012 |
| WO | WO 2012/052899 A1 | 4/2013 |
| WO | WO 2014/100501 A1 | 6/2014 |
| WO | WO 2014/114723 A1 | 7/2014 |
| WO | WO 2015/164374 A1 | 10/2015 |
| WO | WO 2016/118933 A1 | 7/2016 |

OTHER PUBLICATIONS

Agelidis, A.M., et al., "Viral Activation of Heparanase Drives Pathogenesis of Herpes Simplex Virus-1", Cell Rep., v. 20, p. 439-450 (2017).
Baburajeev et al. (2017) BMC Cancer, 17: 235.
Bamoharram, F. F. et al: 'Dawson Heteropolyacid: A Green, Eco-Friendly, and Reusable Catalyst for One-Pot Synthesis of 4-Aminoquinazolines', Synthesis and Reactivity in Inorganic, Metal-Organic, and Nano-Metal Chemistry (2013), 43(5), pp. 539-542.
Barthlein et al. (2003) J Pediatric Surgery, 38(9): 1296-1304.
Basappa et al. (2010) Cancer Letters, 297: 231-243.
Benezra et al. (2002) J Cell Physiol, 192(3): 245-358.
Bentolila et al. (2000) J Med Chem, 43(13): 2591-2600.
Berge, S.M., et al., "Pharmaceutical Salts", J. of Pharm. Sci., v. 66, p. 1-19 (1977).
Cancer-cure, 2022, https://www.healthline.com/health/is-there-a-cure-for-cancer.
Cancer-Prevention, 2022, https://www.cancerresearchuk.org/about-cancer/causes-of-cancer/can-cancer-be-prevented-0.
CAS Registry No. 21580-54-1, STN entry date: Nov. 16, 1984; Chemical Name: 4-Quinazolinamine, 6,7-dimethoxy-2-phenyl.
CAS Registry No. 361154-65-6, STN entry date: Oct. 9, 2001; Chemical Name: 4-Quinazolinamine, 6, 7-dimethoxy-2-( 4-methyl-1-piperazinyl)-N-(2-phenylethyl)-.
CAS Registry No. 422531-79-1, STN entry date: May 29, 2002, Chemical name: 2( IH)-Quinazolinethione, 4-[[2-( IH-indol-3-yl)ethyl]amino ]-.
CAS Registry No. 439097-17-3, STN entry date: Jul. 17, 2002, Chemical name: 2( 1 H)-Quinazolinethione, 3 ,4-dihydro-4-imino-6, 7-dimethoxy-3-[3-( 4-morpholinyl)propyl]-.
CAS Registry No. 477848-75-2, STN entry date: Dec. 31, 2002, Chemical name: 2( 1 H)-Quinazolinethione, 3 ,4-dihydro-4-imino-6, 7-dimethoxy-3-(2-phenylethyl)-.
CAS Registry No. 691858-06-7, STN entry date: Jun. 11, 2004, Chemical name: 4(3H)-Quinazolinimine, 6, 7-dimethoxy-3-(2-phenylethyl)-2-[[[ 4-( trifluoromethyl)phenyl]methyl]thio ]-.
CAS Registry No. 740066-32-4, STN entry date: Sep. 5, 2004; Chemical Name: 1,4-Benzodioxin-2-carboxamide, N-[2-[( 4-amino-6, 7-dimethoxy-2- quinazolinyl)amino ]ethyl]-2,3-dihydro-.
CAS Registry No. 860610-60-2, STN entry date: Aug. 17, 2005, Chemical name: 2( 1 H)-Quinazolinethione, 3-amino-3 ,4-dihydro-4-imino-6, 7-dimethoxy-.
CAS Registry No. 860610-62-4, STN entry date: Aug. 17, 2005, Chemical name: 4(3H)-Quinazolinimine, 3-[ (2-chlorophenyl)methyl ]-6, 7-dimethoxy-2-[[[3-( trifluoromethyl)phenyl]methyl]thio ]-.
CAS Registry No. 896670-06-7, STN entry date: Jul. 28, 2006, Chemical name: 2( 1 H)-Quinazolinethione, 3 ,4-dihydro-4-imino-3-[2-( 1 H-indol-3-yl)ethyl]-.
CAS Registry No. 1095750-67-6, STN entry date: Jan. 25, 2009; Chemical Name:2,4-Quinazolinediamine, N2,N4-bis[( 4-fluorophenyl)methyl]-6, 7-dimethoxy-.
CAS Registry No. 1317296-43-7, STN entry date: Aug. 14, 2011; Chemical Name: Benzenesulfonamide, N-[2-[ ( 4-amino-6, 7-dimethoxy-2-quinazolinyl)amino ]ethyl]-2,5-dimethyl-.
CAS Registry No. 1317535-37-7; STN Entry Date Aug. 14, 2011; Benzamide, N-[2-[(4-amino-6,7-dimethoxy-2-quinazolinyl)amino]ethyl]-4-(trifluoromethyl)-.
CAS Registry No. 1319000-50-4; STN Entry Date Aug. 17, 2011; Benzamide, N-[2-[(4-amino-6,7-dimethoxy-2-quinazolinyl)amino]ethyl]-3-fluoro-4-methyl-.
CAS Registry No. 1347928-14-6; STN Entry Date Dec. 4, 2011; 2-Furancarboxamide, N-[3-[[6,7-dimethoxy-4-(methylamino)-2-quinazolinyl]amino]propyl]tetrahydro-.
CAS Registry No. 1417397-54-6, STN entry date: Jan. 24, 2013; Chemical Name: 4-Quinazolinamine, 6-ethoxy-2-(3-pyridinyl)-N-(2-pyridinylmethyl)-.
CAS Registry No. 1609893-59-5, STN entry date: Jun. 7, 2014; Chemical Name: 4-Quinazolinamine, 2-(2,3-dihydro-7-benzofuranyl)-6, 7-dimethoxy-.
CASPI (2006) Drug Discovery Today: Disease Models, 3(1): 3-9.
Chen et al. (2007) J Agric Food Chem, 55: 6910-6917.
Chen, M., et al., "Parainflammation, chronic inflammation, and age-related macular degeneration", J. Leuk. Biol., v. 98, n. 5, p. 713-725 (2015).
Chinnery, H.R., et al., "Macrophage physiology in the eye", Eur. J. Physiol., v. 469, p. 501-515 (2017).
Cho et al., Discovery of 2-Aryloxy-4-Amino-Qunazoline Derivatives as Novel Protease-Activated Receptor 2 (PAR2) Antagoists.
Coombe-et-al., Front. Oneal., 2019, 60 pages.
Cornish et al. (2005) Vis Neurosci, 22: 447-459.
Courtney et al. (2004) Bioorg Med Chem Lett, 14(12): 3269-3273.
Courtney, S.M et al., "Furanyl-1,3-thiazol-2-yl and benzoxazol-5-yl acetic acid derivatives: novel classes of heparanase inhibitor", Bioorg Med Chem Lett, 15(9):2295-9 (2005).
Curcio et al. (1998) Invest Ophthalmol Vis Sci, 39: 1085-1096.
Diabetes-cure, 2022, https://diabetesresearch .org/type-1-diabetes-cure/.
Diabetes-Prevention, 2022, https://www.cdc.gov/diabetes/basics/what-is-type-1-diabetes.html#:~:text=Currently%2C%20no%20one%20knows%20how,Getting%20regular%20health%20checkups.
Dithmer et al., "Fucoidan Reduces Secretion and Expression of Vascular Endothelial Growth Factor in the Retinal Pigment Epithelium and Reduces Angiogenesis In Vitro", PLOS One (2014), vol. 9, No. 2, p. e89150, 10 Pages.
Dolomanov, et al. (2009) J. Appl. Cryst., 42: 339-341.
Dost, J. et al., "Preparation of 1,3,4,-Oxadiazol-2-carboxylic Acid Derivatives", J. Prakt. Chem., v. 327, n. 1, p. 109-116 (1985).
Dredge, K., et al., "PG545, a dual heparanase and angiogenesis inhibitor, induces potent anti-tumour and anti-metastatic efficacy in preclinical models", British Journal of Cancer v. 104, p. 635-642 (2011).
Elkin, M. et al. "Heparanase as mediator of angiogenesis: mode of action", FASEB J., v. 15, n. 9, p. 1661-3 (2001).
Ferro et al., "Discovery of PG545: A Highly Potent and Simultaneous Inhibitor of Angiogenesis, Tumor Growth, and Metastasis", Journal of Medicinal Chemistry (2012), vol. 55, pp. 3804-3813.

(56) References Cited

OTHER PUBLICATIONS

Forest et al. (2015) Disease Models and Mechanisms, 8: 421-427.
Francis, J.E., et al., "Structure-Activity Profile of a Series of Novel Triazoloquinazoline Adenosine Antagonists", J. Med. Chem. v. 31, p. 1014-1020 (1988).
Freeman (1997) *Biochem J*, 325: 229-237.
Freeman et al. (2005) *J Biol Chem*, 280(10): 8842-8849.
Gagliardi et al. (1998) *Cancer Chemother Pharmacol*, 41: 117-124.
Giardinà, D. et al., "Structure-Activity Relationships in Prazosin-Related Compounds. Effect of Replacing a Piperazine Ring with an Alkanediamine Moiety on $\alpha_1$-Adrenoreceptor Blocking Activity", J. Med. Chem., v. 32, n. 1 (1989).
Gonzalez et al., "Demonstration of Inhibiory Effect of Oral Shark Cartilage on Basic Fibroblast Growth Facotr-Induced Angiogenesis in the Rabbit Cornea", Biol Pharm Bull, v. 24, No. 2, p. 151-154 (2001).
Gozalbes et al. (2013) *Bioorg Med Chem*, 21(7): 1944-1951.
Grzyb, J.Z., "Carbamoylimidazolium and thiocarbamoylimidazolium salts: novel reagents for the synthesis of ureas, thioureas, carbamates, thiocarbamates and amides", Tetrahedron, v. 61, n. 30, p. 7153 (2005).
Guo et al. (2017) *Veterinary Microbiology*, 201: 231-239.
Gutter-Kapon, L., et al., "Heparanase is required for activation and function of macrophages", PNAS, v. 113, n. 48, p. E7808-E7817 (Nov. 29, 2016).
Häcker, H-G et al., "Analogs of a 4-Aminothieno[2,3-d] Pyrimidine Lead (QB13) as Modulators of P-Glycoprotein Substrate Specificity" Bioorganic & Med. Chem. Letters, v. 19, p. 6102-6105 (2009).
Hammond, E., et al., "Development of a colorimetric assay for heparanase activity suitable for kinetic analysis and inhibitor screening", Anal Biochem., v. 396, p. 112-116 (2010).
Hammond et al. (2013) FEBS Open Bio, 3: 346-351.
Hamoud-et-al., 2017, https://www.ncbi.nlm.nih.gov/pmc/articles/PMC5684525/.
He, et al., "Hypoxia Increases Heparanase-Dependent Tumor Cell Invasion, Which Can Be Inhibited by Antiheparanase Antibodies", Cancer Research (2004), vol. 64, pp. 3928-3933.
Ilan, N., et al. "Regulation, function and clinical significance of heparanase in cancer metastasis and angiogenesis", Int. J. Biochem. Cell Biol. 38, 2018-39 (2006).
Ishai-Michaeli, R. et al., "Heparanase activity expressed by platelets, neutrophils, and lymphoma cells releases active fibroblast growth factor from extracellular matrix", Cell Regul. Oct. 1990; 1(11):833-842.
Ishida et al. (2004) *J Antibiot (Tokyo)*, 57: 136-142.
Ishida et al. (2004) Mol Cancer Ther, 3(9): 1069-1077.
Ishida et al. (2004) *Chem Biol*, 11(3): 367-377.
Janik-Papis, K., et al., "Role of oxidative mechanisms in the pathogenesis of age-related macular degeneration", Klinika Oczna, v. 111, n. 4-6, p. 168-173 (2008).
Jiang, et al. (2015) Curr Eye Res, 40(8): 761-771.
Josefsen, K., et al., "Fluorescence-activated cell sorted rat islet cells and studies of the insulin secretory process", J. Endocrinol., v. 149, n. 1, p. 145-154 (1996).
Jyothirmayi, G., et al., "Doxazosin Prevents Proteinuria and Glomerular Loss of Heparan Sulfate in Diabetic Rats", Hypertension, v. 27, n. 5, p. 1108-1114 (1996).
Karamichos, et al. (2012) J Funct Biomater, 3(4): 760-775.
Karoli et al. (2005) *J Med Chem*, 48(26): 8229-8236.
Kawase et al. (1996) *J Antibiot (Tokyo)*, 49(1): 61-64.
Kirschfink (2003) Clin Vaccine Immunol, 10(6): 982-989.
Klauser et al. "Biochemical studies on sulfated lactobionic acid amides", (1991) *Semin Thromb Hemost*, 17(Suppl 1): 118-125.
Klein, R., et al., "The Wisconsin Epidemiologic Study of Diabetic Retinopathy a Comparison of Retinopathy in Younger and Older Onset Diabetic Persons", Adv. Exp. Med. Biol., v. 189, p. 321-335 (1985).
Klein, R., et al., "Prevalence of age-related macular degeneration in the US population", Arch Ophthalmol., v. 129, n. 1, p. 75-80 (Jan. 2011).
Knickelbein, J.E., et al., "Inflammatory Mechanisms of Age-related Macular Degeneration", Int. Ophthalmol. Clin., v. 55, n. 3, p. 63-78 (2015).
Ko et al. (2000) *J Antibiot (Tokyo)*, 53(2): 211-214.
Kumagai, et al., "Sodium pentosan polysulfate resulted in cartilage improvement in knee osteoarthritis—An open clinical trial-", BMC Clinical Pharmacology (2010), vol. 10, No. 1, Article 7, 9 Pages.
Lafond, et al. (2017) Expert Opinion on Drug Delivery, 14(4): 539-550.
Laha, J.K. et al., "Palladium-catalyzed regioselective C-2 arylation of 7-azaindoles, indoles, and pyrroles with arenes" Chem. Commun., v. 52, p. 4329-4332 (2016).
Lapierre et al. (1996) *Glycobiology*, 6(3): 355-366.
Lee, R., et al., "Epidemiology of diabetic retinopathy, diabetic macular edema and related vision loss", Eye and Vis (Lond), 2:17 (2015).
Lee, S.J et al., "Discovery of Potent Cyclic GMP Phosphodiesterase Inhibitors. 2-Pyridyl- and 2-Imidazolylquinazolines Possessing Cyclic GMP Phosphodiesterase and Thromboxane Synthesis Inhibitory Activities", *J Med Chem*. 1995, 38 (18), pp. 3547-3557.
Levidiotus et al. (2004) *J Am Soc Nephrol*, 15(1): 68-78.
Li, L., et al., "The microglia in healthy and diseased retina", Exp Eye Res., v. 136, p. 116-130, Jul. 2015.
Liu, M. et al., "Evaluation of the Antitumor Efficacy of RNAi-Mediated Inhibition of CDC20 and Heparanase in an Orthotopic Liver Tumor Model", Cancer Biother. Radiopharm. 30, 233 9 (2015).
Ma et al, "Phosphomannopentaose sulfate (PI-88) inhibits retinal leukostasis in diabetic rat", Biochemical and Biophysical Research Communications, (2009), vol. 380, Issue 2, pp. 402-406.
Marchetti et al. (1997) J Biol Chem, 272(25): 15891-15897.
Marchetti et al. (2003) *Int J Cancer*, 104(2): 167-174.
Matera, R., "Design and Synthesis of Novel Non Peptidomimetic Beta-Secretase Inhibitors in the Treatment of Alzheimer's Disease", Doctoral Research, Universita di Bologna (2009).
Mckenzie, E.A.., "Heparanase: a target for drug discovery in cancer and inflammation", *Br. J. Pharmacol*. May 2007; 151(1): 1-14.
Mi et al. (2014) Drug Des Devel Ther, 8: 2311-2319.
Mintel GNPD, "Dry Eye Lubricant Eye Drops", Available from the Internet, <URL http://www.gnpd.com/sinatra/recordpage/I 877 871/>, Published Sep. 2012 according to Mintel GNPD.
Mitragotri (2005) Nat Rev Drug Discov, 4: 255-260.
Moreno, E. et al., "Sulfur and selenium derivatives of quinazoline and pyrido[2,3-d]pyrimidine: Synthesis and study of their potential cytotoxic activity in vitroSulfur and selenium derivatives of quinazoline and pyrido[2,3-d]pyrimidine: Synthesis and study of their potential cytotoxic activity in vitro", Eur. J. of Med Chem., v. 47, p. 283-298, (Jan. 2012).
Myler et al. (2006) J Biochem, 139(3): 339-345.
Naggi et al. (2005) *J Biol Chem*, 280(13): 12103-12113.
Naik N., et al., "Novel Indole-2-Carboxylic Acid Analogues: Synthesis and a New Light in to their Antioxidant Potentials", Eur. J. Chem., 3(2), 214 (2012).
Natoli, et al. (2008) Mol Vis, 14: 1983-1994.
Natoli, et al. (2016) Exp Eye Res, 147: 114-127.
Ni et al. (2016) Molecules, 21(11): 1602.
Nishimura et al. (2000) *J Org Chem*, 65(1): 2-11.
Niu et al. (2015) Carbohydrate Polymers, 125: 76-84.
Nugent, J et al., "Solvent-Free Synthesis of Cyanoformamides from Carbamoyl Imidazoles", Eur. J. Org. Chem., v. 2017, n. 34, p. 5110-5118 (2017).
O'Koren, E.G., et al., "Fate mapping reveals that microglia and recruited monocyte-derived macrophages are definitively distinguishable by phenotype in the retina", Sci. Rep., 6. art. No. 20636 (2016).
Pan et al. (2006) *Bioorg Med Chem Lett*, 16(2): 409-412.
Pangborn A., et al., "Safe and Convenient Procedure for Solvent Purification", Organometallics, v. 15, n.5 p. 1518 (1996).
Papadopoulos, et al. (2012) Angiogenesis, 15(2): 171-185.
Parish et al. (1999) Cancer Res, 59: 3433-3441.
Parish, C.R., "The role of heparan sulphate in inflammation", Nat. Rev. Immuno., v. 6, p. 633-643 (2006).

(56) References Cited

OTHER PUBLICATIONS

Pazdera, P. et al. "Preparation and cyclization of 3-substituted 1-(2-cyanophenyl)-thioureas" Chemical Papers (1989) vol. 43( 6) pp. 77 I-781.
Pennisi, et al. (2012) Mol Aspects Med, 33(4): 487-509.
Perez-Balbuena et al, "Efficacy of a fixed combination of 0.09 % xanthan gum/0.1 % chondroitin sulfate preservative free vs polyethylene glycol/propylene glycol in subjects with dry eye disease: a multicenter randomized controlled trial", BMC Ophthalmology (2016), vol. 16, p. 164, 6 Pages, Published Sep. 20, 2016.
Pfeiffer, W-D, et al., "Synthesis and Reactivity of 1,2,4-Triazolo{1,5-c] Quinazolines", J. Heterocyclic Chem., v. 36, p. 1327 (1999).
Rangasamy, S., et al., "Chemokine mediated monocyte trafficking into the retina: role of inflammation in alteration of the blood-retinal barrier in diabetic retinopathy", PLoS One, v. 9, n. 10, e108508 (Oct. 20, 2014).
Rezzola et al. (2014) Angiogenesis, 17(3): 429-442.
Rivara, S., et al., "Heparanase: a rainbow pharmacological target associated to multiple pathologies including rare diseases", Future Med Chem., v. 8, n. 6, p. 647-680 (2016).
RN 116784-56-6, registry database compound, 1988.
RN 1319122-09-2, registry database compound, 2011.
RN1317296-43-7, Oct. 14, 2011, registry database compound.
Robaa, Dina, et al. "Identification and Structure-Activity Relationship Studies of Small-Molecule Inhibitors of the Methyllysine Reader Protein Spindlin1." ChemMedChem, (2016) vol. 11(20) pp. 2327-2338 X compound le, p. 2336.
Robertson, W.M., et al., "Synthesis and evaluation of a series of C5'-substituted duocarmycin SA analogs", Bioorg. Med. Chem. Lett., v. 20, p. 2722 (2010).
Roy et al. (2014) *J Med Chem*, 57(11): 4511-4520.
Rutar, M., et al., "Brief Exposure to Damaging Light Causes Focal Recruitment of Macrophages, and Long-Term Destabilization of Photoreceptors in the Albino Rat Retina", Curr. Eye Res., v. 35, n. 7, p. 631-643 (2010).
Rutar, M., et al. (2011) Invest Ophthalmol Vis Sci, 52: 5347-5358.
Rutar, M., et al., "Small interfering RNA-mediated suppression of Ccl2 in Müller cells attenuates microglial recruitment and photoreceptor death following retinal degeneration", *J. Neuroinflammation*, v. 9, n 1, p. 221 (2012).
Rutar, M., et al. (2014) PLoS One, v. 9, n. 4: e93343.
Saiki et al. (1990) *Cancer Res*, 50: 3631-3637.
Schröder, S., et al., "Activated monocytes and granulocytes, capillary nonperfusion, and neovascularization in diabetic retinopathy", Am. J. Pathol., v. 139, n. 1, p. 81-100 (1991).
Seijas, J. A., et al., "Microwave enhanced synthesis of 4-aminoquinazolines", Tetrahedron Letters, v. 41, iss. 13, p. 2215-2217 (2000Seijas J. A et al. (Tetrahedron Lett. 2000, 41, 2215-2217).
Sheldrick, (2015) Acta Cryst., A71: 3-8.
Shelley et al. (2009) Arch Ophthalmol, 127: 483-492.
Shiozawa et al. (1995) J Antibiot (Tokyo), 48(5): 357-362.
Smits, R.A., et al., "Discovery of Quinazolines ad Histamine H4 Receptor Inverse Agonists Using a Scaffold Hopping Approach", J. Med. Chem. v. 51, p. 7855-7865 (2008).
Song et al., "Effect of sulodexide in patients with non-proliferative diabetic retinopathy: diabetic retinopathy sulodexide study (DRESS)", Graefe's Archive for Clinical and Experimental Ophthalmology (2015), vol. 253, pp. 829-837.
Still, W.C., et al., "Rapid chromatographic technique for preparative separations with moderate resolution", J. Org. Chem., v. 43, n. 14, p. 2923 (1978).
Suhara et al. (1996) *Tetrahedron Letters*, 37(10): 1575-1578.
Suhara et al. (1996) *Tetrahedron Letters*, 37(15): 2549-2552.
Suhara et al. (2002) *Bioorg Med Chem*, 10(6): 1999-2013.
Takahashi et al. (2001) *Tetrahedron*, 57(32): 6915-6926.
Temkin et al. (2004) *J Allergy Clin Immunol*, 113(4): 703-709.
Tressler et al. (1996) In Molecular, Cellular, and Clinical Aspects of Angiogenesis, Plenum Press New York, p. 199.
Trost, B.M. et al., "A Stereodivergent Strategy to Both Product Enantiomers from the Same Enantiomer of a Stereoinducing Catalyst: Agelastatin A", Chem. Euro. J., v. 15, n, 28, p. 6910 (2009).
Van Lookeren Campagne, M., et al., "Mechanisms of age-related macular degeneration and therapeutic opportunities", J. Pathol., v. 232, n. 2, p. 151-164 (2014).
Watterson, S.H., et al., "Potent and Selective Agonists of Sphingosine 1-Phosphate 1 (S1P1): Discovery and SAR of a Novel Isoxazole Based Series", J. of Med. Chem., v. 59, n. 6, p. 2820-2840 (2016).
Weissman et al. (2016) *PNAS*, 113(3): 704-709.
Xu et al. (2006) *Bioorg Med Chem Lett*, 16(2): 404-408.
Yang et al. (2009) *Cancer Immunol Immunother*, 58(9): 1387-1396.
Zammit et al. (2007) *Org Biomol Chem*, 5: 2826-2834.
Zderic, et al. (2004) J Ultrasound Med, 23: 1349-1359.
Zester et al. (2004) *Journal of Cell Science*, 117: 2249-2258.
Zhenhua, L., et al., "Facile and Efficient Cyclization of Anthranilonitrile to 2,4-Dichloroquinazoline by Bis(trichloromethyl) Carbonate and Catalytic Amount Triphenylphosphine Oxide", Heterocycles,, v. 85, n. 6, p. 1417-1426 (2012).
Zhong, et al. (2012) Heterocycles, 85: 1417-1426.
Ziolkowski et al. (2012) *J Clin Invest*, 122(1): 132-141.

A.

B.

C.

Data in (d) represents mean +/- S.D. * P<0.001

HEPARANASE INHIBITORS AND USE THEREOF

RELATED APPLICATIONS

This application is a U.S. National Phase of International Application No. PCT/AU2017/000271 filed Dec. 13, 2017 titled "Heparanase inhibitors and use thereof" which claims priority from U.S. Provisional Patent Application Ser. No. 62/433,639 filed 13 Dec. 2016 titled "Heparanase inhibitors and use thereof", and Australian Provisional Patent Application No 2017902346 filed 20 Jun. 2017, titled "Methods of treating ocular disorders", the entire contents of which are hereby incorporated by cross reference.

FIELD OF THE INVENTION

The present invention broadly relates to functionalised quinazoline compounds, pharmaceutical compositions comprising such compounds, and the use of such compounds as heparanase inhibitors for the treatment of a disease or condition related to heparanse activity. The invention further relates to processes for preparing the compounds.

BACKGROUND OF THE INVENTION

Heparanase is an endo-β-glucuronidase enzyme that is implicated in a wide variety of inflammatory and proliferative diseases, including Type 1 diabetes, Type 2 diabetes, diabetic nephropathy, nephritis, glomerulonephritis, and other cell-mediated autoimmune inflammation indications, cancer, allergy, dermatitis/psoriasis, macular degeneration, retinitis pigmentosa, pancreatitis, among others. Therefore, a drug that inhibits heparanse may be useful in the treatment of those diseases.

One example of a heparanase mediated disease is Type 1 diabetes. Type 1 diabetes is an autoimmune disease in which the insulin-producing beta cells of the Islets of Langerhans in the pancreas are destroyed by the body's immune cells, particularly T-cells. A major effect of this is lack of production of the hormone insulin, leading to abnormally high sugar levels in the blood (hyperglycaemia). While insulin therapy protects Type 1 diabetes patients from dying from diabetic coma, precise and sustained control of blood sugar levels is rarely, if ever, achieved. Over time, the resulting fluctuations in blood sugar levels lead to severe secondary blood vessel complications and disorders, which can result in kidney disease, heart disease, blindness, nerve damage (neuropathy), gangrene and stroke.

Type 1 diabetes affects 10-15% of people with diabetes and the incidence of Type 1 diabetes is also on the rise. In the period 1999-2005 the rate of new cases in those aged 0-14 increased by 25% (18.1 up to 22.6 per 100,000). The overall level of diabetes has a substantial impact on healthcare costs with the direct healthcare expenditures. There is currently no treatment available that can prevent or modify the progression of Type 1 diabetes. Given the seriousness of the disease, there is an urgent need for therapeutic drugs that mitigate the disease processes that lead to Type 1 diabetes.

Recent studies have demonstrated that insulin-producing islet beta cells unconditionally require the glycosaminoglycan polysaccharide heparan sulfate (HS) for their survival. HS is found in the extracellular matrix. HS chains matured by modifications such as deacetylation and sulfation can interact with a variety of secreted and transmembrane proteins, allowing signalling between cells.

The inventors have found that the normal HS content of islet beta cells is severely compromised and ultimately ablated during Type 1 diabetes onset/progression and during the isolation of islets for transplantation, which is a known treatment for Type 1 diabetes. The HS-degrading enzyme, heparanase (HPSE), a glycoside hydrolase that breaks down HS, plays a previously unrecognised role in the autoimmune destruction of islet cells in the development of Type 1 diabetes in mice. HPSE is produced predominantly by inflammatory cells present or infiltrating the islets.

The degradation of HS by HPSE also activates signal cascades that increase cell growth, mobility and angiogenesis. (Ishai-Michaeli, et al. Heparanase activity expressed by platelets, neutrophils, and lymphoma cells releases active fibroblast growth factor from extracellular matrix. *Cell Regul.* 1, 833-42 (1990). Elkin, M. et al. Heparanase as mediator of angiogenesis: mode of action. *FASEB J.* 15, 1661-3 (2001). HPSE is also required for inflammatory and immune cells to cross basement membrane of blood vessel cell wall (Parish C R, The role of heparan sulfate in inflammation. *Nat. Rev. Immunol.* 6, 633-43 (2006)). Hence HPSE is upregulated in tumour and cancer cells, where its overexpression has been strongly correlated with metastasis and increased mortality. (Ilan, N., et al. Regulation, function and clinical significance of heparanase in cancer metastasis and angiogenesis. *Int. J. Biochem. Cell Biol.* 38, 2018-39 (2006)). A clear link has now been established between heparanase expression and the process of tumourigenesis in a wide range of cancers, including bladder, brain, breast, colon, gastric, oral, oesophageal, pancreatic, prostate, thyroid and acute myeloid leukemia. (McKenzie, E. A. *Br J Pharmacol.* 2007 May; 151(1): 1-14). Inhibition of HPSE has also been shown to have a significant anti-tumor and anti-metastatic effect and HPSE is a well-characterised drug target in oncology. (Dredge, K. et al. PG545, a dual heparanase and angiogenesis inhibitor, induces potent anti-tumour and anti-metastatic efficacy in preclinical models. *Br. J. Cancer* 104, 635-42 (2011). Liu, M. et al. Evaluation of the Antitumor Efficacy of RNAi-Mediated Inhibition of CDC20 and Heparanase in an Orthotopic Liver Tumor Model. *Cancer Biother. Radiopharm.* 30, 233-9 (2015)).

Three HPSE-inhibiting drugs have been assessed in clinical trials. Two of these, namely PI-88 and ST0001, have been shown to have significant efficacy in preclinical models of Type 1 diabetes, diabetic nephropathy and nephritis. However, all three HPSE inhibitors currently in development have potential safety issues that have adversely impacted their ability to be used as effective therapeutic agents. For example, PI-88 (Muparfostat, Progen Pharmaceuticals) which is a non-cleavable competitive inhibitor of heparanase, has poor efficacy as a therapeutic agent due to a number of factors, including an anti-coagulant activity that can result in uncontrolled bleeding. In addition, PI-88 also has a short half-life of approximately 30 minutes and also binds other proteins including Platelet Factor 4, which can give rise to heparin-induced thrombocytopenia.

Another inflammatory condition with increasing prevalence and incidence is age-related macular degeneration (AMD). Anti-VEGF agents are currently used in the management of many retinal disorders, especially those in which neovascularization is the primary pathology, including wet or exudative AMD. Several investigational anti-VEGF drugs have received FDA approval for use in treating AMD and related ocular conditions in humans, including pegaptanib sodium (Macugen, Pfizer Inc., New York, NY, USA), ranibizumab (Lucentis, Genentech, San Francisco, CA, USA), aflibercept (Eylea, Regeneron Pharmaceuticals, Tarrytown, NY, USA) and bevacizumab (Avastin, Roche). Anti-VEGF intravitreal injections have dramatically altered the prognosis of AMD and improved chances of preserving useful vision in afflicted patients. However, whilst VEGF inhibitors are efficacious in advanced and late stages of AMD, currently there is no known treatment for early stage AMD.

There remains a need for alternative therapies, preferably small molecule drugs, for treating inflammatory diseases and disorders.

Throughout this specification, unless the context requires otherwise, the word "comprise", or variations such as "comprises" or "comprising", will be understood to imply the inclusion of a stated element, integer or step, or group of elements, integers or steps, but not the exclusion of any other element, integer or step, or group of elements, integers or steps. The term "consisting of" means "consisting only of", that is, including and limited to the stated element(s), integer(s) or step(s), and excluding any other element(s), integer(s) or step(s). The term "consisting essentially of" means the inclusion of the stated element(s), integer(s) or step(s), but other element(s), integer(s) or step(s) that do not materially alter or contribute to the working of the invention may also be included.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this specification.

SUMMARY OF THE INVENTION

The present inventors have identified small molecule heparanase inhibitors suitable for use in the treatment of a variety of conditions related to heparanase activity.

A first aspect of the invention relates to compounds of general formula (I):

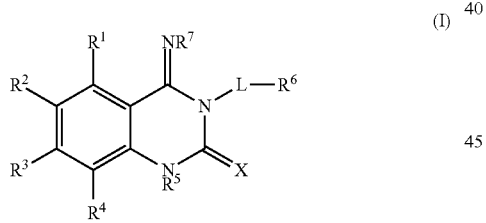

(I)

or a salt, hydrate, solvate, tautomer or stereoisomer thereof,
wherein:
X is S or O;
$R^1$ is selected from H, hydroxyl, halo, $C_{1-6}$alkyl, $C_{1-4}$alkoxy, O—$CH_2$phenyl, O-phenyl;
$R^2$ is selected from H, hydroxyl, halo, $C_{1-6}$alkyl, $C_{1-4}$alkoxy, O—$CH_2$phenyl, O-phenyl;
$R^3$ is selected from H, hydroxyl, halo, $C_{1-6}$alkyl, $C_{1-4}$alkoxy, O—$CH_2$phenyl, O-phenyl;
$R^4$ is selected from H, hydroxyl, halo, $C_{1-6}$alkyl, $C_{1-4}$alkoxy, O—$CH_2$phenyl, O-phenyl;
or $R^1$ and $R^2$, or $R^2$ and $R^3$, or $R^3$ and $R^4$ together form $C_{1-3}$alkylenedioxy;
$R^5$ is selected from H, $C_{1-6}$ alkyl, $C_{1-3}$alkylC(O)O$C_{1-4}$alkyl and $C_{1-3}$alkyl$C_{6-10}$aryl optionally substituted with 1 or 2 groups independently selected from halo$C_{1-3}$alkyl and halo$C_{1-3}$alkoxy;

L is selected from $C_{1-6}$ alkyl, azetidinyl, $C_{1-6}$ alkyl-indolyl, NH, $C_{1-6}$ alkyl-NHC(O)O, azetidinyl-C(O)—, $C_{1-6}$alkyl-NHC(O)-indolyl, $C_{1-6}$alkyl-NHSO$_2$—, or is absent;
$R^6$ is selected from H, halo, hydroxyl, $C_{1-6}$alkyl, $C_{1-6}$alkenyl, $C_{1-6}$alkynyl, $C_{6-10}$aryl optionally substituted with 1 or 2 $R^X$ groups, $C_{1-9}$ heteroaryl optionally substituted with 1 or 2 $R^X$ groups, $C_{2-5}$ heterocycloalkyl optionally substituted with 1 or 2 $R^X$ groups, C(O)-(heterocycloalkyl) optionally substituted with 1 or 2 $R^X$ groups, C(O)($C_{2-5}$heterocycloalkyl) optionally substituted with 1 or 2 $R^X$ groups, C(O)NH$R^Y$, or is absent;
each $R^X$ is independently selected from hydroxyl, halo, nitro, NR'R", $C_{1-4}$alkyl, $C_{3-6}$cycloalkyl, halo$C_{1-4}$alkyl, $C_{1-4}$alkoxy, $C_{6-10}$aryl optionally substituted with 1 or 2 $R^Y$ groups, $C_{1-9}$heteroaryl, $C_{1-4}$alkyl-($C_{1-9}$heteroaryl), C(O)O$C_{1-4}$alkyl, C(O)NH$R^Y$, $C_{2-5}$heterocycloalkyl optionally substituted with 1 or 2 $C_{1-4}$alkyl groups, C(O)-(heterocycloalkyl) optionally substituted with 1 or 2 $C_{1-4}$alkyl groups, or two adjacent $R^X$ groups together form $C_{1-3}$alkylenedioxy;
$R^Y$ is selected from H, hydroxyl, halo, $C_{1-4}$ alkyl, halo$C_{1-4}$ alkyl, $C_{1-4}$ alkoxy, $C_{1-4}$ alkylheterocycloalkyl, C(O)—($C_{1-4}$ alkylheterocycloalkyl), $C_{1-4}$alkylNR'R";
R' and R" are independently selected from H, $C_{1-4}$alkyl, $C_{1-4}$ alkylheterocycloalkyl;
$R^7$ is selected from H, $C_{1-4}$ alkyl and $C_{1-6}$ alkyl$C_{1-9}$ heteroaryl.

In preferred embodiments each heteroaryl and each heterocycloalkyl group comprises at least one nitrogen heteroatom.

In preferred embodiments X is S.

In preferred embodiments $R^5$ is H or $C_{1-6}$ alkyl.

A second aspect of the invention relates to compounds of general formula (II):

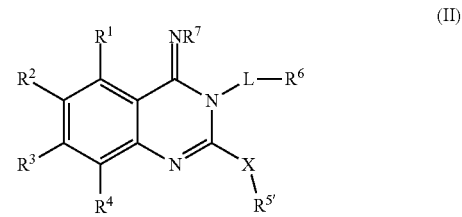

(II)

or a salt, hydrate, solvate, tautomer or stereoisomer thereof,
wherein:
X is S or O;
$R^1$ is selected from H, hydroxyl, halo, $C_{1-6}$alkyl, $C_{1-4}$alkoxy, O—$CH_2$phenyl, O-phenyl;
$R^2$ is selected from H, hydroxyl, halo, $C_{1-6}$alkyl, $C_{1-4}$alkoxy, O—$CH_2$phenyl, O-phenyl;
$R^3$ is selected from H, hydroxyl, halo, $C_{1-6}$alkyl, $C_{1-4}$alkoxy, O—$CH_2$phenyl, O-phenyl;
$R^4$ is selected from H, hydroxyl, halo, $C_{1-6}$alkyl, $C_{1-4}$alkoxy, O—$CH_2$phenyl, O-phenyl;
or $R^1$ and $R^2$, or $R^2$ and $R^3$, or $R^3$ and $R^4$ together form $C_{1-3}$alkylenedioxy;
$R^{5'}$ is selected from H, $C_{1-6}$ alkyl, $C_{1-3}$alkylC(O)O$C_{1-4}$alkyl and $C_{1-3}$alkyl$C_{6-10}$aryl optionally substituted with 1 or 2 groups independently selected from halo$C_{1-3}$alkyl and halo$C_{1-3}$alkoxy;

L is selected from $C_{1-6}$ alkyl, azetidinyl, $C_{1-6}$ alkyl-indolyl, NH, $C_{1-6}$ alkyl-NHC(O)O, azetidinyl-C(O)—, $C_{1-6}$ alkyl-NHC(O)-indolyl, $C_{1-6}$alkyl-NHSO$_2$—, or is absent;

$R^6$ is selected from H, halo, hydroxyl, $C_{1-6}$alkyl, $C_{1-6}$alkenyl, $C_{1-6}$alkynyl, $C_{6-10}$aryl optionally substituted with 1 or 2 $R^X$ groups, $C_{1-9}$ heteroaryl optionally substituted with 1 or 2 $R^X$ groups, $C_{2-5}$ heterocycloalkyl optionally substituted with 1 or 2 $R^X$ groups, C(O)-(heterocycloalkyl) optionally substituted with 1 or 2 $R^X$ groups, C(O)($C_{2-5}$heterocycloalkyl) optionally substituted with 1 or 2 $R^X$ groups, C(O)NHR$^Y$, or is absent;

each $R^X$ is independently selected from hydroxyl, halo, nitro, NR'R", $C_{1-4}$alkyl, $C_{3-6}$cycloalkyl, halo$C_{1-4}$alkyl, $C_{1-4}$alkoxy, $C_{6-10}$aryl optionally substituted with 1 or 2 $R^Y$ groups, $C_{1-9}$heteroaryl, $C_{1-4}$alkyl-($C_{1-9}$heteroaryl), C(O)O$C_{1-4}$ alkyl, C(O)NHR$^Y$, $C_{2-5}$heterocycloalkyl optionally substituted with 1 or 2 $C_{1-4}$alkyl groups, C(O)-(heterocycloalkyl) optionally substituted with 1 or 2 $C_{1-4}$alkyl groups, or two adjacent $R^X$ groups together form $C_{1-3}$alkylenedioxy;

$R^Y$ is selected from H, hydroxyl, halo, $C_{1-4}$ alkyl, halo$C_{1-4}$ alkyl, $C_{1-4}$ alkoxy, $C_{1-4}$ alkylheterocycloalkyl, C(O)—($C_{1-4}$ alkylheterocycloalkyl), $C_{1-4}$alkylNR'R";

R' and R" are independently selected from H, $C_{1-4}$alkyl, $C_{1-4}$ alkylheterocycloalkyl;

$R^7$ is selected from H, $C_{1-4}$ alkyl and $C_{1-6}$ alkyl$C_{1-9}$ heteroaryl.

In preferred embodiments each heteroaryl and each heterocycloalkyl group comprises at least one nitrogen heteroatom.

In preferred embodiments X is S.

In a third aspect the present invention relates to compounds of general formula (III):

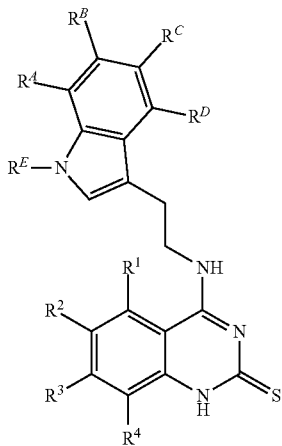

(III)

wherein groups $R^1$, $R^2$, $R^3$, and $R^4$ are as defined for formulae (I) and (II);

$R^A$, $R^B$, $R^C$ and $R^D$ are independently selected from H, OH, $C_{1-3}$ alkyl, O$C_{1-3}$ alkyl, C(O)—(N-heterocycloalkyl) (e.g., C(O)morpholinyl), C(O)piperazinyl) optionally substituted with 1 or 2 $C_{1-3}$ alkyl groups; N-heteroaryl (e.g., 3-pyridyl, 4-pyridyl, 2,1,3-benzoxadiazolyl, pyrazolyl) optionally substituted with 1 or 2 groups selected from OH, halo, $C_{1-3}$ alkyl, O$C_{1-3}$ alkyl; phenyl optionally substituted with 1 or 2 groups selected from OH, halo, $C_{1-3}$ alkyl, O$C_{1-3}$ alkyl, C(O)NH$C_{1-3}$ alkyl-[N($C_{1-3}$ alkyl)$_2$], C(O)(heterocycloalkyl) (e.g., morpholinyl, piperazinyl, piperidinyl) optionally substituted with 1 or 2 $C_{1-3}$ alkyl groups;

$R^E$ is H, $C_{1-3}$alkyl, or C(O)-heterocycloalkyl (e.g., C(O)—(N-morpholino)).

In another aspect the invention relates to a pharmaceutical composition comprising a compound of formula (I), formula (II) or formula (III), or a salt, hydrate, solvate, tautomer or stereoisomer thereof, together with one or more pharmaceutically acceptable carriers, diluents or excipients.

Compounds of general formula (I), formula (II) and formula (III) according to the present invention are heparanase inhibitors and the invention also relates to the treatment of diseases or conditions involving heparanase activity. Accordingly, another aspect of the present invention relates to a method of treatment of a disease or condition associated with heparanase activity in a subject, the method comprising administering to the subject an effective amount of a compound of formula (I), or a compound of formula (II), or a compound of formula (III), or a salt, hydrate, solvate, tautomer or stereoisomer thereof, or a pharmaceutical composition thereof.

In a further aspect the present invention relates to the use of a compound of formula (I), or a compound of formula (II), or a compound of formula (III), or a salt, hydrate, solvate, tautomer or stereoisomer thereof, or a pharmaceutical composition thereof in the manufacture of a medicament for treating a disease or condition associated with heparanase activity.

In another aspect the present invention relates to the use of a compound of formula (I), or a compound of formula (II), or a compound of formula (III), or a salt, hydrate, solvate, tautomer or stereoisomer thereof, or a pharmaceutical composition thereof for the treatment of a disease or condition associated with heparanase activity in a subject.

In a preferred embodiment, the treatment of disease by compounds of the present invention involves at least heparanase inhibition.

In preferred embodiments the disease or condition associated with heparanase activity is selected from Type 1 diabetes, Type 2 diabetes, nephritis, glomerulonephritis, cell-mediated autoimmune inflammation, diabetic nephropathy, gestational diabetes, diabetic ketoacidosis, hyperglycemia, hyperosmolar state, hypoglycemia, diabetic coma, diabetic cardiomyopathy, diabetic neuropathy, diabetic foot, diabetic retinopathy, diabetic myonecrosis, diabetic encephalopathy, and an ocular inflammatory disorder. In other preferred embodiments the disease or condition is selected from Type 1 diabetes, Type 2 diabetes, diabetic nephropathy, nephritis, glomerulonephritis, and cell-mediated autoimmune inflammation indications involving heparanase. In particularly preferred embodiments the disease or condition is selected from Type 1 diabetes and Type 2 diabetes. In other preferred embodiments the disease or condition is selected from Type 1 diabetes, Type 2 diabetes, diabetic nephropathy, nephritis, glomerulonephritis, and cell-mediated autoimmune inflammation indications involving heparanase. In other preferred embodiments the disease or condition is an ocular inflammatory disorder. In particularly preferred embodiments the disease or condition is selected from Type 1 diabetes and Type 2 diabetes.

In other embodiments the disease or condition related to heparanase activity is selected from cancer, allergies, dermatitis, psoriasis, macular degeneration, retinitis pigmentosa and pancreatitis.

Other aspects and embodiments of the present invention relate to processes for preparing compounds of the invention as disclosed herein.

Definitions

The following are some definitions of terms used in the art that may be helpful in understanding the description of the present invention. These are intended as general definitions and should in no way limit the scope of the present invention to those terms alone, but are put forth for a better understanding of the following description.

Unless the context requires otherwise or specifically stated to the contrary, integers, steps, or elements of the invention recited herein as singular integers, steps or elements clearly encompass both singular and plural forms of the recited integers, steps or elements.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps, features, compositions and compounds.

In the context of this specification the term "alkyl" includes within its meaning monovalent ("alkyl") and divalent ("alkylene") straight chain or branched chain saturated aliphatic groups having from 1 to 6 carbon atoms, denoted $C_{1-6}$alkyl. The alkyl group may be $C_{1-4}$alkyl. The alkyl group may be $C_{1-3}$alkyl. The alkyl group may be $C_{1-2}$alkyl. Thus, for example, the term alkyl includes, but is not limited to, methyl, ethyl, 1-propyl, isopropyl, 1-butyl, 2-butyl, isobutyl, tert-butyl, amyl, 1,2-dimethylpropyl, 1,1-dimethylpropyl, pentyl, isopentyl, hexyl, 4-methylpentyl, 1-methylpentyl, 2-methylpentyl, 3-methylpentyl, 2,2-dimethylbutyl, 3,3-dimethylbutyl, 1,2-dimethylbutyl, 1,3-dimethylbutyl, 1,2,2-trimethylpropyl, 1,1,2-trimethylpropyl, and the like.

In the context of this specification the term "alkenyl" includes within its meaning monovalent ("alkenyl") and divalent ("alkenylene") straight or branched chain unsaturated aliphatic hydrocarbon groups having from 2 to 6 carbon atoms and at least one double bond anywhere in the chain, denoted $C_{2-6}$alkenyl. The alkenyl group may be $C_{2-4}$alkenyl. The alkenyl group may be $C_{2-3}$ alkenyl. Unless indicated otherwise, the stereochemistry about each double bond may be independently cis or trans, or E or Z as appropriate. Examples of alkenyl groups include but are not limited to ethenyl, vinyl, allyl, 1-methylvinyl, 1-propenyl, 2-propenyl, 2-methyl-1-propenyl, 2-methyl-1-propenyl, 1-butenyl, 2-butenyl, 3-butentyl, 1,3-butadienyl, 1-pentenyl, 2-pententyl, 3-pentenyl, 4-pentenyl, 1,3-pentadienyl, 2,4-pentadienyl, 1,4-pentadienyl, 3-methyl-2-butenyl, 1-hexenyl, 2-hexenyl, 3-hexenyl, 1,3-hexadienyl, 1,4-hexadienyl, 2-methylpentenyl, and the like.

In the context of this specification the term "alkynyl" includes within its meaning monovalent ("alkynyl") and divalent ("alkynylene") straight or branched chain unsaturated aliphatic hydrocarbon groups having from 2 to 6 carbon atoms and having at least one triple bond, denoted $C_{2-6}$alkynyl. The alkynyl group may be $C_{2-4}$alkynyl. The alkyl group may be $C_{2-3}$alkynyl. Examples of alkynyl groups include but are not limited to ethynyl, 1-propynyl, 1-butynyl, 2-butynyl, 1-methyl-2-butynyl, 3-methyl-1-butynyl, 1-pentynyl, 1-hexynyl, methylpentynyl, and the like.

In the context of this specification the term "alkoxy" refers to straight chain or branched alkoxy (O-alkyl) groups, wherein alkyl is as defined above. Examples include methoxy, ethoxy, n-propoxy, isopropoxy, sec-butoxy, tert-butoxy, and the like.

In the context of this specification the term "aryl" as a group or part of a group denotes (i) an optionally substituted monocyclic, or fused polycyclic, aromatic carbocycle (ring structure having ring atoms that are all carbon) that may have from 6-10 atoms per ring, denoted $C_{6-10}$aryl. Examples of aryl groups include phenyl, naphthyl, phenanthryl and the like; (ii) an optionally substituted partially saturated bicyclic aromatic carbocyclic moiety in which a phenyl and a $C_{5-7}$cycloalkyl or $C_{5-7}$cycloalkenyl group are fused together to form a cyclic structure, such as tetrahydronaphthyl, indenyl or indanyl. The group may be a terminal group or a bridging group.

In the context of this specification the term "cycloalkyl" refers to a saturated or partially saturated, monocyclic, fused or spiro polycyclic, carbocycle that may contain from 3 to 9 carbon atoms per ring, such as cyclopropyl, cyclobutyl, cyclopentyl, cyclohexyl, spiro[3.3]heptane, and the like, unless otherwise specified. It includes monocyclic systems such as cyclopropyl and cyclohexyl, bicyclic systems such as decalin, and polycyclic systems such as adamantane. The group may be a terminal group or a bridging group.

In the context of this specification the term "cycloalkenyl" means a non-aromatic monocyclic or multicyclic ring system containing at least one carbon-carbon double bond and may have from 5-10 carbon atoms per ring, denoted $C_{5-10}$ cycloalkenyl. Exemplary monocyclic cycloalkenyl rings include cyclopentenyl, cyclohexenyl or cycloheptenyl. The cycloalkenyl group may be substituted by one or more substituent groups. The group may be a terminal group or a bridging group.

The term "$C_{1-3}$alkylenedioxy" as used herein refers to an —O(CH$_2$)$_{1-3}$O— group wherein the oxygen atoms of the alkylenedioxy group are attached to two adjacent carbon atoms of the parent molecular moiety forming a 5-, 6- or 7-membered ring. Exemplary alkylenedioxy groups are methylenedioxy and 1,2-ethylenedioxy.

In the context of this specification the terms "halogen" or "halo" are synonymous and refer to fluorine, chlorine, bromine or iodine.

In the context of this specification the term "heterocycloalkyl" includes within its meaning monovalent ("heterocycloalkyl") and divalent ("heterocycloalkylene"), saturated, monocyclic, bicyclic, fused or spiro polycyclic, hydrocarbon radicals having from 3 to 8 ring atoms, wherein from 1 to 5, or from 1 to 3, typically 1 or 2 ring atoms are heteroatoms independently selected from O, N, NH, or S. The heterocycloalkyl group may be $C_{3-6}$ heterocycloalkyl. The heterocycloalkyl group may be $C_{3-5}$heterocycloalkyl. Representative examples of heterocycloalkyl groups include aziridinyl, azetidinyl, pyrrolidinyl, piperidinyl, piperazinyl, quinuclidinyl, morpholinyl, diazaspiro[3.3]heptane (e.g., 2,6-diazaspiro[3.3]heptane), tetrahydrothiophenyl, tetrahydrofuranyl, tetrahydropyranyl, and the like. In one or more embodiments the heterocycloalkyl group is an N-heterocycloalkyl having one or more nitrogen heteroatoms, e.g., 1, 2, 3 or 4 nitrogen heteroatoms depending on the particular structure. N-heterocycloalkyl groups may also have heteroatoms other than nitrogen, but are characterized by having at least one nitrogen heteroatom. Exemplary N-heterocycloalkyl groups include aziridinyl, azetidinyl, pyrrolidinyl, piperidinyl, piperazinyl, morpholinyl, 2,6-diazaspiro[3.3]heptane among others. The heterocycloalkyl group may be a terminal group or a bridging group and may be attached through a heteroatom or any carbon ring atom.

In the context of this specification the term "heteroaryl" either alone or as part of a group means a monocyclic heteroaryl group having a 5- or 6-membered aromatic ring having one or more heteroatoms as ring atoms in the aromatic ring with the remainder of the ring atoms being carbon atoms, or a 8-10 membered bicyclic heteroaryl consisting of a monocyclic heteroaryl fused to a phenyl, or a monocyclic heteroaryl fused to a cycloalkyl, or a monocyclic heteroaryl fused to a cycloalkenyl, or a monocyclic heteroaryl fused to a monocyclic heteroaryl. The monocyclic heteroaryl and the bicyclic heteroaryl may be connected to the parent molecular moiety through any carbon atom or any nitrogen atom contained within the monocyclic heteroaryl or the bicyclic heteroaryl. Representative examples of monocyclic heteroaryl include, but are not limited to, furyl, imidazolyl, isoxazolyl, isothiazolyl, oxadiazolyl, oxazolyl (e.g., 1,3-oxazolyl, 1,2-oxazolyl), pyridinyl (e.g., 2-, 3-, 4-pyridinyl), pyridazinyl, pyrimidinyl, pyrazinyl, pyrazolyl, pyrrolyl, tetrazolyl, thiadiazolyl, thiazolyl, thienyl, triazolyl (e.g., 1,2,3-triazolyl, 1,2,4-triazolyl), and triazinyl. Representative examples of bicyclic heteroaryl include, but are not limited to, benzimidazolyl, benzofuranyl, benzothienyl, benzoxadiazolyl (e.g., 2,1,3-benzoxadiazolyl), cinnolinyl, dihydroquinolinyl, dihydroisoquinolinyl, furopyridinyl, indazolyl, indolyl (e.g., 2- or 3-indolyl), isoquinolinyl (e.g., 1-, 3-, 4-, or 5-isoquinolinyl), naphthyridinyl (e.g., 1,5-naphthyridinyl, 1,7-naphthyridinyl, 1,8-naphthyridinyl, etc), pyrrolopyridinyl (e.g., pyrrolo[2,3-b]pyridinyl), quinolinyl (e.g., 2-, 3-, 4-, 5-, or 8-quinolinyl), quinoxalinyl, tetrahydroquinolinyl, and thienopyridinyl. In one or more embodiments the heteroaryl group is an N-heteroaryl group having one or more nitrogen heteroatoms, e.g., 1, 2, 3 or 4 nitrogen heteroatoms depending on the particular structure. N-heteroaryl groups may also have heteroatoms other than nitrogen, but N-heteroaryl groups are characterized by having at least one nitrogen heteroatom. Exemplary N-heteroaryl groups include imidazolyl, indolyl, (e.g., 2- or 3-indolyl), naphthyridinyl, pyrazinyl, pyridyl (e.g., 2-, 3- or 4-pyridyl), pyrrolyl, pyrimidinyl, quinolinyl (e.g., 2-, 3-, 4-, 5-, or 8-quinolinyl), isoquinolinyl, quinazolinyl, quinoxalinyl, triazinyl, among others. The heteroaryl group may be a terminal group or a bridging group and may be attached through a heteroatom or any carbon ring atom.

The term "heteroatom" or variants such as "hetero-" as used herein refers to O, N, NH and S.

The term "inhibitor" as used herein refers to an agent that decreases, inhibits or impairs at least one function or biological activity of a target molecule. As used herein, the term "heparanase inhibitor" refers to an agent that decreases, inhibits or impairs at least one function or biological activity of heparanase. Heparanase inhibitors may decrease, inhibit or impair heparanase catalytic activity, heparanase protein binding, heparanase-mediated modulation of gene transcription, heparanase-mediated initiation of cell signaling and/or angiogenesis. In particular embodiments, the heparanase inhibitor decreases, inhibits or impairs one or more biological activities of heparanase, including heparanase catalytic activity. In particular embodiments, the heparanase inhibitor is an inhibitor of the type 1 heparanase isoform. The heparanase inhibitor may also inhibit complement fixation, macrophage activation, oxidative damage and/or growth factor activity. In preferred embodiments, the heparanase inhibitor inhibits one or both of macrophage, preferably microglial, activation and complement fixation. Heparanase inhibitors according to the present invention may be selective or non-selective inhibitors. In various embodiments, heparanase inhibitors according to the present invention are selective heparanase inhibitors.

The term "optionally substituted" as used throughout the specification denotes that the group may or may not be further substituted or fused (so as to form a polycyclic system), with one or more non-hydrogen substituent groups. Suitable chemically viable optional substituents for a particular functional group will be apparent to those skilled in the art. Typical optional substituents include $C_{1-4}$ alkyl, $C_{2-4}$ alkenyl, OH, halogen, O($C_{1-4}$ alkyl), CN, $NO_2$, NR'R" wherein R' and R" are independently selected from H and $C_1$-$C_3$ alkyl; CONR'R", SH, S($C_{1-3}$ alkyl), $SO_2$($C_{1-3}$alkyl), $CH_2$—($C_{1-3}$alkoxy), $C_{1-3}$ alkylenedioxy, $C_{6-10}$ aryl, —$CH_2$-phenyl, O—$CH_2$-phenyl, hydroxy($C_{1-3}$ alkyl), halo($C_{1-3}$ alkyl), $CO_2H$, $CO_2$($C_{1-4}$ alkyl), among others. Presently preferred optional substituents include halogen, OH, $NH_2$, $C_{1-3}$ alkyl, $C_{1-3}$ alkoxy, —$CH_2$—($C_{1-3}$alkoxy), $CH_2OH$, halo-($C_{1-3}$)alkyl, e.g., $CF_3$, halo-($C_{1-3}$)alkoxy, e.g, $OCF_3$, phenyl, and —$CH_2$-phenyl.

Certain compounds of the disclosed embodiments may exist as single stereoisomers, racemates, and/or mixtures of enantiomers and/or diastereomers. All such single stereoisomers, racemates, enantiomers, diastereomers and mixtures thereof, are intended to be within the scope of the subject matter of the invention.

Additionally, general formula (I) is intended to cover, where applicable, solvated as well as unsolvated forms of the compounds. Thus, each formula includes compounds having the indicated structure, including the hydrated or solvated form, as well as the non-hydrated and non-solvated forms. The term "solvate" is used herein to describe a molecular complex comprising the compound of the invention and one or more pharmaceutically acceptable solvent molecules, for example, ethanol. The term "hydrate" is employed when the solvent is water.

The term "pharmaceutically acceptable salt" refers to those salts which, within the scope of sound medical judgement, are suitable for use in contact with the tissues of humans and animals without undue toxicity, irritation, allergic response and the like, and are commensurate with a reasonable benefit/risk ratio. Pharmaceutically acceptable salts are well known in the art. S. M. Berge et al. describe pharmaceutically acceptable salts in detail in J. Pharmaceutical Sciences, 1977, 66:1-19. For a review on suitable salts, see Handbook of Pharmaceutical Salts: Properties, Selection, and Use by Stahl and Wermuth (Wiley-VCH, 2002). Methods for making pharmaceutically acceptable salts of compounds of the invention are known to one of skill in the art. The salts can be prepared in situ during the final isolation and purification of the compounds of the invention, or separately by reacting the free base function with a suitable organic acid. Suitable pharmaceutically acceptable acid addition salts of the compounds of the present invention may be prepared from an inorganic acid or from an organic acid. Examples of such inorganic acids are hydrochloric, hydrobromic, hydroiodic, nitric, carbonic, sulfuric, and phosphoric acid. Appropriate organic acids may be selected from aliphatic, cycloaliphatic, aromatic, heterocyclic carboxylic and sulfonic classes of organic acids, examples of which are formic, acetic, propionic, succinic, glycolic, gluconic, lactic, malic, tartaric, citric, ascorbic, glucoronic, fumaric, maleic, pyruvic, alkyl sulfonic, arylsulfonic, aspartic, glutamic, benzoic, anthranilic, mesylic, methanesulfonic, salicylic, p-hydroxybenzoic, phenylacetic, mandelic, ambonic, pamoic, pantothenic, sulfanilic, cyclohexylaminosulfonic, stearic, algenic, β-hydroxybutyric, galactaric, and galacturonic acids. Suitable pharmaceutically acceptable base addition salts of the compounds of the present invention include metallic salts made from lithium, sodium, potassium, magnesium, calcium, aluminium, and zinc, and organic salts made from organic bases such as choline, diethanolamine, morpholine. Alternatively, suitable pharmaceutically acceptable base addition salts of the compounds of the present invention include organic salts made from N,N'-dibenzylethylenediamine, chloroprocaine, choline, diethanolamine, ethylenediamine, meglumine (N-methylglucamine), procaine, ammonium salts, quaternary salts such as tetramethylammonium salt, amino acid addition salts such as salts with glycine and arginine. In the case of compounds that are solids, it will be understood by those skilled in the art that the inventive compounds, agents and salts may exist in different crystalline or polymorphic forms, all of which are intended to be within the scope of the present invention and specified formulae.

The term "stereoisomer" as used herein refers to any two or more isomers that have the same molecular constitution and differ only in the three dimensional arrangement of their atomic groupings in space. Stereoisomers may be diastereoisomers or enantiomers. It will be recognized that the compounds described herein may possess asymmetric centers and are therefore capable of existing in more than one stereoisomeric form. The invention thus also relates to compounds in substantially pure isomeric form at one or more asymmetric centers e.g., greater than about 90% ee, such as about 95% or 97% ee or greater than 99% ee, as well as mixtures, including racemic mixtures, thereof. Such isomers may be naturally occurring or may be prepared by asymmetric synthesis, for example using chiral intermediates, or by chiral resolution.

The terms "treating", "treatment" and "therapy" are used herein to refer to curative therapy, prophylactic therapy, palliative therapy and preventative therapy. Thus, in the context of the present disclosure the term "treating" encompasses curing, ameliorating or tempering the severity of a medical condition or one or more of its associated symptoms.

The terms "therapeutically effective amount" or "pharmacologically effective amount" or "effective amount" refer to an amount of an agent sufficient to produce a desired therapeutic or pharmacological effect in the subject being treated. The terms are synonymous and are intended to qualify the amount of each agent that will achieve the goal of improvement in disease severity and/or the frequency of incidence over treatment of each agent by itself while preferably avoiding or minimising adverse side effects, including side effects typically associated with other therapies. Those skilled in the art can determine an effective dose using information and routine methods known in the art.

A "pharmaceutical carrier, diluent or excipient" includes, but is not limited to, any physiological buffered (i.e., about pH 7.0 to 7.4) medium comprising a suitable water soluble organic carrier, conventional solvents, dispersion media, fillers, solid carriers, coatings, antibacterial and antifungal agents, isotonic and absorption delaying agents. Suitable water soluble organic carriers include, but are not limited to, saline, dextrose, corn oil, dimethylsulfoxide, and gelatin capsules. Other conventional additives include lactose, mannitol, corn starch, potato starch, binders such as microcrystalline cellulose, cellulose derivatives such as hydroxypropylmethylcellulose, acacia, gelatins, disintegrators such as sodium carboxymethylcellulose, and lubricants such as talc or magnesium stearate.

"Subject" includes any human or non-human mammal. Thus, in addition to being useful for human treatment, the compounds of the present invention may also be useful for veterinary treatment of mammals, including companion animals and farm animals, such as, but not limited to dogs, cats, horses, cows, sheep, and pigs. In preferred embodiments the subject is a human.

In the context of this specification the term "administering" and variations of that term including "administer" and "administration", includes contacting, applying, delivering or providing a compound or composition of the invention to a subject by any appropriate means.

DETAILED DESCRIPTION OF EMBODIMENTS OF THE INVENTION

Figure 1:
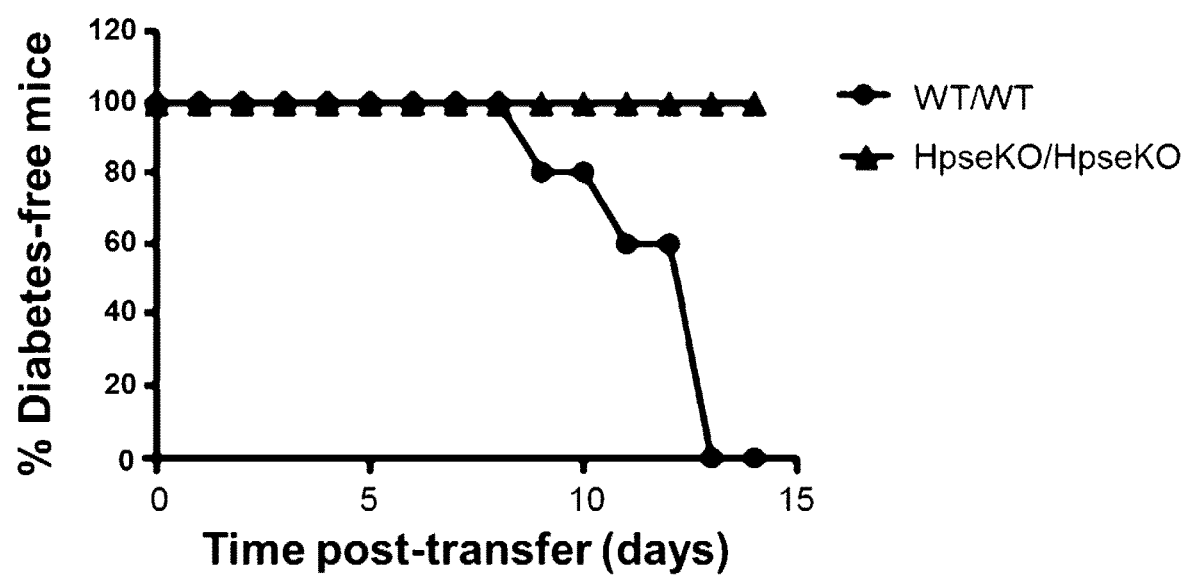
FIG. 1. Wild-type (WT) RIP-OVAhi mice become diabetic within 2 weeks after transfer of (WT) activated OT-II and naïve OT-I tg T cells. In contrast, transfer of heparanase-deficient (Hpse KO) OT-II and OT-1 tg T cells into heparanase-deficient RIP-OVAhi mice confirmed that Type 1 diabetes induction is heparanase-dependent.

The present invention relates to functionalized dihydro- and tetrahydro-quinazoline compounds as defined herein, and to the use of such compounds in the treatment of diseases or conditions associated with heparanase activity. In preferred embodiments, the compounds of the invention are heparanase inhibitors.

In one aspect the present invention relates to compounds of general formula (I) or general formula (II):

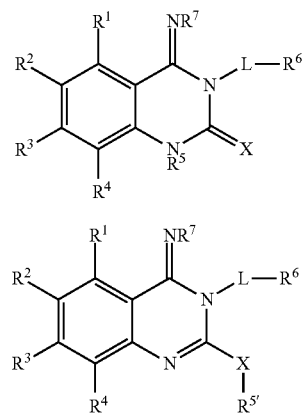

or a salt, hydrate, solvate, tautomer or stereoisomer thereof,
wherein:
X is S or O;
$R^1$ is selected from H, hydroxyl, halo, $C_{1-6}$ alkyl, $C_{1-4}$ alkoxy, O—$CH_2$phenyl, O-phenyl;
$R^2$ is selected from H, hydroxyl, halo, $C_{1-6}$ alkyl, $C_{1-4}$ alkoxy, O—$CH_2$phenyl, O-phenyl;
$R^3$ is selected from H, hydroxyl, halo, $C_{1-6}$ alkyl, $C_{1-4}$ alkoxy, O—$CH_2$phenyl, O-phenyl;
$R^4$ is selected from H, hydroxyl, halo, $C_{1-6}$ alkyl, $C_{1-4}$ alkoxy, O—$CH_2$phenyl, O-phenyl;
or $R^1$ and $R^2$, or $R^2$ and $R^3$, or $R^3$ and $R^4$ together form $C_{1-3}$ alkylenedioxy;
$R^5$ and $R^{5'}$ are independently selected from H, $C_{1-6}$ alkyl, $C_{1-3}$alkylC(O)OC$_{1-4}$alkyl and $C_{1-3}$alkylC$_{6-10}$aryl optionally substituted with 1 or 2 groups independently selected from haloC$_{1-3}$alkyl and haloC$_{1-3}$alkoxy;
L is selected from $C_{1-6}$ alkyl, azetidinyl, $C_{1-6}$ alkyl-indolyl, NH, $C_{1-6}$alkyl-NHC(O)O, azetidinyl-C(O)—, $C_{1-6}$ alkyl-NHC(O)-indolyl, $C_{1-6}$ alkyl-NHSO$_2$—, or is absent;
$R^6$ is selected from H, halo, hydroxyl, $C_{1-6}$alkyl, $C_{1-6}$alkenyl, $C_{1-6}$alkynyl, $C_{6-10}$aryl optionally substituted with 1 or 2 $R^X$ groups, $C_{1-9}$heteroaryl optionally substituted with 1 or 2 $R^X$ groups, $C_{2-5}$heterocycloalkyl optionally substituted with 1 or 2 $R^X$ groups, C(O)($C_{1-9}$heteroaryl) optionally substituted with 1 or 2 $R^X$ groups, C(O)($C_{2-5}$ heterocycloalkyl) optionally substituted with 1 or 2 $R^X$ groups, C(O)NHR$^Y$, or is absent;
each $R^X$ is independently selected from hydroxyl, halo, nitro, NR'R'', $C_{1-4}$ alkyl, $C_{3-6}$ cycloalkyl, haloC$_{1-4}$ alkyl, $C_{1-4}$alkoxy, $C_{6-10}$ aryl optionally substituted with 1 or 2 $R^Y$ groups, $C_{1-9}$ heteroaryl, $C_{1-4}$ alkyl-($C_{1-9}$heteroaryl), C(O)OC$_{1-4}$ alkyl, C(O)NHR$^Y$, $C_{2-5}$heterocycloalkyl optionally substituted with 1 or 2 $C_{1-4}$ alkyl groups, C(O)-(heterocycloalkyl) optionally substituted with 1 or 2 $C_{1-4}$ alkyl groups, or two adjacent $R^X$ groups together form $C_{1-3}$alkylenedioxy;
$R^Y$ is selected from H, hydroxyl, halo, $C_{1-4}$ alkyl, haloC$_{1-4}$ alkyl, $C_{1-4}$ alkoxy, $C_{1-4}$ alkylheterocycloalkyl, C(O)—($C_{1-4}$ alkylheterocycloalkyl), $C_{1-4}$ alkylNR'R'';
R' and R'' are independently selected from H, $C_{1-4}$alkyl, and $C_{1-4}$ alkylheterocycloalkyl;
$R^7$ is selected from H, $C_{1-4}$ alkyl, $C_{1-6}$ alkylC$_{1-9}$ heteroaryl.

In preferred embodiments each heteroaryl and each heterocycloalkyl group comprises at least one nitrogen heteroatom.

In preferred embodiments X is S.

In preferred embodiments the salt is a pharmaceutically acceptable salt.

In one or more embodiments, each heteroaryl is independently selected from indolyl (e.g., N-indolyl, 2-indolyl, 3-indolyl), pyridyl (e.g., 2-pyridyl, 3-pyridyl, 4-pyridyl), pyrazolyl, pyrrolyl, benzoxadiazolyl, triazolyl, oxazolyl, oxadiazolyl, each of which may be optionally substituted with 1 or 2 $R^X$ groups.

In one or more embodiments, each heterocycloalkyl is independently selected from aziridinyl, morpholinyl, piperidinyl, piperazinyl, each of which may be optionally substituted with 1 or 2 $R^X$ groups.

In one or more embodiments $R^1$ and $R^4$ are H. In one or more embodiments $R^2$ and $R^3$ are independently H, halo, or $C_{1-4}$alkoxy. In one or more embodiments $R^2$ and $R^3$ are not both H. In one or more embodiments $R^2$ and $R^3$ are both $C_{1-4}$alkoxy e.g., methoxy, ethoxy. In one or more embodiments $R^2$ and $R^3$ together are methylenedioxy.

In one or more embodiments $R^5$ or $R^{5'}$ is independently H. In one or more embodiments $R^5$ or $R^{5'}$ is independently a $C_{1-6}$ alkyl group, e.g., methyl, ethyl. In one or more embodiments $R^5$ or $R^{5'}$ is independently $C_{1-3}$alkylC(O)OC$_{1-3}$alkyl. In one or more embodiments $R^5$ or $R^{5'}$ is independently a benzyl group optionally substituted with 1 or 2 groups selected from $CF_3$ and $OCF_3$.

In one or more embodiments L is $C_{1-3}$ alkyl, $C_{1-3}$ alkylNHC(O)—, or azetidinyl. In one or more embodiments L is $C_{1-6}$ alkyl-NHC(O)-indolyl.

In or more embodiments $R^6$ is a group selected from indolyl (e.g., 2-indolyl or 3-indolyl), phenyl, pyridyl (e.g., 2-pyridyl, 3-pyridyl or 4-pyridyl), N-morpholinyl, N-piperidinyl, N-piperazinyl, pyrrolyl, diazolyl, triazolyl (e.g., 4-triazolyl), pyrazolyl (e.g., N(1)-pyrazolyl); oxazolyl, ozadiazolyl, benzodiazolyl and pyrrolopyridinyl (e.g., pyrrolo[2,3-b]pyridinyl), wherein each group is optionally substituted with 1 or 2 $R^X$ groups.

In one or more embodiments $R^7$ is H or $C_{1-4}$ alkyl. In more or more embodiments, $R^7$ is $C_{1-6}$ alkylC$_{1-9}$ heteroaryl. In one or more embodiments, $R^7$ is $C_{1-2}$ alkyl-(2-indolyl) or $C_{1-2}$ alkyl-(3-indolyl).

In one or more embodiments L is absent and $R^6$ is selected from $C_{1-6}$alkyl, $C_{1-6}$alkenyl. $C_{1-6}$ alkynyl, and $C_{2-5}$heterocycloalkyl (e.g., piperidinyl, piperazinyl or morpholinyl) optionally substituted with 1 or 2 $R^X$ groups.

In one or more embodiments L is NH and $R^6$ is H or phenyl.

In one or more embodiments L is $C_{1-2}$alkyl and $R^6$ is indolyl (e.g., 2-indolyl or 3-indolyl) optionally substituted with 1 or 2 $R^X$ groups. In one or more embodiments L is $C_{1-2}$ alkyl-NHC(O)— and $R^6$ is $C_{1-9}$ heteroaryl (e.g., indolyl, pyrrolyl, pyridinyl, oxazolyl, oxadiazolyl) optionally substituted with 1 or 2 $R^X$ groups, $R^5$ or $R^{5'}$ is independently H and $R^7$ is H.

In one or more embodiments L is $C_{1-2}$ alkyl-NHC(O)— and $R^6$ is $C_{1-9}$ heteroaryl (e.g., indolyl, pyrrolyl, pyridinyl, oxazolyl, oxadiazolyl) optionally substituted with 1 or 2 $R^X$ groups. In one or more embodiments, L is $C_{1-3}$ alkylNHC(O)— and $R^6$ is indolyl (e.g., 2-indolyl or 3-indolyl) optionally substituted with 1 or 2 $R^X$ groups or 3-indolyl optionally substituted with 1 or 2 $R^X$ groups. In one or more embodiments L is $C_{1-6}$ alkyl-NHC(O)— and $R^6$ is $C_{1-9}$ heteroaryl (e.g., pyrrolyl, pyridinyl, oxazolyl, oxadiazolyl) optionally substituted with 1 or 2 $R^X$ groups. In one or more embodiments L is $C_{1-3}$ alkylNHC(O)— and $R^6$ is indolyl (e.g., 2-indolyl or 3-indolyl) optionally substituted with a pyridinyl group (e.g., 2-, 3- or 4-pyridinyl). In one or more embodiments L is $C_{1-6}$ alkyl-NHC(O)— and $R^6$ is $C_{1-9}$ heteroaryl (e.g., pyrrolyl, pyridinyl, oxazolyl, oxadiazolyl) optionally substituted with 1 or 2 $R^X$ groups, $R^5$ or $R^{5'}$ is independently selected from $C_{1-3}$ alkyl, $C_{1-3}$alkylC(O)OC$_{1-4}$alkyl and $C_{1-3}$alkylC$_{6-10}$ aryl optionally substituted with 1 or 2 groups independently selected from haloC$_{1-3}$alkyl (e.g., CF$_3$) and haloC$_{1-3}$alkoxy (e.g., OCF$_3$), and $R^7$ is H.

In one or more embodiments L is $C_{1-3}$ alkyl-NHC(O)-indolyl and $R^6$ is selected from phenyl optionally substituted with 1 or 2 $R^X$ groups, $C_{3-8}$ heteroaryl optionally substituted with 1 or 2 $R^X$ groups, C(O)($C_{3-8}$ heteroaryl) optionally substituted with 1 or 2 $R^X$ groups, C(O)($C_{2-5}$heterocycloalkyl) optionally substituted with 1 or 2 $R^X$ groups, C(O)NHR$^Y$, or is absent. In one or more embodiments L is $C_{1-3}$ alkyl-NHC(O)-indolyl and $R^6$ is selected from phenyl optionally substituted with C(O)NHR$^Y$, C(O)-(heterocycloalkyl) optionally substituted with 1 or 2 $C_{1-4}$ alkyl groups (e.g., methyl, ethyl).

In one or more embodiments L is $C_{1-2}$ alkyl-NHC(O)-indolyl, $R^6$ is pyridyl, and $R^5$ or $R^{5'}$ is independently selected from H, $C_{1-6}$ alkyl, $C_{1-3}$alkylC(O)OC$_{1-4}$alkyl and $C_{1-3}$alkylC$_{6-10}$aryl optionally substituted with 1 or 2 groups independently selected from haloC$_{1-3}$alkyl or haloC$_{1-3}$alkoxy.

In one or more embodiments L is azetidinylC(O)— and $R^6$ is indolyl (e.g., 2-indolyl or 3-indolyl) optionally substituted with 1 or 2 $R^X$ groups. In one or more embodiments L is azetidinylC(O)— and $R^6$ is 2-indolyl optionally substituted with a $C_{1-9}$ heteroaryl group. In one or more embodiments L is azetidinylC(O)— and $R^6$ is 2-indolyl optionally substituted with a pyridinyl group (e.g., 2-, 3- or 4-pyridinyl). In one or more embodiments L is azetidinylC(O)— and $R^6$ is 2-indolyl optionally substituted with a $C_{1-9}$ heteroaryl group, $R^5$ or $R^{5'}$ is independently H and $R^7$ is H. In one or more embodiments L is azetidinylC(O)— and $R^6$ is 2-indolyl optionally substituted with a $C_{1-9}$ heteroaryl group, $R^5$ or $R^{5'}$ is independently selected from $C_{1-3}$ alkyl, $C_{1-3}$alkylC(O)OC$_{1-4}$alkyl and $C_{1-3}$alkylC$_{6-10}$aryl optionally substituted with 1 or 2 groups independently selected from haloC$_{1-3}$alkyl and haloC$_{1-3}$alkoxy, and $R^7$ is H.

In one or more embodiments, $R^5$ or $R^{5'}$ is independently H and $R^7$ is H.

In one or more embodiments, $R^5$ or $R^{5'}$ is independently H and $R^7$ is $C_{1-2}$alkyl-(3-indolyl).

In one or more embodiments each $R^X$ is independently selected from hydroxyl, halo, $C_{1-3}$ alkyl, $C_{1-4}$alkoxy, C(O) OC$_{1-4}$ alkyl, phenyl, NR'R" wherein R' and R" are independently selected from H and $C_{1-3}$ alkyl, morpholinyl optionally substituted with 1 or 2 $C_{1-3}$ alkyl groups, piperazinyl optionally substituted with 1 or 2 $C_{1-3}$ alkyl groups, C(O) morpholinyl optionally substituted with 1 or 2 $C_{1-3}$alkyl groups, $C_{6-10}$aryl optionally substituted with 1 or 2 C(O)—($C_{1-4}$alkylheterocycloalkyl) groups, C(O)piperazinyl optionally substituted with 1 or 2 $C_{1-3}$ alkyl groups, or two adjacent $R^X$ groups together form methylenedioxy or 1,2-ethylenedioxy. In one or more embodiments $R^X$ is pyridyl (e.g., 2-, 3- or 4-pyridyl).

In one or more embodiments the invention relates to compounds of formula (IA) or formula (IB), formula (IC), formula (IIA), or formula (IIB) or a salt, hydrate, solvate, tautomer or stereoisomer thereof:

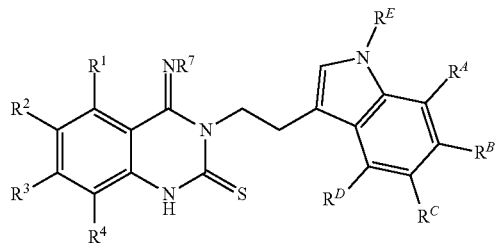

(IA)

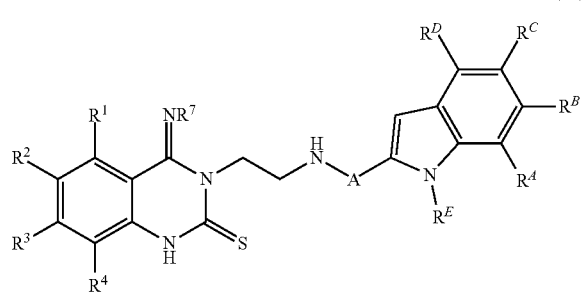

(IB)

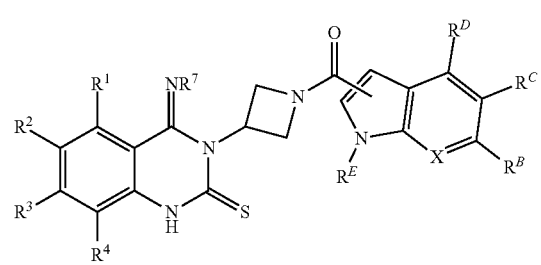

(IC)

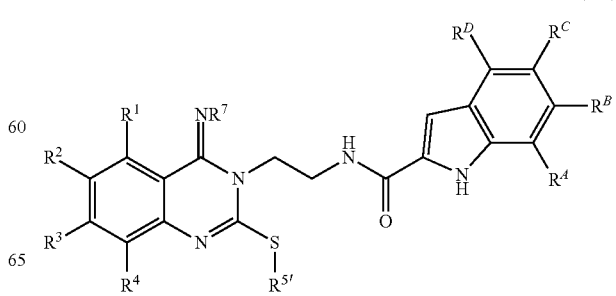

(IIA)

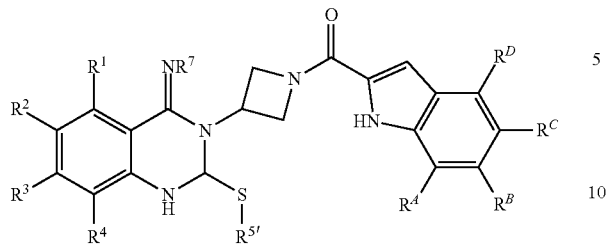

(IIB)

wherein:

R¹ and R⁴ are both H;

R² is H, halo, $C_{1-3}$alkoxy, O—CH₂phenyl, O-phenyl;

R³ is H, halo, $C_{1-3}$alkoxy, O—CH₂phenyl, O-phenyl;

R⁷ is H or $C_{1-3}$ alkyl;

A is C=O or SO₂;

X is C or N;

$R^E$ is H, $C_{1-3}$alkyl, or C(O)-heterocycloalkyl (e.g., C(O)—(N-morpholino));

$R^{5'}$ is H, $C_{1-6}$ alkyl, $C_{1-3}$alkylC(O)OC$_{1-3}$alkyl or $C_{1-3}$ alkylC$_{6-10}$ aryl optionally substituted with 1 or 2 groups independently selected from haloC$_{1-3}$alkyl or haloC$_{1-3}$ alkoxy;

$R^A$, $R^B$, $R^C$ and $R^D$ are independently selected from H, OH, $C_{1-3}$ alkyl, OC$_{1-3}$ alkyl, C(O)—(N-heterocycloalkyl) (e.g., C(O)morpholinyl), C(O)piperazinyl) optionally substituted with 1 or 2 $C_{1-3}$ alkyl groups; N-heteroaryl (e.g., 3-pyridyl, 4-pyridyl, 2,1,3-benzoxadiazolyl, pyrazolyl) optionally substituted with 1 or 2 groups selected from OH, halo, $C_{1-3}$ alkyl, OC$_{1-3}$ alkyl; phenyl optionally substituted with 1 or 2 groups selected from OH, halo, $C_{1-3}$ alkyl, OC$_{1-3}$ alkyl, C(O) NHC$_{1-3}$ alkyl-[N(C$_{1-3}$ alkyl)₂], C(O)(heterocycloalkyl) (e.g., morpholinyl, piperazinyl, piperidinyl) optionally substituted with 1 or 2 $C_{1-3}$ alkyl groups.

It will be apparent to those skilled in the art that general formulae (IA)-(IC) are subsets of general formula (I), and formulae (IIA) and (IIB) are a subsets of general formula (II).

In one or more embodiments $R^A$ and $R^D$ are H. In one or more embodiments, $R^A$, $R^C$ and $R^D$ are H. In one or more embodiments, $R^A$, $R^B$, $R^C$ and $R^D$ are H.

In on or more embodiments $R^E$ is H. In one or more embodiments $R^E$ is $C_{1-3}$alkyl.

In one or more embodiments A is C=O.

Those skilled in the art will recognise that when the linker group L comprises an amide or cyclic moiety (e.g., a heterocycloalkyl, cycloalkyl moiety), rotation of the groups attached to the linker will be restricted. In one or more embodiments of the invention, such compounds may have increased activity.

Another aspect of the invention relates to compounds of general formula (III):

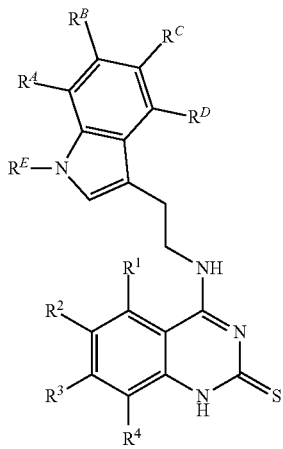

(III)

or a salt, hydrate, solvate, tautomer or stereoisomer thereof, wherein groups R¹, R², R³, R⁴, $R^A$, $R^B$, $R^C$, $R^D$, and $R^E$ are as defined for formulae (I) and (II), formulae (IA)-(IC) and formulae (IIA)-(IIB), including the preferred embodiments.

Those skilled in the art will recognise that general formula (III) is based on a tautomeric form of the imine group of general formula (I), wherein the amine group has been alkylated.

For the avoidance of doubt, throughout this specification a general reference to 'a compound of the invention' refers to compounds of general formula (I), general formulae (IA)-(IC), general formula (II), general formulae (IIA)-(IIB), general formula (III) and salts, hydrates, solvates, tautomers or stereoisomers thereof unless expressly stated otherwise. For convenience, a reference to 'a compound of formula (I)' or 'a compound of general formula (I)' includes compounds of general formulae (IA)-(IC) and salts, hydrates, solvates, tautomers or stereoisomers thereof unless expressly stated otherwise. Similarly, a reference to 'a compound of formula (II)' or 'a compound of general formula (II)' includes compounds of general formulae (IIA)-(IIB) and salts, hydrates, solvates, tautomers or stereoisomers thereof unless expressly stated otherwise.

Compounds of the invention, or salts, hydrates, solvates, tautomers or stereoisomers thereof may be prepared using methods known to those skilled in the art, the illustrative reaction schemes and General Procedures disclosed herein, the specific methods described in the Examples section, or by routine modifications thereof. The present invention also encompasses any one or more of these processes for preparing the compounds of the invention, in addition to any novel intermediates used therein.

Suitable reagents and reaction conditions for performing reactions will be known to the skilled person and are described in the literature and text books, including for example March, J. *Advanced Organic Chemistry*, 4th Ed (John Wiley & Sons, New York, 1992) and *Vogel's Textbook of Practical Organic Chemistry*, 5th Ed (John Wiley & Sons, New York, 1989).

The reaction schemes presented below are illustrative of general methods that may be employed to prepare the compounds of the invention. Alternative methods, including routine modifications of the methods disclosed herein, will be apparent to those skilled in the art. Groups R¹, R², R³, R⁴, R⁵, $R^{5'}$, R⁶, $R^A$, $R^B$, $R^C$, $R^D$ are as previously defined for general formula (I), general formula (II) and general formula (III).

Compounds of general formula (I) may be prepared via the condensation reaction described by Pazdera, P., et al, *Chem. Papers,* 1989, 43, 771 which involves the condensation of a 2-isothiocyanatobenzonitrile 1 (X=S) or 2-isocyanatobenzonitrile 1 (X=O) with a primary amine 2 as illustrated in Scheme 1:

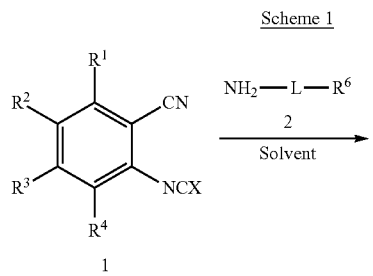

The reaction scheme depicted in Scheme 1 is versatile and allows ready access to the 4-imino-3,4-dihydroquinazoline-2(1H)-thione (X=S) or 4-imino-3,4-dihydroquinazoline-2(1H)-one (X=O) scaffold, with substituent groups $R^1$-$R^4$ in formula (I) derived from the benzonitrile reactant 1. Advantageously, such reactions may be performed in one-pot.

Typical solvents include but are not limited to alcohols (e.g., ethanol, propanol), tetrahydrofuran, petroleum spirit/dichloromethane mixtures.

The reaction is typically performed at a temperature in the range of about 20° C. to about 100° C., e.g., about 20° C. to about 80° C., or about 25° C. to about 80° C.

An exemplary reaction scheme for preparing compounds of general formula (I) is shown in Scheme 1A in which linker L is an alkylene and $R^6$ is an optionally substituted 3-indole.

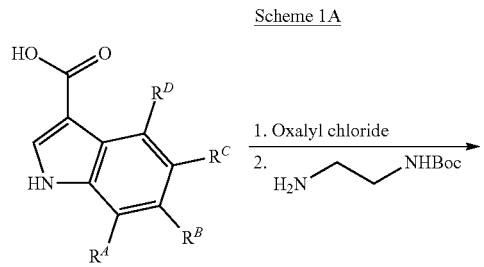

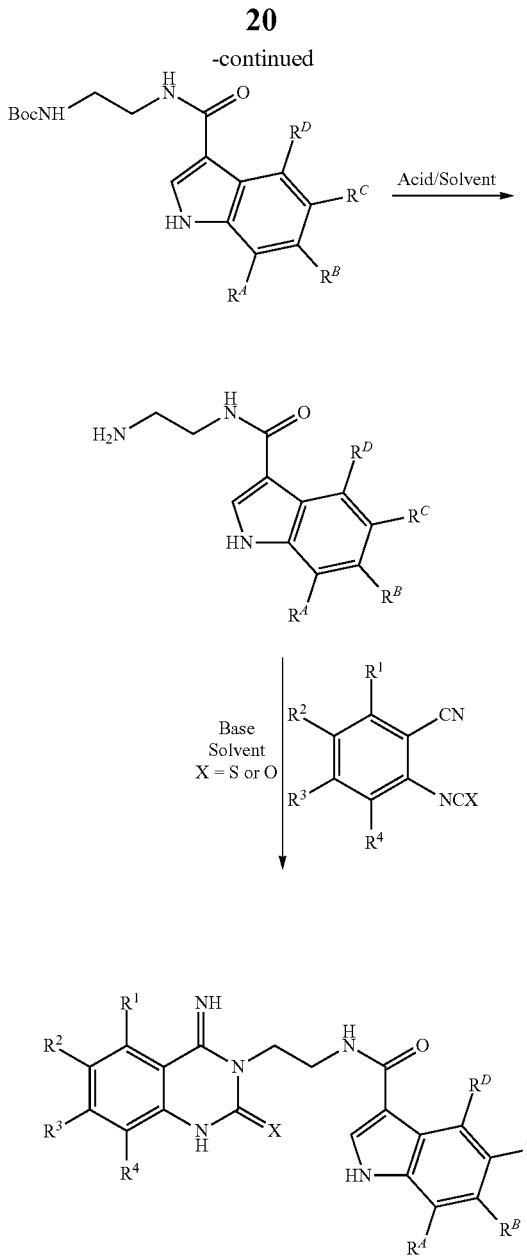

Scheme 1A

Suitable acids for removal of the t-butoxycarbonyl (Boc) protecting group from the amine in step 2 of Scheme 1A include but are not limited to an inorganic acid such as hydrochloric acid or trifluoracetic acid, and suitable solvents include alcohols such as methanol or ethanol, dioxane, tetrahydrofuran or acetonitrile. Suitable bases for the condensation reaction shown in the third step include but are not limited to triethylamine, diisopropylethylamine, 2,6-dimethylpyridine, and suitable solvents include alcohols e.g., methanol, ethanol, propanol, tetrahydrofuran, and petroleum spirit/dichloromethane mixtures. The reactions are typically carried out at temperatures below 60° C., typically at room temperature.

Another exemplary reaction scheme for preparing compounds of general formula (I) is depicted in Scheme 1B:

Scheme 1B

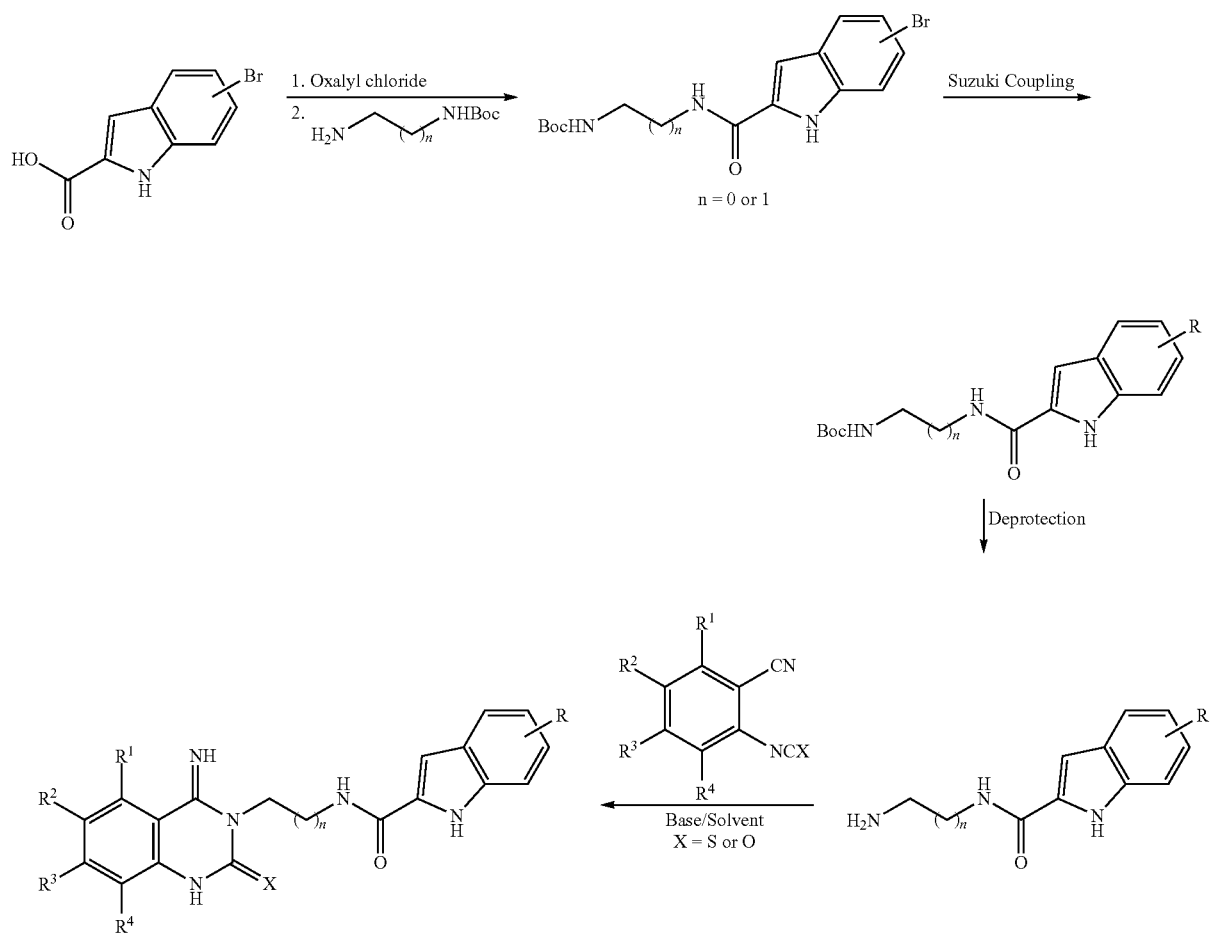

The Suzuki coupling step to introduce functionality onto the indole ring is well known to those skilled in the art and can be performed, for example, by reacting aryl bromide with a boronic acid or ester in base, e.g., potassium carbonate, sodium carbonate in a degassed mixture of dimethoxyethane, water and ethanol, followed by addition of bis(triphenylphosphine)palladium(II) dichloride. The reaction mixture is typically heated to a temperature above 100° C. The deprotection step to remove the Boc protecting group from the amine is also well known in the art and suitable conditions include trifluoroacetic acid/$CH_2Cl_2$, or hydrochloric acid/dioxane. The final step typically may use a base such as triethylamine, diisopropylethylamine, 2,6-dimethylpyridine, among others, and suitable solvents include alcohols e.g., methanol, ethanol, propanol, tetrahydrofuran, and petroleum spirit/dichloromethane mixtures. The reactions are typically carried out at temperatures below 60° C., typically at room temperature.

Another exemplary reaction scheme useful in the preparation of compounds of general formula (I) is depicted in Scheme 1C below:

Scheme 1C

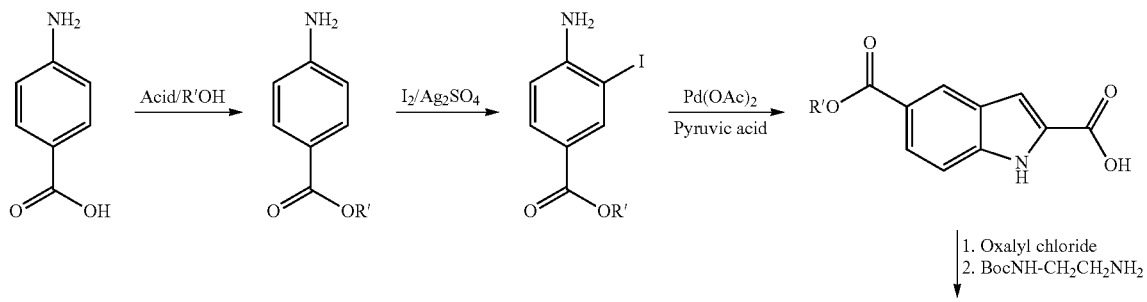

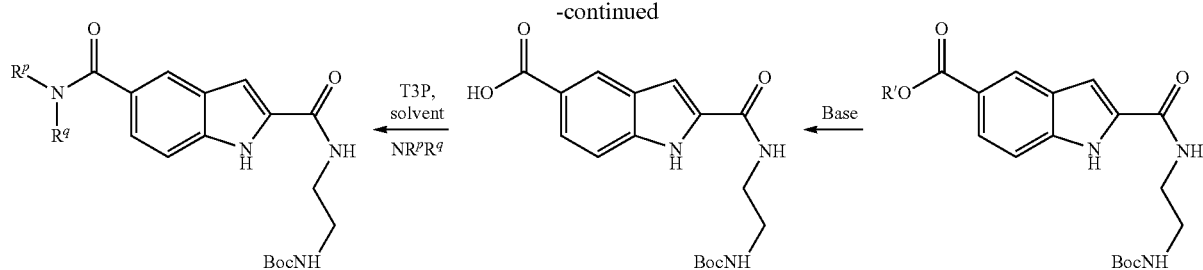

Scheme 1C illustrates methods for introducing amide functionality at the 5-position of the indole ring. In various embodiments the groups R$^p$ and R$^q$ together with the nitrogen atom to which they are attached may form a morpholinyl, piperazinyl or piperidinyl ring. The first step shown in Scheme 1C involves standard methodology to protect the carboxylic acid as an ester. Suitable alcohols (R'OH) include methanol, ethanol, butanol (e.g., n-butanol), etc. A suitable base for use in the fifth step to convert the ester into a carboxylic acid without removing the Boc protecting group includes but is not limited to lithium hydroxide. A suitable exemplary solvent for the sixth step which involves formation of the amide bond, is N,N-dimethylformamide. The amide product shown in Scheme 1C may then be deprotected to remove the Boc protecting group and reacted with a 2-isothiocyanatobenzonitrile (X=S) or 2-isocyanatobenzonitrile (X=O) following the general procedures known in the art, including those described above for Scheme 1, Scheme 1A and Scheme 1B.

Compounds of general formula (II) may be prepared from compounds of general formula (I) (when R$^5$=H). For example, as illustrated in general Scheme 2, a compound of formula (I) represented by quinazoline compound 3 is first treated with base to form an intermediate thioamide enolate (X=S) or an amide enolate (X=O), followed by a nucleophilic substitution reaction with a halide compound 4 (R$^{5'}$—X') (where X'=Cl, Br, I) to afford the compound of general formula (II).

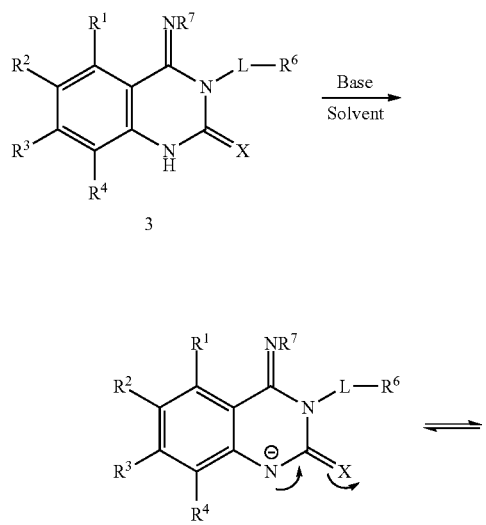

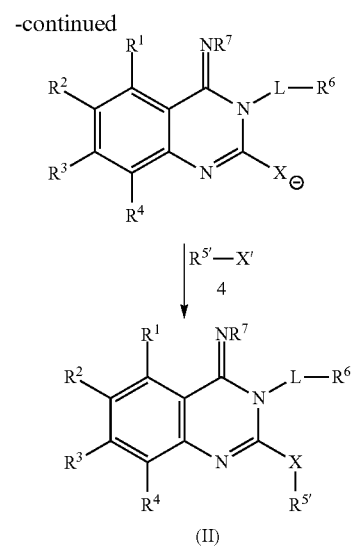

An exemplary reaction scheme for preparing compounds of general formula (II) is shown in Scheme 2A in which linker L is an alkyl amide, R$^6$ is an optionally substituted 2-indole and R$^{5'}$—X' is methyl iodide.

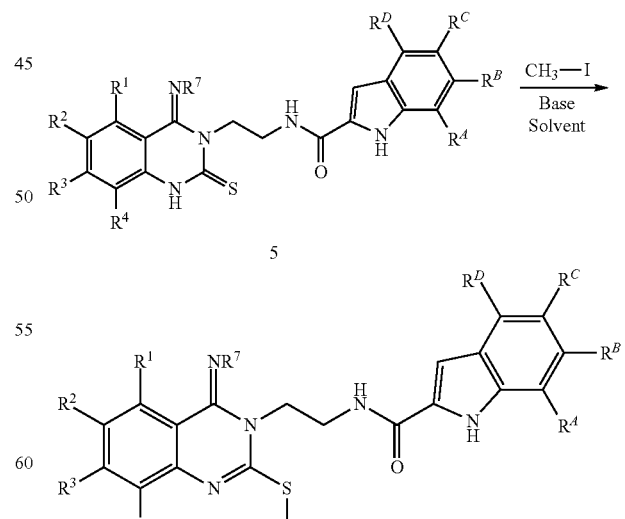

As illustrated in Scheme 2A, a quinazoline compound 5 of general formula (I) is reacted with a base (e.g., potassium carbonate) in a suitable solvent such as acetone. The reaction mixture is stirred, typically at room temperature, until substantially complete. The reaction will typically require at least 2-4 hours, more typically about 12-48 hours, although longer periods may be required for large scale reactions. If necessary, routine methods of purification such as flash column chromatography can be used to isolate compounds of general formula (II).

Compounds of general formula (III) may be prepared by performing a nucleophilic reaction at the 4-position of the dihydroquinazoline 6 (X=S or O) according to the method described in *Eur J Med Chem* 2012 47 283 and Lee et al. *J Med Chem.* 1995, 38 (18), pp 3547-3557, as illustrated in general Scheme 3:

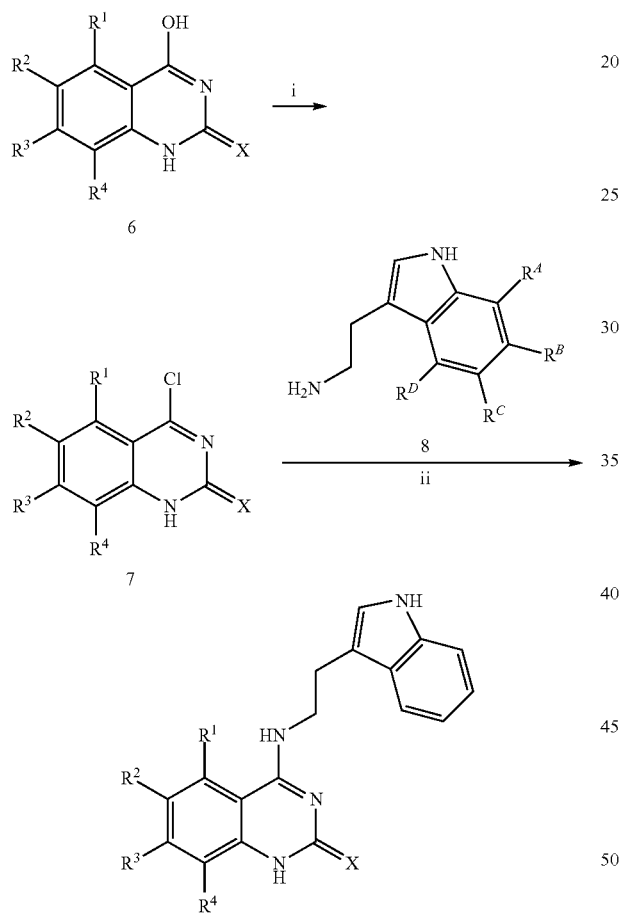

i. POCl₃/solvent, reflux; ii. benzylamine in ethanol

Suitable solvents for step i include, for example, DMF, THF. Typically the reaction mixture is heated at reflux until substantially complete. Step ii is typically performed by heating the reaction mixture at temperatures above 60° C., typically about 75° C. until the reaction is judged to be substantially complete. Typical reaction times are about 2-24 hours, e.g., about 12 hours or 15 hours, depending on the scale of the reaction.

In an alternative procedure, compounds of general formula (III) may be prepared by thionation of the corresponding 2-chloroquinazoline 9 as illustrated in Scheme 4:

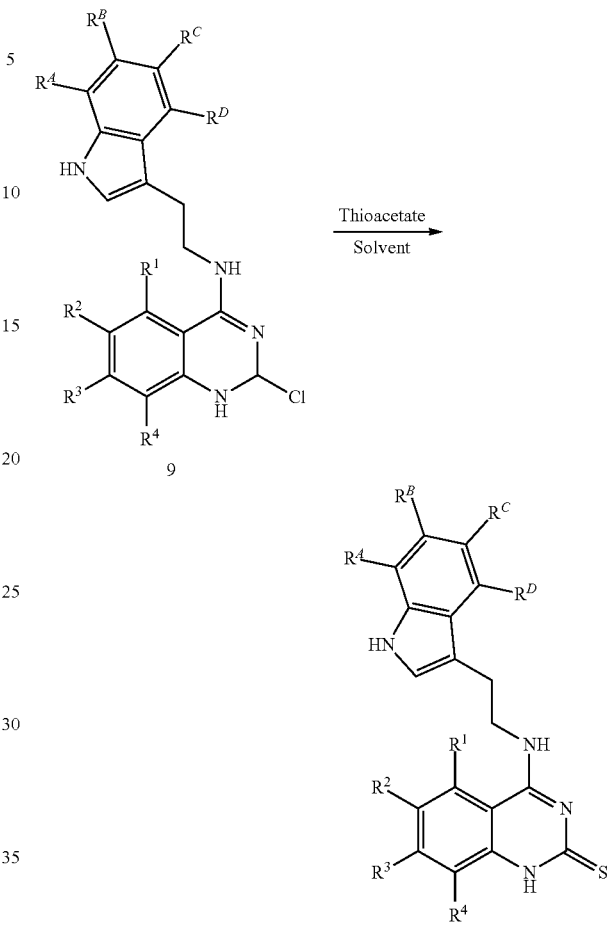

As illustrated in Scheme 4, a 2-chloro-4-amino substituted dihydro-quinazoline 6 is reacted with a salt of thioacetate (e.g., potassium thioacetate) in a suitable solvent such as dioxane or THF. The reaction mixture is typically heated to a temperature above 60° C., typically above 100° C., more typically about 120° C. and the reaction is allowed to proceed for a period of time sufficient for the reaction to proceed substantially to completion. Those skilled in the art know how to monitor the progress of a chemical reaction using standard techniques, such as Thin Layer Chromatography (TLC), ¹H NMR, etc. The reaction will typically require at least 1 hour, more typically about 3 hours, although longer periods may be required for large scale reactions. When the reaction is judged to be sufficiently complete, the reaction mixture is typically cooled, and the reaction solvent removed (e.g., under vacuum), after which the residue is treated with ammonia in a protic solvent such as methanol. The compound of general formula (III) may then be isolated using routine methods such as flash column chromatography.

Where appropriate or necessary, protecting groups may be employed at any stage in the synthesis of compounds of the invention. Similarly, those skilled in the art will also appreciate that compounds of the invention can also be prepared with certain protecting groups that are useful for purification or storage that can be removed before administration to a patient. Thus, this invention also encompasses compounds of the invention containing protective groups. Suitable protecting groups and their use are well known to those skilled in the art and include, for example, protecting groups described in Peter G. M. Wuts, Theodora W. Greene, "Greene's Protective Groups in Organic Synthesis", 4$^{th}$ Edition. (John Wiley & Sons, Inc., 2007). The protection and deprotection of functional groups is also described in "Protective Groups in Organic Chemistry", edited by J. W. F. McOmie, Plenum Press (1973).

Those skilled in the art will recognise the versatility of the reactions illustrated in the above Schemes, which can provide access to a wide range of substituted dihydro and tetrahydro quinazoline compounds of general formulae (I), (II) and (III). The methods described above are merely representative and routine modifications and variations that would be apparent to persons skilled in the art fall within the broad scope and ambit of the invention disclosed herein.

Compounds of general formula (I), general formula (II) or general formula (III) may be isolated or purified using standard techniques known to those skilled in the art. Such techniques include precipitation, crystallisation, recrystallization, column chromatography (including flash column chromatography), HPLC, formation of salts, lyophilisation, among others. Suitable solvents for use in these techniques will be known or can be readily ascertained by those skilled in the art using routine practices.

Salts, including pharmaceutically acceptable salts of compounds of the invention may be prepared by methods known to those skilled in the art, including for example:
(i) by reacting the compound of the invention with the desired acid or base;
(ii) by removing an acid- or base-labile protecting group from a suitable precursor of the compound of the invention or by ring-opening a suitable cyclic precursor, for example, a lactone or lactam, using the desired acid or base; or
(iii) by converting one salt of the compound of the invention into another salt by reaction with an appropriate acid or base, or by means of a suitable ion exchange column.

The above reactions are typically carried out in solution. Suitable solvent systems (including mixed solvent systems) are well known to those skilled in the art and those skilled in the art can readily select or determine a suitable solvent system using routine methods taking into consideration the nature of the compound, the particular salt being formed, and the amount of the compound. Exemplary solvent systems include methanol, ethanol, water, acetone, tetrahydrofuran, dichloromethane, pentane, hexane, diethyl ether, ethyl acetate, and any mixture of two or more such solvents. The resulting salt may precipitate out and be collected by filtration or may be recovered by evaporation of the solvent. The degree of ionisation in the resulting salt may vary from completely ionised to almost non-ionised.

In Vitro Screening Assays

The present disclosure also includes in vitro screening assays for assessing the heparanase inhibitor activity of test compounds.

Suitable assays for determining heparanase inhibitory activity are known in the art, see, for example, the in vitro assays described in Rivara et al. (2016) *Future Med Chem*, 8(6): 647-680. For example, the method may include contacting a preparation comprising heparanase and a heparanase substrate (e.g. heparan sulfate or fondaparinux) with a test compound and detecting the amount of the intact substrate in comparison to a reference level of intact substrate in the absence of the test compound, or detecting the modulation of the activity of a downstream target of the intact heparanase substrate. Detecting the amount of intact substrate or modulation may be achieved using techniques including, but not limited to, ELISA, cell-based ELISA, inhibition ELISA, western blots, RIA, immunoprecipitation, immunostaining, a solid-phase labeled substrate assay such as a solid phase radio- or fluorescently-labeled or biotinylated substrate, an ultrafiltration assay, proximity assays such as HTRF and scintillation proximity assays, fluorescent assays using e.g. fluorescent substrate-heparanase substrate conjugates such as fluorescein or rhodamine, colorimetric assays and fluorescent immunoassays, all of which are well known to those skilled in the art.

In some embodiments, test compounds may be screened using commercially available assays, illustrative examples of which include Cisbio heparanse assay toolbox (Biotin-Heparan sulfate-Eu cryptate; Catalogue No. 61BHSKAA; Cisbio Bioassays, Codolet France), Amsbio heparanase assay kit (Catalogue No. Ra001-BE-K; AMS Biotechnology Ltd, Abington UK) and InSight heparanase activity kit (Catalogue No. INS-26-4-0000-10; InSight Biopharmaceuticals, Rehovot, Israel).

Heparanase inhibitor compounds according to the present invention may elicit their heparanase inhibitory activity through one or more modes of action. For example, heparanase inhibitor compounds may decrease, inhibit or impair any one or more of heparanase catalytic activity, heparanase protein binding, heparanase-mediated modulation of gene transcription, heparanase-mediated initiation of cell signaling and/or angiogenesis.

Pharmaceutical Use

Compounds of general formula (I), general formula (II) and general formula (III) according to the present invention are heparanase inhibitors and the invention also relates to a method of treating a condition or disease related to heparanase activity. Thus, an embodiment of the present invention relates to a method of treatment of a disease or condition associated with heparanase activity in a subject, the method comprising administering to the subject an effective amount of a compound of general formula (I), general formula (II) or general formula (III), or a pharmaceutical composition thereof.

A further embodiment of the invention relates to the use of a compound of formula (I) or a salt, hydrate, solvate, tautomer or stereoisomer thereof or a pharmaceutical composition thereof in the manufacture of a medicament for treating a disease or condition associated with heparanase activity.

In another aspect the present invention relates to the use of a compound of formula (I) or a salt, hydrate, solvate, tautomer or stereoisomer thereof or a pharmaceutical composition thereof for the treatment of a disease or condition associated with heparanase activity in a subject.

The expression "a disease or condition associated with heparanase activity" means that the heparanase enzyme plays a role in the disease or condition. However, other enzymes, pathways and mechanisms may also be implicated in the disease of condition. The compounds of the present invention may be an inhibitor of one or more activities of heparanase, including, but not limited to, heparanase catalytic activity. Furthermore, compounds of the present invention may partially or substantially inhibit any one or more heparanase activities.

In preferred embodiments the subject is a human.

In various embodiments the disease or condition is selected from Type 1 diabetes, Type 2 diabetes, nephritis, glomerulonephritis, cell-mediated autoimmune inflammation, diabetic nephropathy, gestational diabetes, diabetic ketoacidosis, hyperglycemia, hyperosmolar state, hypoglycemia, diabetic coma, diabetic cardiomyopathy, diabetic neuropathy, diabetic foot, diabetic retinopathy, diabetic myonecrosis, and diabetic encephalopathy. In other embodiments the disease or condition related to heparanase activity is selected from cancer, allergies, dermatitis, psoriasis, an ocular inflammatory disorder, such as, macular degeneration, retinitis pigmentosa and pancreatitis.

In preferred embodiments the disease or condition is selected from Type 1 diabetes, Type 2 diabetes, diabetic nephropathy, nephritis, glomerulonephritis, and cell-mediated autoimmune inflammation indications involving heparanase. In particularly preferred embodiments the disease is Type 1 diabetes or Type 2 diabetes.

In another aspect the invention relates to a method of controlling blood glucose levels in a subject, the method comprising administering to the subject an effective amount of a compound of general formula (I), general formula (II), or general formula (III), or a pharmaceutical composition thereof.

In a further aspect the invention relates to a method of treating or preventing rejection of a pancreatic islet transplant in a subject, the method comprising administering to the subject an effective amount of a compound of general formula (I), general formula (II), or general formula (III) or a pharmaceutical composition thereof.

In another aspect the invention relates to a method of preserving beta-cell function in a subject, the method comprising administering to the subject an effective amount of a compound of general formula (I), general formula (II), or general formula (III), or a pharmaceutical composition thereof.

Ocular inflammatory disorders such as diabetic retinopathy, age-related macular degeneration (AMD), retinitis pigmentosa, uveitis and viral corneal inflammation, occur wholly or in part from progressive inflammation in the eye. In a diseased eye, excessive macrophage activation and accumulation in particular tissues, such as the activation and accumulation of microglia in the sub-retinal space in degenerative disorders, can disrupt the immune privilege of the eye (Li et al. (2015) *Experimental Eye Research*, 136: 116-130). Heparanase has been shown to be important for ocular inflammation associated with viral infection of the cornea (Agelidis et al (2017) *Cell*, 20:439-450) as well as for the activation of macrophages (Gutter-Kapon et al. (2016) *PNAS*, 113(48): E7808-E781). Activated macrophages, including retinal microglia, produce different kinds of products including complement proteins, pro-inflammatory cytokines, reactive oxygen species, growth factors and other products, which can result in a chronic local inflammation and can typically lead to further damage (Li et al. (2015) *Experimental Eye Research*, 136: 116-130). For example, in the pathogenesis of AMD, microglia activated by cell death migrate to the damaged area to phagocytose cellular debris but also secrete molecules that kill neighboring photoreceptors around the area of primary degeneration (Li et al. (2015) *Experimental Eye Research*, 136: 116-130). Ocular macrophage, including microglial, activation is therefore an important target for the treatment and prevention of ocular inflammatory disorders. Accordingly, drugs that target heparanase, such as heparanase inhibitors, may prevent or reduce macrophage activation and may be useful for treating ocular inflammatory disorders, such as diabetic retinopathy and AMD among others.

As described in the applicant's co-pending PCT application filed 13 Dec. 2017, titled "Heparanase inhibitors and use thereof" which claims priority from U.S. provisional application Ser. No. 62/433,652, and co-pending PCT application filed 13 Dec. 2017, titled "Methods of treating ocular disorders" which claims priority from Australian Provisional Patent Application No 2017902346 filed 20 Jun. 2017, compounds possessing heparanase inhibitory activity are useful for treating ocular inflammatory disease such as age-related macular degeneration.

Thus, in another aspect the invention relates to a method for treating, or inhibiting the progression or development of, an ocular inflammatory disorder in a subject, the method comprising administering to the subject a compound of general formula (I) or a pharmaceutical composition thereof. The ocular inflammatory disorder may be any disorder of the eye which has an inflammatory component. Exemplary ocular inflammatory disorders include, but are not limited to, age-related macular degeneration (AMD) including the exudative or 'wet' AMD, dry AMD, diabetic retinopathy, retinitis pigmentosa, retinal vein occlusion, retinoblastoma, uveitis, macular edema, dry eye, viral infection and/or keratoconus; especially AMD, diabetic retinopathy and retinitis pigmentosa. In preferred embodiments, the ocular inflammatory disorder is AMD or diabetic retinopathy, preferably AMD. In preferred embodiments, the ocular inflammatory disorder is dry AMD. In other preferred embodiments the ocular inflammatory disorder is wet AMD. Although acute ocular inflammatory disorders are contemplated by the invention, in particularly preferred embodiments, the ocular inflammatory disorder is a chronic disorder.

Pharmaceutical Formulations

The compounds of the invention described herein may be administered as a formulation comprising a pharmaceutically effective amount of the compound, in association with one or more pharmaceutically acceptable excipients including carriers, vehicles and diluents. The term "excipient" herein means any substance, not itself a therapeutic agent, used as a diluent, adjuvant, or vehicle for delivery of a therapeutic agent to a subject or added to a pharmaceutical composition to improve its handling or storage properties or to permit or facilitate formation of a solid dosage form such as a tablet, capsule, or a solution or suspension suitable for oral, parenteral, intradermal, subcutaneous, or topical application. Excipients can include, by way of illustration and not limitation, diluents, disintegrants, binding agents, adhesives, wetting agents, polymers, lubricants, glidants, stabilizers, and substances added to mask or counteract a disagreeable taste or odor, flavors, dyes, fragrances, and substances added to improve appearance of the composition. Acceptable excipients include (but are not limited to) stearic acid, magnesium stearate, magnesium oxide, sodium and calcium salts of phosphoric and sulfuric acids, magnesium carbonate, talc, gelatin, acacia gum, sodium alginate, pectin, dextrin, mannitol, sorbitol, lactose, sucrose, starches, gelatin, cellulosic materials, such as cellulose esters of alkanoic acids and cellulose alkyl esters, low melting wax, cocoa butter or powder, polymers such as polyvinyl-pyrrolidone, polyvinyl alcohol, and polyethylene glycols, and other pharmaceutically acceptable materials. Examples of excipients and their use is described in *Remington's Pharmaceutical Sciences*, 20th Edition (Lippincott Williams & Wilkins, 2000). The choice of excipient will to a large extent depend on factors such as the particular mode of administration, the effect of the excipient on solubility and stability, and the nature of the dosage form.

The compounds and pharmaceutical compositions of the invention may be formulated for oral, injectable, rectal, parenteral, subcutaneous, intravenous, topical, intravitreal or intramuscular delivery. Non-limiting examples of particular formulation types include tablets, capsules, caplets, powders, granules, injectables, ampoules, vials, ready-to-use solutions or suspensions, lyophilized materials, creams, lotions, ointments, drops, suppositories and implants. Solid formulations such as the tablets or capsules may contain any number of suitable pharmaceutically acceptable excipients or carriers described above. The compounds of the invention may also be formulated for sustained delivery.

Tablets and capsules for oral administration may be in unit dose presentation form, and may contain conventional excipients such as binding agents, for example, acacia, gelatin, sorbitol, tragacanth, or polyvinylpyrrolidone; fillers, for example lactose, sugar, maize-starch, calcium phosphate, sorbitol or glycine; tabletting lubricants, for example, magnesium stearate, talc, polyethylene glycol or silica; disintegrants, for example, potato starch; or acceptable wetting agents such as sodium lauryl sulphate. The tablets may be coated according to methods well known in normal pharmaceutical practice.

Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example, sorbitol, methyl cellulose, glucose syrup, gelatin, hydroxyethyl cellulose, carboxymethyl cellulose, aluminium stearate gel or hydrogenated edible fats, emulsifying agents, for example, lecithin, sorbitan monooleate, or acacia; non-aqueous vehicles (which may include edible oils), for example, almond oil, oily esters such as glycerin, propylene glycol, or ethyl alcohol; preservatives, for example, methyl or propyl p-hydroxybenzoate or sorbic acid; and, if desired, conventional flavouring or colouring agents.

For parenteral administration, including intravenous, intramuscular, subcutaneous, intravitreal, or intraperitoneal administration, fluid unit dosage forms may be prepared by combining the compound and a sterile vehicle, typically a sterile aqueous solution which is preferably isotonic with the blood of the recipient. Depending on the vehicle and concentration used, the compound may be either suspended or dissolved in the vehicle or other suitable solvent. In preparing solutions, the compound may be dissolved in water for injection and filter sterilized before filling into a suitable vial or ampoule and sealing. Advantageously, agents such as a local anaesthetic, preservative and buffering agents can be dissolved in the vehicle. To enhance the stability, the composition may be frozen after filling into the vial and the water removed under vacuum. The dry lyophilized powder may then be sealed in the vial and an accompanying vial of water for injection or other suitable liquid may be supplied to reconstitute the liquid prior to use. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. A surfactant or wetting agent may be included in the composition to facilitate uniform distribution of the compound.

In one or more preferred embodiments the compounds of the invention are formulated as an injectable solution, suspension or emulsion. In preferred embodiments, the compounds of the invention are formulated for intravitreal injection into the eye of a subject. Such formulations may be particularly preferred for treatment of ocular inflammatory disorders, such as age-related macular degeneration (AMD) including the exudative or 'wet' and 'dry' form of AMD, diabetic retinopathy, retinitis pigmentosa, retinal vein occlusion, retinoblastoma, uveitis, macular edema, dry eye, viral infection and/or keratoconus; especially AMD, diabetic retinopathy and retinitis pigmentosa.

In preferred embodiments, ophthalmic formulations, including intravitreal formulations and other ophthalmic formulations, such as eye drops, typically may comprise one or more co-solvent(s), such as one or more organic co-solvents; one or more tonicity agent(s); a buffering system comprising one or more buffering agents; a stabilizing agent; pH between about 3-8. In preferred embodiments, the organic co-solvent may be polysorbate, for example, polysorbate 20 or polysorbate 80, polyethylene glycol (PEG), for example, PEG 3350, or propylene glycol, or a combination thereof; the tonicity agent may be, for example, sodium chloride or potassium chloride; the stabilizing agent may be sucrose, sorbitol, glycerol, trehalose, or mannitol; and the buffering agent may be, for example, phosphate buffer, such as a sodium phosphate buffer.

Intravitreal formulations are preferably sterile, isotonic and preferably have a pH within the range pH 3-8, preferably pH 5-7 or pH 3-5. Such formulations may contain one or more buffers as part of a buffer system, however, the concentration of buffers is preferably kept as low as possible. Buffer stressing studies may be carried out to select the minimal buffer amount needed to safely maintain the desired pH range. Exemplary intravitreal formulations are described in Shikari H, Samant P M. Intravitreal injections: A review of pharmacological agents and techniques. *J Clin Ophthalmol Res* 2016; 4:51-9.

In preferred embodiments, ophthalmically acceptable formulations may be lyophilizable. Lyophilizable formulations can be reconstituted into solutions, suspensions, emulsions, or any other suitable form for administration or use. Lyophilizable formulations are typically first prepared as liquids, then frozen and lyophilized. The total liquid volume before lyophilization can be less, equal to, or more than, the final reconstituted volume of the lyophilized formulation. The lyophilization process is well known to those of ordinary skill In the art, and typically Includes sublimation of water from a frozen formulation under controlled conditions. Lyophilized formulations typically can be stored at a wide range of temperatures. For example, lyophilized formulations may be stored below 25° C., for example, refrigerated at 2-8° C., or at room temperature (e.g., approximately 25° C.). Preferably, lyophilized formulations are stored below about 25° C., more preferably, at about 4-20° C.; below about 4° C.; or below about 0° C.

Lyophilized formulations are preferably reconstituted with a solution consisting primarily of water (e.g., USP WFI, or water for injection) or bacteriostatic water (e.g., USP WFI with 0.9% benzyl alcohol). Alternatively, solutions comprising buffers and/or excipients and/or one or more pharmaceutically acceptable carriers may be used. The liquid that is to undergo freeze-drying or lyophilization preferably comprises all components desired in a final reconstituted liquid formulation.

The pharmaceutical compositions of the invention may be administered locally to an eye using a variety of routes including, but not limited to, topical, through an ocular implant or direct injection into the eye. In particular embodiments, the pharmaceutical composition of the invention is administered locally to the eye using intravitreal injection, subconjunctival injection, sub-tenon injection, retrobulbar injection, suprachoroidal injection, intrascleral injection, intracorneal injection, subretinal injection or intracameral injection; especially intravitreal injection. In some embodiments, the composition is administered using a microneedle, for example, through intrascleral or intracorneal injection.

In some embodiments, the composition is administered using an ocular implant, for example, a biodegradable implant such as those made from, for example, polylactic acid (PLA), polyglycolic acid, poly(lactide-co-glycolide) (PLGA), cross-linked gelatin derivatives, hypromellose, polyesters and/or polycaprolactones; or a non-biodegradable implant such as those made from, for example, polyvinyl alcohol, ethylene vinyl acetate, silicon and/or polysulfone capillary fiber.

In some embodiments, the composition of the invention is formulated in a sustained release formulation or depot. Exemplary sustained release formulations or depots include a microsphere; matrix; emulsion; lipid-based; polymer-based; nanomicelle; micelle; nanovesicle such as a liposome, noisome, transfersome, discome, pharmacosome, emulsome or spanlastic, especially a liposome; microparticle; nanoparticle such as a nanocapsule or nanosphere composed of e.g. lipids, proteins, natural or synthetic polymers such as albumin, sodium alginate, chitosan, PLGA, PLA and/or polycaprolactone; or in situ gel such as an in situ hydrogel drug delivery system.

In some embodiments, the composition of the invention is formulated for topical administration to the eye. Thus, the composition may be in the form of an eye drop, gel or ointment; especially an eye drop. The composition may be in a single unit dose or multiple unit dose form.

The amount of therapeutically effective compound that is administered and the dosage regimen for treating a disease condition with the compounds and/or pharmaceutical compositions of the present invention depends on a variety of factors, including the age, weight, sex, and medical condition of the subject, the severity of the disease, the route and frequency of administration, the particular compound employed, as well as the pharmacokinetic properties (e.g., adsorption, distribution, metabolism, excretion) of the individual treated, and thus may vary widely. Such treatments may be administered as often as necessary and for the period of time judged necessary by the treating physician. One of skill in the art will appreciate that the dosage regime or therapeutically effective amount of the compound to be administrated may need to be optimized for each individual. The pharmaceutical compositions may contain active ingredient in the range of about 0.1 mg to 2000 mg, typically in the range of about 0.5 mg to 500 mg and more typically between about 1 mg and 200 mg. A daily dose of about 0.01 mg/kg to 100 mg/kg body weight, typically between about 0.1 mg/kg and about 50 mg/kg body weight, may be appropriate, depending on the route and frequency of administration. The daily dose will typically be administered in one or multiple, e.g., two, three or four, doses per day.

The compounds of the present invention may be administered along with a pharmaceutical carrier, diluent or excipient as described above. Alternatively, or in addition, the compounds may be administered in combination with other agents, for example, other antidiabetic therapeutic agents, or VEGF inhibitor drugs.

The terms "combination therapy" or "adjunct therapy" in defining use of a compound of the present invention and one or more other pharmaceutical agents, are intended to embrace administration of each agent in a sequential manner in a regimen that will provide beneficial effects of the drug combination, and is intended as well to embrace co-administration of these agents in a substantially simultaneous manner, such as in a single formulation having a fixed ratio of these active agents, or in multiple, separate formulations of each agent.

In accordance with various embodiments of the present invention one or more compounds of formula (I), formula (II), or formula (III) may be formulated or administered in combination with one or more other therapeutic agents. Thus, in accordance with various embodiments of the present invention, one or more compounds of formula (I), formula (II), or formula (III) may be included in combination treatment regimens with surgery and/or other known treatments or therapeutic agents, and/or adjuvant or prophylactic agents.

A number of agents are available in commercial use, in clinical evaluation and in pre-clinical development, which could be selected for treatment of Type 1 diabetes, Type 2 diabetes, diabetic nephropathy, nephritis, glomerulonephritis, and other cell-mediated autoimmune inflammation indications, cancer, psoriasis, dermatitis, allergy, macular degeneration, retinitis pigmentosa and pancreatitis as part of combination drug therapy. Suitable agents which may be used in combination therapy will be recognized by those of skill in the art. Suitable agents are listed, for example, in the Merck Index, *An Encyclopaedia of Chemicals, Drugs and Biologicals,* $12^{th}$ Ed., 1996, and subsequent editions, the entire contents of which are incorporated herein by reference.

For example, when used in the treatment of Type 1 diabetes or Type 2 diabetes, compounds of the present invention may be administered with an additional anti-diabetic agent, or combinations thereof, such as: biguanides (e.g., metformin), insulin secretagogues (e.g., sulfonylureas and glinides), glitazones, non-glitazone PPARy agonists, PPARp agonists, inhibitors of DPPIV, inhibitors of PDE5, inhibitors of GSK-3, glucagon antagonists, inhibitors of f-1,615 BPase (Metabasis/Sankyo), GLP-1/analogs (AC 2993, also known as exendin-4), insulin and insulin mimetics (Merck natural products). Other examples include PKC-p inhibitors, AGE breakers, SGLT2 inhibitors, T cell inhibitors (including anti-CD3 monoclonal antibodies), B cell inhibitors (including anti-CD20 monoclonal antibodies such as Rituximab), CTLA-4-Ig (Abatacept/Bristol-Myers Squibb) and inflammatory cytokine inhibitors including blocking monoclonal antibodies, among others.

In other embodiments, when used for the treatment of ocular inflammatory disorders, such as, for example, age-related macular degeneration (AMD), the compound of formula (I) may be administered in combination with a growth factor inhibitor. Suitable growth factor inhibitors include, but are not limited to, a vascular endothelial growth factor (VEGF) inhibitor, such as ranibizumab, aflibercept, bevacizumab, pegaptanib, conbercept, abicipar pegol (MP0112) and MP0250; a platelet derived growth factor (PDGF) inhibitor, such as E10030 (anti-PDGF PEGylated aptamer), trapidil and pegpleranib; and pharmaceutically acceptable salts and combinations thereof. In some embodiments, the one or more pharmaceutically active agent is a VEGF inhibitor selected from the group consisting of ranibizumab, aflibercept, bevacizumab, pegaptanib, conbercept and pharmaceutically acceptable salts and combinations thereof.

Combination regimens may involve the active agents being administered together, sequentially, or spaced apart as appropriate in each case. Combinations of active agents including compounds of the invention may be synergistic.

The co-administration of compounds of the invention may be effected by the compounds being in the same unit dose as another active agent, or the compounds and one or more other active agent(s) may be present in individual and discrete unit doses administered at the same, or at a similar time, or at different times according to a dosing regimen or schedule. Sequential administration may be in any order as required, and may require an ongoing physiological effect of the first or initial compound to be current when the second or later compound is administered, especially where a cumulative or synergistic effect is desired.

Embodiments of the invention will now be discussed in more detail with reference to the examples which are provided for exemplification only and which should not be considered limiting on the scope of the invention in any way.

EXAMPLES

Abbreviations

BOC refers to a t-butoxycarbonyl group
T3P® refers to propylphosphonic anhydride solution (>50 wt. % in ethyl acetate)
DIPEA refers to diisopropylethylamine
DEA refers to diethylamine
DCM refers to dichloromethane
THF refers to tetrahydrofuran
DMF refers to N,N-dimethyformamide
DMSO refers to dimethyl sulfoxide
EtOAc refers to ethyl acetate
rt refers to room temperature General Procedures Unless otherwise specified, proton ($^1$H) and carbon ($^{13}$C) NMR spectra were recorded at room temperature in base-filtered CDCl$_3$ with a Bruker spectrometer operating at 400 MHz for proton and 100 MHz for carbon nuclei. For $^1$H NMR spectra, signals arising from the residual protio forms of the solvent were used as the internal standards. $^1$H NMR spectroscopic data are recorded as follows: chemical shift (δ) [multiplicity, coupling constant(s) J (Hz), relative integral] where multiplicity is defined as: s=singlet; d=doublet; t=triplet; q=quartet; m=multiplet; br=broad or combinations of thereof. The signal due to residual CHCl$_3$ appearing at δH=7.26 ppm and the central resonance of the CDCl$_3$ "triplet" appearing at δC=77.0 ppm were used to reference $^1$H and $^{13}$C NMR spectra, respectively. The quintet due to residual DMSO-d$_5$ appearing at δH=2.50 ppm and the central resonance of the DMSO-d$_6$ "multiplet" appearing at δC=39.52 ppm were used to reference 1H and $^{13}$C NMR spectra, respectively. Infrared spectra (IR: max) were recorded with a Perkin-Elmer 1800 series FTIR spectrometer or a Perkin-Elmer UATR Spectrum Two FTIR spectrometer. Samples were analyzed as thin films on KBr plates or compressed and flattened on a diamond window. Low-resolution ESI mass spectra were recorded on a single quadrupole liquid chromatograph-mass spectrometer, while high-resolution measurements were conducted on a time-of-flight instrument. Low- and high-resolution EI mass spectra were recorded with a magnetic-sector machine. Melting points were measured with an Optimelt automated melting point system and are uncorrected. Analytical thin layer chromatography (TLC) was performed on aluminium-backed 0.2 mm thick silica gel 60 F254 plates. Eluted plates were visualized with a 254 nm UV lamp and/or by treatment with a suitable dip followed by heating. These dips included phosphomolybdic acid/ceric sulfate/sulfuric acid (concd.)/water (37.5 g:7.5 g:37.5 g:720 mL) or potassium permanganate/potassium carbonate/5% sodium hydroxide aqueous solution/water (3 g:20 g:5 mL:300 mL). Flash chromatographic separations were carried out according to protocols defined by Still et al. *J. Org. Chem.* 1978, 43, 2923 with silica gel 60 (40-63 μm) as the stationary phase and with the AR- or HPLC-grade solvents indicated.

Microwave reactions were conducted with a CEM Explorer microwave reactor. Microwave vessels were sealed with a snap-cap and irradiated for the time and at the temperatures specified, typically with a ramp time of 1 minute to the specified temperature at a maximum power of 200 W.

Starting materials and reagents were generally available from the Sigma-Aldrich, Merck, TCI, Strem, AK Scientific or Lancaster chemical companies and were used as supplied. Drying agents and other inorganic salts were purchased from the AJAX, BDH or Unilab chemical companies. Tetrahydrofuran (THF), diethyl ether, methanol and dichloromethane were dried by using a Glass Contour solvent purification system that is based upon a technology originally described by Grubbs et al. *Organometallics* 1996, 15, 1518. Where necessary, reactions were performed under nitrogen.

I. SYNTHESIS EXAMPLES

General Experimental Procedures

General Procedure A

Preparation of 2-isothiocyanatobenzonitriles

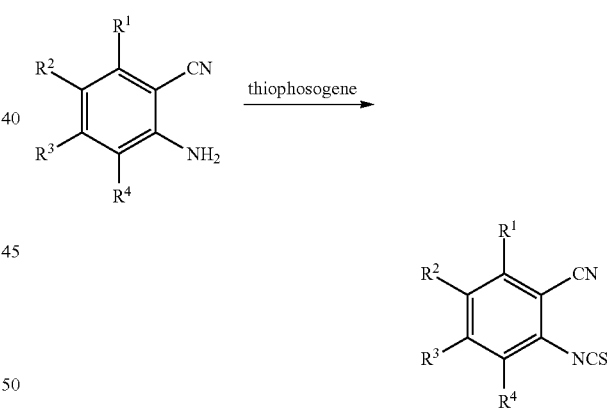

Following the procedure of Calestani, G et al. (*Tetrahedron*, 2001, 57 (33), 7221) a magnetically stirred mixture of thiophosgene (1.35 mL, 17.5 mmol) in DCM (2 mL) and water (4 mL) was treated dropwise with a solution of the substituted amino-benzonitrile (14.3 mmol) in DCM (15 mL). The mixture was stirred for two hours and was then transferred to a separatory funnel and the aqueous layer extracted with DCM (20 mL). The organic layers were combined, washed with water (2×20 mL) then dried over Na$_2$SO$_4$. The DCM was removed with a gentle stream of nitrogen with heating at 40° C. and the residue obtained was then held under high vacuum (1 mmHg) for 4 h to afford the desired 2-isothiocyanatobenzonitrile which may be used without further purification.

General Procedure B

Reaction of Primary Amines with 2-isothiocyanatobenzonitriles

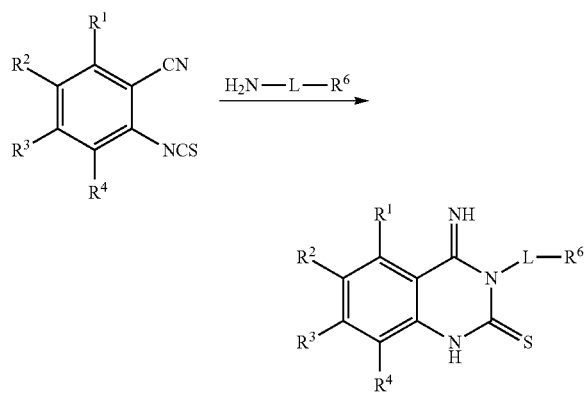

Following a modified procedure analogous to that reported by Pazdera, P (*Chem. Papers* 1989, 43 (3), 465), a magnetically stirred solution of substituted 2-isothiocyanatobenzonitrile (1.36 mmol) in a mixture of DCM and petroleum Spirit (2.5 mL: 2.5 mL) was treated with a solution of primary amine in DCM (7 mL). The mixture was stirred for 0.5 h and then pet. spirit (15 mL) was added. The solid was collected by vacuum filtration and then magnetically stirred in a solution of ethanol (30 mL) and heated at 70° C. for 2 h. The mixture was cooled to 0° C. and the solid was collected by vacuum filtration, washed with ethanol (10 mL) and dried at the pump (1 mmHg).

General Procedure C

Reaction of Primary Amines with 2-isothiocyanatobenzonitriles—Alternative Procedure

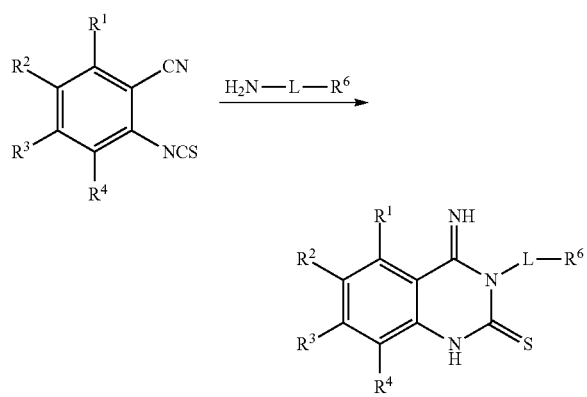

Crude amine hydrochloride (0.27 mmol) suspended in ethanol (6 mL), was treated with triethylamine (96 μL, 0.68 mmol) and then a solution of 2-isothiocyanato-4,5-dimethoxybenzonitrile (50 mg, 0.27 mmol) in DCM (3 mL) was added. The mixture was stirred at rt for 1 h then concentrated by a gentle stream of nitrogen and re-suspended in ethanol (5 mL). The mixture was heated at reflux for 4 h and the precipitate that formed was collected and washed with ethanol (15 mL) then ether (10 mL) and dried at the pump.

General Procedure D

Suzuki Cross-Coupling Procedure

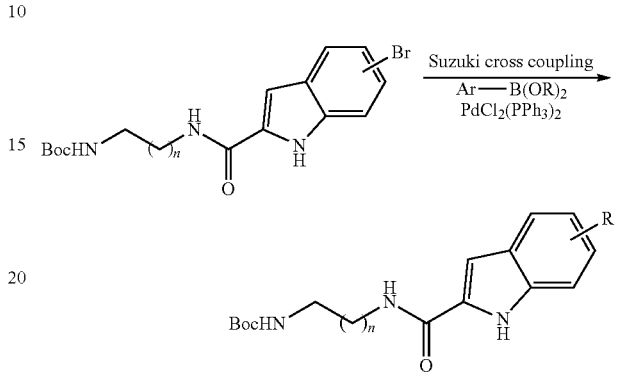

A 10 mL snap-cap microwave vessel, fitted with a magnetic stirring bar, was charged with a mixture of boronic acid or ester (77.2 μmol), aryl bromide or triflate (52.3 μmol) and potassium carbonate (38 mg, 274 μmol) then treated with a degassed mixture of dimethoxyethane, water and ethanol (7:3:2, 1 mL). Bis(triphenylphosphine)palladium(II) dichloride (1.8 mg, 5 mol %) was added and the mixture was sparged with nitrogen for 0.05 hr, sealed then subjected to microwave irradiation (120° C./0.33 h, ramp time 1 minute, maximum power 200 W). The mixture was treated with water (1 mL) and extracted with EtOAc (3×2 mL) and the combined organic layers washed with brine and concentrated under a gentle stream of nitrogen. The residue obtained was subjected to flash column chromatography [silica, 1:10 v/v MeOH/DCM elution (unless otherwise specified) to give, after concentration of the appropriate fractions the desired compound.

General Procedure E

Boc Deprotection with Hydrogen Chloride in Dioxane

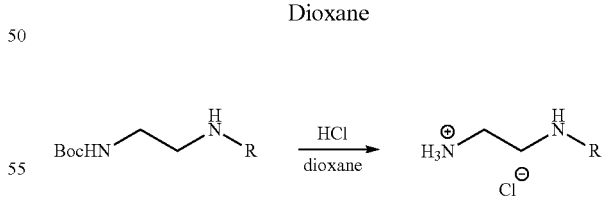

A solution of hydrogen chloride (2 mL, 4M in dioxane) at 4° C. was added to the Boc-protected compound and magnetically stirred for 1 h at rt. Diethyl ether (5 mL) was added and the mixture vigorously stirred for 0.05 h then magnetic stirring was ceased and the precipitate or gum allowed to settle. The solvent was decanted off the precipitate and this procedure was repeated a further 3 times and the resulting compound placed under high vacuum for 3 hours and used without further purification.

General Procedure F

Boc Deprotection with Trifluoroacetic Acid in Dichloromethane

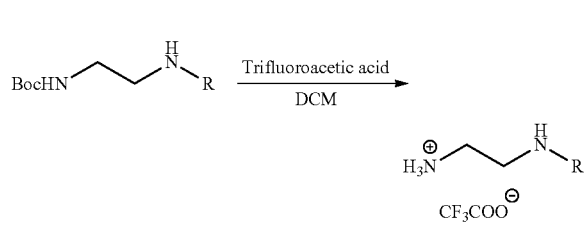

A magnetically stirred suspension of Boc-protected compound (1.80 mmol) in DCM (4 mL) maintained at 0° C. was treated with trifluoroacetic acid (1 mL) and magnetically stirred for 2 h. The cold bath was removed and the mixture was then stirred for a further 1 h at rt. The solvent was removed with a gentle stream of nitrogen and the remaining gum was triturated with diethyl ether (3×10 mL) then placed under high vacuum for 1 h to afford the amine trifluoroacetate salt as a powder and used directly without further purification.

General Procedure G

Preparation of Amides with T3P®

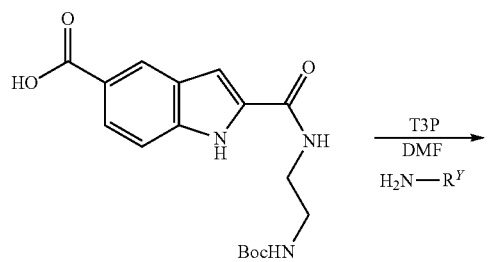

A magnetically stirred mixture of carboxylic acid (100 mg, 0.29 mmol) in DMF (1 mL) was sequentially treated with, triethylamine (320 μL, 2.30 mmol), propylphosphonic anhydride (T3P®) (366 μL, 0.58 mmol, 50% wt in EtOAc) and amine (0.29 mmol). The reaction was stirred for 24 h at 18° C. and then the mixture was concentrated in vacuo and purified by flash chromatography.

General Procedure H

Acid Chloride Formation and Amine Addition

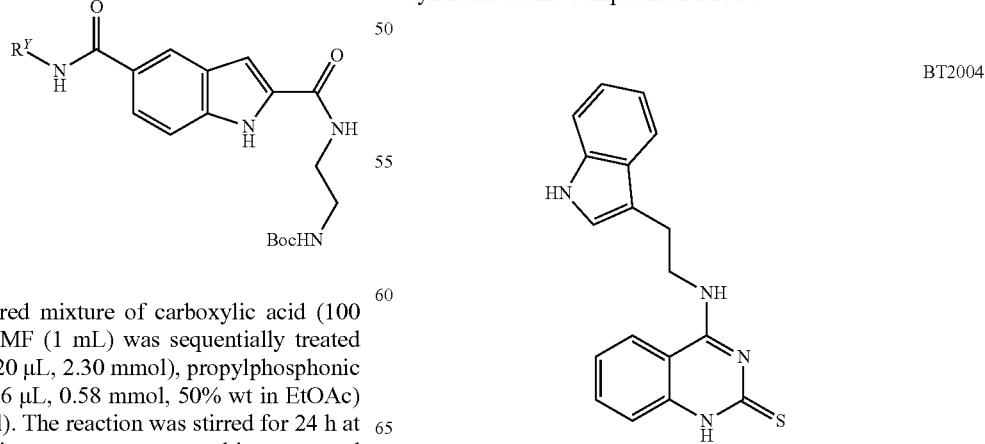

A magnetically stirred suspension of carboxylic acid (6.25 mmol) in DCM (30 mL) at 0° C. was treated with oxalyl chloride (563 μL, 6.57 mmol) dropwise, followed by DMF (1 drop). The mixture was stirred at 0° C. for 1 h and then the cold-bath was removed and stirring was continued at rt for 2.5 hr. The clear solution was then concentrated with a gentle stream of nitrogen with heating, in a water bath at 40° C. The resulting cream coloured powder was then placed under high vacuum (1 mm Hg) for 1 hr and redissolved in THF (20 mL) and added transferred dropwise by syringe to a magnetically stirred, ice-cold solution of amine (6.25 mmol) and N,N-diisopropylethylamine (1.75 mL, 12.5 mmol) in DCM (20 mL). After 1 hr at 0° C. the cold bath was removed and stirred a further one hr at 18° C. then a solution of sodium hydrogen carbonate (50 mL, half saturated) was added and the DCM and THF were removed in vacuo. The precipitate was collected by vacuum filtration and washed with water (200 mL) and was dried under high vacuum for 18 hours.

General Procedure I

Thionation of 2-chloroquinazolines

The general procedure is illustrated with respect to the synthesis of the compound BT2004:

A 10 mL sealed-tube was charged with 2-chloro-4-amino substituted quinazoline (100 mg, 0.31 mmol), potassium thioacetate (106 mg, 0.93 mmol) and dioxane (3 mL). The magnetically stirred mixture was heated at 120° C. for three hours and then the solvent was removed in vacuo. An ammoniacal solution of methanol (1 mL, saturated) was added and then the solution was subjected to flash column chromatography [silica, 1:10 v/v MeOH/DCM elution] to give, after concentration of the appropriate fractions the compound BT2004 (47 mg, 47%) as a tan solid. $^1$H NMR (DMSO-$d_6$, 400 MHz) δ 12.37 (s, 1H), 10.83 (s, 1H), 8.83 (t, J=5.7 Hz, 1H), 8.08 (d, J=8.2 Hz, 1H), 7.74 (d, J=7.9 Hz, 1H), 7.65 (t, J=7.9 Hz, 1H), 7.38 (d, J=8.3 Hz, 1H), 7.34 (d, J=8.2 Hz, 1H), 7.27 (t, J=7.6 Hz, 1H), 7.20 (s, 1H), 7.07 (t, J=7.6 Hz, 1H), 6.98 (t, J=7.4 Hz, 1H), 3.86-3.78 (m, 2H), 3.07 (app. t, J=7.5 Hz, 2H); $^{13}$C NMR (DMSO-$d_6$, 100 MHz) δ 180.9, 156.5, 141.2, 136.7, 134.4, 127.7, 123.8, 123.7, 123.1, 121.4, 119.2, 118.8, 116.0, 112.1, 111.8, 110.3, 42.1, 24.9; (+)-LRESIMS m/z (rel. int.) 343 (100) [M+Na]$^+$, 321 (60) [M+H]$^+$; (+)-HRESIMS calcd. for $C_{18}H_{16}N_4S$ [M+H]$^+$ 321.1168, found 321.1176; $v_{max}$ 1621, 1604, 1569, 1538, 1372, 1356, 1333, 1278, 1218, 1193, 1124, 954 cm$^{-1}$.

General Procedure J

The general procedure is illustrated with respect to the synthesis of the compound BT2152:

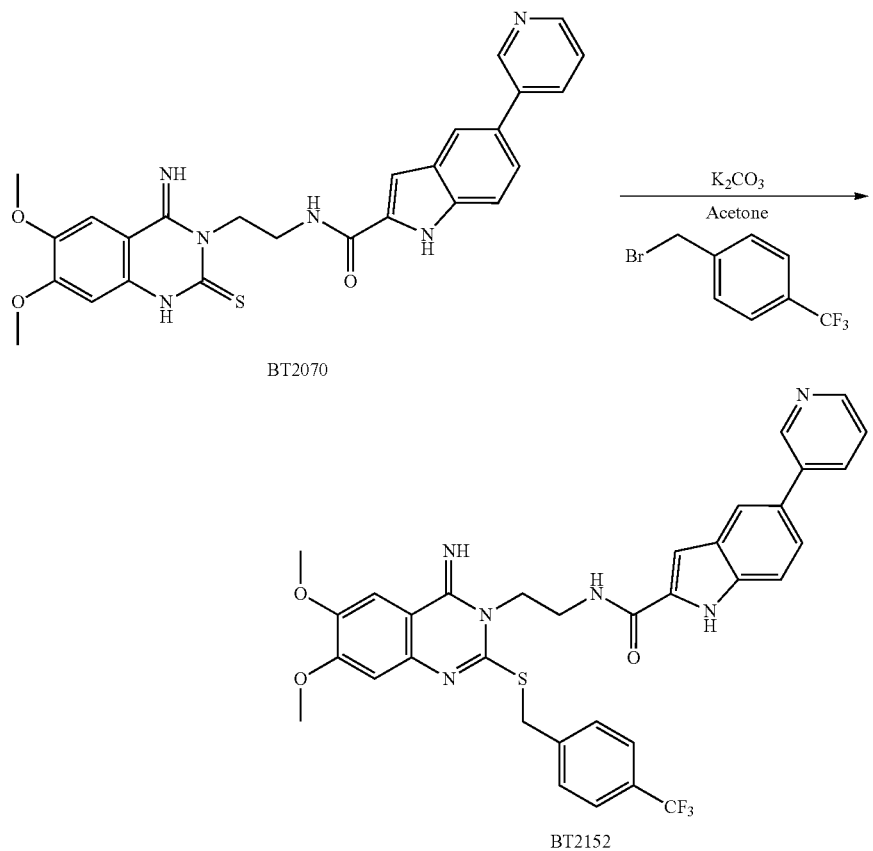

A mixture of BT2070 (50 mg, 0.10 mmol), potassium carbonate (28 mg, 0.20 mmol) in acetone (1.5 mL) at rt was treated with 1-(bromomethyl)-4-(trifluoromethyl)benzene (24 μL, 0.10 mmol) in one portion. The mixture was stirred for 24 h and then the mixture was purified by flash column chromatography [silica, 1:20 v/v ammoniacal MeOH/DCM elution] to give, after concentration of the appropriate fractions, BT2152 as a white powder (11 mg, 17%). $^1$H NMR (DMSO-$d_6$, 400 MHz) δ 11.73 (s, 1H), 8.91 (d, J=2.0 Hz, 1H), 8.82 (app. t, J=5.9 Hz, 1H), 8.52 (dd, J=4.7, 1.6 Hz, 1H), 8.48 (br s, 1H), 8.07 (ddd, J=8.0, 2.4, 1.6 Hz, 1H), 7.98 (s, 1H), 7.65 (s, 1H), 7.58 (dd, J=8.8, 1.7 Hz, 1H), 7.54 (d, J=8.8 Hz, 1H), 7.47 (dd, J=8.0, 4.7 Hz, 1H), 7.39 (d, J=8.0 Hz, 2H), 7.28 (d, J=8.0 Hz, 2H), 7.12 (d, J=2.0 Hz, 1H), 6.86 (s, 1H), 4.42 (s, 2H), 4.34-4.27 (s, 2H), 3.86 (s, 3H), 3.85 (s, 3H), 3.71-3.64 (m, 2H). (+)-LRESIMS m/z (rel. int.) 659 (100) [M+H]$^+$; $v_{max}$ 1623, 1601, 1547, 1510, 1328, 1233, 1106, 1018, 799 cm$^{-1}$.

Experimental Procedures and Product Characterization

Preparation (i).
2-Isothiocyanato-4,5-dimethoxybenzonitrile

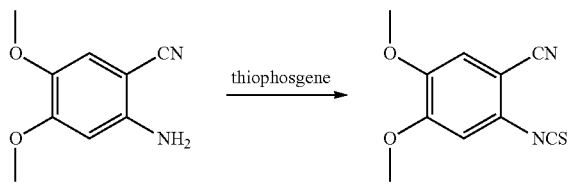

Prepared according to General Procedure A, from reaction of 2-amino-4,5-dimethoxybenzonitrile (2.50 g, 14.3 mmol) and thiophosgene (1.35 mL, 17.5 mmol) to afford 2-Isothiocyanato-4,5-dimethoxybenzonitrile as a pale-orange powder (2.60 g, 84%). $^1$H NMR (CDCl$_3$, 400 MHz) δ 6.96 (s, 1H), 6.75 (s, 1H), 3.93 (s, 3H), 3.90 (s, 3H); $^{13}$C NMR (CDCl$_3$, 100 MHz) δ 153.4, 148.1, 139.8, 128.9, 115.8, 113.6, 109.4, 101.0, 56.5, 56.4; LRMS (EI, 70 eV) m/z (rel. int.) 220 (100, M+), 205 (65), 177 (39), 119 (28); HREIMS calcd. for C$_{10}$H$_8$N$_2$O$_2$S [M+·] 220.0301, found 220.0312; $v_{max}$ 3311, 2221, 1713, 1598, 1527, 1406, 1239, 1213, 1191, 1118, 1000, 688 cm$^{-1}$.

Preparation (ii).
5-Methoxy-2-isothiocyanatobenzonitrile

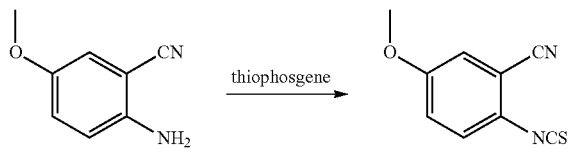

Prepared according to General Procedure A, from reaction of 2-amino-5-methoxybenzonitrile (492 mg, 3.32 mmol) and thiophosgene (318 μL, 4.15 mmol) to afford 5-methoxy-2-isothiocyanatobenzonitrile (402 mg, 64%) as a tan powder and used without further purification. $^1$H NMR (CDCl$_3$, 400 MHz) δ 7.26 (d, J=8.7 Hz, 1H), 7.12-7.07 (m, 2H), 3.84 (s, 2H); $^{13}$C NMR (CDCl$_3$, 100 MHz) δ 157.8, 139.7, 128.2, 127.1, 120.5, 117.3, 115.3, 110.3, 56.0; (+)-LRESIMS m/z (rel. int.) 191 (100) [M+H]$^+$; $v_{max}$ 2235, 2093, 1603, 1567, 1487, 1299, 1229, 1159, 1112, 1027, 939, 868, 824 cm$^{-1}$.

Preparation (iii).
5-Iodo-2-isothiocyanatobenzonitrile

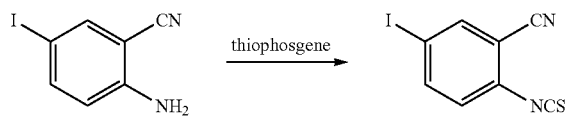

Prepared according to General Procedure A from reaction of 2-amino-5-iodobenzonitrile (2.44 g, 10.0 mmol) and thiophosgene (960 μL, 12.5 mmol) to afford 5-iodo-2-isothiocyanatobenzonitrile (1.88 g, 64%) as an orange powder and used without further purification. $^1$H NMR (CDCl$_3$, 400 MHz) δ 7.93 (d, J=2.0 Hz, 1H), 7.88 (dd, J=8.5, 2.0 Hz, 1H), 7.07 (d, J=8.5 Hz, 1H); $^{13}$C NMR (CDCl$_3$, 100 MHz) δ 143.0, 142.1, 141.6, 134.5, 128.2, 113.9, 111.3, 90.2; LRMS (EI, 70 eV) m/z (rel. int.) 286 (100, M+), 159 (54); HREIMS calcd. for C$_8$H$_3$IN$_2$S [M+] 285.9056, found 285.9062; $v_{max}$ 2233, 2063, 1468, 1072, 935, 819 cm$^{-1}$.

Preparation (iv).
5-Bromo-2-isothiocyanatobenzonitrile

Prepared according to General Procedure A, from reaction of 2-amino-5-bromobenzonitrile (1.97 g, 10.0 mmol) and thiophosgene (960 μL, 12.5 mmol) to afford 5-bromo-2-isothiocyanatobenzonitrile (1.52 g, 64%) as a yellow powder and used without further purification. $^1$H NMR (CDCl$_3$, 400 MHz) δ 7.75 (d, J=2.2 Hz, 1H), 7.70 (dd, J=8.6, 2.2 Hz, 1H), 7.22 (d, J=8.6 Hz, 1H); $^{13}$C NMR (CDCl$_3$, 100 MHz) δ 142.1, 137.2, 135.8, 134.0, 128.2, 120.0, 114.1, 111.1; LRMS (EI, 70 eV) m/z (rel. int.) 240 (100, M+·), 238 (97, M+·), 159 (47); HREIMS calcd. for C$_8$H$_3$$^{79}$BrN$_2$S [M+·] 237.9195, found 237.9203; $v_{max}$ 2230, 2034, 1476, 1462, 888, 830 cm$^{-1}$.

Preparation (v): Phenyl (2-cyano-4,5-dimethoxyphenyl)carbamate

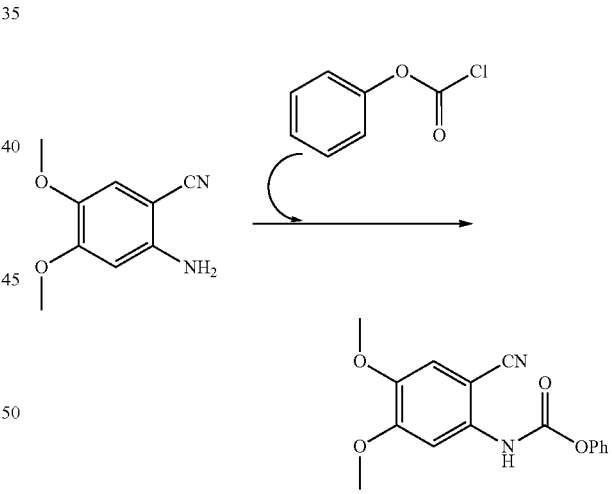

Following a procedure analogous to that used by Vovk, M. B. (*Russ. J. Org. Chem.* 2007, 43 (2), 312): A magnetically stirred solution of 2-amino-4,5-dimethoxybenzonitrile (500 mg, 2.81 mmol) in toluene (3 mL) at 0° C. was treated with a solution of phenyl chloroformate (388 μL, 3.09 mmol) in toluene (5 mL) dropwise. The mixture was then refluxed for 3 h and cooled to rt over 18 h. The precipitate was collected by vacuum filtration and washed with ether (30 mL) to afford phenyl (2-cyano-4,5-dimethoxyphenyl)carbamate (347 mg, 41-61%) as a beige powder. $^1$H NMR (CDCl$_3$, 400 MHz) δ 7.90 (s, 1H), 7.48-7.37 (m, 2H), 7.39 (s, 1H), 7.33-7.25 (m, 1H), 7.25-7.17 (m, 2H), 6.97 (s, 1H), 3.92 (s, 3H), 3.88 (s, 3H); $^{13}$C NMR (CDCl$_3$, 100 MHz) δ 153.9, 151.5, 150.1, 145.3, 136.1, 129.6 (2C), 126.2, 121.5 (2C), 116.7, 112.9, 103.2, 91.8 56.3, 56.3; $v_{max}$ 3312, 2221, 1712, 1598, 1527, 1511, 1492, 1406, 1357, 1238, 1213, 1190, 1118, 1026, 999, 874, 793, 725, 688 cm$^{-1}$.

Preparation (vi): tert-Butyl (2-(5-bromo-1H-indole-2-carboxamido)ethyl)carbamate

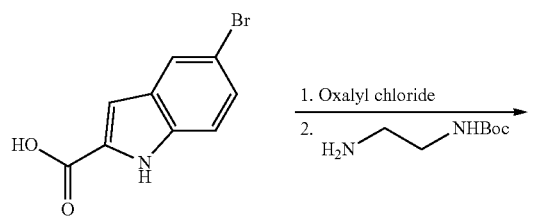

Following General Procedure H, 5-bromo-1H-indole-2-carboxylic acid (1.50 g, 6.25 mmol) was converted to 5-bromo-1H-indole-2-carbonyl chloride and reacted with tert-butyl (2-aminoethyl)carbamate (1.00 g, 6.25 mmol) to afford tert-butyl (2-(5-bromo-1H-indole-2-carboxamido) ethyl)carbamate (2.17 g, 91%) as a white powder. $^1$H NMR (DMSO-d$_6$, 400 MHz) δ 11.78 (s br, 1H), 8.57 (t, J=5.7 Hz, 1H), 7.84 (d, J=2.0 Hz, 1H), 7.39 (d, J=8.7 Hz, 1H), 7.28 (dd, J=8.7, 2.0 Hz, 1H), 7.08 (s, 1H), 6.92 (t, J=5.7 Hz, 1H), 3.32 (app. q, J=6.3 Hz, 2H), 3.13 (app. q, J=6.3 Hz, 2H), 1.37 (s, 9H); $^{13}$C NMR (DMSO-d$_6$, 100 MHz) 2 signals obscured by DMSO-d$_6$ δ 160.9, 155.7, 135.0, 133.1, 128.9, 125.8, 123.6, 114.3, 112.1, 101.9, 77.7, 28.2 (3C); (+)-LRESIMS m/z (rel. int.) 404 (100) [M+H], 406 (100) [M+H]$^+$; (+)-HRESIMS calcd. for C$_{16}$H$_{20}$N$_3$O$_3$Na$^{81}$Br [M+Na]$^+$ 406.0560, found 406.0561; $v_{max}$ 3357, 3269, 1684, 1629, 1546, 1531, 1367, 1275, 1252, 1167, 880, 797, 768 cm$^{-1}$.

Preparation (vii): tert-Butyl (2-(6-bromo-1H-indole-2-carboxamido)ethyl)carbamate

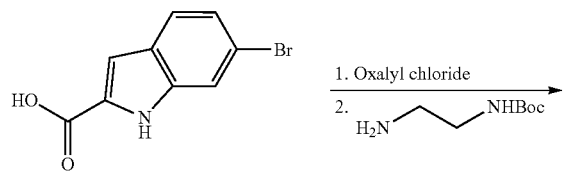

Following a procedure analogous to General Procedure H, 6-bromo-1H-indole-2-carboxylic acid (1.00 g, 4.17 mmol) was converted to 6-bromo-1H-indole-2-carbonyl chloride and reacted with tert-butyl (2-aminoethyl)carbamate (0.73 g, 4.56 mmol) to afford tert-butyl (2-(6-bromo-1H-indole-2-carboxamido)ethyl)carbamate (1.20 g, 76%) as a white solid. 1H NMR (DMSO-d$_6$, 400 MHz) δ 11.71 (s, 1H), 8.55 (t, J=5.3 Hz, 1H), 7.59 (d, J=8.1 Hz, 1H), 7.58 (s, 1H), 7.15 (dd, J=8.1, 1.9 Hz, 1H), 7.10 (s, 1H), 6.92 (t, J=5.3 Hz, 1H), 3.29 (app. q, J=6.2 Hz, 2H), 3.11 (app. q, J=6.2 Hz, 2H), 1.37 (s, 9H); $^{13}$C NMR (DMSO-d$_6$, 100 MHz) δ 160.9, 155.7, 137.1, 132.6, 126.1, 123.4, 122.7, 115.9, 114.7, 102.5, 77.7, 39.7, 39.2, 28.2 (3C); (+)-LRESIMS m/z (rel. int.) 404 (100), 406 (100) [M+Na]$^+$; (+)-HRESIMS calcd. for C$_{16}$H$_{20}^{79}$BrN$_3$NaO$_3$ [M+Na]$^+$404.0586, found 404.0589; $v_{max}$ 1696, 1647, 1549, 1365, 1289, 1247, 1152 cm$^{-1}$.

Preparation (viii): tert-Butyl (3-(6-bromo-1H-indole-2-carboxamido)propyl)carbamate

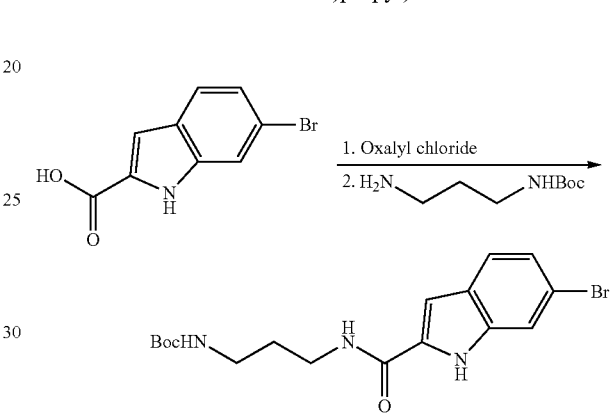

Following a procedure analogous to General Procedure H, 6-bromo-1H-indole-2-carboxylic acid (1.00 g, 4.17 mmol) was converted to 6-bromo-1H-indole-2-carbonyl chloride and reacted with N-(3-aminopropyl)-6-bromo-1H-indole-2-carboxamide (0.73 g, 4.17 mmol) to afford tert-butyl (3-(6-bromo-1H-indole-2-carboxamido)propyl)carbamate (0.88 g, 53%) as a white solid. $^1$H NMR (DMSO-d$_6$, 400 MHz) δ 11.71 (s, 1H), 8.52 (t, J=5.7 Hz, 1H), 7.58 (d, J=8.4 Hz, 1H), 7.58 (d, J=1.2 Hz, 1H), 7.15 (dd, J=8.4, 1.7 Hz, 1H), 7.11 (d, J=1.2 Hz, 1H), 6.83 (t, J=5.3 Hz, 1H), 3.28 (app. q, J=6.8 Hz, 2H), 2.99 (app. q, J=6.5 Hz, 2H), 1.68-1.61 (m, J=6.8 Hz, 2H), 1.37 (s, 9H); $^{13}$C NMR (DMSO-d$_6$, 100 MHz) δ 160.7, 155.6, 137.1, 132.7, 126.1, 123.3, 122.7, 115.9, 114.7, 102.3, 77.5, 37.7, 36.6, 29.7, 28.3. (3C); (+)-LRESIMS m/z (rel. int.) 396 (100), 398 (100) [M+H]$^+$; (+)-HRESIMS calcd. for C$_{17}$H$_{23}^{79}$BrN$_3$O$_3$[M+H]$^+$ 396.0917, found 396.0917; $v_{max}$ 3381, 3269, 2979, 1686, 1615, 1549, 1523, 1365, 1267, 1168, 906, 861, 814, 788, 732 cm$^{-1}$.

Preparation (ix): tert-Butyl (1-(5-bromo-1H-indole-2-carbonyl)azetidin-3-yl)carbamate

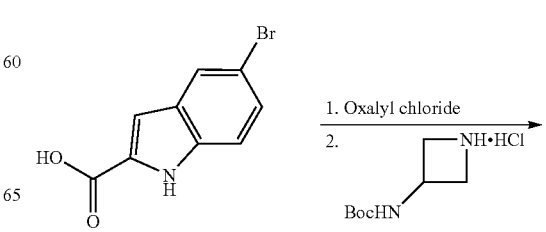

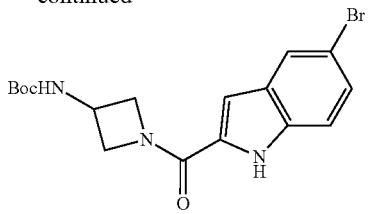

Following a procedure analogous to General Procedure H, 5-bromo-1H-indole-2-carboxylic acid (0.74 g, 3.08 mmol) was converted to 5-bromo-1H-indole-2-carbonyl chloride and reacted with 3-N-Boc-amino-azetidine hydrochloride (0.64 g, 3.08 mmol) to afford tert-butyl (1-(5-bromo-1H-indole-2-carbonyl)azetidin-3-yl)carbamate (1.12 g, 92%) as a white solid. $^1$H NMR (DMSO-$d_6$, 400 MHz) δ 11.82 (s, 1H), 7.82 (s, 1H), 7.65 (d, J=6.7 Hz, 1H), 7.39 (d, J=8.8 Hz, 1H), 7.33-7.29 (m, 1H), 6.79 (s, 1H), 4.75-4.69 (m, 1H), 4.48-4.37 (m, 1H), 4.36-4.23 (m, 2H), 3.99-3.89 (m, 1H), 1.40 (s, 9H); $^{13}$C NMR (DMSO-$d_6$, 100 MHz) δ 161.0, 154.8, 134.6, 130.5, 129.2, 126.2, 123.8, 114.3, 112.1, 103.8, 78.3, 59.6, 55.6, 40.7, 28.2 (3C). (+)-LRESIMS m/z (rel. int.) 394 (100), 396 (100) [M+H]$^+$; (+)-HRESIMS calcd. for $C_{17}H_{21}^{79}BrN_3O_3$[M+H]$^+$ 394.0761, found 394.0765; $v_{max}$ 3360, 3225, 1680, 1603, 1532, 1455, 1410, 1272, 1169, 800, 767, 639 cm$^{-1}$.

Preparation (x): 
5-(Methoxycarbonyl)-1H-indole-2-carboxylic acid

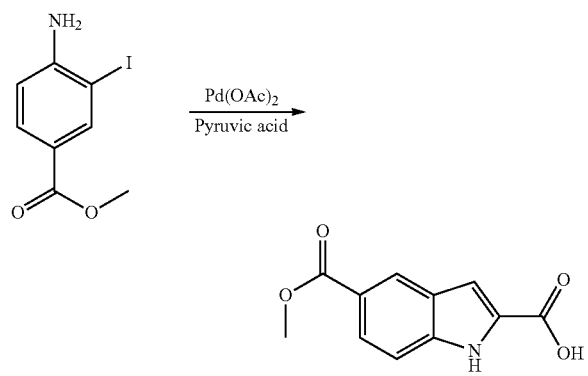

The title compound was prepared following a procedure analogous to that used by Boger et. al. (*Bioorg. Med. Chem. Lett.* 2010, 20, 2722). A mixture of methyl 4-amino-3-iodobenzoate (2.92 g, 10.5 mmol), DMF (30 mL), DABCO (3.55 g, 31.5 mmol) and pyruvic acid (2.18 mL, 31.5 mmol) was degassed by sparging with a gentle stream of nitrogen for 10 minutes and then palladium(II) acetate (12 mg, 52.5 μmol) was added. The mixture was sparged with nitrogen for a further minute and then heated at 105° C. under an atmosphere of nitrogen for 6 hours. The reaction was cooled to rt and the mixture was acidified to pH 2-3 with an aqueous solution of HCl (1M) and water added (100 mL). The resulting precipitate was collected to afford 5-(methoxycarbonyl)-1H-indole-2-carboxylic acid (1.37 g, 59%) as a tan solid and used without further purification. $^1$H NMR (DMSO-$d_6$, 400 MHz) δ 13.15 (s br, 1H), 12.14 (s, 1H), 8.38 (s, 1H), 7.84 (d, J=8.5 Hz, 1H), 7.51 (d, J=8.5 Hz, 1H), 7.26 (s, 1H), 3.85 (s, 3H); $^{13}$C NMR (CDCl$_3$, 100 MHz) δ 166.9, 162.5, 139.6, 130.3, 126.5, 125.0, 124.8, 121.6, 112.6, 108.9, 51.9. $v_{max}$ 3324, 1695, 1661, 1433, 1340, 1301, 1256, 1202, 1191, 923, 761 cm$^{-1}$.

Preparation (xi): [2-((2-((tert-butoxycarbonyl)amino)ethyl)carbamoyl)-1H-indole-5-carboxylic acid

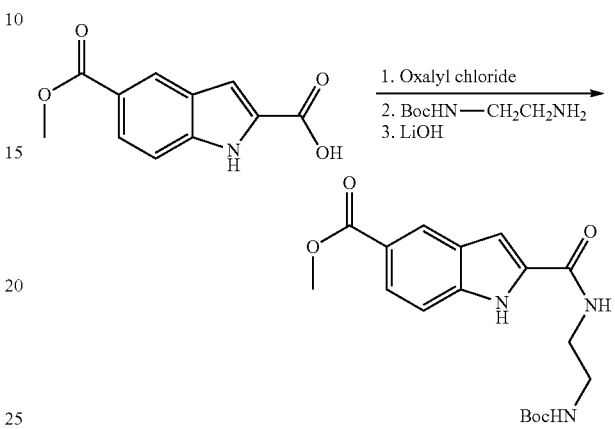

Following a procedure analogous to General Procedure H, 5-(methoxycarbonyl)-1H-indole-2-carboxylic acid (1.18 g, 4.25 mmol) was converted to its acid chloride and reacted with tert-butyl (2-aminoethyl)carbamate. The resulting amide (1.49 g, 4.12 mmol) was then suspended in a solution of methanol/THF/water (3:3:9, 30 mL) and treated with lithium hydroxide monohydrate (3.47 g, 82.7 mmol) and stirred at 18° C. for 1 hour. The mixture was then heated at 55° C. for two hours and the methanol and THF removed in vacuo. Water (100 mL) was added and the mixture transferred to a separatory funnel and washed with EtOAc (2×30 mL) and the aqueous layer brought to pH 3 with an aqueous solution of HCl (2M). The precipitated solid was collected and washed with water (100 mL) to afford the desired carboxylic acid product (1.33 g, 93%) as a beige coloured powder which was used without further purification. $^1$H NMR (DMSO-$d_6$, 400 MHz) δ 12.51 (s, 1H), 11.92 (s, 1H), 8.59 (t, J=5.7 Hz, 1H), 8.30 (s, 1H), 7.78 (dd, J=8.6, 1.6 Hz, 1H), 7.47 (d, J=8.6 Hz, 1H), 7.23 (s, 1H), 6.92 (t, J=5.7 Hz, 1H), 3.35-3.29 (m, 2H), 3.15-3.09 (m, 2H), 1.37 (s, 9H); $^{13}$C NMR (DMSO-$d_6$, 100 MHz) δ 168.1, 160.9, 155.7, 138.7, 133.3, 126.6, 124.4, 124.2, 122.3, 112.0, 103.7, 77.7, 39.7, 39.3, 28.2 (3C); (+)-LRESIMS m/z (rel. int.) 370 (100) [M+Na]$^+$; (+)-HRESIMS calcd. for $C_{17}H_{21}N_3NaO_5$ [M+Na]$^+$ 370.1373, found 370.1376; $v_{max}$ 3277, 1686, 1640, 1560, 1338, 1259, 1169, 760 cm$^{-1}$.

Preparation (xii): Morpholine-4-carbonyl cyanide

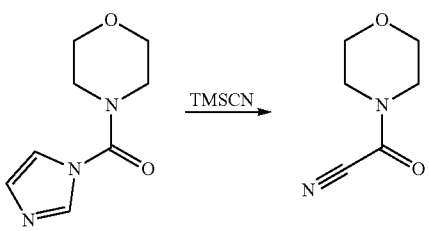 [SMILES: "TMSCN" ; O=C(N1CCOCC1)n1ccnc1 ; N#CC(=O)N1CCOCC1]

Following a method analogous to that reported by Schwartz et al. (Eur. J. Org. Chem 2017, 34, 5110), in a fully operational and well maintained fume cupboard, behind a safety shield, a 10 mL sealed tube vessel fitted with a magnetic stirring-bar was charged with a mixture of trimethylsilyl cyanide (452 µL, 3.62 mmol, CAUTION!) and (1H-imidazol-1-yl)(morpholino)methanone (624 mg, 3.44 mmol) prepared by the method described by Grzyb, J. A.; et al. *Tetrahedron* 2005, 61, 7153. The vessel was sealed under an atmosphere of nitrogen and heated with magnetic stirring at 100° C. in an oil bath for 18 h. The sealed tube was cooled and the contents dissolved in DCM (5 mL) and poured into a saturated aqueous solution of sodium bicarbonate (5 mL) and extracted into DCM (2×15 mL). The combined organic layers were washed with brine (5 mL), dried ($Na_2SO_4$) and concentrated in vacuo. The resulting residue was subjected to flash column chromatography [silica, 1:1 v/v EtOAc/pet. spirit elution] to give, after concentration of the appropriate fractions morpholine-4-carbonyl cyanide as a white solid (433 mg, 90%). Mp. 59-61° C.; $^1$H NMR ($CDCl_3$, 500 MHz) 3.77-3.74 (m, 4H), 3.70-3.68 (m, 2H), 3.64-3.62 (m, 2H); $^{13}$C NMR ($CDCl_3$, 125 MHz) 143.3, 109.9, 66.5, 65.9, 47.0, 42.6; LRMS (EI, 70 eV) m/z (rel. int.) 140 (87, M+·), 113 (30), 110 (59), 86 (35), 56 (100), 54 (93); HREIMS calcd. for $C_6H_8N_2O_2$ [M+·] 140.0580, found 140.0586; $v_{max}$ 2871, 2233, 1669, 1448, 1434, 1273, 1246, 1113, 1036, 958, 854, 721, 628 cm$^{-1}$.

Preparation (xiii): tert-butyl (2-(6-bromopicolinamido)ethyl)carbamate

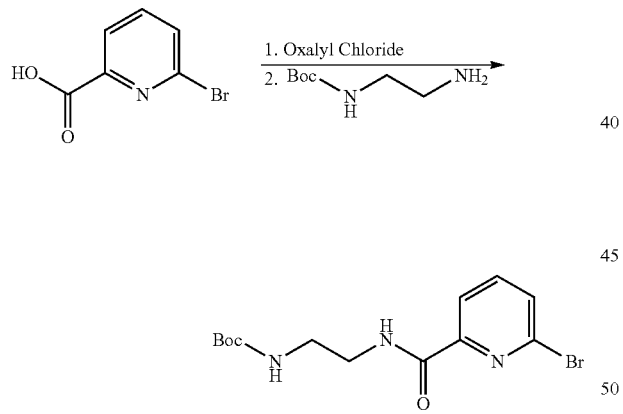

Following a procedure analogous to General Procedure H, 6-bromopicolinic acid (2.00 g, 9.90 mmol) was converted to 6-bromopicolinoyl chloride with oxalyl chloride (0.88 mL, 10.40 mmol) and reacted with tert-butyl (2-aminoethyl) carbamate (1.59 g, 9.90 mmol) to afford tert-butyl (2-(6-bromopicolinamido)ethyl)carbamate (2.41 g, 70%) as a white powder. $^1$H NMR (400 MHz, DMSO-$d_6$) δ 8.66 (t, J=5.0 Hz, 1H), 8.03 (d, J=7.8 Hz, 1H), 7.93 (app. t, J=7.8 Hz, 1H), 7.85 (d, J=7.8 Hz, 1H), 6.92 (t, J=4.7 Hz, 1H), 3.34 (app. q, J=6.0 Hz 2H), 3.12 (app. q, J=5.8 Hz, 2H), 1.36 (s, 9H). (+)-LRESIMS m/z (rel. int.) 366 (100) $C_{13}H_{18}^{79}BrN_3NaO_3$ [M+Na]$^+$, 368 (98) $C_{13}H_{18}^{81}BrN_3NaO_3$ [M+Na]$^+$; $v_{max}$ 3331, 1695, 1657, 1526, 1428, 1271, 1168, 1120, 677 cm$^{-1}$.

Preparation (xiv): tert-butyl (1-(6-bromo-1H-indole-2-carbonyl)azetidin-3-yl)carbamate

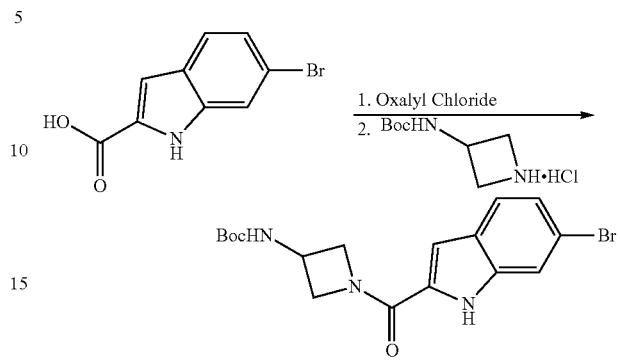

Following a procedure analogous to General Procedure H, 6-bromo-1H-indole-2-carboxylic acid (1.00 g, 4.17 mmol) was converted to 6-bromo-1H-indole-2-carbonyl chloride and reacted with 3-N-Boc-amino-azetidine hydrochloride (0.96 g, 4.58 mmol) to afford tert-butyl (1-(6-bromo-1H-indole-2-carbonyl)azetidin-3-yl)carbamate (1.08 g, 66%) as a tan solid. $^1$H NMR (400 MHz, DMSO-$d_6$) δ 11.75 (s, 1H), 7.65 (d, J=7.3 Hz, 1H), 7.62-7.56 (m, 2H), 7.17 (dd, J=8.6, 1.8 Hz, 1H), 6.83 (d, J=1.5 Hz, 1H), 4.73 (app. t, J=7.6 Hz, 1H), 4.49-4.36 (m, 1H), 4.34-4.32 (m, 2H), 3.93 (dd, J=10.3, 5.3 Hz, 1H), 1.40 (s, 9H); $^{13}$C NMR (100 MHz, DMSO-$d_6$) δ 161.1, 154.8, 136.7, 130.1, 126.4, 123.6, 122.8, 116.4, 114.7, 104.6, 78.3, 59.6, 55.6, 40.7, 28.2 (3C). (+)-LRESIMS m/z (rel. int.) 416 (95) $C_{17}H_{20}^{79}BrN_3NaO_3$ [M+Na]$^+$, 418 (100) $C_{17}H_{20}^{81}BrN_3NaO_3$ [M+Na]$^+$; $v_{max}$ 3355, 3237, 1606, 1680, 1531, 1456, 1342, 1167, 815, 645 cm$^{-1}$.

Synthesis Example 1—BT1057

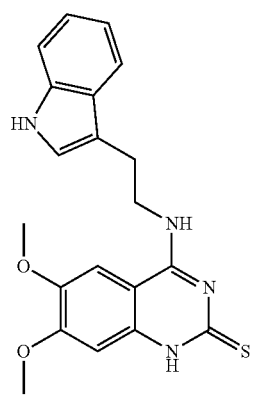 [SMILES: COc1cc2[nH]c(=S)nc(NCCc3c[nH]c4ccccc34)c2cc1OC]

Prepared according to General Procedure I from reaction of N-(2-(1H-indol-3-yl)ethyl)-2-chloro-6,7-dimethoxyquinazolin-4-amine (70 mg, 0.18 mmol) with potassium thioacetate (60 mg, 0.53 mmol) to afford a residue that was subjected to flash column chromatography [silica, 1:20-1:10 v/v MeOH/DCM elution] to give, after concentration of the appropriate fractions the compound BT1057 as a white powder (51 mg, 76%). $^1$H NMR (DMSO-$d_6$, 400 MHz) δ 12.18 (s, 1H), 10.84 (s, 1H), 8.54 (t, J=5.4 Hz, 1H), 7.74 (d, J=7.8 Hz, 1H), 7.55 (s, 1H), 7.34 (d, J=8.1 Hz, 1H), 7.20 (d, J=2.0 Hz, 1H), 7.07 (t, J=7.5 Hz, 1H), 6.98 (t, J=7.4 Hz, 1H), 6.94 (s, 1H), 3.82 (s, 3H), 3.82 (s, 3H), 3.80-3.78 (m, 2H), 3.08-3.02 (m, 2H); (+)-LRESIMS m/z (rel. int.) 403 (100) [M+Na]$^+$; (+)-HRESIMS calcd. for $C_{20}H_{21}N_4O_2S$ [M+H]$^+$ 381.1380, found 381.1385; $v_{max}$ 3391, 3303, 1625, 1609, 1577, 1539, 1511, 1345, 1266, 1205, 1155, 739, 608 cm$^{-1}$.

Synthesis Example 2—BT2011

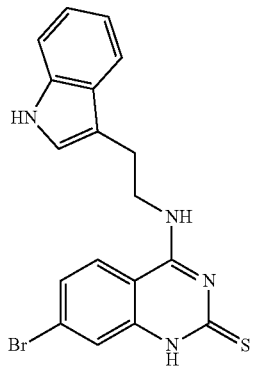 [SMILES: S=c1nc(NCCc2c[nH]c3ccccc23)c2ccc(Br)cc2[nH]1]

Prepared according to General Procedure C from reaction of N-(2-(1H-indol-3-yl)ethyl)-7-bromo-2-chloroquinazolin-4-amine (25 mg, 62 μmol) with potassium thioacetate (20 mg, 124 μmol) to afford a residue that was subjected to flash column chromatography [silica, 1:20 v/v ammoniacal MeOH/DCM elution] to give, after concentration of the appropriate fractions the compound BT2011 as a white powder (18 mg, 73%). $^1$H NMR (DMSO-d$_6$, 400 MHz) δ 12.37 (s, 1H), 10.83 (s, 1H), 8.92 (t, J=5.6 Hz, 1H), 8.01 (d, J=8.7 Hz, 1H), 7.72 (d, J=8.0 Hz, 1H), 7.55 (d, J=2.0 Hz, 1H), 7.46 (dd, J=8.7, 2.0 Hz, 1H), 7.34 (d, J=8.1 Hz, 1H), 7.20 (d, J=2.3 Hz, 1H), 7.07 (t, J=7.5 Hz, 1H), 6.97 (t, J=7.5 Hz, 1H), 3.84-3.74 (m, 2H), 3.05 (t, J=7.5 Hz, 2H); (+)-LRESIMS m/z (rel. int.) 399 (20), 401 (20) [M+H]$^+$, 421 (100), 423 (100) [M+Na]$^+$; (+)-HRESIMS calcd. for $C_{18}H_{16}^{79}BrN_4S$ [M+H]$^+$ 399.0274, found 399.0280. $v_{max}$ 3399, 1604, 1540, 1482, 1333, 1216, 1188, 1144, 754, 740 cm$^{-1}$.

Synthesis Example 3—BT2012

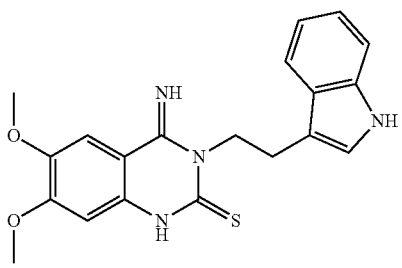 [SMILES: COc1cc2[nH]c(=S)n(CCc3c[nH]c4ccccc34)c(=N)c2cc1OC]

Prepared according to General Procedure B, from reaction of 2-isothiocyanato-4,5-dimethoxybenzonitrile (300 mg, 1.36 mmol) and tryptamine (218 mg, 1.36 mmol) to afford BT2012 as a cream powder (395 mg, 76%). $^1$H NMR (DMSO-d$_6$, 400 MHz) δ 11.92 (s br, 1H), 10.83 (s, 1H), 9.18 (s, 1H), 7.94 (d, J=8.0 Hz, 1H), 7.64 (s, 1H), 7.35 (d, J=8.0 Hz, 1H), 7.19 (s, 1H), 7.12-7.04 (m, 1H), 7.02-6.95 (m, 1H), 6.86 (s, 1H), 4.92-4.78 (m, 2H), 3.84 (s, 3H), 3.80 (s, 3H), 3.18-3.09 (m, 2H); $^{13}$C NMR (DMSO-d$_6$, 100 MHz) δ 172.8, 153.8, 153.3, 146.6, 136.3, 131.9, 127.4, 122.9, 121.0, 119.0, 118.2, 111.4, 111.2, 107.1, 106.5, 98.4, 56.3, 55.8, 47.8, 21.6; (+)-LRESIMS m/z (rel. int.) 380 (100) [M+H]$^+$; (+)-HRESIMS calcd. for $C_{20}H_{21}N_4O_2S$ [M+H]$^+$ 381.1380, found 381.1386. $v_{max}$ 3181, 3122, 1632, 1583, 1551, 1515, 1456, 1441, 1401, 1350, 1285, 1265, 1243, 1163, 1126, 1011 cm$^{-1}$.

Synthesis Example 4—BT2014

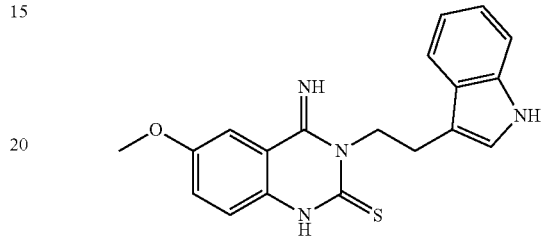

Prepared according to General Procedure B, from reaction of 2-isothiocyanato-5-methoxybenzonitrile (33 mg, 0.16 mmol) and tryptamine (27 mg, 0.17 mmol) to afford BT2014 as a cream powder (24 mg, 42%). $^1$H NMR (DMSO-d$_6$, 400 MHz) δ 12.10 (s br, 1H), 10.84 (s, 1H), 9.53 (s br, 1H), 7.94 (d, J=7.8 Hz, 1H), 7.71 (d, J=1.7 Hz, 1H), 7.36 (d, J=7.8 Hz, 1H), 7.29-7.17 (m, 3H), 7.08 (t, J=7.5 Hz, 1H), 7.00 (t, J=7.5 Hz, 1H), 4.92-4.80 (m, 2H), 3.83 (s, 3H), 3.20-3.09 (m, 2H); $^{13}$C NMR (DMSO-d$_6$, 100 MHz) δ 173.0, 156.1, 153.3, 136.3, 129.7, 127.4, 122.7, 121.4, 121.0, 119.1, 118.2, 117.4, 115.6, 111.5, 111.3, 108.3, 55.9, 47.7, 21.7. (+)-LRESIMS m/z (rel. int.) 351 (100) [M+H]$^+$; (+)-HRESIMS calcd. for $C_{19}H_{19}N_4OS$ [M+H]$^+$ 351.1274, found 351.1281. $v_{max}$ 3307, 1619, 1581, 1542, 1504, 1460, 1349, 1260, 1234, 1158, 1057, 993, 814 cm$^{-1}$.

Synthesis Example 5—BT2015

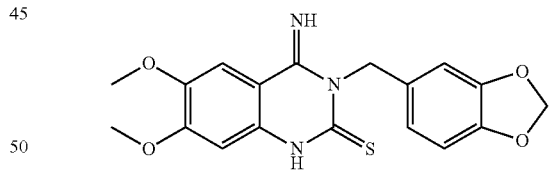

Prepared according to General Procedure B, from reaction of 2-isothiocyanato-4,5-dimethoxybenzonitrile (50 mg, 0.23 mmol) and piperonyl amine (34 mg, 0.23 mmol) to afford BT2015 as a cream powder (34 mg, 40%). $^1$H NMR (DMSO-d$_6$, 400 MHz) δ 12.02 (s br, 1H), 9.09 (s, 1H), 7.55 (s, 1H), 6.93 (s, 1H), 6.86 (s, 1H), 6.85-6.82 (m, 1H), 6.80 (d, J=8.0 Hz, 1H), 5.95 (s, 2H), 5.78 (s br, 2H), 3.80 (s, 3H), 3.79 (s, 3H); $^{13}$C NMR (DMSO-d$_6$, 100 MHz) one signal obstructed or overlapping δ 173.8, 153.3 (br), 146.9, 146.5, 145.8, 131.3 (br), 130.6 (br), 120.5 (br), 108.1 (br), 107.8, 107.4 (br), 100.7, 98.3 (br), 56.1, 55.7, 49.1; (+)-LRESIMS m/z (rel. int.) 372 (100) [M+H]$^+$; (+)-HRESIMS calcd. for $C_{18}H_{18}N_3O_4S$ [M+H]$^+$ 372.1013, found 372.1021; $v_{max}$ 3275, 1628, 1577, 1552, 1516, 1502, 1437, 1242, 1188, 1134, 1030, 1001, 924, 821 cm$^{-1}$.

Synthesis Example 6—BT2017

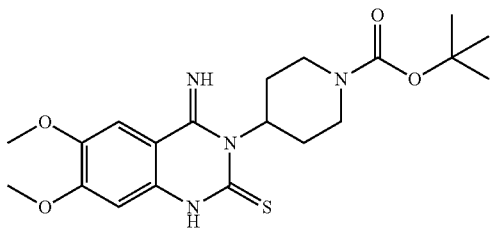 [SMILES: COc1cc2[nH]c(=S)n(C3CCN(C(=O)OC(C)(C)C)CC3)c(=N)c2cc1OC]

A mixture of 2-isothiocyanato-4,5-dimethoxybenzonitrile (30 mg, 0.14 mmol), 4-amino-1-Boc-piperidine (55 mg, 0.27 mmol) and triethyl amine (38 µL, 0.27 mmol) in DCM (3 mL) was stirred for 24 h. The solid was collected and washed with DCM (3 mL) to afford BT2017 as a cream powder (50 mg, 87%). $^1$H NMR (DMSO-$d_6$, 400 MHz) δ 11.85 (s, 1H), 9.13 (s, 1H), 7.50 (s, 1H), 6.81 (s, 1H), 6.08-5.96 (m, 1H), 4.16-3.94 (m, 2H), 3.80 (s, 3H), 3.77 (s, 3H), 3.07-2.94 (m, 2H), 2.87-2.61 (m, 2H), 1.60-1.52 (m, 2H), 1.42 (s, 9H); $^{13}$C NMR (DMSO-$d_6$, 100 MHz) δ 174.6, 153.9, 153.7, 152.8, 146.4, 130.3, 108.8, 107.0, 98.0, 78.5, 59.7 (br), 56.1, 55.7, 44.4-43.3 (br, 2C), 28.1 (3C), 26.4 (2C); (+)-LRESIMS m/z (rel. int.) 421 (100) [M+H]$^+$; (+)-HRESIMS calcd. for $C_{20}H_{29}N_4O_4S$ [M+H]$^+$ 421.1904, found 421.1900; $v_{max}$ 1690, 1638, 1542, 1511, 1418, 1234, 1136, 1126, 1010 cm$^{-1}$.

Synthesis Example 7—BT2018

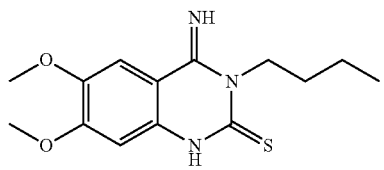 [SMILES: CCCCn1c(=S)[nH]c2cc(OC)c(OC)cc2c1=N]

Prepared according to General Procedure B, from reaction of 2-isothiocyanato-4,5-dimethoxybenzonitrile (50 mg, 0.23 mmol) and n-butylamine (68 µL, 0.68 mmol) to afford BT2018 as a white powder (39 mg, 87%). $^1$H NMR (DMSO-$d_6$, 400 MHz) δ 11.84 (s br, 1H), 9.00 (s br, 1H), 7.56 (s, 1H), 6.82 (s, 1H), 4.62-4.49 (m, 2H), 3.82 (s, 3H), 3.78 (s, 3H), 1.73-1.62 (m, 2H), 1.39-1.28 (m, 2H), 0.92 (t, J=7.3 Hz, 3H); (+)-LRESIMS m/z (rel. int.) 294 (100) [M+H]$^+$; (+)-HRESIMS calcd. for $C_{14}H_{20}N_3O_2S$ [M+H]$^+$ 294.1271, found 294.1274; $v_{max}$ 3272, 1629, 1577, 1516, 1436, 1354, 1258, 1239, 1110, 1022, 822, 764 cm$^{-1}$.

Synthesis Example 8—BT2020

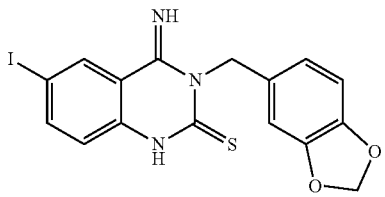 [SMILES: N=c1c2cc(I)ccc2[nH]c(=S)n1Cc1ccc2c(c1)OCO2]

Prepared according to General Procedure B, from reaction of 5-iodo-2-isothiocyanatobenzonitrile (50 mg, 0.17 mmol) and piperonylamine (26 mg, 0.17 mmol) to afford BT2020 as a white powder (37 mg, 48%). $^1$H NMR (DMSO-$d_6$, 400 MHz) δ 12.27 (s br, 1H), 9.63 (s br, 1H), 8.48 (s, 1H), 7.86 (dd, J=8.5, 1.8 Hz, 1H), 7.06 (d, J=8.5 Hz, 1H), 6.92 (s, 1H), 6.83 (dd, J=8.2, 0.8 Hz, 1H), 6.79 (d, J=8.2 Hz, 1H), 5.95 (s, 2H), 5.73 (s br, 2H); (+)-LRESIMS m/z (rel. int.) 438 (100) [M+H]$^+$; (+)-HRESIMS calcd. for $C_{16}H_{13}N_3O_2SI$ [M+H]$^+$ 437.9768, found 437.9774; $v_{max}$ 3279, 1608, 1538, 1503, 1446, 1249, 1187, 1042, 952, 814, 620 cm$^{-1}$.

Synthesis Example 9—BT2021

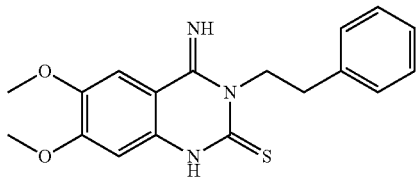 [SMILES: COc1cc2[nH]c(=S)n(CCc3ccccc3)c(=N)c2cc1OC]

Prepared according to General Procedure B, from reaction of 2-isothiocyanato-4,5-dimethoxybenzonitrile (50 mg, 0.23 mmol) and 2-phenylethan-1-amine (28 mg, 0.23 mmol) to afford BT2021 as a white powder (32 mg, 36%). $^1$H NMR (DMSO-$d_6$, 400 MHz) δ 11.90 (s br, 1H), 9.12 (s br, 1H), 7.60 (s, 1H), 7.37-7.29 (m, 4H), 7.26-7.21 (m, 1H), 6.84 (s, 1H), 4.84-4.71 (m, 2H), 3.83 (s, 3H), 3.80 (s, 3H); 3.00 (t, J=8.2 Hz, 2H); (+)-LRESIMS m/z (rel. int.) 342 (100) [M+H]$^+$; (+)-HRESIMS calcd. for $C_{18}H_{20}N_3O_2S$ [M+H]$^+$ 342.1271, found 342.1270; $v_{max}$ 3274, 1630, 1577, 1552, 1516, 1436, 1351, 1279, 1238, 1253, 1010, 820, 704 cm$^{-1}$.

Synthesis Example 10—BT2022

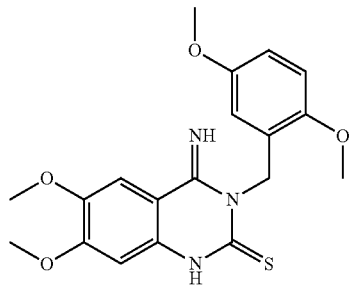

A mixture of 2-isothiocyanato-4,5-dimethoxybenzonitrile (30 mg, 0.14 mmol), 2,5-dimethoxybenzyl amine (46 mg, 0.27 mmol) and triethyl amine (38 µL, 0.27 mmol) in DCM (3 mL) was stirred for 24 h. The solid was collected and washed with DCM (3 mL) to afford BT2022 as a white powder (47 mg, 87%). $^1$H NMR poor resolution of signals (DMSO-$d_6$, 400 MHz) δ 11.93 (s br, 1H), 9.03 (s br, 1H), 7.58 (s br, 1H), 6.91 (s br, 2H), 6.74 (s br, 1H), 6.18 (s br, 1H), 5.74 (s br, 2H), 3.81 (m, 9H), 3.57 (s, 3H); (+)-LRESIMS m/z (rel. int.) 388 (100) [M+H]$^+$; (+)-HRESIMS calcd. for $C_{19}H_{22}N_3O_4S$ [M+H]$^+$ 388.1326, found 388.1325; $v_{max}$ 1642, 1550, 1505, 1433, 1396, 1280, 1226, 1174, 1118, 1050, 997, 820 cm$^{-1}$.

Synthesis Example 11—BT2023

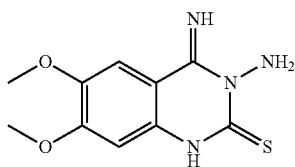 [SMILES: COc1cc2[nH]c(=S)n(N)c(=N)c2cc1OC]

Prepared according to General Procedure B, from reaction of 2-isothiocyanato-4,5-dimethoxybenzonitrile (50 mg, 0.23 mmol) and hydrazine monohydrate (34 mg, 0.68 mmol) to afford BT2023 as a white powder (55 mg, 96%). $^1$H NMR (DMSO-$d_6$, 400 MHz) δ 10.74-8.64 (br m, 2H), 7.76 (s, 1H), 6.92 (s, 1H), 6.38 (s, 2H), 3.89 (s, 3H), 3.85 (s, 3H); (+)-LRESIMS m/z (rel. int.) 253 (100) [M+H]$^+$; (+)-HRESIMS calcd. for $C_{10}H_{13}N_4O_2S$ [M+H]$^+$ 253.0754, found 253.0754; $v_{max}$ 1622, 1554, 1502, 1402, 1337, 1289, 1236, 1199, 1105, 991, 847, 755, 644 cm$^{-1}$.

Synthesis Example 12—BT2024

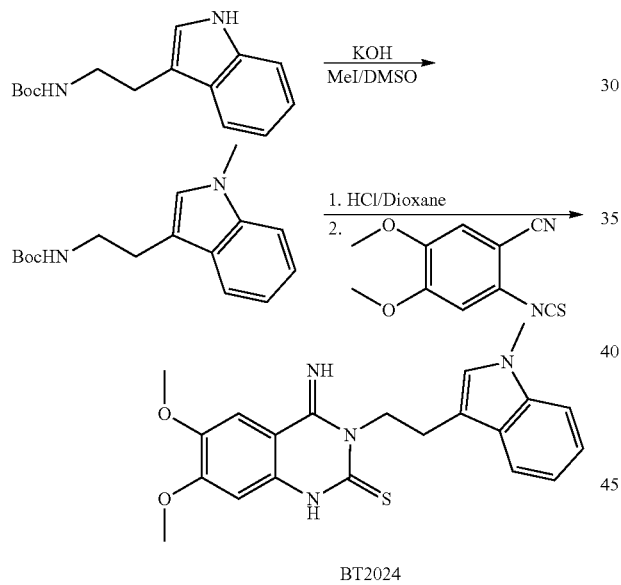

BT2024

A magnetically stirred solution of tert-butyl (2-(1H-indol-3-yl)ethyl)carbamate (200 mg, 0.77 mmol) and potassium hydroxide (101 mg, 1.54 mmol) in DMSO (3 mL) was treated with methyl iodide (72 μL, 1.15 mmol) and stirred for 18 h. The mixture was diluted with water (10 mL) and extracted with EtOAc (3×15 mL) and the combined organic layers washed with brine (15 mL). The solvent was removed in vacuo and the residue subjected to flash column chromatography [silica, 1:3 v/v EtOAc/Pet spirit elution] to give, after concentration of the appropriate fractions, tert-butyl (2-(1-methyl-1H-indol-3-yl)ethyl)carbamate (154 mg, 73%) as a thick pale yellow oil. 1H NMR (CDCl$_3$, 400 MHz) δ 7.60 (d, J=7.9 Hz, 1H), 7.34-7.27 (m, 1H), 7.23 (ddd, J=8.1, 6.9, 1.1 Hz, 1H), 7.11 (ddd, J=7.9, 7.0, 1.0 Hz, 1H), 6.89 (s, 1H), 3.76 (s, 2H), 3.46 (d, J=6.3 Hz, 2H), 2.94 (t, J=6.8 Hz, 1H), 1.44 (s, 9H). Spectroscopic data were identical with those reported. t-Butyl (2-(1-methyl-1H-indol-3-yl)ethyl)carbamate (154 mg, 0.56 mmol) was treated with a solution of hydrogen chloride (2 mL, 4M in dioxane) and magnetically stirred for 3 h. The solvent was removed with a gentle stream of nitrogen and the remaining gum was triturated with ether (3×10 mL) then placed under high vacuum for 1 h to afford the amine hydrochloride as a cream coloured gum and used directly without further purification. A mixture of triethylamine (88 μL, 0.64 mmol), the crude amine hydrochloride formed directly above, and DCM (1 mL) was added to a magnetically stirred solution of 2-isothiocyanato-4,5-dimethoxybenzonitrile (35 mg, 0.16 mmol) in a mixture of DCM and pet. spirit (0.75 mL:0.75 mL). The mixture was stirred for 0.5 h and then pet. spirit (5 mL) was added. The solid was allowed to settle and the solvent was decanted and then ethanol (5 mL) was added and the mixture heated at 70° C. for 2 h. The mixture was cooled to rt and the solid was collected by vacuum filtration, washed with ethanol (5 mL) and dried at the pump (1 mmHg) to afford BT2024 as a cream powder (43 mg, 69%). $^1$H NMR (DMSO-$d_6$, 400 MHz) δ 10.90 (s br, 2H), 7.89 (d, J=7.8 Hz, 1H), 7.81 (s, 1H), 7.39 (d, J=8.2 Hz, 1H), 7.25 (s, 1H), 7.15 (t, J=7.6 Hz, 1H), 7.03 (t, J=7.8 Hz, 1H), 6.91 (s, 1H), 4.93-4.79 (m, 2H), 3.86 (s, 3H), 3.84 (s, 3H), 3.76 (s, 3H), 3.12 (app. t, J=8.4 Hz, 2H); $^{13}$C NMR (DMSO-$d_6$, 100 MHz) δ 172.4, 154.5, 153.5, 146.9, 136.6, 132.6, 127.7, 127.6, 121.1, 119.1, 118.3, 110.1, 109.5, 106.9, 105.6, 98.2, 56.4, 55.9, 48.1, 32.2, 21.3; (+)-LRESIMS m/z (rel. int.) 395 (100) [M+H]$^+$; (+)-HRESIMS calcd. for $C_{21}H_{23}N_4O_2S$ [M+H]$^+$ 395.1536, found 395.1544; $v_{max}$ 1628, 1579, 1541, 1515, 1441, 1400, 1263, 1246, 1129, 1015, 738 cm$^{-1}$.

Synthesis Example 13—BT2025

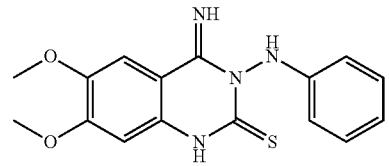 [SMILES: COc1cc2[nH]c(=S)n(Nc3ccccc3)c(=N)c2cc1OC]

Prepared according to General Procedure B, from reaction of 2-isothiocyanato-4,5-dimethoxybenzonitrile (30 mg, 0.14 mmol) and phenyl hydrazine monohydrate (15 mg, 0.14 mmol) to afford BT2025 as a white powder (21 mg, 47%). $^1$H NMR (DMSO-$d_6$, 400 MHz) δ 9.15 (s br, 1H), 8.99 (s br, 1H), 8.61 (s br, 1H), 7.60 (s, 1H), 7.22 (t, J=7.7 Hz, 2H), 6.90 (t, J=7.4 Hz, 1H), 6.83 (s, 1H), 6.65 (d, J=8.0 Hz, 2H), 3.88 (s, 3H), 3.83 (s, 3H); (+)-LRESIMS m/z (rel. int.) 329 (100) [M+H]$^+$; (+)-HRESIMS calcd. for $C_{16}H_{17}N_4O_2S$ [M+H]$^+$ 329.1067, found 329.1067; $v_{max}$ 3415, 3070, 1625, 1551, 1503, 1495, 1434, 1285, 1231, 990, 844 cm$^{-1}$.

Synthesis Example 14—BT2026

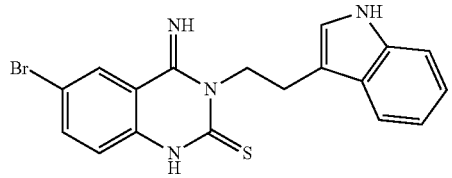 [SMILES: N=c1c2cc(Br)ccc2[nH]c(=S)n1CCc1c[nH]c2ccccc12]

Prepared according to General Procedure B, from reaction of 5-bromo-2-isothiocyanatobenzonitrile (300 mg, 1.25 mmol) and tryptamine (201 mg, 1.25 mmol) to afford BT2026 as a cream powder. $^1$H NMR (DMSO-$d_6$, 400 MHz) δ; (+)-LRESIMS m/z (rel. int.) 399 (100), 401 (100) [M+H]$^+$; (+)-HRESIMS calcd. for $C_{18}H_{16}N_4S^{79}Br$ [M+H]$^+$ 399.0274, found 399.0274; $v_{max}$ 3468, 3249, 1633, 1603, 1538, 1450, 1329, 1156, 1146, 848, 803, 750 cm$^{-1}$.

Synthesis Example 15—BT2027

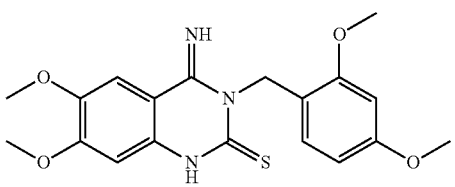

Prepared according to General Procedure B, from reaction of 2-isothiocyanato-4,5-dimethoxybenzonitrile (35 mg, 0.16 mmol), 2,4-dimethoxybenzylamine hydrochloride (32 mg, 0.16 mmol) and triethylamine (22 μL, 0.16 mmol) to afford BT2027 as a white powder (21 mg, 47%). $^1$H NMR (DMSO-$d_6$, 400 MHz) δ 10.76 (s br, 2H), 7.88 (s, 1H), 6.99 (s, 1H), 6.66 (d, J=8.4 Hz, 1H), 6.62 (d, J=2.4 Hz, 1H), 6.39 (dd, J=8.4, 2.4 Hz, 1H), 5.72 (s br, 2H), 3.88 (s, 3H), 3.86 (s, 6H), 3.73 (s, 3H); (+)-LRESIMS m/z (rel. int.) 388 (100) [M+H]$^+$; (+)-HRESIMS calcd. for $C_{19}H_{22}N_3O_4S$ [M+H]$^+$ 388.1326, found 388.1333; $v_{max}$ 1676, 1642, 1617, 1547, 1508, 1434, 1244, 1209, 1156, 1117, 1031, 823 cm$^{-1}$.

Synthesis Example 16—BT2028

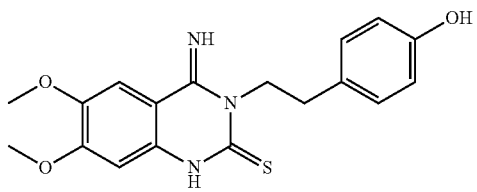 [SMILES: COc1cc2[nH]c(=S)n(CCc3ccc(O)cc3)c(=N)c2cc1OC]

Prepared according to General Procedure B, from reaction of 2-isothiocyanato-4,5-dimethoxybenzonitrile (35 mg, 0.16 mmol), tyramine hydrochloride (28 mg, 0.16 mmol) and triethylamine (22 μL, 0.16 mmol) to afford a residue that was further triturated with ethanol (2 mL) to provide BT2028 as a cream powder (13 mg, 23%). $^1$H NMR (DMSO-$d_6$, 400 MHz) δ 11.95 (s br, 1H), 9.20 (s, 1H), 9.10 (s br, 1H), 7.60 (s, 1H), 7.12 (d, J=8.0 Hz, 2H), 6.84 (s, 1H), 6.71 (d, J=8.0 Hz, 2H), 4.76-4.65 (m, 2H), 3.83 (s, 3H), 3.79 (s, 3H), 2.87 (app. t, J=8.2 Hz, 2H); (+)-LRESIMS m/z (rel. int.) 358 (100) [M+H]$^+$; (+)-HRESIMS calcd. for $C_{18}H_{20}N_3O_3S$ [M+H]$^+$ 358.1220, found 358.1219; $v_{max}$ 1629, 1580, 1550, 1512, 1438, 1354, 1248, 1235, 1212, 1126, 1008, 823, 767 cm$^{-1}$.

Synthesis Example 17—BT2032

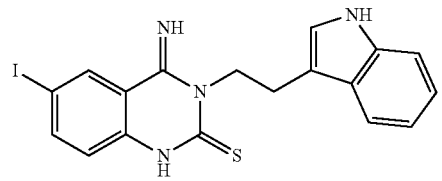 [SMILES: N=c1c2cc(I)ccc2[nH]c(=S)n1CCc1c[nH]c2ccccc12]

Prepared according to General Procedure B, from reaction of 2-isothiocyanato-5-iodobenzonitrile (300 mg, 1.1 mmol) with tryptamine (168 mg, 1.1 mmol) to afford BT2032 as a cream powder (235 mg, 66%). $^1$H NMR (DMSO-$d_6$, 400 MHz) δ 12.19 (s, 1H), 10.84 (s, 1H), 9.70 (s, 1H), 8.55 (s, 1H), 7.90-7.85 (m, 2H), 7.35 (d, J=8.0 Hz, 1H), 7.19 (s, 1H), 7.11-7.05 (m, 2H), 6.99 (t, J=7.4 Hz, 1H), 4.86-4.76 (m, 2H), 3.11 (t, J=8.3 Hz, 2H); (+)-LRESIMS m/z (rel. int.) 447 (100) [M+H]$^+$; (+)-HRESIMS calcd. for $C_{18}H_{16}N_4SI$ [M+H]$^+$ 447.0135, found 447.0140; $v_{max}$ 3451, 3279, 1621, 1599, 1582, 1528, 1460, 1381, 1323, 1286, 1154, 1145, 1038, 817, 741 cm$^{-1}$.

Synthesis Example 18—BT2033

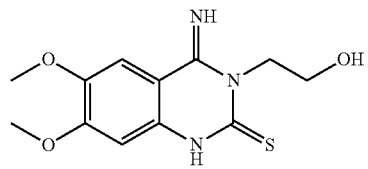 [SMILES: COc1cc2[nH]c(=S)n(CCO)c(=N)c2cc1OC]

Prepared according to General Procedure B, from reaction of 2-isothiocyanato-4,5-dimethoxybenzonitrile (200 mg, 0.91 mmol) with 2-aminoethan-1-ol (55 μL, 0.91 mmol) to afford BT2033 as a white powder (179 mg, 23%). $^1$H (DMSO-$d_6$, 400 MHz) δ 11.90 (s br, 1H), 9.02 (s br, 1H), 7.57 (s, 1H), 6.82 (s, 1H), 4.95 (s br, 1H), 4.75-4.63 (m, 2H), 3.81 (s, 3H), 3.79 (s, 3H), 3.73-3.65 (m, 2H); (−)-LRESIMS m/z (rel. int.) 280 (100) [M−H]−; (−)-HRESIMS calcd. for $C_{12}H_{14}N_3O_3S$ [M−H]− 280.0761, found 280.0757; $v_{max}$ 3514, 3266, 1631, 1584, 1549, 1518, 1437, 1396, 1280, 1263, 1232, 1096, 1058, 1012, 821 cm$^{-1}$. A portion of the product (20 mg) was suspended in DCM (2 mL) and trifluoroacetic acid (100 μL) added. The mixture was concentrated under a gentle stream of nitrogen over 24 h to afford the trifluoroacetate salt of BT2033. $^1$H (DMSO-$d_6$, 400 MHz) TFA salt δ 13.75 (s br, 1H), 10.36 (s, 1H), 9.69 (s br, 1H), 8.68 (s br, 1H), 7.80 (s, 1H), 6.99 (s, 1H), 4.88-4.64 (m, 2H), 3.90 (s, 3H), 3.88-3.84 (m, 2H), 3.85 (s, 3H); $^{13}$C (DMSO-$d_6$, 100 MHz) TFA salt δ 171.4, 158.5 (q, JC-F=35.3 Hz) 157.2, 155.7, 147.7, 135.3, 116.0 (q, JC-F=292.9 Hz), 105.4, 102.2, 97.7, 57.0, 56.4, 56.4, 51.2.

Synthesis Example 19—BT2034

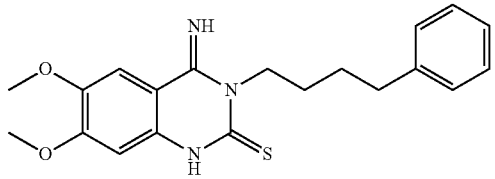 [SMILES: COc1cc2[nH]c(=S)n(CCCCc3ccccc3)c(=N)c2cc1OC]

Prepared according to General Procedure B, from reaction of 2-isothiocyanato-4,5-dimethoxybenzonitrile (35 mg, 0.16 mmol) with 4-phenylbutan-1-amine (34 mg, 0.23 mmol) to afford BT2034 as a white powder (11 mg, 13%). $^1$H NMR (DMSO-d$_6$, 400 MHz) δ 11.81 (s br, 1H), 8.99 (s br, 1H), 7.55 (s, 1H), 7.32-7.11 (m, 5H), 6.82 (s, 1H), 4.68-4.53 (m, 2H), 3.82 (s, 3H), 3.78 (s, 3H), 2.63 (app. t, J=7.6 Hz, 2H), 1.78-1.69 (m, 2H), 1.67-1.57 (m, 2H); (+)-LRESIMS m/z (rel. int.) 370 (100) [M+H]$^+$; (+)-HRESIMS calcd. for C$_{20}$H$_{24}$N$_3$O$_2$S [M+H]$^+$ 370.1584, found 370.1584; ν$_{max}$ 3270, 2981, 1629, 1579, 1551, 1517, 1462, 1267, 1240, 1212, 1123, 1021, 820, 697 cm$^{-1}$.

Synthesis Example 20—BT2035

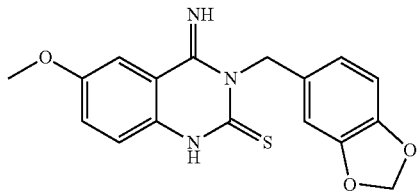 [SMILES: COc1ccc2[nH]c(=S)n(Cc3ccc4c(c3)OCO4)c(=N)c2c1]

Prepared according to General Procedure B, from reaction of 2-isothiocyanato-5-methoxybenzonitrile (33 mg, 0.16 mmol) with piperonyl amine (25 mg, 0.17 mmol) to afford BT2035 as a white powder (35 mg, 64%). $^1$H NMR (DMSO-d$_6$, 400 MHz) δ 12.14 (s br, 1H), 9.45 (s, 1H), 7.64 (s, 1H), 7.26 (s, 1H), 7.19 (dd, J=8.9, 2.6 Hz, 1H), 6.94 (s, 1H), 6.85 (d, J=7.9 Hz, 1H), 6.80 (d, J=8.0 Hz, 1H), 5.95 (s, 2H), 5.78 (s, 2H), 3.80 (s, 3H); $^{13}$C NMR (DMSO-d$_6$, 100 MHz) δ 173.6, 156.2, 153.4, 146.8, 145.8, 131.3, 129.6, 121.5, 120.6, 117.4, 115.5, 108.3, 108.2, 107.8, 100.7, 55.9, 49.2; (+)-LRESIMS m/z (rel. int.) 342 (100) [M+H]$^+$; (+)-HRESIMS calcd. for C$_{17}$H$_{16}$N$_3$O$_3$S [M+H]$^+$ 342.0907, found 342.0911; ν$_{max}$ 3259, 1621, 1544, 1502, 1443, 1238, 1164, 1040, 969, 813, 723, 621 cm$^{-1}$.

Synthesis Example 21—BT2037

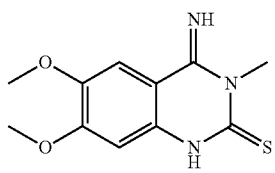

Prepared according to General Procedure B, from reaction of 2-isothiocyanato-4,5-dimethoxybenzonitrile (35 mg, 0.16 mmol) with methylamine (159 μL, 0.32 mmol, 2M solution in MeOH) to afford BT2037 as a white powder (19 mg, 48%). $^1$H NMR (DMSO-d$_6$, 400 MHz) δ 11.91 (s, 1H), 9.06 (s, 1H), 7.58 (s, 1H), 6.83 (s, 1H), 3.82 (s, 3H), 3.82 (s, 3H), 3.80 (s, 3H); (+)-LRESIMS m/z (rel. int.) 252 (100) [M+H]$^+$; (+)-HRESIMS calcd. for C$_{11}$H$_{14}$N$_3$O$_2$S [M+H]$^+$ 252.0801, found 252.0804; ν$_{max}$ 3276, 1631, 1584, 1552, 1518, 1438, 1277, 1264, 1235, 1090, 820, 764, 661 cm$^{-1}$.

Synthesis Example 22—BT2038

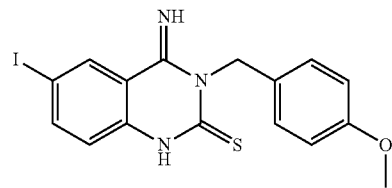 [SMILES: COc1ccc(Cn2c(=S)[nH]c3ccc(I)cc3c2=N)cc1]

Prepared according to General Procedure B, from reaction of 5-iodo-2-isothiocyanatobenzonitrile (200 mg, 0.70 mmol) with 4-methoxybenzylamine (96 mg, 0.70 mmol) to afford BT2038 as a white powder (202 mg, 68%). $^1$H NMR (DMSO-d$_6$, 400 MHz) δ 12.26 (s, 1H), 9.63 (s, 1H), 8.50 (s, 1H), 7.86 (dd, J=8.5, 1.8 Hz, 1H), 7.28 (d, J=8.7 Hz, 2H), 7.07 (d, J=8.5 Hz, 1H), 6.82 (d, J=8.7 Hz, 2H), 5.76 (s, 2H), 3.70 (s, 3H); (+)-LRESIMS m/z (rel. int.) 424 (100) [M+H]$^+$; (+)-HRESIMS calcd. for C$_{16}$H$_{15}$N$_3$OSI [M+H]$^+$ 423.9975, found 423.9972; ν$_{max}$ 1606, 1580, 1512, 1387, 1250, 1183, 1177, 1026, 963, 949, 818, 604 cm$^{-1}$.

Synthesis Example 23—BT2039

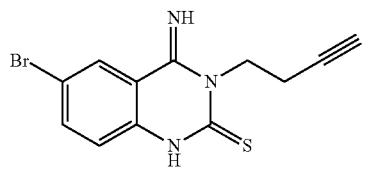 [SMILES: C#CCCn1c(=S)[nH]c2ccc(Br)cc2c1=N]

Prepared according to General Procedure B, from reaction of 5-bromo-2-isothiocyanatobenzonitrile (100 mg, 0.42 mmol) with but-3-yn-1-amine (29 mg, 0.42 mmol) to afford BT2039 as a tan powder (32 mg, 25%). $^1$H NMR (DMSO-d$_6$, 400 MHz) δ 12.24 (s, 1H), 9.65 (s, 1H), 8.41 (d, J=2.1 Hz, 1H), 7.71 (dd, J=8.7, 2.1 Hz, 1H), 7.17 (d, J=8.7 Hz, 1H), 4.71-4.62 (m, 2H), 2.88 (t, J=2.7 Hz, 1H), 2.59 (ddd, J=9.3, 7.0, 2.7 Hz, 2H); $^{13}$C NMR (DMSO-d$_6$, 100 MHz) δ 174.1, 151.8, 135.8, 134.6, 128.5, 117.9, 116.5, 116.0, 81.3, 72.6, 45.4, 15.1; (+)-LRESIMS m/z (rel. int.) 308 (100), 310 (100) [M+H]$^+$; (+)-HRESIMS calcd. for C$_{12}$H$_{11}$N$_3$S$^{79}$Br [M+H]$^+$ 307.9852, found 307.9861; ν$_{max}$ 3274, 3258, 1603, 1586, 1533, 1463, 1381, 1278, 1150, 822, 657 cm$^{-1}$.

Synthesis Example 24—BT2040

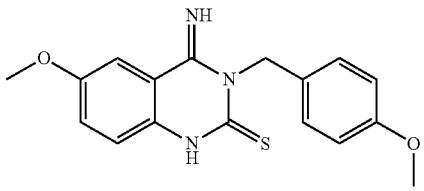

Prepared according to General Procedure B, from reaction of 2-isothiocyanato-5-methoxybenzonitrile (33 mg, 0.16 mmol) with 4-methoxybenzylamine (23 mg, 0.17 mmol) to afford BT2040 as a white powder (16 mg, 31%). $^1$H NMR (DMSO-d$_6$, 400 MHz) δ 12.14 (s, 1H), 9.44 (s, 1H), 7.64 (s, 1H), 7.30 (d, J=8.3 Hz, 2H), 7.27-7.16 (m, 2H), 6.82 (d, J=8.3 Hz, 2H), 5.81 (s, 2H), 3.80 (s, 3H), 3.70 (s, 3H); (+)-LRESIMS m/z (rel. int.) 328 (100) [M+H]$^+$; (+)-HRESIMS calcd. for $C_{17}H_{18}N_3O_2S$ [M+H]$^+$ 328.1114, found 328.1116; v$_{max}$ 3267, 1617, 1589, 1542, 1507, 1440, 1276, 1241, 1176, 1033, 967, 812, 724, 613 cm$^{-1}$.

Synthesis Example 25—BT2041

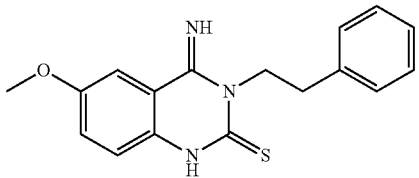 [SMILES: COc1ccc2[nH]c(=S)n(CCc3ccccc3)c(=N)c2c1]

Prepared according to General Procedure B, from reaction of 2-isothiocyanato-5-methoxybenzonitrile (33 mg, 0.16 mmol) with 2-phenylethan-1-amine (20 mg, 0.17 mmol) to afford BT2041 as a white powder (15 mg, 30%). $^1$H NMR (DMSO-d$_6$, 400 MHz) δ 12.10 (s, 1H), 9.47 (s, 1H), 7.68 (s, 1H), 7.36-7.31 (m, 4H), 7.27-7.16 (m, 3H), 4.77 (app. t, J=8.1 Hz, 2H), 3.82 (s, 3H), 3.01 (app. t, J=8.2 Hz, 2H); v$_{max}$ 3279, 1628, 1583, 1538, 1496, 1438, 1354, 1250, 1238, 1163, 1143, 1033, 991, 820, 750 cm$^{-1}$.

Synthesis Example 26—BT2042

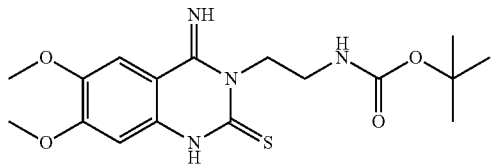 [SMILES: COc1cc2[nH]c(=S)n(CCNC(=O)OC(C)(C)C)c(=N)c2cc1OC]

Prepared according to General Procedure B, from reaction of 2-isothiocyanato-4,5-dimethoxybenzonitrile (30 mg, 0.14 mmol) with tert-butyl (2-aminoethyl)carbamate (23 mg, 0.14 mmol) to afford BT2042 as a white powder (8 mg, 16%). $^1$H NMR (DMSO-d$_6$, 400 MHz) δ 11.89 (s, 1H), 9.05 (s, 1H), 7.59 (s, 1H), 6.82 (s, 1H), 4.75-4.66 (m, 2H), 3.82 (s, 3H), 3.78 (s, 3H), 3.35-3.29 (m, 2H), 1.34 (s, 9H); (+)-LRESIMS m/z (rel. int.) 381 (100) [M+H]$^+$; (+)-HRESIMS calcd. for $C_{17}H_{25}N_4O_4S$ [M+H]$^+$ 381.1591, found 381.1599; v$_{max}$ 3381, 3302, 1688, 1635, 1600, 1506, 1460, 1438, 1339, 1279, 1238, 1203, 1164, 1127, 1088, 824, 759, 629 cm$^{-1}$.

Synthesis Example 27—BT2043

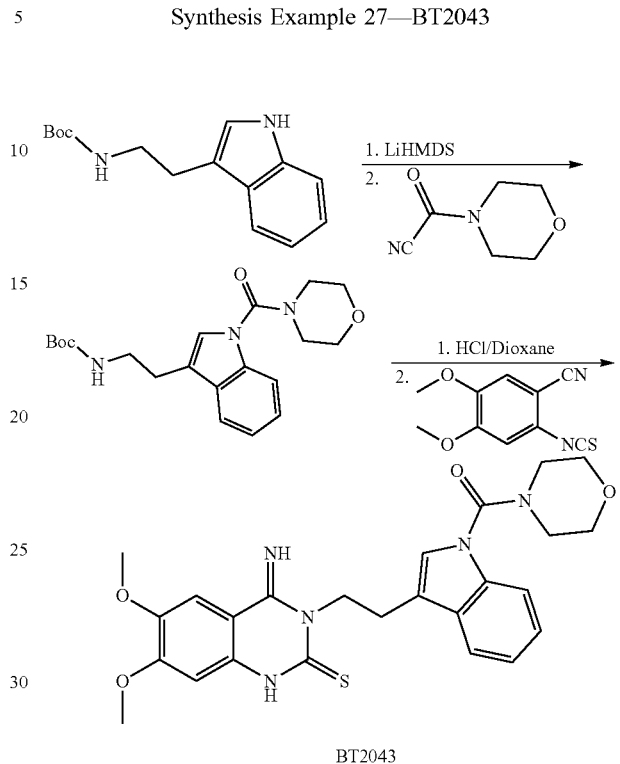

BT2043 t-Butyl (2-(1-(morpholine-4-carbonyl)-1H-indol-3-yl)ethyl)carbamate: A magnetically stirred solution of Boc-tryptamine (179 mg, 0.69 mmol) in THF (5 mL) at 0° C. was treated with a solution of lithium bis(trimethylsilyl)amide (760 μL, 0.76 mmol, 1M in THF) dropwise. The reaction was stirred for 0.5 h and was then treated in one portion with morpholine-4-carbamoyl cyanide see bottom of document (96 mg, 0.69 mmol) and stirred for 1 h. The reaction was poured onto ice cold sodium hydrogen carbonate (20 mL, half saturated) and the mixture extracted with EtOAc (3×15 mL). The combined organic layers were washed with brine, dried (Na$_2$SO$_4$) and concentrated in vacuo to afford a residue that was subjected to flash column chromatography [silica, 1:3 v/v EtOAc/pet. spirit elution] to give, after concentration of the appropriate fractions the morpholine-indoleamide (196 mg, 72%) as a white powder. $^1$H NMR (CDCl$_3$, 400 MHz) δ 7.69 (d, J=8.2 Hz, 1H), 7.57 (d, J=7.8 Hz, 1H), 7.34-7.29 (m, 1H), 7.22 (t, J=7.5 Hz, 1H), 7.15 (s, 1H), 4.62 (s, 1H), 3.84-3.74 (m, 4H), 3.67-3.53 (m, 4H), 3.50-3.43 (m, 2H), 2.92 (app. t, J=6.9 Hz, 2H), 1.44 (s, 9H); $^{13}$C NMR (CDCl$_3$, 100 MHz) δ 155.9, 154.3, 135.7, 129.5, 124.0, 123.5, 121.9, 119.2, 117.0, 113.5, 79.3, 66.7 (2C), 47.1 (2C), 40.3, 28.4, 25.7; (+)-LRESIMS m/z (rel. int.) 396 (100) [M+Na]$^+$; (+)-HRESIMS calcd. for $C_{20}H_{27}N_3O_4Na$ [M+Na]$^+$ 396.1894, found 396.1907; v$_{max}$ 3352, 2971, 2927, 1703, 1674, 1517, 1452, 1413, 1365, 1270, 1241, 1166, 1114, 993, 746 cm$^{-1}$. A sample of the above compound (186 mg) was treated with a solution of hydrogen chloride (2 mL, 4M in dioxane) and magnetically stirred for 1 h. The solvent was removed with a gentle stream of nitrogen and the remaining gum was triturated with ether (3×10 mL) then placed under high vacuum for 1 h to afford the amine hydrochloride as a cream coloured gum and a portion of which used directly without further purification. A mixture of triethylamine (44 μL, 0.32 mmol), the amine hydrochloride formed directly above (49 mg, 0.16 mmol, crude) and DCM (1.5 mL) was added to a magnetically stirred solution of 2-isothiocyanato-4,5-dimethoxybenzonitrile (35 mg, 0.16 mmol) in a mixture of DCM and pet. spirit (1.5 mL:1.5 mL). The mixture was stirred for 0.5 h and then pet. spirit (5 mL) was added. The solid was allowed to settle and the solvent was decanted and then ethanol (5 mL) was added and the mixture heated at 70° C. for 2 h. The mixture was cooled to rt and the solid was collected by vacuum filtration, washed with ethanol (5 mL) and dried at the pump (1 mmHg) to afford BT2043 as a cream powder (32 mg, 41%). $^1$H NMR (DMSO-$d_6$) δ 11.78 (s br, 1H), 9.60 (s br, 1H), 7.99 (d, J=7.7 Hz, 1H), 7.71 (s, 1H), 7.66 (d, J=8.2 Hz, 1H), 7.44 (s, 1H), 7.32-7.24 (m, 1H), 7.24-7.16 (m, 1H), 6.88 (s, 1H), 4.95-4.85 (m, 2H), 3.85 (s, 3H), 3.82 (s, 3H), 3.71-3.62 (m, 4H), 3.57-3.48 (m, 4H), 3.15 (app. t, J=8.1 Hz, 2H); $^{13}$C NMR (DMSO-$d_6$, 100 MHz) three signals obstructed, overlapping or not resolved δ 172.8, 153.9 (br), 153.3, 153.2, 146.7, 135.3, 129.2, 124.3, 123.5, 121.3, 119.7, 115.6, 107.1, 106.3 (br), 98.4, 65.9 (2C), 56.3, 55.8, 47.1, 46.4 (2C), 21.2; (+)-LRESIMS m/z (rel. int.) 494 (100) [M+H]$^+$; (+)-HRESIMS calcd. for $C_{25}H_{28}N_5O_4S$ [M+H]+ 494.1857, found 494.1862; $v_{max}$ 1682, 1630, 1575, 1548, 1517, 1452, 1398, 1281, 1256, 1234, 1120, 1008, 823, 737 cm$^{-1}$.

Synthesis Example 28—BT2045

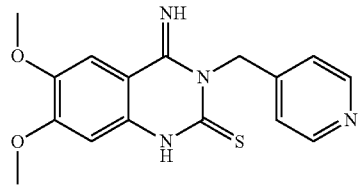 [SMILES: COc1cc2[nH]c(=S)n(Cc3ccncc3)c(=N)c2cc1OC]

Prepared according to General Procedure B, from reaction of 2-isothiocyanato-4,5-dimethoxybenzonitrile (50 mg, 0.23 mmol) with pyridin-4-ylmethanamine (24.5 mg, 0.23 mmol) to afford BT2045 as a white powder (60 mg, 80%). $^1$H NMR (DMSO-$d_6$, 400 MHz) δ 12.15 (s br, 1H), 9.09 (s, 1H), 8.44 (d, J=5.8 Hz, 2H), 7.60 (s, 1H), 7.20 (d, J=5.8 Hz, 2H), 6.89 (s, 1H), 5.86 (s br, 2H), 3.81 (m, 6H); $^{13}$C NMR (DMSO-$d_6$, 100 MHz) one signal obstructed, overlapping or not resolved δ 173.8, 153.3, 153.1 (br), 149.3 (2C), 146.6, 130.8 (br), 121.7 (2C), 107.4, 107.0, 98.6, 56.2, 55.7, 49.2; (+)-LRESIMS m/z (rel. int.) 329 (100) [M+H]$^+$; (+)-HRESIMS calcd. for $C_{16}H_{17}N_4O_2S$ [M+H]$^+$329.1067, found 329.1081; $v_{max}$ 1634, 1552, 1514, 1550, 1279, 1240, 998, 936, 847, 820, 763, 643 cm$^{-1}$.

Synthesis Example 29—BT2046

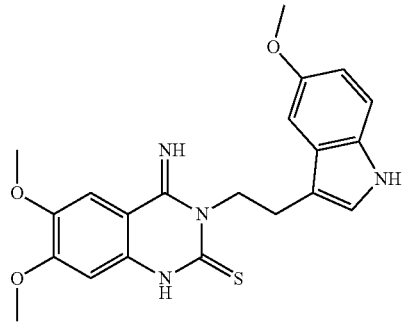 [SMILES: COc1ccc2[nH]cc(CCn3c(=S)[nH]c4cc(OC)c(OC)cc4c3=N)c2c1]

Prepared according to General Procedure B, from reaction of 2-isothiocyanato-4,5-dimethoxybenzonitrile (50 mg, 0.23 mmol) with 5-methoxytryptamine (43 mg, 0.23 mmol) to afford BT2046 as a white powder (51 mg, 80%). $^1$H NMR (DMSO-$d_6$, 400 MHz) δ 11.93 (s, 1H), 10.65 (s, 1H), 9.18 (s, 1H), 7.64 (s, 1H), 7.55 (s, 1H), 7.23 (d, J=8.7 Hz, 1H), 7.14 (s, 1H), 6.87 (s, 1H), 6.72 (dd, J=8.7, 1.9 Hz, 1H), 4.88-4.78 (m, 2H), 3.85 (s, 3H), 3.80 (s, 3H), 3.79 (s, 3H), 3.15-3.05 (m, 2H); $^{13}$C NMR (DMSO-$d_6$, 100 MHz) two signals obstructed, overlapping or not resolved δ 173.2, 153.2 (br), 152.9, 146.5, 131.4, 130.8 (br), 127.8, 123.4, 111.9, 111.2, 111.1, 107.3 (br), 101.1, 98.3 (br), 56.2, 55.7, 55.3, 47.4, 21.9; (+)-LRESIMS m/z (rel. int.) 411 (100) [M+H]$^+$; 433 (13) [M+Na]$^+$; (+)-HRESIMS calcd. for $C_{21}H_{23}N_4O_3S$ [M+H]$^+$ 411.1485, found 411.1489; $v_{max}$ 3394, 3326, 1630, 1545, 1514, 1439, 1347, 1234, 1211, 1125, 1006, 792, 772 cm$^{-1}$.

Synthesis Example 30—BT2049

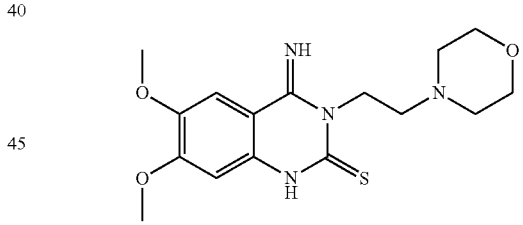

Prepared according to General Procedure B, from reaction of 2-isothiocyanato-4,5-dimethoxybenzonitrile (50 mg, 0.23 mmol) with 2-morpholinoethan-1-amine (31 mg, 0.24 mmol) to afford a residue that was subjected to flash column chromatography [silica, 1:20 v/v MeOH/DCM elution] to give, after concentration of the appropriate fractions BT2049 as a white powder (38 mg, 48%). $^1$H NMR (DMSO-$d_6$, 400 MHz) δ 11.90 (s br, 1H), 9.04 (s, 1H), 7.57 (s, 1H), 6.82 (s, 1H), 4.77-4.68 (m, 2H), 3.81 (s, 3H), 3.78 (s, 3H), 3.57 (app. t, J=4.6 Hz, 4H), 2.63 (t, J=7.4 Hz, 2H), 2.54-2.46 (m, 4H); $^{13}$C NMR (DMSO-$d_6$, 100 MHz) two signals obstructed, overlapping or not resolved δ 173.3 (br), 153.1 (br), 146.4, 130.6 (br), 107.3 (br), 98.1 (br), 66.2 (2C), 56.1, 55.7, 53.8 (br), 53.6 (2C), 43.9 (br); (+)-LRESIMS m/z (rel. int.) 351 (100) [M+H]$^+$; (+)-HRESIMS calcd. for $C_{16}H_{23}N_4O_3S$ [M+H]$^+$ 351.1485, found 351.1492; $v_{max}$ 3318, 1619, 1592, 1532, 1510, 1435, 1344, 1275, 1230, 1113, 1068, 1005, 868, 848, 776 cm$^{-1}$.

Synthesis Example 31—BT2050

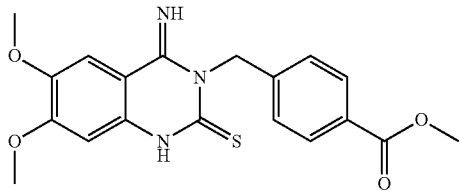 [SMILES: COC(=O)c1ccc(Cn2c(=S)[nH]c3cc(OC)c(OC)cc3c2=N)cc1]

Prepared according to General Procedure B, from reaction of 2-isothiocyanato-4,5-dimethoxybenzonitrile (50 mg, 0.23 mmol) with methyl 4-(aminomethyl)benzoate hydrochloride (48 mg, 0.24 mmol) and triethylamine (33 µL, 0.24 mmol) to afford BT2050 as a white powder (52 mg, 59%). $^1$H NMR (DMSO-$d_6$, 400 MHz) δ 12.11 (s br, 1H), 9.09 (s, 1H), 7.88 (d, J=8.3 Hz, 2H), 7.59 (s, 1H), 7.37 (d, J=8.3 Hz, 2H), 6.88 (s, 1H), 5.92 (s br, 2H), 3.83 (s, 3H), 3.81 (m, 6H); (+)-LRESIMS m/z (rel. int.) 386 (100) [M+H]$^+$; (+)-HRESIMS calcd. for $C_{19}H_{20}N_3O_4S$ [M+H]$^+$ 386.1169, found 386.1175; $v_{max}$ 3326, 1706, 1634, 1594, 1551, 1516, 1437, 1274, 1240, 1194, 1106, 1002, 937, 820, 757 cm$^{-1}$.

Synthesis Example 32—BT2055

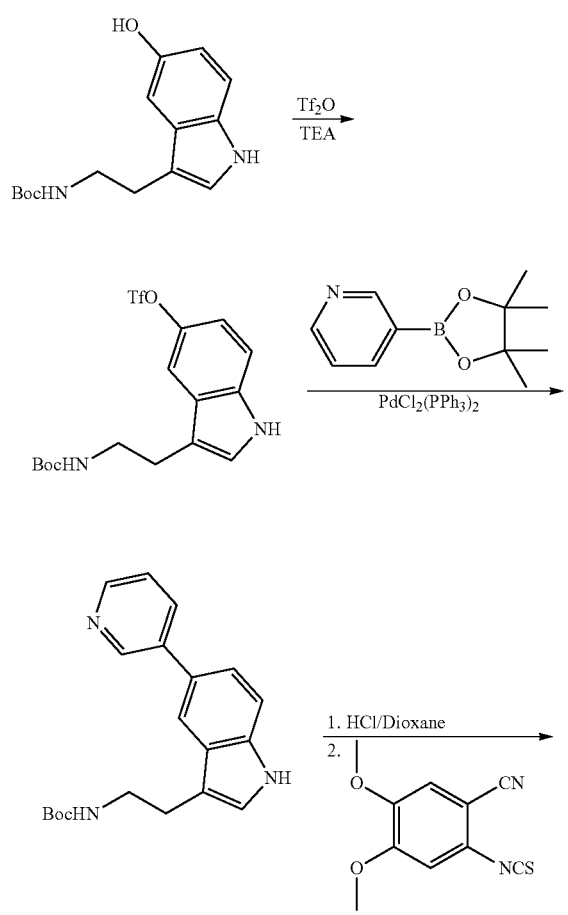

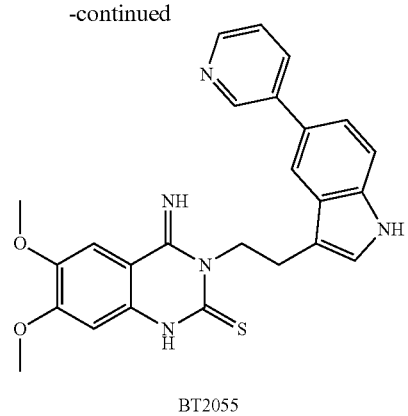

BT2055

A magnetically stirred solution of tert-butyl (2-(5-hydroxy-1H-indol-3-yl)ethyl)carbamate (600 mg, 2.20 mmol) in DCM (12 mL) at −78° C. was treated sequentially with triethylamine (TEA) (370 µL, 2.64 mmol) and trifluoromethanesulfonic anhydride (425 µL, 2.53 mmol). The reaction was stirred for 6 h and then quenched with half saturated aqueous solution of sodium bicarbonate (10 mL). The mixture was extracted with DCM (3×30 mL) and the combined organic layers dried ($Na_2SO_4$) and concentrated in vacuo to afford the desired triflate as a thick colourless oil (550 mg, 61%) which was used directly in the next step without further purification. $^1$H NMR (CDCl$_3$, 400 MHz) δ 8.40 (s, 1H), 7.47 (d, J=2.4 Hz, 1H), 7.37 (d, J=8.8 Hz, 1H), 7.13 (s, 1H), 7.09 (dd, J=8.8, 2.4 Hz, 1H), 4.63 (s, 1H), 3.52-3.40 (m, 2H), 2.92 (t, J=6.9 Hz, 2H), 1.44 (s, 9H); $^{13}$C NMR (CDCl$_3$, 100 MHz) δ 156.0, 143.5, 135.1, 127.8, 124.5, 120.5, 118.86 (q, JC-F=320.8 Hz), 117.3, 115.3, 114.2, 112.2, 111.3, 79.4, 40.9, 28.4 (3C), 25.7, 21.1; (+)-LRESIMS m/z (rel. int.) 431 (100) [M+Na]$^+$; (+)-HRESIMS calcd. for $C_{16}H_{19}N_2O_5F_3NaS$ [M+Na]$^+$ 431.0859, found 431.0866; $v_{max}$ 3425, 3258, 1691, 1520, 1413, 1244, 1204, 1139, 931, 887, 799 cm$^{-1}$. A portion of the above compound (75 mg, 0.18 mmol), was subjected to a palladium catalysed Suzuki-Miyaura reaction and reacted with 3-pyridineboronic acid pinacol ester (56 mg, 0.28 mmol) according to General Procedure D to afford a residue that was subjected to flash column chromatography [silica, 1:1 v/v EtOAc/Pet. spirit elution] to give, after concentration of the appropriate fractions tert-butyl (2-(5-(pyridin-3-yl)-1H-indol-3-yl)ethyl)carbamate (55 mg, 89%) as a beige powder. $^1$H NMR (CDCl$_3$, 400 MHz) δ 8.91 (d, J=2.0 Hz, 1H), 8.56 (dd, J=4.8, 1.6 Hz, 1H), 8.27 (s, 1H), 7.94 (dt, J=7.9, 2.0 Hz, 1H), 7.79 (s, 1H), 7.47 (d, J=8.4 Hz, 1H), 7.42 (dd, J=8.4, 1.7 Hz, 1H), 7.36 (ddd, J=7.9, 4.8, 0.9 Hz, 1H), 7.11 (d, J=1.4 Hz, 1H), 4.66 (s, 1H), 3.57-3.43 (m, 2H), 3.00 (t, J=6.7 Hz, 2H), 1.41 (s, 9H). A portion of the above material (48 mg, 0.14 mmol) was treated with a solution of hydrogen chloride (3 mL, 4M in dioxane) and magnetically stirred at 0° C. for 2 then 3 h at rt. Ether (10 mL) was added and the solvent decanted to afford a gum which was triturated with ether (5 mL). The residue was placed under high vacuum for 3 h to afford 2-(5-(pyridin-3-yl)-1H-indol-3-yl) ethan-1-amine dihydrochloride (37 mg, 84%) as a cream coloured gum and used directly without further purification. A mixture of triethylamine (133 µL, 0.81 mmol), aminedihydrochloride (37 mg, 0.14 mmol, crude from above), DCM (2 mL) and ethanol (1 mL) was added to a magnetically stirred solution of 2-isothiocyanato-4,5-dimethoxybenzonitrile (30 mg, 0.14 mmol) in a mixture of DCM and pet.

spirit (1 mL:1 mL). The mixture was stirred for 1 h and then pet. spirit (5 mL) was added. The solid was collected by filtration then dissolved in ethanol (2.5 mL) was added and the mixture heated at 70° C. for 2 h. The mixture was cooled to rt and the solid was collected by vacuum filtration, washed with ethanol (5 mL) and dried at the pump (1 mmHg) to afford BT2055 as a cream powder (22 mg, 36%). $^1$H NMR (DMSO-$d_6$, 400 MHz) δ 12.06 (s br, 1H), 11.02 (s, 1H), 9.44 (s br, 1H), 8.90 (s, 1H), 8.51 (d, J=4.0 Hz, 1H), 8.22 (s, 1H), 8.03 (d, J=7.9 Hz, 1H), 7.70 (s, 1H), 7.50-7.40 (m, 2H), 7.30 (s, 1H), 6.87 (s, 1H), 4.98-4.86 (m, 2H), 3.85 (s, 3H), 3.82 (s, 3H), 3.20 (t, J=8.1 Hz, 2H); (+)-LRESIMS m/z (rel. int.) 458 (100) [M+H]$^+$; 480 (17) [M+Na]$^+$; (+)-HRESIMS calcd. for $C_{25}H_{24}N_5O_2S$ [M+H]$^+$ 458.1645, found 458.1650. $v_{max}$ 1627, 1585, 1563, 1515, 1442, 1400, 1280, 1251, 1212, 1129, 1005, 788, 771, 634 cm$^{-1}$.

Synthesis Example 33—BT2058

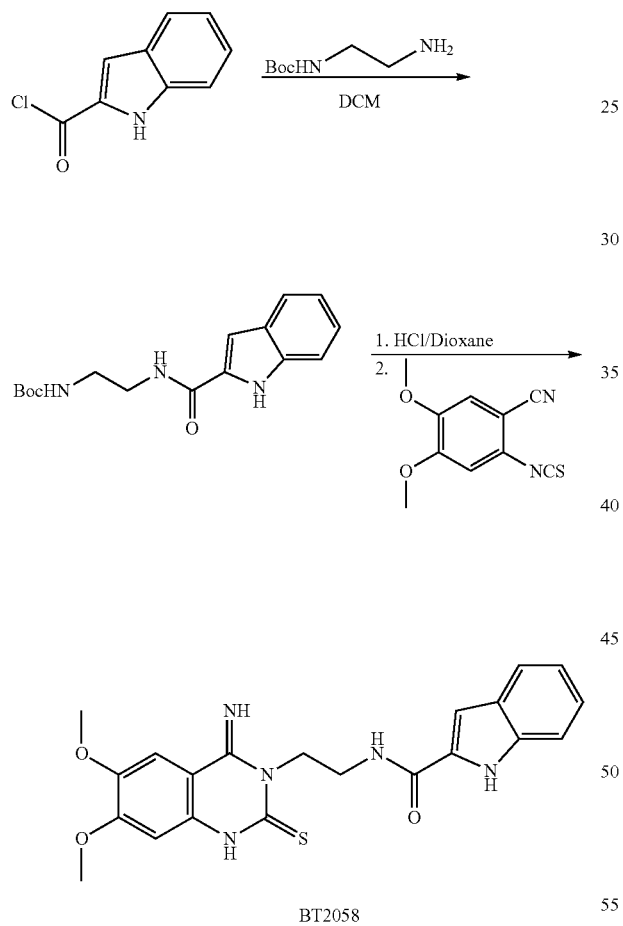

BT2058

A magnetically stirred solution of 1H-indole-2-carbonyl chloride, prepared according to Kumarb et. al. (*Eur. J. Chem.* 2012, 3(2), 214), (350 mg, 1.95 mmol) in DCM (5 mL) at −10° C. was treated dropwise with a solution of pyridine (1 mL), DIPEA (272 μL, 1.95 mmol) and tert-butyl (2-aminoethyl)carbamate (312 mg, 1.95 mmol) in DCM (20 mL). The mixture was allowed to warm to rt over 18 h and then the mixture was diluted with DCM (30 mL) and washed with aqueous HCl (2×10 mL, 0.2M) followed by a half saturated aqueous solution of sodium bicarbonate (2×15 mL) then brine (10 mL). The organic layer was dried ($Na_2SO_4$) and concentrated in vacuo to afford a solid that was subjected to flash column chromatography [silica, 1:20 v/v MeOH/DCM elution] to give, after concentration of the appropriate fractions, tert-butyl (2-(1H-indole-2-carboxamido)ethyl)carbamate (296 mg, 50%) as a tan coloured solid. $^1$H NMR (CDCl$_3$, 400 MHz) one NH not observed δ 9.19 (s, 1H), 7.65 (d, J=8.0 Hz, 1H), 7.43 (d, J=8.2 Hz, 1H), 7.29 (d, J=7.2 Hz, 1H), 7.14 (t, J=7.5 Hz, 1H), 6.90 (s, 1H), 5.02-4.93 (m, 1H), 3.63-3.54 (m, 2H), 3.50-3.39 (m, 2H), 1.45 (s, 9H); (+) LRESIMS m/z (rel. int.) 326 (100) [M+Na]$^+$; (+)-HRESIMS calcd. for $C_{16}H_{21}N_3NaO_3$ [M+Na]$^+$ 326.1475, found 326.1481; $v_{max}$ 3308, 3226, 1694, 1609, 1541, 1422, 1280, 1254, 1152, 1018, 825, 745 cm$^{-1}$.

tert-Butyl (2-(1H-indole-2-carboxamido)ethyl)carbamate (100 mg, 0.33 mmol) was treated with a solution of hydrogen chloride (2 mL, 4M in dioxane) and magnetically stirred for 1 h at 4° C. then a further 0.5 h at rt. Ether (5 mL) was added to precipitate the product and the remaining gum was triturated with ether (3×5 mL) then placed under high vacuum for 1 h to afford N-(2-aminoethyl)-1H-indole-2-carboxamide hydrochloride as a cream coloured gum and used directly without further purification. A mixture of triethylamine (66 μL, 0.47 mmol), N-(2-aminoethyl)-1H-indole-2-carboxamide hydrochloride (57 mg, 0.24 mmol, crude from above) and DCM (2 mL) was added to a magnetically stirred solution of 2-isothiocyanato-4,5-dimethoxybenzonitrile (50 mg, 0.27 mmol) in a mixture of DCM and pet. spirit (1 mL:1 mL). The mixture was stirred for 1 h and then pet. spirit (5 mL) was added. The solid was collected by vacuum filtration then suspended in ethanol (5 mL) and the mixture heated at 70° C. for 1 h. The mixture was cooled to rt and the solid was collected by vacuum filtration, washed with ethanol (5 mL) and dried at the pump (1 mmHg) to afford BT2058 as a cream powder (32 mg, 33%). $^1$H NMR (DMSO-$d_6$, 400 MHz) δ 11.93 (s br, 1H), 11.56 (s, 1H), 9.78 (s br, 1H), 8.80 (s, 1H), 7.73 (s, 1H), 7.60 (d, J=7.9 Hz, 1H), 7.42 (d, J=8.2 Hz, 1H), 7.17 (t, J=7.6 Hz, 1H), 7.07 (s, 1H), 7.03 (t, J=7.5 Hz, 1H), 6.89 (s, 1H), 5.01-4.73 (m, 2H), 3.84 (s, 6H), 3.76-3.65 (m, 2H); (+)-LRESIMS m/z (rel. int.) 424 (100) [M+H]$^+$; (+)-HRESIMS calcd. for $C_{21}H_{22}N_5O_3S$ [M+H]$^+$ 424.1438, found 424.1442. $v_{max}$ 3243, 1623, 1557, 1545, 1512, 1282, 1189, 1020, 766, 738 cm$^{-1}$.

Synthesis Example 34—BT2061

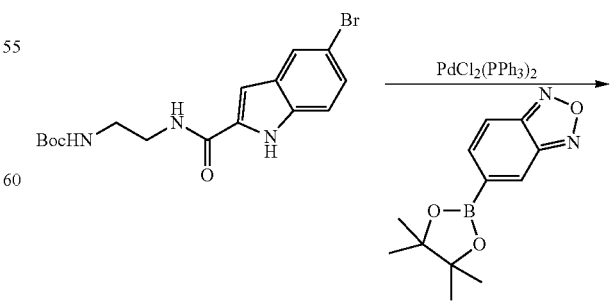

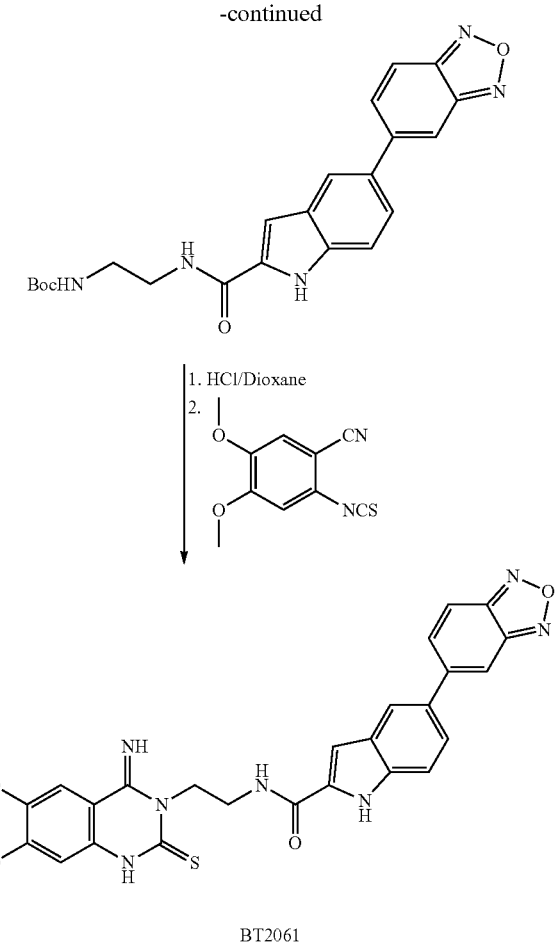

tert-Butyl (2-(5-(benzo[c][1,2,5]oxadiazol-5-yl)-1H-indole-2-carboxamido)ethyl)carbamate was prepared and purified according to General Procedure D from reaction of benzo[c][1,2,5]oxadiazole-5-boronic acid pinacol ester (96 mg, 0.39 mmol) and tert-butyl (2-(5-bromo-1H-indole-2-carboxamido)ethyl)carbamate (100 mg, 0.26 mmol) to afford after flash chromatography, tert-butyl (2-(5-(benzo[c][1,2,5]oxadiazol-5-yl)-1H-indole-2-carboxamido)ethyl)carbamate (94 mg, 85%) as a white powder. $^1$H NMR (DMSO-d$_6$, 400 MHz) δ 11.80 (s, 1H), 8.60 (t, J=5.3 Hz, 1H), 8.25 (t, J=1.3 Hz, 1H), 8.20-8.15 (m, 1H), 8.12-8.11 (m, 2H), 7.71 (dd, J=8.6, 1.9 Hz, 1H), 7.56 (d, J=8.6 Hz, 1H), 7.22 (s, 1H), 6.94 (t, J=5.8 Hz, 1H), 3.37-3.39 (m, 2H), 3.18-3.10 (m, 2H), 1.07 (s, 9H); (+)-LRESIMS m/z (rel. int.) 444 (100) [M+Na]$^+$; (+)-HRESIMS calcd. for C$_{22}$H$_{23}$N$_5$NaO$_4$ [M+Na]$^+$ 444.1642, found 444.1642; v$_{max}$ 3360, 3295, 2979, 1683, 1615, 1535, 1519, 1251, 1166, 1152, 1004, 795, 773 cm$^{-1}$. A portion of the above material (98 mg, 0.23 mmol) was treated with a solution of hydrogen chloride (3 mL, 4M in dioxane) and magnetically stirred at rt for 1 h. Ether (5 mL) was added and the solvent decanted to afford a gum which was triturated with ether (5 mL). The residue was placed under high vacuum for 3 h to afford the amine hydrochloride (75 mg, 91%) as a cream solid and used directly without further purification. $^1$H NMR (DMSO-d$_6$, 400 MHz) δ 11.89 (s, 1H), 8.94 (t, J=5.6 Hz, 1H), 8.28-8.23 (m, 1H), 8.20 (d, J=1.8 Hz, 1H), 8.14-8.08 (m, 2H), 7.73 (dd, J=8.7, 1.8 Hz, 1H), 7.57 (d, J=8.6 Hz, 1H), 7.35-7.33 (m, 1H), 4.76 (s br, 3H), 3.62-3.53 (m, 2H), 3.09-2.96 (m, 2H); (+)-LRESIMS m/z (rel. int.) 322 (100) [M+H]$^+$; (+)-HRESIMS calcd. for C$_{17}$H$_{16}$N$_5$O$_2$ [M+H]$^+$ 322.1299, found 322.1304. A portion of the crude amine hydrochloride formed above (50 mg, 0.14 mmol) was then reacted with triethylamine (58 μL, 0.42 mmol) and 2-isothiocyanato-4,5-dimethoxybenzonitrile (31 mg, 0.14 mmol) according to General Procedure C to afford BT2061 as a white powder (35 mg, 47%). $^1$H NMR (DMSO-d$_6$, 400 MHz) 1H not observed or obscured δ 11.76 (s br, 2H), 9.14 (s, 1H), 8.70 (s, 1H), 8.24 (s, 1H), 8.17-8.08 (m, 2H), 7.71 (d, J=7.9 Hz, 1H), 7.65-7.52 (m, 2H), 7.19 (s, 1H), 6.85 (s, 1H), 4.95-4.85 (m, 2H), 3.82 (s, 3H), 3.79 (s, 3H), 3.77-3.70 (m, 2H); (+)-LRESIMS m/z (rel. int.) 542 (100) [M+H]$^+$; (+)-HRESIMS calcd. for C$_{27}$H$_{24}$N$_7$O$_4$S [M+H]+ 542.1605, found 542.1611. v$_{max}$ 3206, 1622, 1542, 1513, 1439, 1344, 1278, 1234, 1020, 770 cm$^{-1}$.

Synthesis Example 35—BT2063

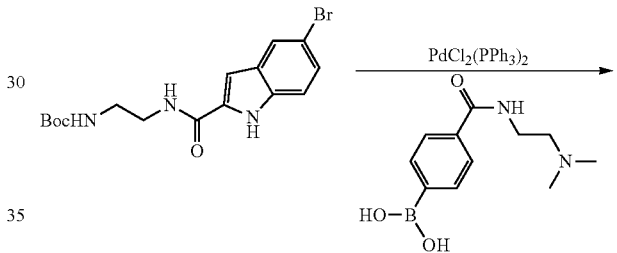

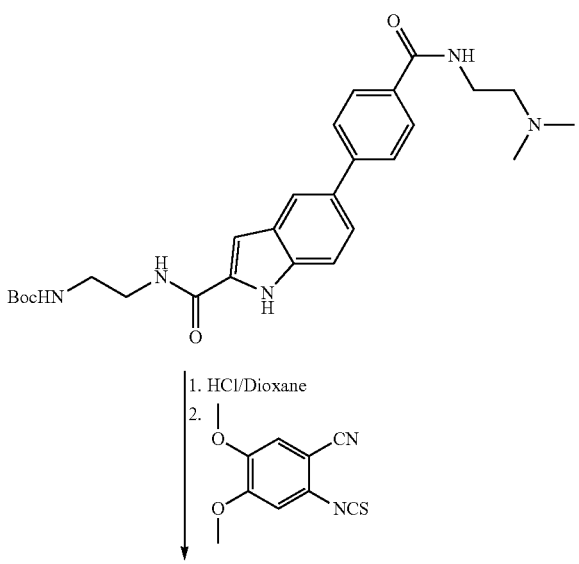

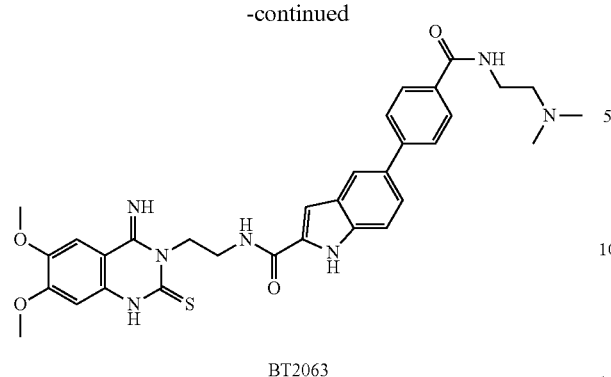

BT2063 tert-Butyl (2-(5-(4-((2-(dimethylamino)ethyl)carbamoyl)phenyl)-1H-indole-2-carboxamido)ethyl)carbamate was prepared according to General Procedure D from reaction of 4-(2-(dimethylamino)ethylcarbamoyl)phenylboronic acid (124 mg, 0.39 mmol) and tert-butyl (2-(5-bromo-1H-indole-2-carboxamido)ethyl)carbamate (100 mg, 0.26 mmol) to afford, after flash column chromatography [silica, 1:10-1:5 v/v ammoniacal MeOH/DCM elution] and concentration of the appropriate fractions, the desired product (90 mg, 70%) as a white powder. $^1$H NMR (DMSO-d$_6$, 400 MHz) δ 11.68 (s, 1H), 8.55 (t, J=5.2 Hz, 1H), 8.40 (t, J=5.6 Hz, 1H), 7.98 (s, 1H), 7.91 (d, J=8.4 Hz, 2H), 7.78 (d, J=8.4 Hz, 2H), 7.56 (dd, J=8.6, 1.6 Hz, 1H), 7.51 (d, J=8.6 Hz, 1H), 7.17 (s, 1H), 6.93 (t, J=5.4 Hz, 1H), 3.41-3.29 (m, 4H), 3.18-3.10 (m, 2H), 2.42 (t, J=6.9 Hz, 2H), 2.19 (s, 6H), 1.38 (s, 9H); (+)-LRESIMS m/z (rel. int.) 494 (100) [M+H]$^+$; (+)-HRESIMS calcd. for C$_{27}$H$_{36}$N$_5$O$_4$ [M+H]$^+$ 494.2762, found 494.2766; ν$_{max}$ 3381, 3229, 1693, 1635, 1607, 1552, 1272, 1166, 764 cm$^{-1}$. The above material (90 mg, 0.18 mmol) was deprotected according to General Procedure E to afford N-(2-aminoethyl)-5-(4-((2-(dimethylamino)ethyl)carbamoyl)phenyl)-1H-indole-2-carboxamide dihydrochloride (76 mg, 91%) as a cream solid and used directly without further purification. A portion of the crude hydrochloride formed above (76 mg, 0.16 mmol) was then reacted with triethylamine (120 µL, 0.86 mmol) and 2-isothiocyanato-4,5-dimethoxybenzonitrile (36 mg, 0.16 mmol) according to General Procedure C to afford BT2063 as a cream powder (31 mg, 32%). $^1$H NMR (DMSO-d$_6$, 400 MHz) δ 11.86 (s br, 1H), 11.68 (s, 1H), 9.33 (s br, 1H), 8.80 (s br, 1H), 8.74 (t, J=5.0 Hz, 1H), 7.98 (s, 1H), 7.97 (d, J=8.1 Hz, 2H), 7.81 (d, J=8.1 Hz, 2H), 7.66 (s, 1H), 7.58 (dd, J=8.6, 1.3 Hz, 1H), 7.52 (d, J=8.6 Hz, 1H), 7.16 (s, 1H), 6.86 (s, 1H), 4.98-4.81 (m, 2H), 3.83 (s, 3H), 3.81 (s, 3H), 3.73 (app. q, J=6.1 Hz, 2H), 3.61 (app. q, J=6.0 Hz, 2H), 3.18-3.08 (m, 2H), 2.73 (s, 6H); (+)-LRESIMS m/z (rel. int.) 614 (100) [M+H]$^+$; (+)-HRESIMS calcd. for C$_{32}$H$_{36}$N$_7$O$_4$S [M+H]$^+$ 614.2544, found 614.2545; ν$_{max}$ 1678, 1626, 1554, 1504, 1441, 1317, 1279, 1234, 1160, 1072, 813, 769 cm$^{-1}$.

Synthesis Example 36—BT2066

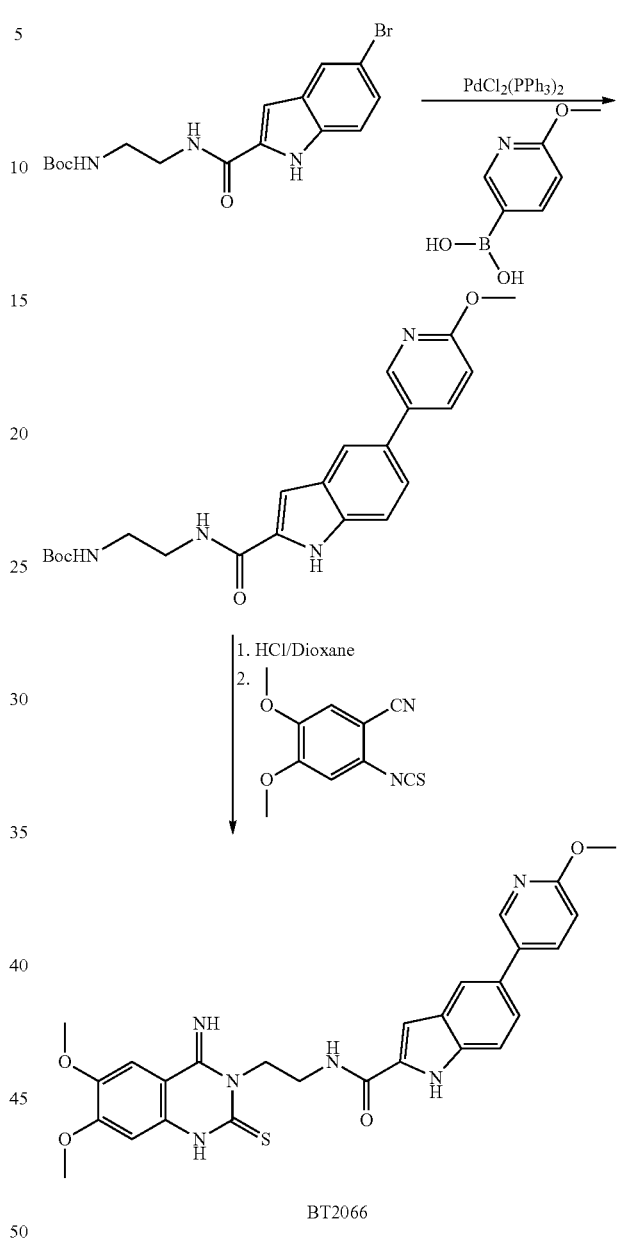

BT2066 tert-Butyl (2-(5-(6-methoxypyridin-3-yl)-1H-indole-2-carboxamido)ethyl)carbamate was prepared and purified according to General Procedure D from reaction of 2-methoxy-5-pyridine boronic acid (60 mg, 0.39 mmol) and tert-butyl (2-(5-bromo-1H-indole-2-carboxamido)ethyl)carbamate (100 mg, 0.26 mmol) to afford the desired compound (75 mg, 70%) as a white powder. $^1$H NMR (DMSO-d$_6$, 400 MHz) δ 11.64 (s, 1H), 8.53 (t, J=5.5 Hz, 1H), 8.47 (s, 1H), 8.06-7.98 (m, 1H), 7.87 (s, 1H), 7.50 (d, J=8.5 Hz, 1H), 7.46 (d, J=8.5 Hz, 1H), 7.15 (s, 1H), 6.97-6.89 (m, 1H), 6.89 (d, J=8.6 Hz, 1H), 3.89 (s, 3H), 3.38-3.27 (m, 2H), 3.13 (app. q, J=6.4 Hz, 2H), 1.38 (s, 9H); $^{13}$C NMR (DMSO-d$_6$, 100 MHz) 2 signals obscured by DMSO-d$_6$ δ 162.4, 161.1, 155.7, 144.4, 137.6, 135.9, 132.5, 130.5, 128.9, 127.7, 122.4, 119.1, 112.9, 110.3, 102.8, 77.7, 53.1, 28.2 (3C); (+)-LRESIMS m/z (rel. int.) 411 (100) [M+H]$^+$; (+)-HRES- IMS calcd. for $C_{22}H_{27}N_4O_4$ [M+H]$^+$ 411.2027, found 411.2029; $v_{max}$ 3314, 3227, 1696, 1613, 1554, 1497, 1367, 1291, 1279, 1151, 1040, 836, 812, 625 cm$^{-1}$. tert-Butyl (2-(5-(6-methoxypyridin-3-yl)-1H-indole-2-carboxamido)ethyl)carbamate (100 mg, 0.41 mmol) was deprotected according to General Procedure E to afford N-(2-aminoethyl)-5-(6-methoxypyridin-3-yl)-1H-indole-2-carboxamide dihydrochloride as a white powder, and used directly without further purification. The crude dihydrochloride formed above (87 mg, 0.27 mmol) in a solution of ethanol (6 mL) was treated with triethylamine (96 µL, 0.68 mmol) and then a solution of 2-isothiocyanato-4,5-dimethoxybenzonitrile (50 mg, 0.27 mmol) in DCM (3 mL) was added. The mixture was stirred at rt for 1 h then concentrated by a gentle stream of nitrogen and suspended in ethanol (5 mL) and refluxed for 4 h. The precipitate formed was collected and washed with ethanol (15 mL) then diethyl ether (10 mL) and dried at the pump to afford BT2066 (33 mg, 27%) as a cream coloured powder. $^1$H NMR (DMSO-d$_6$, 400 MHz) δ 11.94 (s, 1H), 11.61 (s, 1H), 9.14 (s, 1H), 8.65 (s, 1H), 8.50-8.44 (m, 1H), 8.03-7.99 (m, 1H), 7.85 (s, 1H), 7.62 (s, 1H), 7.49 (d, J=8.5 Hz, 1H), 7.46 (d, J=8.0 Hz, 1H), 7.11 (s, 1H), 6.89 (d, J=8.6 Hz, 1H), 6.84 (s, 1H), 4.94-4.84 (s, 2H), 3.89 (s, 3H), 3.82 (s, 3H), 3.79 (s, 3H), 3.79-3.66 (m, 2H); (+)-LRESIMS m/z (rel. int.) 531 (100) [M+H]$^+$; (+)-HRESIMS calcd. for $C_{27}H_{27}N_6O_4S$ [M+H]+ 531.1809, found 542.1816. $v_{max}$ 3209, 1625, 1551, 1513, 1438, 1280, 1238, 1020, 804, 765, 738 cm$^{-1}$.

Synthesis Example 37—BT2068

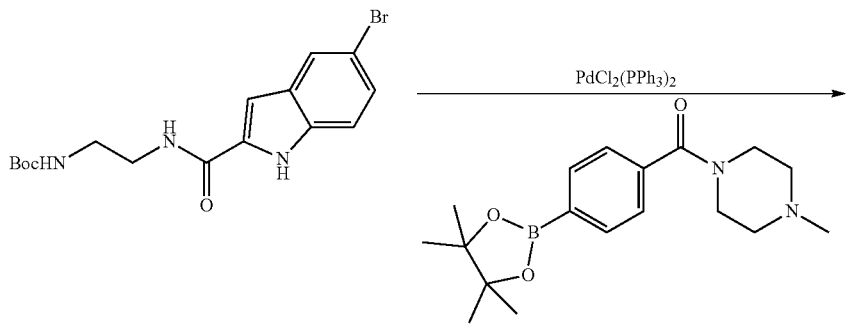

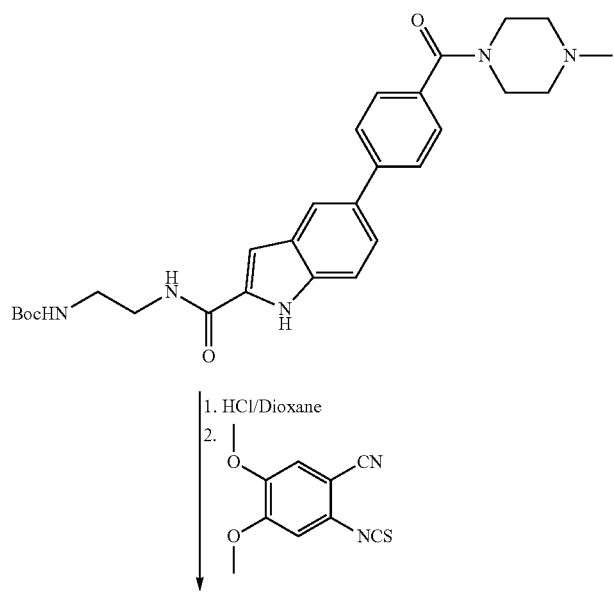

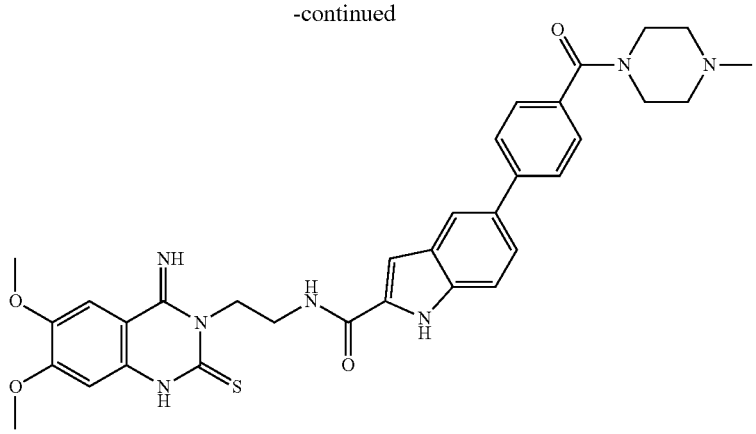

BT2068 tert-Butyl (2-(5-(4-(4-methylpiperazine-1-carbonyl)phenyl)-1H-indole-2-carboxamido)ethyl)carbamate was prepared and purified according to General Procedure D from reaction of [4-(4-methylpiperazine-1-carbonyl)phenyl]boronic acid pinacol ester (130 mg, 0.39 mmol) and tert-butyl (2-(5-bromo-1H-indole-2-carboxamido)ethyl)carbamate (100 mg, 0.26 mmol) to afford the desired compound (72 mg, 54%) as a white powder. $^1$H NMR (DMSO-d$_6$, 400 MHz) δ 11.68 (s, 1H), 8.55 (t, J=5.5 Hz, 1H), 7.94 (s, 1H), 8.05 (d, J=8.0 Hz, 2H), 7.55-7.50 (m, 2H), 7.45 (d, J=8.0 Hz, 2H), 7.17 (s, 1H), 6.93 (t, J=5.5 Hz, 1H), 3.65-3.33 (m, 6H), 3.14 (app. q, J=5.7 Hz, 2H), 2.38-2.28 (m, 4H), 2.20 (s, 3H), 1.38 (s, 9H); $^{13}$C NMR (DMSO-d$_6$, 100 MHz) 2 signals obscured by DMSO-d$_6$ δ 168.9, 161.1, 155.7, 142.5, 136.2, 133.7, 132.6, 131.2, 127.7, 127.6 (2C), 127.6, 126.5 (2C), 122.7, 119.6, 112.8, 102.9, 77.7, 54.6 (br, 2C), 45.6, 28.2 (3C); (+)-LRESIMS m/z (rel. int.) 506 (100) [M+H]$^+$; (+)-HRESIMS calcd. for $C_{28}H_{36}N_5O_4$ [M+H]$^+$ 506.2762, found 506.2759; $v_{max}$ 3257, 1691, 1625, 1605, 1557, 1522, 1423, 1293, 1246, 1170, 1128, 1004, 808, 764 cm$^{-1}$. The Boc protected compound (100 mg, 0.20 mmol) was deprotected according to General Procedure E to afford the corresponding amine dihydrochloride (87 mg, 91%) as a white powder, and used directly without further purification. The crude dihydrochloride formed above (87 mg, 0.18 mmol) was reacted with triethylamine (76 µL, 0.55 mmol) and 2-isothiocyanato-4,5-dimethoxybenzonitrile (40 mg, 0.18 mmol) according to General Procedure C to afford BT2068 (25 mg, 22%) as a white powder. $^1$H NMR (DMSO-d$_6$, 400 MHz) 1H obscured or overlapping δ 11.95 (s br, 1H), 11.66 (s br, 1H), 9.14 (s br, 1H), 8.68 (s br, 1H), 7.93 (s, 1H), 7.74 (d, J=7.6 Hz, 2H), 7.61 (s br, 1H), 7.56-7.49 (m, 2H), 7.45 (d, J=7.6 Hz, 2H), 7.15 (s br, 1H), 4.97-4.84 (m, 2H), 3.82 (s, 3H), 3.79 (s, 3H), 3.78-3.71 (m, 2H), 3.66-3.48 (m, 4H), 2.38-2.27 (s br, 4H), 2.21 (s, 3H); $^{13}$C NMR (DMSO-d$_6$, 100 MHz) complex spectrum due to slow rotation δ 173.8 (br), 168.9, 161.0 (br), 154.1 (br), 153.1 (br), 146.4, 142.5, 136.2, 133.7 (br), 132.9, 131.3, 130.7 (br), 127.7, 127.6 (br), 126.5 (br), 122.7, 119.6, 112.9, 107.4 (br), 102.9 (br), 98.2 (br), 56.2, 55.7, 54.6 (br), 46.1 (br), 45.6, 36.6 (br). (+)-LRESIMS m/z (rel. int.) 626 (100) [M+H]$^+$; (+)-HRESIMS calcd. for $C_{33}H_{36}N_7O_4S$ [M+H]$^+$ 626.2544, found 626.2552; $v_{max}$ 3216, 1624, 1545, 1513, 1436, 1278, 1235, 1188, 1021, 851, 805, 762 cm$^{-1}$.

Synthesis Example 38—BT2070

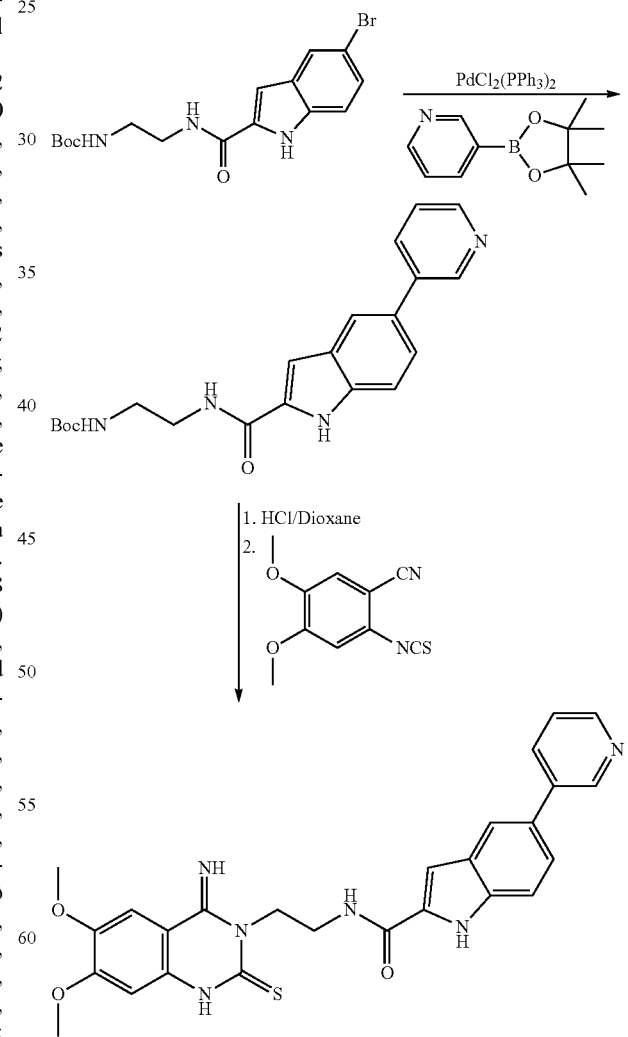

BT2070 tert-Butyl (2-(5-(pyridin-3-yl)-1H-indole-2-carboxamido)ethyl)carbamate was prepared and purified according to General Procedure D from reaction of 3-pyridylboronic acid pinacol ester (80 mg, 0.39 mmol) and tert-butyl (2-(5-bromo-1H-indole-2-carboxamido)ethyl)carbamate (100 mg, 0.26 mmol) to afford after flash chromatography, the desired compound (62 mg, 62%) as a white powder. $^1$H NMR (DMSO-$d_6$, 400 MHz) δ 11.71 (s, 1H), 8.92 (d, J=2.2 Hz, 1H), 8.56 (t, J=5.5 Hz, 1H), 8.51 (dd, J=4.7, 1.4 Hz, 1H), 8.08 (dt, J=8.0, 2.2 Hz, 1H), 7.98 (s, 1H), 7.54 (s, 2H), 7.45 (dd, J=8.0, 4.7 Hz, 1H), 7.18 (d, J=1.4 Hz, 1H), 6.94 (t, J=5.5 Hz, 1H), 3.33 (app. q, J=6.7 Hz, 2H), 3.14 (app. q, J=6.7 Hz, 2H), 1.38 (s, 9H); $^{13}$C NMR (DMSO-$d_6$, 100 MHz) 2 signals obscured by DMSO-$d_6$ δ 161.1, 155.7, 147.7, 147.5, 136.7, 136.2, 133.9, 132.7, 128.9, 127.8, 123.7, 122.6, 119.9, 113.0, 102.9, 77.7, 28.2 (3C); (+)-LRESIMS m/z (rel. int.) 381 (100) [M+H]$^+$; (+)-HRESIMS calcd. for $C_{21}H_{25}N_4O_3$ [M+H]$^+$ 381.1921, found 381.1926; $v_{max}$ 3371, 3222, 2974, 1686, 1634, 1564, 1528, 1330, 1267, 1168, 795 cm$^{-1}$. The Boc protected compound (97 mg, 0.25 mmol) was deprotected according to General Procedure E to afford the corresponding amine dihydrochloride (75 mg, 85%) as a white powder, and used directly without further purification. The crude dihydrochloride formed above (75 mg, 0.21 mmol) was reacted with triethylamine (118 µL, 0.85 mmol) and 2-isothiocyanato-4,5-dimethoxybenzonitrile (47 mg, 0.21 mmol) according to General Procedure C to afford BT2070 (18 mg, 17%) as a white powder. $^1$H NMR (DMSO-$d_6$, 400 MHz) δ 11.96 (s br, 1H), 11.68 (s, 1H), 9.17 (s br, 1H), 8.91 (s, 1H), 8.72 (s br, 1H), 8.52 (d, J=4.0 Hz, 1H), 8.09 (dt, J=7.9, 4.0 Hz, 1H), 7.96 (s, 1H), 7.62 (s, 1H), 7.55-7.53 (m, 2H), 7.46 (dd, J=7.9, 4.7 Hz, 1H), 7.15 (s, 1H), 6.85 (s, 1H), 4.89 (s br, 2H), 3.82 (s, 3H), 3.80 (s, 3H), 3.76-3.69 (m, 2H); (+)-LRESIMS m/z (rel. int.) 501 (100) [M+H]$^+$; (+)-HRESIMS calcd. for $C_{26}H_{25}N_6O_3S$ [M+H]$^+$ 501.1703, found 501.1709. $v_{max}$ 3202, 1623, 1546, 1512, 1437, 1396, 1279, 1233, 1186, 1018, 796, 762 cm$^{-1}$.

Synthesis Example 39—BT2071

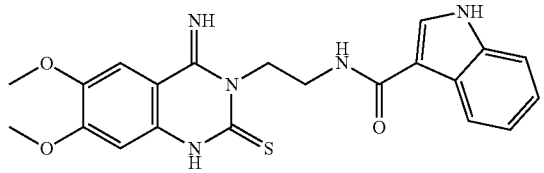 [SMILES: COc1cc2[nH]c(=S)n(CCNC(=O)c3c[nH]c4ccccc34)c(=N)c2cc1OC]

Following a procedure analogous to that used in General Procedure H, 1H-indole-3-carboxylic acid (400 mg, 2.48 mmol) was converted to 1H-indole-3-carbonyl chloride and reacted with tert-butyl (2-aminoethyl)carbamate (397 mg, 2.48 mmol) to afford tert-butyl (2-(1H-indole-3-carboxamido)ethyl)carbamate (352 mg, 47%) as a white solid. $^1$H NMR (CD$_3$OD, 400 MHz) NH protons not observed δ 8.13-8.05 (m, 1H), 7.85 (s, 1H), 7.45-7.38 (m, 1H), 7.21-7.11 (m, 2H), 3.47 (app. t, J=6.1 Hz, 2H), 3.29 (app. t, J=6.1 Hz, 2H), 1.41 (s, 9H); $^{13}$C NMR (CD$_3$OD, 100 MHz) δ 168.8, 158.9, 138.1, 129.2, 126.9, 123.4, 121.9, 121.7, 112.8, 111.8, 80.2, 41.3, 40.8, 28.7; (+)-LRESIMS m/z (rel. int.) 326 (100) [M+Na]$^+$; (+)-HRESIMS calcd. for $C_{16}H_{21}N_3O_3Na$ [M+Na]$^+$ 326.1475, found 326.1481; $v_{max}$ 3357, 3222, 1684, 1611, 1547, 1495, 1441, 1321, 1234, 1210, 1151, 1105, 777, 739 cm$^{-1}$. A portion of the Boc protected compound (136 mg, 0.45 mmol) was deprotected according to General Procedure E to afford (100 mg, 93%) as a grey gum, and used directly without further purification. The crude hydrochloride formed above (65 mg, 0.27 mmol) was reacted with triethylamine (118 µL, 0.85 mmol) and 2-isothiocyanato-4,5-dimethoxybenzonitrile (47 mg, 0.21 mmol) according to General Procedure C to afford BT2071 (41 mg, 36%) as a pale yellow solid. 1H NMR (DMSO-$d_6$, 400 MHz) 1H obscured or overlapping δ 11.97 (s br, 1H), 11.56 (s br, 1H), 9.23 (s br, 1H), 8.12 (d, J=7.7 Hz, 1H), 7.99 (s, 1H), 7.60 (s, 1H), 7.43 (d, J=7.7 Hz, 1H), 7.19-7.07 (m, 2H), 6.83 (s, 1H), 4.86 (s br, 2H), 3.83 (s, 3H), 3.81 (s, 3H), 3.70-3.62 (m, 2H); (+)-LRESIMS m/z (rel. int.) 424 (100) [M+H]$^+$; (+)-HRESIMS calcd. for $C_{21}H_{22}N_5O_3S$ [M+H]$^+$ 424.1438, found 424.1445; $v_{max}$ 1704, 1620, 1503, 1440, 1207, 1064, 743 cm$^{-1}$.

Synthesis Example 40—BT2072

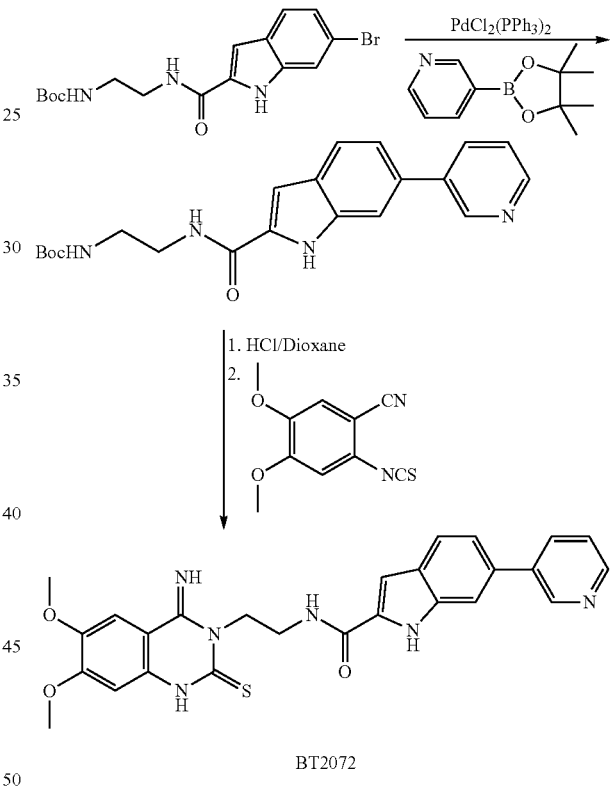

BT2072 tert-Butyl (2-(6-(pyridin-3-yl)-1H-indole-2-carboxamido)ethyl)carbamate was prepared and purified according to General Procedure D from reaction of 3-pyridylboronic acid pinacol ester (80 mg, 0.39 mmol) and tert-butyl (2-(5-bromo-1H-indole-2-carboxamido)ethyl)carbamate (100 mg, 0.26 mmol) to afford after flash chromatography the desired compound (53 mg, 53%) as a white powder. $^1$H NMR (DMSO-$d_6$, 400 MHz) δ 11.73 (s, 1H), 8.87 (d, J=1.7 Hz, 1H), 8.62-8.49 (m, 2H), 8.09-8.00 (m, 1H), 7.74 (d, J=8.3 Hz, 1H), 7.68 (s, 1H), 7.48 (dd, J=8.0, 4.7 Hz, 1H), 7.39 (d, J=8.4 Hz, 1H), 7.14 (s, 1H), 6.94 (t, J=5.2 Hz, 1H), 3.36-3.29 (m, 2H), 3.13 (q, J=6.5 Hz, 2H), 1.38 (s, 9H); $^{13}$C NMR (DMSO-$d_6$, 100 MHz) two signals obscured by DMSO-$d_6$ δ 161.0, 155.7, 147.9, 147.7, 136.9, 136.7, 134.1, 132.8, 132.3, 127.0, 123.8, 122.2, 119.2, 110.4, 102.4, 77.7, 28.2 (3C); (+)-LRESIMS m/z (rel. int.) 381 (100) [M+H]$^+$, 403

(80) [M+Na]+; (+)-HRESIMS calcd. for C21H25N4O3 [M+H]+ 381.1921, found 381.1927; $v_{max}$ 3355, 3310, 1684, 1640, 1533, 1270, 1239, 1165, 991, 791 cm$^{-1}$. Boc-protected compound (96 mg, 0.25 mmol) was deprotected according to General Procedure E to afford (78 mg, 88%) as a white powder, and used directly without further purification. (+)-LRESIMS m/z (rel. int.) 281 (100) [M+H]+; (+)-HRESIMS calcd. for C16H17N4O [M+H]+ 281.1397, found 281.1404. A suspension of the crude hydrochloride formed above (72 mg, 0.20 mmol) was suspended in ethanol (4 mL) and treated with triethylamine (113 μL, 0.82 mmol) and sonicated until the mixture became clear. 2-Isothiocyanato-4,5-dimethoxybenzonitrile (45 mg, 0.20 mmol) was added in portion and stirred for 0.5 h at rt and then heated at 70° C. for 4 h. The precipitate was collected by vacuum filtration and was subjected to flash column chromatography [silica, 1:10 v/v MeOH/DCM elution] to give, after concentration of the appropriate fractions BT2072 (15 mg, 15%) as a cream powder. H NMR (DMSO-de, 400 MHz) δ 11.96 (s br, 1H), 11.71 (s br, 1H), 9.15 (s, 1H), 8.87 (s br, 1H), 8.68 (s, 1H), 8.55 (dd, J=4.7, 1.2 Hz, 1H), 8.09-8.01 (m, 1H), 7.73 (d, J=8.3 Hz, 1H), 7.68 (s, 1H), 7.62 (s, 1H), 7.49 (dd, J=8.3, 4.7 Hz, 1H), 7.39 (d, J=8.5 Hz, 1H), 7.10 (s, 1H), 6.84 (s, 1H), 4.89 (s br, 2H), 3.82 (s, 3H), 3.79 (s, 3H), 3.78-3.67 (m, 2H); (+)-LRESIMS m/z (rel. int.) 501 (100) [M+H]+; (+)-HRES-IMS calcd. for C26H25N6O3S [M+H]+ 501.1703, found 501.1707; $v_{max}$ 3215, 1625, 1550, 1514, 1459, 1436, 1282, 1237, 1022, 809, 633 cm$^{-1}$.

Synthesis Example 41—BT2073

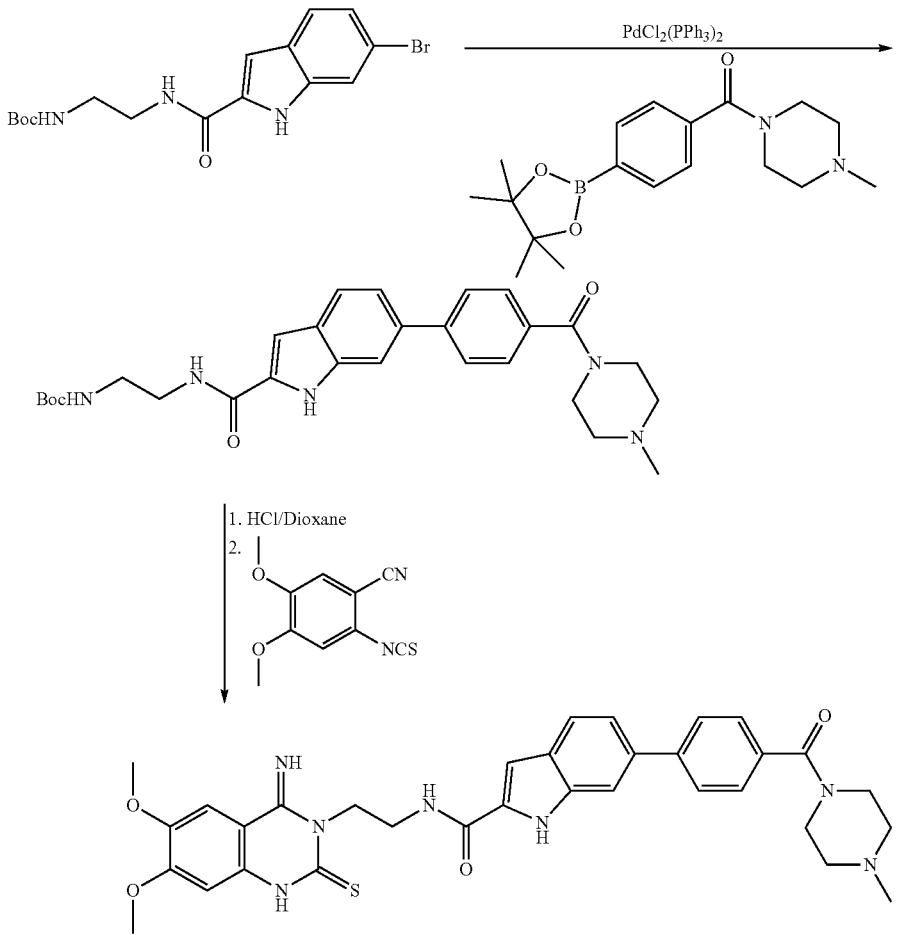

BT2073 tert-Butyl (2-(6-(4-(4-methylpiperazine-1-carbonyl)phenyl)-1H-indole-2-carboxamido)ethyl)carbamate was prepared and purified according to General Procedure D from reaction of [4-(4-Methylpiperazine-1-carbonyl)phenyl]boronic acid pinacol ester (130 mg, 0.39 mmol) and tert-butyl (2-(5-bromo-1H-indole-2-carboxamido)ethyl)carbamate (100 mg, 0.26 mmol) to afford the desired compound (88 mg, 66%) as a white powder. $^1$H NMR (DMSO-d6, 400 MHz) δ 11.72 (s, 1H), 8.55 (t, J=5.9 Hz, 1H), 7.74-7.66 (m, 1H), 7.71 (d, J=8.0 Hz, 2H), 7.68 (s, 1H), 7.48 (d, J=8.1 Hz, 2H), 7.38 (d, J=8.0 Hz, 1H), 7.12 (s, 1H), 6.94 (t, J=5.5 Hz, 1H), 3.69-3.26 (m, 6H), 3.13 (app. q, J=6.3 Hz, 2H), 2.41-2.28 (m, 4H), 2.20 (s, 3H), 1.38 (s, 9H); (+)-LRESIMS m/z (rel. int.) 506 (100) [M+H]+; (+)-HRESIMS calcd. for C28H36N5O4 [M+H]+ 506.2762, found 506.2769; $v_{max}$ 3229, 2788, 1716, 1618, 1493, 1434, 1291, 1266, 1166, 1000, 829, 779 cm$^{-1}$. The Boc-protected compound (95 mg, 0.19 mmol) was deprotected according to General Procedure E to afford a white powder, and used directly without further purification. $^1$H NMR (DMSO-d6, 400 MHz) δ 11.83 (s, 1H), 11.30 (s, 1H), 8.95 (t, J=5.6 Hz, 1H), 8.16 (s, 3H), 7.76 (d, J=8.0 Hz, 2H), 7.74 (d, J=8.2 Hz, 1H), 7.70 (s, 1H), 7.56 (d, J=8.0 Hz, 2H), 7.40 (dd, J=8.2, 1.5 Hz, 1H), 7.28 (d, J=1.5 Hz, 1H), 3.58 (app. q, J=5.9 Hz, 2H), 3.51-3.35 (m, 4H), 3.17-3.06 (m, 4H), 3.06-2.99 (m, 2H), 2.77 (s, 3H); (+)-LRESIMS m/z (rel. int.) 406 (100) [M+H]$^+$; (+)-HRESIMS calcd. for $C_{23}H_{28}N_5O_2$ [M+H]$^+$ 406.2238, found 406.2244. The crude dihydrochloride formed above (78 mg, 0.16 mmol) was reacted with triethylamine (91 μL, 0.65 mmol) and 2-isothiocyanato-4,5-dimethoxybenzonitrile (36 mg, 0.16 mmol) according to General Procedure C to afford BT2073 (81 mg, 81%) as a pale yellow solid. $^1$H NMR (DMSO-d$_6$, 400 MHz) δ 11.90 (s br, 1H), 11.68 (s, 1H), 9.15 (s, 1H), 8.66 (s, 1H), 7.72 (d, J=8.0 Hz, 2H), 7.71-7.66 (m, 2H), 7.62 (s, 1H), 7.48 (d, J=8.0 Hz, 2H), 7.38 (d, J=8.3 Hz, 1H), 7.08 (s, 1H), 6.84 (s, 1H), 4.97-4.83 (m, 2H), 3.82 (s, 3H), 3.79 (s, 3H), 3.77-3.70 (m, 2H), 3.69-3.48 (m, 4H), 2.43-2.26 (m, 4H), 2.20 (s, 3H); (+)-LRESIMS m/z (rel. int.) 626 (100) [M+H]$^+$; (+)-HRESIMS calcd. for $C_{33}H_{36}N_7O_4S$ [M+H]$^+$ 626.2544, found 626.2547; ν$_{max}$ 3195, 1622, 1562, 1542, 1515, 1442, 1365, 1235, 1192, 1018, 834 cm$^{-1}$.

Synthesis Example 42—BT2075

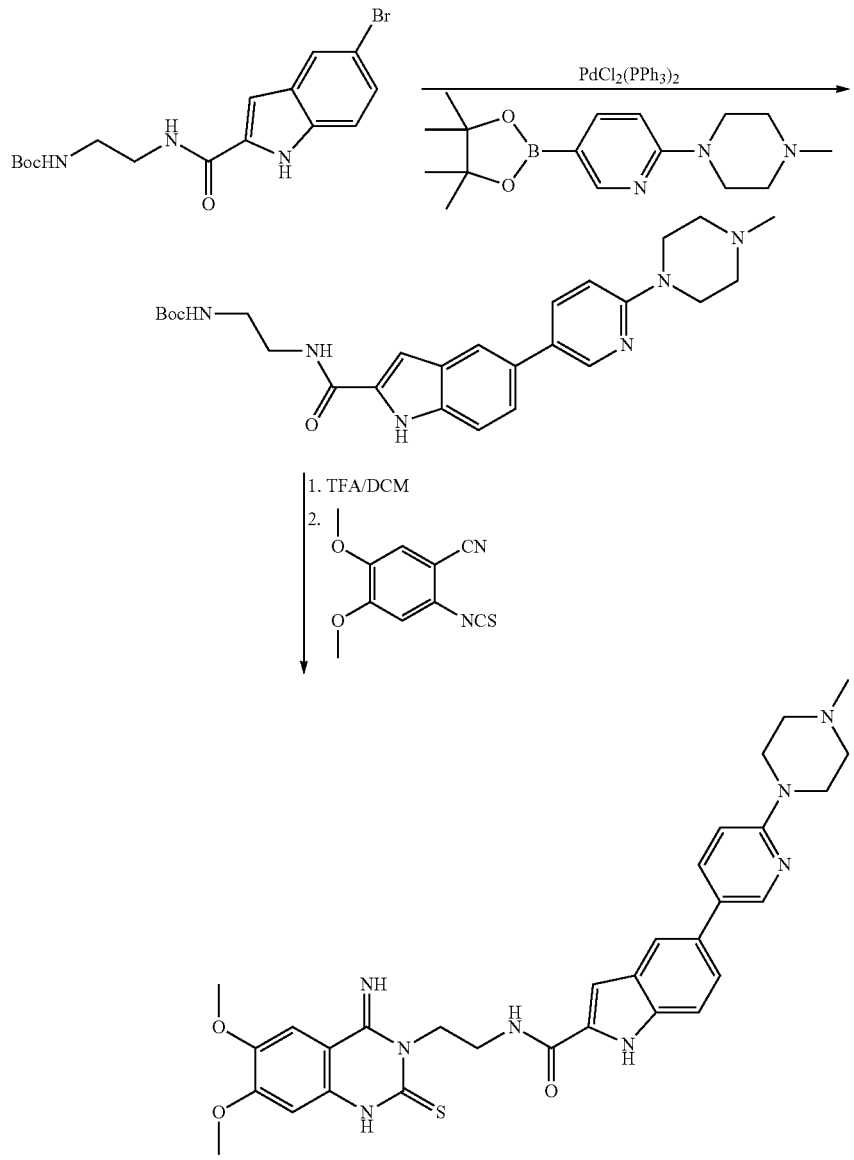

BT2075 tert-Butyl (2-(5-(6-(4-methylpiperazin-1-yl)pyridin-3-yl)-1H-indole-2-carboxamido)ethyl)carbamate was prepared according to General Procedure D from reaction of 2-(piperazin-1-yl)pyridine-5-boronic acid pinacol ester (119 mg, 0.39 mmol) and tert-butyl (2-(5-bromo-1H-indole-2-carboxamido)ethyl)carbamate (100 mg, 0.26 mmol) to afford after flash column chromatography [silica, 1:10 v/v ammoniacal MeOH/DCM elution] and concentration of the appropriate fractions, the desired compound (62 mg, 49%) as a white powder. $^1$H NMR (DMSO-d$_6$, 400 MHz) δ 11.58 (s, 1H), 8.50 (t, J=5.6 Hz, 1H), 8.44 (d, J=2.5 Hz, 1H), 7.85 (dd, J=8.8, 2.5 Hz, 1H), 7.81 (s, 1H), 7.47 (d, J=8.6 Hz, 1H), 7.43 (dd, J=8.6, 1.5 Hz, 1H), 7.12 (s, 1H), 6.94 (d, J=5.3 Hz, 1H), 6.90 (d, J=8.8 Hz, 1H), 3.51 (t, J=5.1 Hz, 4H), 3.38-3.27 (m, 2H), 3.12 (app. q, J=6.0 Hz, 2H), 2.45-2.37 (m, 4H), 2.22 (s, 3H), 1.38 (s, 9H); $v_{max}$ 3376, 3319, 2933, 1683, 1633, 1529, 1241, 1168, 810 cm$^{-1}$. A magnetically stirred suspension of tert-butyl (2-(5-(6-(4-methylpiperazin-1-yl)pyridin-3-yl)-1H-indole-2-carboxamido)ethyl)carbamate (86 mg, 1.80 mmol) in DCM (4 mL) maintained at 0° C. was treated with trifluoroacetic acid (1 mL) and magnetically stirred for 2 h. The cold bath was removed and the mixture stirred at rt for 1 h and then the solvent was removed with a gentle stream of nitrogen and the remaining gum was triturated with ether (3×10 mL) then placed under high vacuum for 1 h to afford the deprotected TFA salt as a beige powder and used directly without further purification. (+)-LRESIMS m/z (rel. int.) 379 (100) [M+H]$^+$; (+)-HRESIMS calcd. for $C_{21}H_{27}N_6O$ [M+H]$^+$ 379.2241, found 379.2245; $v_{max}$ 1673, 1647, 1548, 1422, 1177, 1131, 1025, 799 cm$^{-1}$. The powder so formed was reacted with triethylamine (150 μL, 1.07 mmol) and 2-isothiocyanato-4,5-dimethoxybenzonitrile (39 mg, 0.18 mmol) according to General Procedure C to afford BT2075 (83 mg, 78%) as a beige powder. $^1$H NMR (DMSO-d$_6$, 400 MHz) δ 11.93 (s, 1H), 11.55 (s, 1H), 9.15 (s, 1H), 8.62 (s, 1H), 8.44 (s, 1H), 7.85 (d, J=8.7 Hz, 1H), 7.79 (s, 1H), 7.62 (s, 1H), 7.50-7.40 (m, 2H), 7.07 (s, 1H), 6.90 (d, J=8.7 Hz, 1H), 6.84 (s, 1H), 4.96-4.83 (m, 2H), 3.82 (s, 3H), 3.79 (s, 3H), 3.77-3.69 (m, 2H), 3.56-3.47 (m, 4H), 2.44-2.39 (m, 4H), 2.22 (s, 3H); (+)-LRESIMS m/z (rel. int.) 599 (100) [M+H]$^+$; (+)-HRESIMS calcd. for $C_{31}H_{35}N_8O_3S$ [M+H]$^+$ 599.2547, found 599.2553; $v_{max}$ 3205, 1610, 1582, 1548, 1514, 1397, 1186, 1019, 859, 805 cm$^{-1}$.

Synthesis Example 43—BT2076

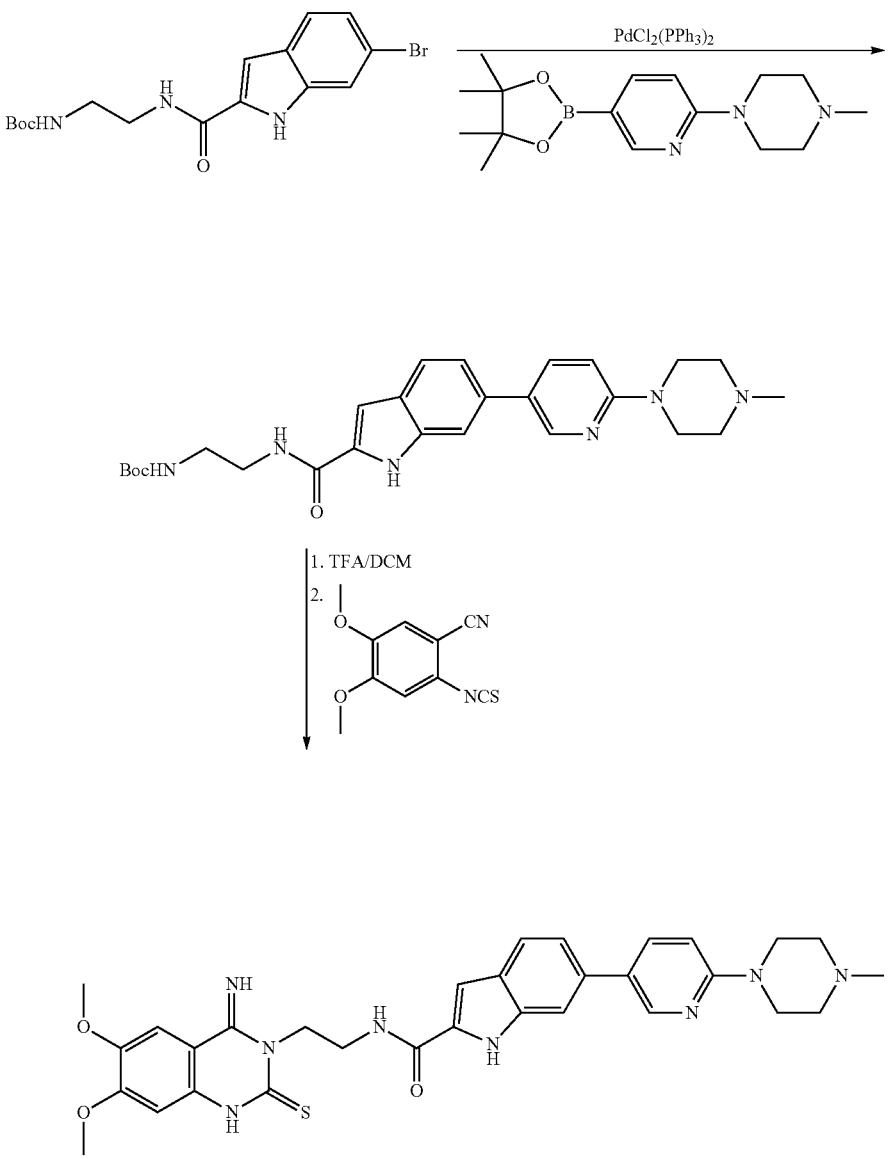

BT2076 tert-Butyl (2-(6-(6-(4-methylpiperazin-1-yl)pyridin-3-yl)-1H-indole-2-carboxamido)ethyl)carbamate was prepared and purified according to General Procedure D from reaction of 2-(piperazin-1-yl)pyridine-5-boronic acid pinacol ester (81 mg, 0.27 mmol) and tert-butyl (2-(6-bromo-1H-indole-2-carboxamido)ethyl)carbamate (100 mg, 0.26 mmol) to afford the desired product (62 mg, 49%) as a cream coloured powder. $^1$H NMR (DMSO-$d_6$, 400 MHz) δ 11.63 (s, 1H), 8.52 (t, J=5.3 Hz, 1H), 8.42 (d, J=2.5 Hz, 1H), 7.82 (dd, J=9.0, 2.5 Hz, 1H), 7.65 (d, J=8.4 Hz, 1H), 7.56 (s, 1H), 7.29 (dd, J=8.4, 1.5 Hz, 1H), 7.09 (s, 1H), 6.95 (d, J=5.5 Hz, 1H), 6.92 (d, J=9.0 Hz, 1H), 3.55-3.49 (m, 4H), 3.35-3.29 (m, 2H), 3.12 (q, J=6.1 Hz, 2H), 2.43-2.39 (m, 4H), 2.22 (s, 3H), 1.38 (s, 9H); (+)-LRESIMS m/z (rel. int.) 479 (100) [M+H]$^+$; (+)-HRESIMS calcd. for $C_{26}H_{35}N_6O_3$ [M+H]$^+$ 479.2765, found 479.2771; $v_{max}$ 3322, 1689, 1633, 1535, 1246, 1167, 1005, 812 cm$^{-1}$. The Boc-protected compound formed directly above (80 mg, 0.17 mmol) was deprotected according to General Procedure F to afford a tan powder, and used directly without further purification. The powder so formed was reacted with triethylamine (232 μL, 1.65 mmol) and 2-isothiocyanato-4,5-dimethoxybenzonitrile (46 mg, 0.21 mmol) according to the procedure used for General Procedure C to afford BT2076 (67 mg, 65%) as a cream powder. $^1$H NMR (DMSO-$d_6$, 400 MHz) δ 11.94 (s br, 1H), 11.55 (s, 1H), 9.15 (s, 1H), 8.62 (s, 1H), 8.42 (s, 1H), 7.82 (d, J=8.7 Hz, 1H), 7.69-7.59 (m, 2H), 7.56 (s, 1H), 7.29 (d, J=8.2 Hz, 1H), 7.05 (s, 1H), 6.92 (d, J=8.7 Hz, 1H), 6.84 (s, 1H), 4.94-4.84 (m, 2H), 3.82 (s, 3H), 3.79 (s, 3H), 3.76-3.67 (m, 2H), 3.58-3.47 (m, 4H), 2.45-2.37 (m, 4H), 2.22 (s, 3H); (+)-LRESIMS m/z (rel. int.) 599 (100) [M+H]$^+$; (+)-HRESIMS calcd. for $C_{31}H_{35}N_8O_3S$ [M+H]$^+$ 599.2547, found 599.2551. A portion of the product (20 mg) was suspended in DCM (2 mL) and trifluoroacetic acid (100 μL) added. The mixture was concentrated under a gentle stream of nitrogen over 24 h to afford the trifluoroacetic acid salt of BT2076. $^1$H NMR (DMSO-$d_6$, 400 MHz) TFA salt δ 13.77 (s, 1H), 11.69-11.60 (m, 1H), 10.57 (s, 1H), 10.31 (s, 1H), 10.05 (s, 1H), 9.01 (t, J=5.9 Hz, 1H), 8.51 (d, J=2.5 Hz, 1H), 8.01 (dd, J=9.0, 2.5 Hz, 1H), 7.88 (s, 1H), 7.85 (s, 1H), 7.52-7.47 (m, 2H), 7.12 (d, J=2.0 Hz, 2H), 7.10 (d, J=9.0 Hz, 1H), 7.01 (s, 1H), 5.60-4.56 (m br, 2H), 4.54-4.35 (m, 2H), 3.91 (s, 3H), 3.86 (s, 3H), 3.81-3.69 (m, 2H), 3.62-3.49 (m, 2H), 3.30-3.02 (m, 4H), 2.87 (s, 3H); $^{13}$C NMR (DMSO-$d_6$, 100 MHz) TFA salt δ 171.6, 162.4, 158.5 (q, JC-F=35.4 Hz), 157.3, 156.2, 155.3, 147.8, 144.3, 136.9, 136.0, 135.4, 131.6, 129.1, 127.7, 127.6, 122.5, 118.7, 116.0 (q, JC-F=292.8 Hz), 113.0, 108.3, 105.4, 103.6, 102.4, 97.8, 56.4 (2C), 52.0, 47.7, 42.4, 42.2, 35.0.

Synthesis Example 44—BT2077

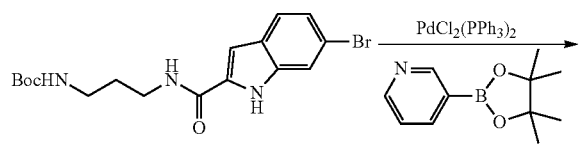

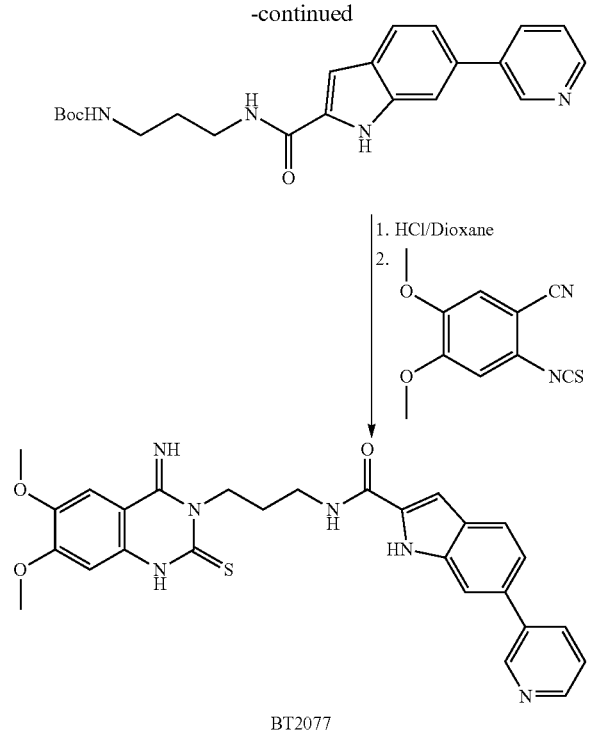

tert-Butyl (3-(6-(pyridin-3-yl)-1H-indole-2-carboxamido)propyl)carbamate was prepared according to General Procedure D from reaction of 3-pyridylboronic acid pinacol ester (80 mg, 0.39 mmol) and tert-butyl (3-(6-bromo-1H-indole-2-carboxamido)propyl)carbamate (104 mg, 0.26 mmol) and purified as follows: After microwave irradiation the solvent was removed in vacuo and water (20 mL) was added. The precipitate which formed was collected and subjected to flash column chromatography [silica, 1:10 v/v MeOH/DCM elution] to give, after concentration of the appropriate fractions the desired compound (66 mg, 64%) as a white solid. $^1$H NMR (DMSO-$d_6$, 400 MHz) δ 11.73 (s, 1H), 8.88 (d, J=1.5 Hz, 1H), 8.55 (dd, J=4.6, 1.0 Hz, 1H), 8.51 (t, J=5.7 Hz, 1H), 8.05 (dt, J=7.8, 1.5 Hz, 1H), 7.74 (d, J=8.3 Hz, 1H), 7.69 (s, 1H), 7.48 (dd, J=7.8, 4.8 Hz, 1H), 7.39 (dd, J=8.3, 1.0 Hz, 1H), 7.14 (s, 1H), 6.85 (t, J=5.8 Hz, 1H), 3.29 (app. q, J=7.0 Hz, 2H), 3.00 (app. q, J=6.6 Hz, 2H), 1.70-1.62 (m, 2H), 1.38 (s, 9H); $^{13}$C NMR (DMSO-$d_6$, 100 MHz) δ160.9, 155.6, 147.9, 147.7, 136.9, 136.7, 134.1, 132.9, 132.3, 127.0, 123.9, 122.2, 119.2, 110.4, 102.2, 77.5, 37.7, 36.6, 29.7, 28.2 (3C); (+)-LRESIMS m/z (rel. int.) 395 (100) [M+H]$^+$, 417 (14) [M+Na]$^+$, 789 (15) [2M+H]$^+$; (+)-HRESIMS calcd. for $C_{22}H_{27}N_4O_3$ [M+H]$^+$ 395.2078, found 395.2084; $v_{max}$ 3355, 1684, 1640, 1534, 1367, 1270, 1239, 1165, 991, 791 cm$^{-1}$. The Boc-protected amine (82 mg, 0.21 mmol) was deprotected following General Procedure F to afford a white powder, and used directly without further purification. The powder so formed was reacted with triethylamine (232 μL, 1.66 mmol) and 2-isothiocyanato-4,5-dimethoxybenzonitrile (46 mg, 0.21 mmol) according to General Procedure C to afford BT2077 (47 mg, 44%) as a white powder. $^1$H NMR (DMSO-$d_6$, 400 MHz) δ 11.89 (s, 1H), 11.74 (s, 1H), 9.11 (s, 1H), 8.88 (d, J=2.0 Hz, 1H), 8.68 (t, J=5.7 Hz, 1H), 8.54 (dd, J=4.7, 1.5 Hz, 1H), 8.05 (ddd, J=7.9, 2.0, 1.7 Hz, 1H), 7.75 (d, J=8.3 Hz, 1H), 7.70 (s, 1H), 7.61 (s, 1H), 7.48 (dd, J=7.9, 4.7 Hz, 1H), 7.39 (dd, J=8.3, 1.7 Hz, 1H), 7.15 (s, 1H), 6.84 (s, 1H), 4.70 (s, 2H), 3.83 (s, 3H), 3.79 (s, 3H), 3.44-3.35 (m, 2H), 2.09-1.98 (m, 2H); $^{13}$C NMR (DMSO-d$_6$, 100 MHz) δ 173.2, 160.7, 153.6 (br), 153.1 (br), 147.9, 147.7, 146.5, 136.9, 136.7, 134.1, 133.0, 132.3, 130.7, 127.1, 123.9, 122.2, 119.2, 110.5, 107.4 (br), 107.2 (br), 102.1, 98.2, 56.2, 55.7, 44.8 (br), 36.6, 26.6; (+)-LRESIMS m/z (rel. int.) 515 (100) [M+H]$^+$; (+)-HRESIMS calcd. for C$_{27}$H$_{27}$N$_6$O$_3$S [M+H]$^+$ 515.1860, found 515.1866; ν$_{max}$ 3144, 1626, 1555, 1517, 1442, 1404, 1284, 1260, 1242, 1107, 1024, 1016, 782, 710 cm−1; A portion of the product (20 mg) was suspended in DCM (2 mL) and trifluoroacetic acid (100 μL) added. The mixture was concentrated under a gentle stream of nitrogen over 24 h to afford the trifluoroacetic acid salt of BT2077. $^1$H NMR (DMSO-d$_6$, 400 MHz) TFA salt δ 13.73 (s, 1H), 11.89 (s, 1H), 10.87 (s, 1H), 10.36 (s, 1H), 9.81 (s, 1H), 9.17 (s, 1H), 8.80 (d, J=5.1 Hz, 1H), 8.71 (t, J=5.7 Hz, 1H), 8.66 (d, J=8.2 Hz, 1H), 7.96 (dd, J=8.2, 5.1 Hz, 1H), 7.85-7.78 (m, 3H), 7.49 (dd, J=8.3, 1.6 Hz, 1H), 7.17 (d, J=1.6 Hz, 1H), 6.98 (s, 1H), 5.71-4.13 (m, 2H), 3.88 (s, 3H), 3.86 (s, 3H), 3.51 (q, J=6.5 Hz, 2H), 2.11-1.99 (m, 2H); $^{13}$C NMR (DMSO-d$_6$, 100 MHz) TFA salt δ 171.0, 160.9, 158.5 (q, JC-F=35.5 Hz), 157.2, 154.7, 147.7, 142.1, 140.8, 139.1, 136.8, 135.3, 133.7, 129.7, 127.9, 126.4, 122.6, 119.2, 116.0 (q, JC-F=292.2 Hz), 111.1, 105.5, 102.5, 102.2, 97.7, 56.4, 56.4, 47.1, 36.2, 25.3.

Synthesis Example 45—BT2078

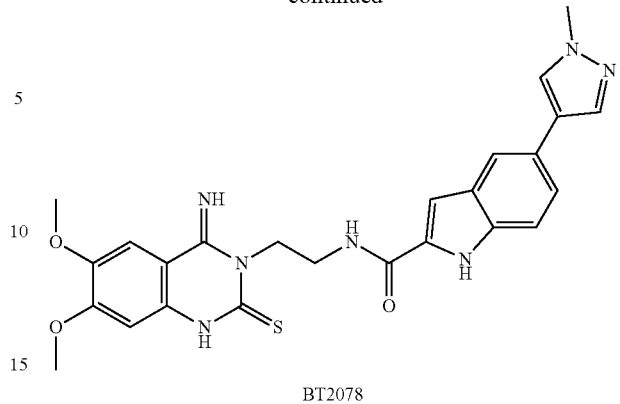

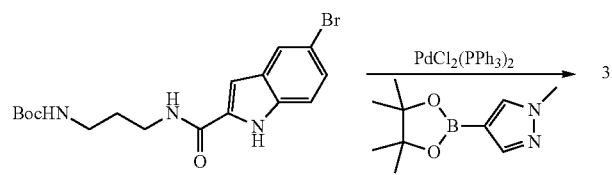

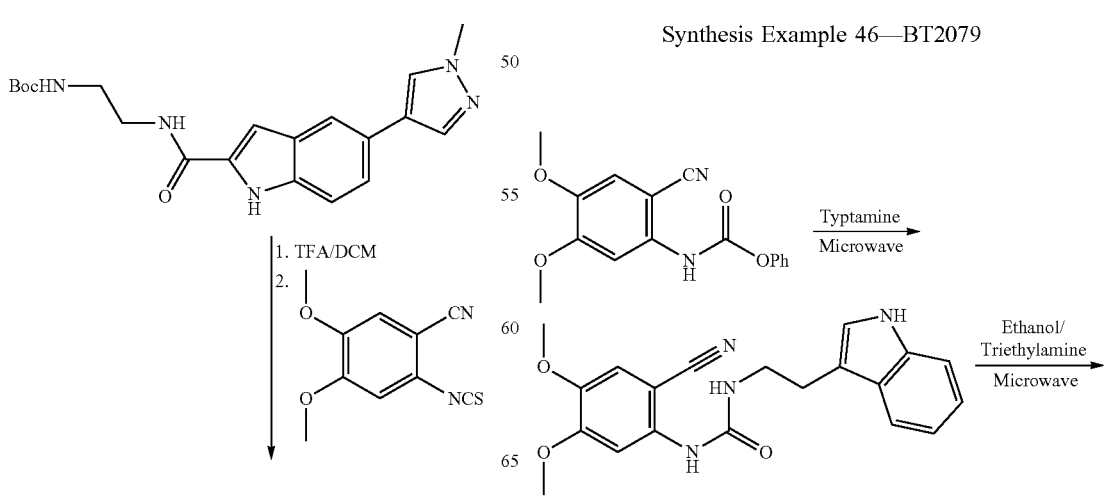

BT2078 tert-Butyl (2-(5-(1-methyl-1H-pyrazol-4-yl)-1H-indole-2-carboxamido)ethyl)carbamate was prepared and purified according to General Procedure D from reaction of 1-methylpyrazole-4-boronic acid pinacol ester (81 mg, 0.39 mmol) and tert-butyl (2-(5-bromo-1H-indole-2-carboxamido)ethyl) carbamate (100 mg, 0.26 mmol) to afford the desired product (95 mg, 95%) as a white powder. $^1$H NMR (DMSO-d$_6$, 400 MHz) δ 11.52 (s, 1H), 8.48 (t, J=5.5 Hz, 1H), 8.05 (s, 1H), 7.81 (s, 1H), 7.76 (s, 1H), 7.39 (s, 2H), 7.05 (s, 1H), 6.93 (t, J=5.4 Hz, 1H), 3.85 (s, 3H), 3.33-3.28 (m, 2H), 3.12 (q, J=6.1 Hz, 2H), 1.38 (s, 9H); (+)-LRESIMS m/z (rel. int.) 384 (100) [M+H]$^+$; (+)-HRESIMS calcd. for C$_{20}$H$_{26}$N$_5$O$_3$ [M+H]+ 384.2030, found 384.2032; ν$_{max}$ 1687, 1639, 1527, 1365, 1269, 1232, 1166, 998, 795 cm$^{-1}$. The Boc-protected compound formed directly above (70 mg, 0.18 mmol) was deprotected according to General Procedure F to afford a white powder, and used directly without further purification. The powder so formed was reacted with triethylamine (202 μL, 1.46 mmol) and 2-isothiocyanato-4,5-dimethoxybenzonitrile (40 mg, 0.18 mmol) according to General Procedure C to afford BT2078 (74 mg, 80%) as a beige solid. $^1$H NMR (DMSO-d$_6$, 400 MHz) δ 11.91 (s br, 1H), 11.52 (s, 1H), 9.15 (s br, 1H), 8.68 (s br, 1H), 8.04 (s, 1H), 7.82 (s, 1H), 7.76 (s, 1H), 7.60 (s, 1H), 7.42-7.37 (m, 2H), 7.05 (s, 1H), 6.83 (s, 1H), 5.02-4.74 (m, 2H), 3.86 (s, 3H), 3.82 (s, 3H), 3.79 (s, 3H), 3.78-3.68 (m, 2H); (+)-LRESIMS m/z (rel. int.) 504 (100) [M+H]$^+$; ν$_{max}$ 3224, 1623, 1545, 1510, 1437, 1395, 1280, 1233, 1191, 1020, 851, 797, 762 cm$^{-1}$.

Synthesis Example 46—BT2079

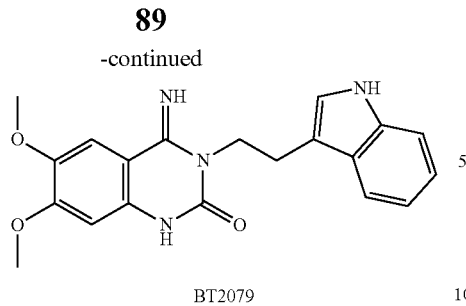

BT2079

A 10 mL snap-cap microwave vessel containing a magnetic stirring-bar was charged with a mixture of phenyl (2-cyano-4,5-dimethoxyphenyl)carbamate (100 mg, 0.34 mmol), tryptamine (54 mg, 0.34 mmol) and acetonitrile (3 mL). The sealed vessel was then subjected to microwave irradiation (100° C./1 h, ramp time 1 minute, maximum power 300 W with $N_2$ cooling during reaction (Powermax)). The vessel was cooled in ice and the resulting crystals collected by vacuum filtration to afford 1-(2-(1H-indol-3-yl)ethyl)-3-(2-cyano-4,5-dimethoxyphenyl)urea as a white solid (92 mg, 76%) and transferred to a 10 mL snap-cap microwave vessel containing a magnetic sirring-bar, ethanol (4 mL) and triethylamine (200 µL). The sealed vessel was then subjected to microwave irradiation (100° C./0.2 h, ramp time 1 minute, maximum power 300 W with $N_2$ cooling during reaction (Powermax)) and after this time TLC analysis revealed incomplete conversion. The mixture was re-subjected to the above microwave conditions for a further 0.17 h and the residue obtained after concentration in vacuo, was subjected to flash column chromatography [silica, 1:10 v/v MeOH/DCM elution] to give, after concentration of the appropriate fractions BT2079 (35 mg, 38%) as a white powder. H NMR (DMSO-$d_6$, 400 MHz) δ 10.80 (s, 1H), 10.51 (s br, 1H), 8.79 (s br, 1H), 7.82 (d, J=8.1 Hz, 1H), 7.61 (s, 1H), 7.34 (d, J=8.1 Hz, 1H), 7.18 (d, J=1.8 Hz, 1H), 7.07 (t, J=7.3 Hz, 1H), 6.98 (t, J=7.3 Hz, 1H), 6.61 (s, 1H), 4.35-4.23 (m, 2H), 3.81 (s, 3H), 3.79 (s, 3H), 3.03-2.95 (m, 2H); $^{13}$C NMR (DMSO-$d_6$, 100 MHz) δ 155.1, 153.2, 150.0, 145.0, 136.3, 132.1, 127.5, 122.7, 121.0, 118.8, 118.2, 111.7, 111.4, 108.0, 105.0, 97.9, 56.2, 55.7, 41.4, 22.8; (+)-LRESIMS m/z (rel. int.) 365 (100) [M+H]$^+$; (+)-HRESIMS calcd. for $C_{20}H_{21}N_4O_3$ [M+H]$^+$ 365.1608, found 365.1615; $v_{max}$ 1683, 1619, 1512, 1466, 1440, 1237, 1112, 1013, 841, 785 cm$^{-1}$.

Synthesis Example 47—BT2080

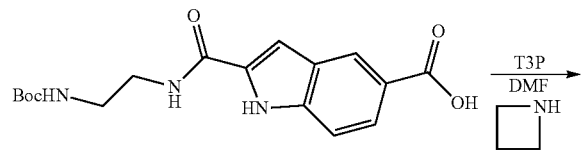

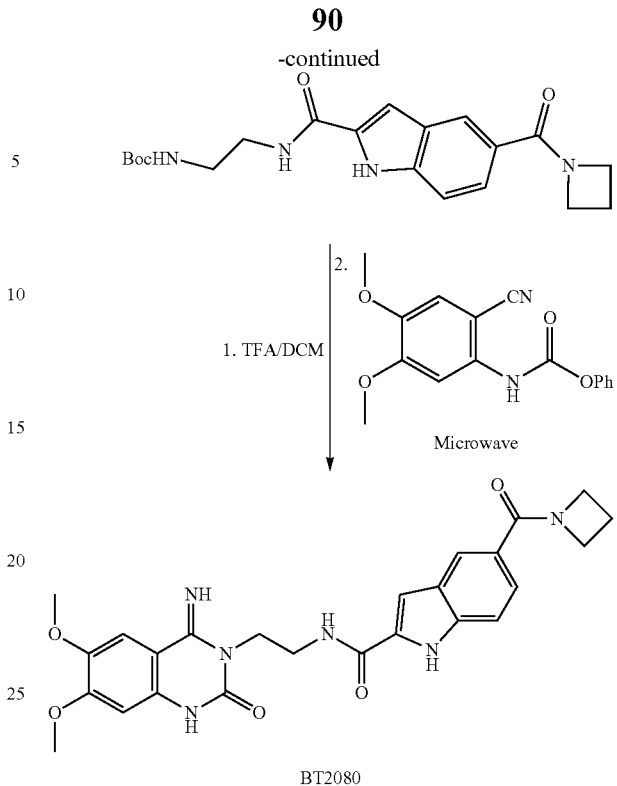

BT2080 tert-Butyl (2-(5-(azetidine-1-carbonyl)-1H-indole-2-carboxamido)ethyl)carbamate was prepared according to General Procedure G from 2-((2-((tert-butoxycarbonyl)amino)ethyl)carbamoyl)-1H-indole-5-carboxylic acid (100 mg, 0.29 mmol) and azetidine hydrochloride (27 mg, 0.29 mmol). The residue obtained after concentration in vacuo, was subjected to flash column chromatography [silica, 1:10 v/v MeOH/DCM elution] to give, after concentration of the appropriate fractions the desired azetidine amide (35 mg, 31%) as a white powder. $^1$H NMR (DMSO-$d_6$, 400 MHz) δ 11.81 (s, 1H), 8.55 (t, J=5.7 Hz, 1H), 7.92 (s, 1H), 7.47 (dd, J=8.6, 1.4 Hz, 1H), 7.43 (d, J=8.6 Hz, 1H), 7.17 (s, 1H), 6.92 (t, J=5.7 Hz, 1H), 4.42-4.25 (m, 2H), 4.12-3.97 (m, 2H), 3.36-3.27 (m, 2H), 3.12 (app. q, J=6.3 Hz, 2H), 2.32-2.19 (m, 2H), 1.37 (s, 9H); (+)-LRESIMS m/z (rel. int.) 387 (100) [M+H]$^+$; (+)-HRESIMS calcd. for $C_{20}H_{27}N_4O_4$ [M+H]$^+$ 387.2027, found 387.2029; $v_{max}$ 1673, 1643, 1594, 1560, 1528, 1422, 1287, 1175, 985, 813, 751 cm$^{-1}$. The Boc-protected compound formed directly above (32 mg, 83 µmol) was deprotected following General Procedure F to afford a white powder, and used directly without further purification. $^1$H NMR (DMSO-$d_6$, 400 MHz) TFA salt δ 11.87 (s, 1H), 8.72 (t, J=5.2 Hz, 1H), 7.95 (s, 1H), 7.88 (s, 3H), 7.48 (d, J=8.6 Hz, 1H), 7.45 (d, J=8.6 Hz, 1H), 7.20 (s, 1H), 4.41-4.27 (m, 2H), 4.14-3.97 (m, 2H), 3.62-3.47 (m, 2H), 3.07-2.95 (m, 2H), 2.32-2.20 (m, 2H). A 10 mL snap-cap microwave vessel containing a magnetic stirring-bar was charged with a mixture of phenyl (2-cyano-4,5-dimethoxyphenyl)carbamate (18.2 mg, 60 µmol), the crude trifluoroacetic acid salt, formed directly above (83 µmol), ethanol (1 mL) and triethylamine (150 µL) then subjected to microwave irradiation (100° C./1 h, ramp time 1 minute, maximum power 300 W with $N_2$ cooling during reaction (Powermax)). The vessel was cooled in ice and the resulting crystals collected by vacuum filtration to afford BT2080 (12 mg, 41%) as a white solid. $^1$H NMR (DMSO-$d_6$, 400 MHz) δ 11.78 (s, 1H), 10.50 (s, 1H), 8.75-8.61 (m, 2H), 7.90 (s, 1H), 7.58 (s, 1H), 7.46 (d, J=8.7 Hz, 1H), 7.42 (d, J=8.7 Hz, 1H), 7.11 (s, 1H), 6.55 (s, 1H), 4.40-4.30 (m, 2H), 4.30-4.19 (m, 2H), 4.11-3.99 (m, 2H), 3.79 (s, 3H), 3.77 (s, 3H), 3.63-3.54 (m, 2H), 2.31-2.21 (m, 2H); (+)-LRESIMS m/z (rel. int.) 491 (100) [M+H]$^+$; (+)-HRESIMS calcd. for $C_{25}H_{27}N_6O_5$ [M+H]$^+$ 491.2037, found 491.2039; $v_{max}$ 3612, 3179, 1690, 1614, 1561, 1513, 1443, 1276, 1213, 1046, 756 cm$^{-1}$.

Synthesis Example 48—BT2081

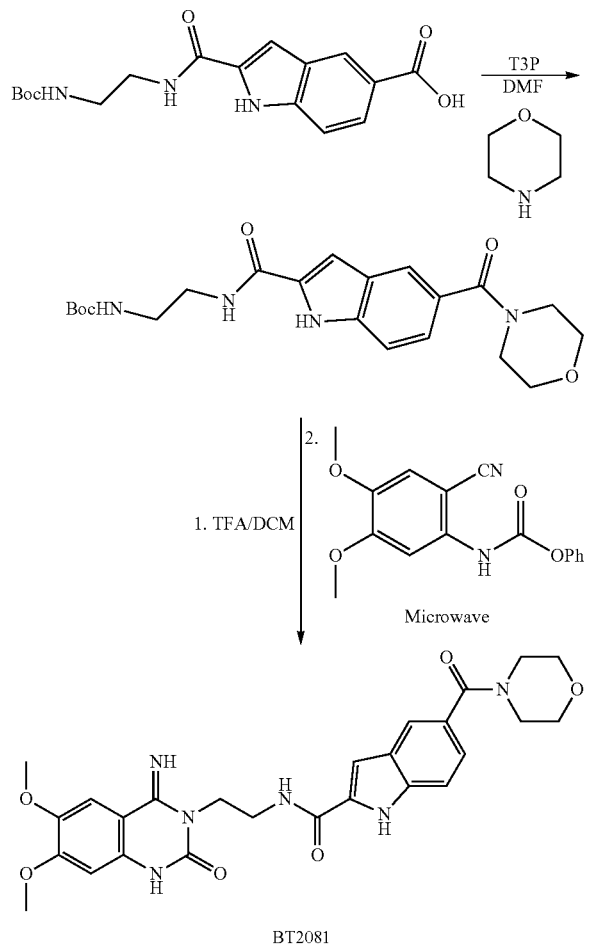

BT2081 tert-Butyl (2-(5-(morpholine-4-carbonyl)-1H-indole-2-carboxamido)ethyl)carbamate was prepared according to General Procedure G from 2-((2-((tert-butoxycarbonyl)amino)ethyl)carbamoyl)-1H-indole-5-carboxylic acid (100 mg, 0.29 mmol) and morpholine (25 mg, 0.29 mmol). The residue obtained after concentration in vacuo, was subjected to flash column chromatography [silica, 1:20 v/v ammoniacal MeOH/DCM elution] to give, after concentration of the appropriate fractions the desired morpholine amide (85 mg, 71%) as a white powder. $^1$H NMR (DMSO-d$_6$, 400 MHz) δ 11.78 (s, 1H), 8.55 (t, J=5.2 Hz, 1H), 7.71 (s, 1H), 7.46 (d, J=8.4 Hz, 1H), 7.23 (d, J=8.4 Hz, 1H), 7.16 (s, 1H), 6.92 (t, J=5.6 Hz, 1H), 3.66-3.57 (m, 4H), 3.56-3.48 (m, 4H), 3.37-3.29 (m, 2H), 3.18-3.09 (m, 2H), 1.37 (s, 9H); (+)-LRESIMS m/z (rel. int.) 417 (50) [M+H]$^+$, 439 (100) [M+Na]$^+$; (+)-HRESIMS calcd. for $C_{21}H_{29}N_4O_5$ [M+H]$^+$ 417.2132, found 417.2137; $v_{max}$ 1704, 1624, 1556, 1421, 1252, 1168, 1114 cm$^{-1}$. The Boc-protected compound formed directly above (50 mg, 0.12 mmol) was deprotected following General Procedure F to afford a white powder, and used directly without further purification. $^1$H NMR (DMSO-d$_6$, 400 MHz) δ 11.84 (s, 1H), 8.71 (t, J=4.9 Hz, 1H), 7.86 (s, 3NH), 7.74 (s, 1H), 7.47 (d, J=8.4 Hz, 1H), 7.25 (d, J=8.4 Hz, 1H), 7.17 (s, 1H), 3.68-3.46 (m, 10H), 3.06-2.97 (m, 2H); $^{13}$C NMR (DMSO-d$_6$, 100 MHz) TFA salt, 1 signal obscured or overlapping δ 170.2, 161.5, 158.25 (q, J=35.8 Hz), 136.8, 132.5, 127.1, 126.3, 122.9, 121.2, 115.89 (q, J=293.2 Hz), 112.2, 103.5, 66.2 (2C), 38.7, 36.7. A 10 mL snap-cap microwave vessel containing a magnetic stirring-bar was charged with a mixture of phenyl (2-cyano-4,5-dimethoxyphenyl)carbamate (26.4 mg, 89 μmol), the crude TFA salt formed directly above (120 μmol), ethanol (2 mL) and triethylamine (167 μL) then subjected to microwave irradiation (100° C./1 h, ramp time 1 minute, maximum power 300 W with N$_2$ cooling during reaction (Powermax)). The vessel was cooled in ice and the resulting crystals collected by vacuum filtration to BT2081 (22 mg, 35%) as a white solid. $^1$H NMR (DMSO-d$_6$, 400 MHz) δ 11.76 (s, 1H), 10.50 (s, 1H), 8.77-8.59 (m, 2H), 7.69 (s, 1H), 7.58 (s, 1H), 7.44 (d, J=8.4 Hz, 1H), 7.23 (d, J=8.4 Hz, 1H), 7.09 (s, 1H), 6.56 (s, 1H), 4.32-4.22 (m, 2H), 3.79 (s, 3H), 3.77 (s, 3H), 3.67-3.47 (m, 10H); (+)-LRESIMS m/z (rel. int.) 521 (100) [M+H]$^+$; (+)-HRESIMS calcd. for $C_{26}H_{29}N_6O_6$ [M+H]$^+$ 521.2143, found 521.2150; $v_{max}$ 1691, 1623, 1558, 1512, 1462, 1419, 1288, 1212, 1114, 1041, 1019, 820, 758 cm$^{-1}$.

Synthesis Example 49—BT2082

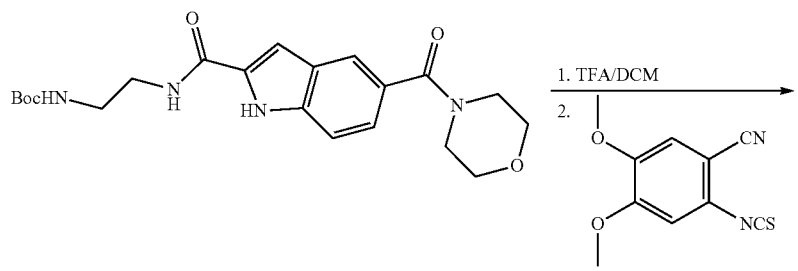

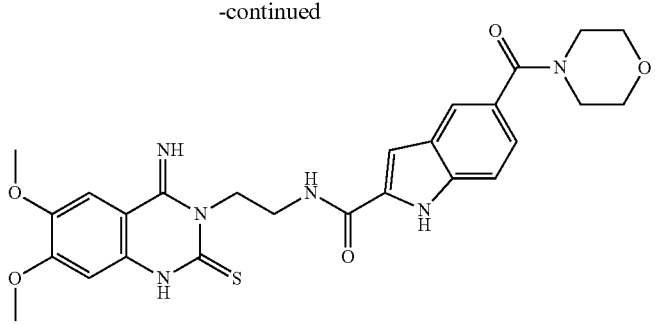

BT2082 tert-Butyl (2-(5-(morpholine-4-carbonyl)-1H-indole-2-carboxamido)ethyl)carbamate (30 mg, 72 µmol) (prepared in Example 48) was deprotected following General Procedure F to afford a white powder, and used directly without further purification. The powder so formed was reacted with triethylamine (60 µL, 0.43 mmol) and 2-isothiocyanato-4,5-dimethoxybenzonitrile (16 mg, 72 µmol) according to General Procedure C to afford BT2082 (31 mg, 80%) as a white solid. $^1$H NMR (DMSO-$d_6$, 400 MHz) δ 11.94 (s, 1H), 11.76 (s, 1H), 9.13 (s, 1H), 8.68 (s, 1H), 7.70 (s, 1H), 7.60 (s, 1H), 7.45 (d, J=8.3 Hz, 1H), 7.23 (d, J=8.3 Hz, 1H), 7.12 (s, 1H), 6.83 (s, 1H), 4.96-4.82 (m, 2H), 3.82 (s, 3H), 3.79 (s, 3H), 3.76-3.70 (m, 2H), 3.66-3.48 (m, 8H); (+)-LRESIMS m/z (rel. int.) 537 (100) [M+H]$^+$; (+)-HRESIMS calcd. for $C_{26}H_{29}N_6O_5S$ [M+H]$^+$ 537.1915, found 537.1920; $v_{max}$ 3213, 1622, 1557, 1514, 1436, 1280, 1016, 756, 580 cm$^{-1}$.

Synthesis Example 50—BT2083

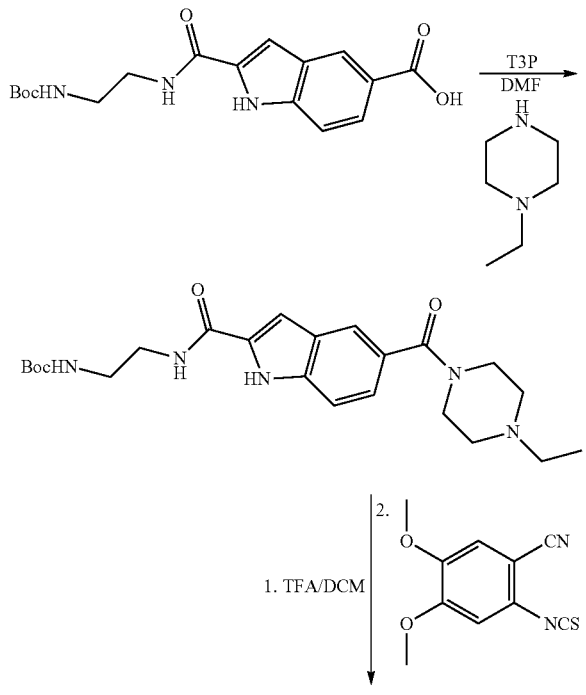

-continued

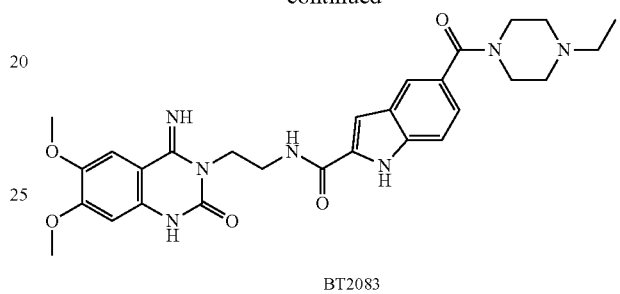

BT2083 tert-Butyl (2-(5-(4-ethylpiperazine-1-carbonyl)-1H-indole-2-carboxamido)ethyl)carbamate was prepared according to the General Procedure G from 2-((2-((tert-butoxycarbonyl)amino)ethyl)carbamoyl)-1H-indole-5-carboxylic acid (100 mg, 0.29 mmol) and 1-ethylpiperazine (36 µL, 0.29 mmol). The residue obtained after concentration in vacuo, was subjected to flash column chromatography [silica, 1:10 v/v ammoniacal MeOH/DCM elution] to give, after concentration of the appropriate fractions the desired amide (36 mg, 29%) as a white powder. $^1$H NMR (DMSO-$d_6$, 400 MHz) δ 11.77 (s, 1H), 8.54 (t, J=5.6 Hz, 1H), 7.67 (s, 1H), 7.45 (d, J=8.4 Hz, 1H), 7.20 (dd, J=8.4, 1.6 Hz, 1H), 7.15 (s, 1H), 6.92 (t, J=5.8 Hz, 1H), 3.61-3.43 (m, 4H), 3.35-3.28 (m, 2H), 3.12 (app. q, J=6.4 Hz, 2H), 2.43-2.30 (m, 4H), 2.36 (q, J=7.1 Hz, 2H) 1.38 (s, 9H), 1.00 (t, J=7.1 Hz, 3H); (+)-LRESIMS m/z (rel. int.) 444 (100) [M+H]$^+$; (+)-HRESIMS calcd. for $C_{23}H_{34}N_5O_4$ [M+H]$^+$ 444.2605, found 444.2607; $v_{max}$ 1704, 1621, 1556, 1424, 1324, 1299, 1252, 1166 cm$^{-1}$. The Boc-protected compound formed directly above (35 mg, 79 µmol) was deprotected following General Procedure F to afford a white powder, and used directly without further purification. The powder so formed was reacted with triethylamine (88 µL, 0.63 mmol) and 2-isothiocyanato-4,5-dimethoxybenzonitrile (17 mg, 79 µmol) according to General Procedure C to afford BT2083 (20 mg, 80%) as a beige solid. $^1$H NMR (DMSO-$d_6$, 400 MHz) δ 11.94 (s br, 1H), 11.75 (s, 1H), 9.13 (s br, 1H), 8.68 (s br, 1H), 7.66 (s, 1H), 7.60 (s, 1H), 7.44 (d, J=8.3 Hz, 1H), 7.20 (d, J=8.3 Hz, 1H), 7.11 (s, 1H), 6.83 (s, 1H), 4.95-4.79 (m, 2H), 3.81 (s, 3H), 3.79 (s, 3H), 3.74-3.69 (m, 2H), 3.55-3.46 (m, 4H), 2.40-2.34 (m, 4H), 2.35 (q, J=7.1 Hz, 2H), 1.00 (t, J=7.1 Hz, 3H); (+)-LRESIMS m/z (rel. int.) 564 (100) [M+H]$^+$; (+)-HRESIMS calcd. for $C_{28}H_{33}N_7O_4S$ [M+H]$^+$ 564.2387, found 564.2393; $v_{max}$ 3197, 1629, 1563, 1549, 1514, 1279, 1016, 754 cm$^{-1}$.

Synthesis Example 51—BT2084

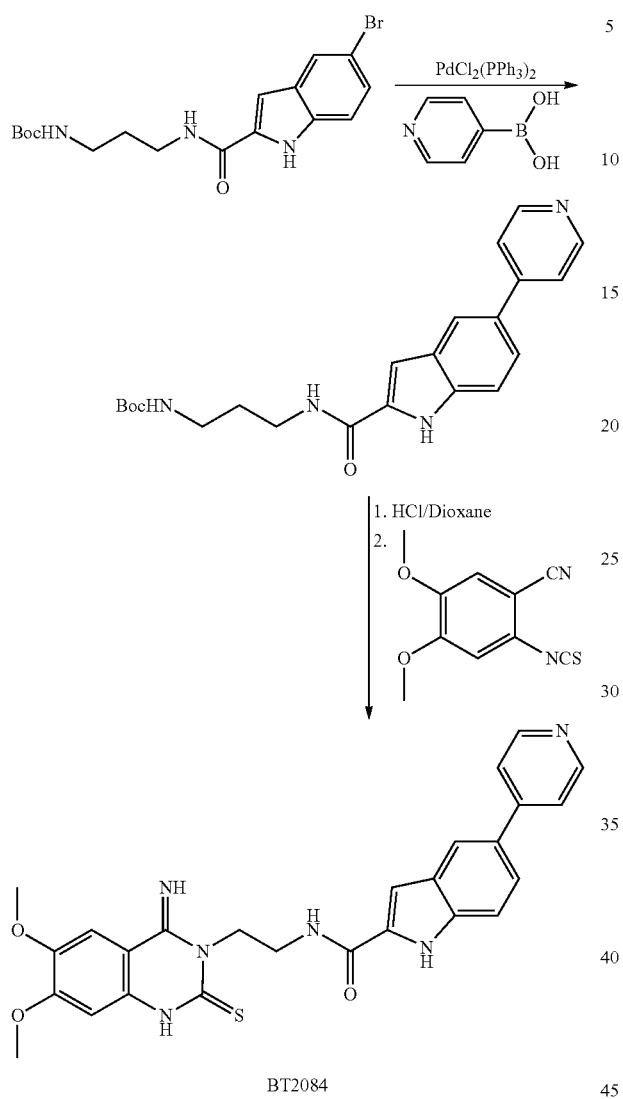

BT2084 tert-Butyl (2-(5-(pyridin-4-yl)-1H-indole-2-carboxamido)ethyl)carbamate was prepared and purified according to General Procedure D from reaction of pyridine-4-boronic acid (48 mg, 0.39 mmol) and tert-butyl (2-(5-bromo-1H-indole-2-carboxamido)ethyl)carbamate (100 mg, 0.26 mmol) to afford the desired product (30 mg, 30%) as a white powder. $^1$H NMR (DMSO-$d_6$, 400 MHz) δ 11.77 (s, 1H), 8.63-8.55 (m, 3H), 8.11 (s, 1H), 7.73 (d, J=5.8 Hz, 2H), 7.63 (dd, J=8.6, 1.5 Hz, 1H), 7.55 (d, J=8.6 Hz, 1H), 7.21 (s, 1H), 6.94 (t, J=5.3 Hz, 1H), 3.37-3.30 (m, 2H), 3.18-3.10 (m, 2H), 1.38 (s, 9H); $^{13}$C NMR (DMSO-$d_6$, 100 MHz) 2C obscured by DMSO-$d_6$ δ 161.0, 155.7, 150.0 (2C), 148.1, 136.9, 132.9, 128.8, 127.7, 122.2, 121.1 (2C), 120.1, 113.0, 103.1, 77.7, 28.2 (3C); (+)-LRESIMS m/z (rel. int.) 381 (100) [M+H]$^+$; (+)-HRESIMS calcd. for $C_{21}H_{25}N_4O_3$ [M+H]$^+$ 381.1921, found 381.1925. The Boc-protected compound (50 mg, 0.13 mmol) was deprotected following General Procedure F to afford a white powder, and used directly without further purification. The powder so formed was reacted with triethylamine (109 μL, 0.79 mmol) and 2-isothiocyanato-4,5-dimethoxybenzonitrile (29 mg, 0.13 mmol) according to General Procedure C to afford BT2084 (52 mg, 79%) as a beige solid. 1H NMR (DMSO-$d_6$, 400 MHz) 1H obscured or overlapping δ 11.75 (s, 1H), 9.09 (s, 1H), 8.76 (s, 1H), 8.59 (d, J=4.8 Hz, 2H), 8.09 (s, 1H), 7.74 (d, J=4.8 Hz, 2H), 7.63 (d, J=8.3 Hz, 1H), 7.60 (s, 1H), 7.53 (d, J=8.3 Hz, 1H), 7.17 (s, 1H), 6.83 (s, 1H), 4.97-4.83 (m, 2H), 3.82 (s, 3H), 3.79 (s, 3H), 3.76-3.68 (m, 2H); (+)-LRESIMS m/z (rel. int.) 501 (100) [M+H]$^+$; $v_{max}$ 3194, 1622, 1626, 1597, 1562, 1558, 1538 cm$^{-1}$.

Synthesis Example 52—BT2085

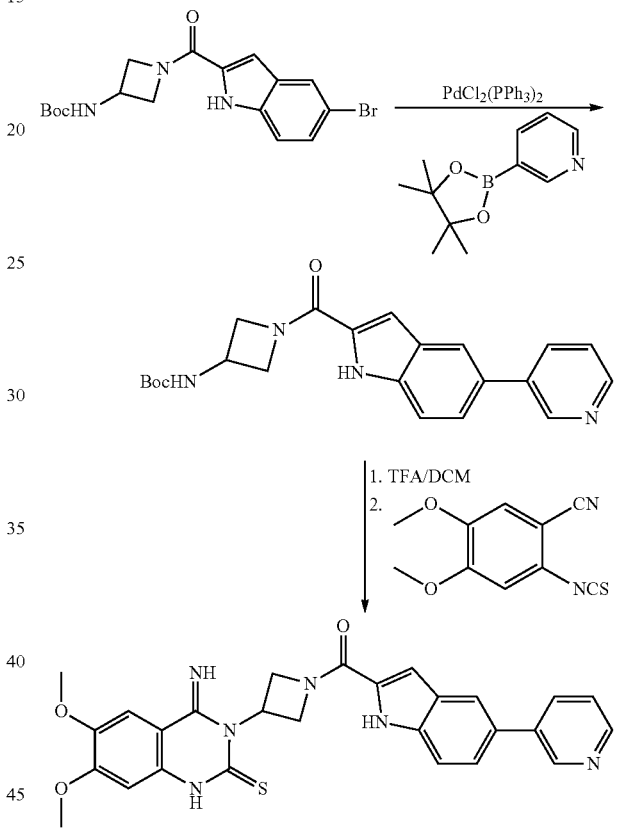

BT2085 tert-Butyl (1-(5-(pyridin-3-yl)-1H-indole-2-carbonyl)azetidin-3-yl)carbamate was prepared according to General Procedure D from reaction of 3-pyridylboronic acid pinacol ester (80 mg, 0.39 mmol) and tert-butyl (1-(5-bromo-1H-indole-2-carbonyl)azetidin-3-yl)carbamate (100 mg, 0.25 mmol) to afford after flash column chromatography [silica, 1:10 v/v ammoniacal MeOH/DCM elution] and concentration of the appropriate fractions the desired compound (35 mg, 30%) as a white powder. $^1$H NMR (DMSO-$d_6$, 400 MHz) δ 11.76 (s, 1H), 8.90 (d, J=2.4 Hz, 1H), 8.53 (dd, J=4.8, 1.7 Hz, 1H), 8.07 (dt, J=7.9, 1.7 Hz, 1H), 7.97 (s, 1H), 7.67 (d, J=7.4 Hz, 1H), 7.62-7.52 (m, 2H), 7.47 (dd, J=7.9, 4.8 Hz, 1H), 6.88 (s, 1H), 4.81-4.71 (m, 1H), 4.54-4.40 (m, 1H), 4.39-4.27 (m, 2H), 4.00-3.91 (m, 1H), 1.41 (s, 9H); (+)-LRESIMS m/z (rel. int.) 393 (100) [M+H]$^+$; (+)-HRESIMS calcd. for $C_{22}H_{25}N_4O_3$ [M+H]+ 393.1921, found 393.1930; $v_{max}$ 3363, 3223, 1682, 1604, 1527, 1455, 1353, 1270, 1169, 877, 793, 767, 641 cm$^{-1}$. The Boc-protected compound (152 mg, 0.39 mmol) was deprotected following General Procedure F to afford a hygroscopic cream coloured viscous paste, and used directly without further purification. The product so formed was reacted with triethylamine (431 µL, 3.09 mmol) and 2-isothiocyanato-4,5-dimethoxybenzonitrile (85 mg, 0.39 mmol) according to General Procedure C to afford BT2085 (138 mg, 70%) as a cream solid. $^1$H NMR (DMSO-$d_6$, 400 MHz) 1H obscured or overlapping δ 12.08 (s, 1H), 11.75 (s, 1H), 9.34 (s, 1H), 8.90 (d, J=1.9 Hz, 1H), 8.51 (dd, J=4.6, 1.1 Hz, 1H) 8.06 (dt, J=8.1, 1.9 Hz, 1H), 7.99 (s, 1H), 7.62-7.53 (m, 3H), 7.46 (dd, J=8.0, 4.6 Hz, 1H), 6.87 (d, J=1.9 Hz, 1H), 6.81 (s, 1H), 5.98-5.90 (m, 1H), 5.02-4.98 (m, 1H), 4.89-4.81 (m, 1H), 4.67-4.59 (m, 1H), 4.44-4.34 (m, 1H), 3.80 (s, 3H), 3.78 (s, 3H); (+)-LRESIMS m/z (rel. int.) 513 (100) [M+H]$^+$; (+)-HRESIMS calcd. for $C_{27}H_{25}N_6O_3S$ [M+H]$^+$ 513.1703, found 513.1702; $v_{max}$ 1623, 1596, 1537, 1514, 1447, 1433, 1389, 1283, 1253, 1235, 1206, 1132, 1011, 791, 730 626 cm$^{-1}$.

Synthesis Example 53—BT2100

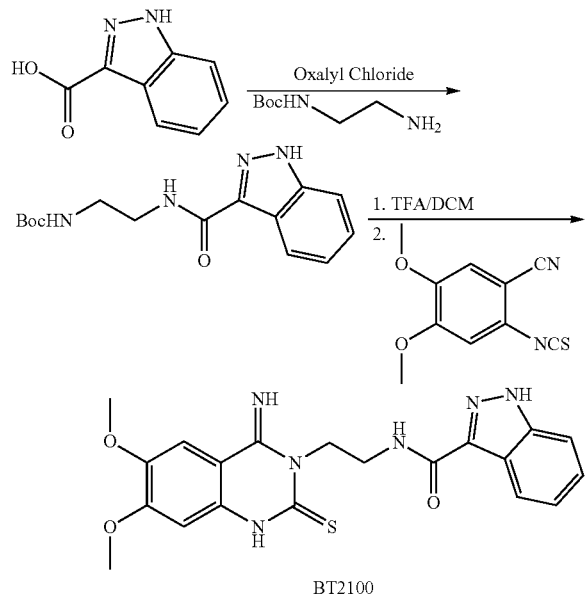

BT2100

A magnetically stirred mixture of 1H-indazole-3-carboxylic acid (100 mg, 0.62 mmol) in DMF (5 mL) was treated sequentially with N-(3-dimethylaminopropyl)-N'-ethylcarbodiimide hydrochloride (EDC) (142 mg, 0.74 mmol), 1-hydroxybenzotriazole hydrate (100 mg, 0.74 mmol) and triethylamine (103 µL, 0.74 mmol) and stirred at rt 0.5 h. tert-Butyl (2-aminoethyl)carbamate (118 mg, 0.74 mmol) was added and the mixture stirred for 60 h then concentrated in vacuo and purified by flash column chromatography [silica, 1:20 v/v MeOH/DCM elution] to give, after concentration of the appropriate fractions, tert-butyl (2-(1H-indazole-3-carboxamido)ethyl)carbamate (32 mg, 14%) as a white powder. $^1$H NMR (400 MHz, Chloroform-d) δ 10.65 (s, 1H), 8.40 (dt, J=8.2, 1.1 Hz, 1H), 7.56 (br s, 1H), 7.53 (d, J=8.4 Hz, 1H), 7.44 (ddd, J=8.4, 6.9, 1.0 Hz, 1H), 7.30 (ddd, J=7.9, 6.9, 1.0 Hz, 1H), 5.06-4.94 (m, 1H), 3.64 (app. q, J=6.1 Hz, 2H), 3.44 (app. q, J=6.0 Hz, 2H), 1.42 (s, 9H); (+)-LRESIMS m/z (rel. int.) 305 (30) [M+H]$^+$, 327 (100) [M+Na]$^+$, 631 (40) [2M+Na]$^+$. The Boc-protected compound formed directly above (32 mg, 0.11 mmol) was deprotected following General Procedure F with TFA (1.0 mL) and DCM (4.0 mL) to afford after trituration with ether (10 mL) TFA salt of N-(2-aminoethyl)-1H-indazole-3-carboxamide as a gum that was used directly in the next step without further purification. The amine TFA-salt (0.11 mmol) was then suspended in ethanol (5 mL) and treated with triethylamine (175 µL, 1.26 mmol) and magnetically stirred for 5 min. The reaction mixture was then treated with a solution of 2-isothiocyanato-4,5-dimethoxybenzonitrile (23 mg, 0.11 mmol) in DCM (3 mL). The mixture was then stirred for 1 h followed by stirring at 75° C. for 1 h. The reaction mixture was cooled and then the precipitate was collected by vacuum filtration and washed with ether (5 mL) to afford BT2100 (24 mg, 51%) as a pale-yellow solid. $^1$H NMR (400 MHz, DMSO-$d_6$) δ 13.48 (s, 1H), 11.95 (s, 1H), 9.12 (s, 1H), 8.51 (s, 1H), 8.13 (d, J=8.6 Hz, 1H), 7.67-7.54 (m, 2H), 7.45-7.33 (m, 1H), 7.28-7.18 (m, 1H), 6.83 (s, 1H), 4.98-4.84 (m, 2H), 3.81 (s, 3H), 3.78 (s, 3H), 3.73-3.78 (m, 2H); (+)-LRESIMS m/z (rel. int.) 425 (100) [M+H]$^+$, $v_{max}$ 2134, 1684, 1647, 1560, 1532, 1500, 1438, 1401, 1233, 1211, 1159, 1211, 1159, 1063 cm$^{-1}$.

Synthesis Example 54—BT2103

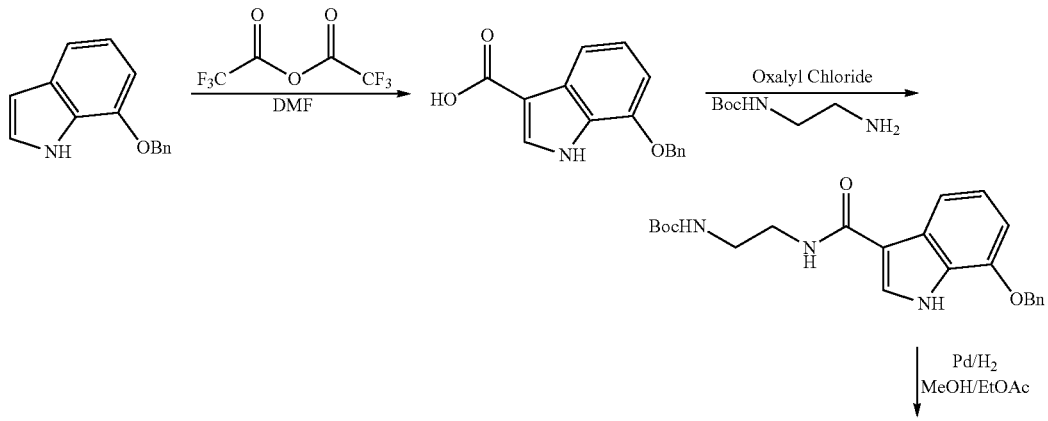

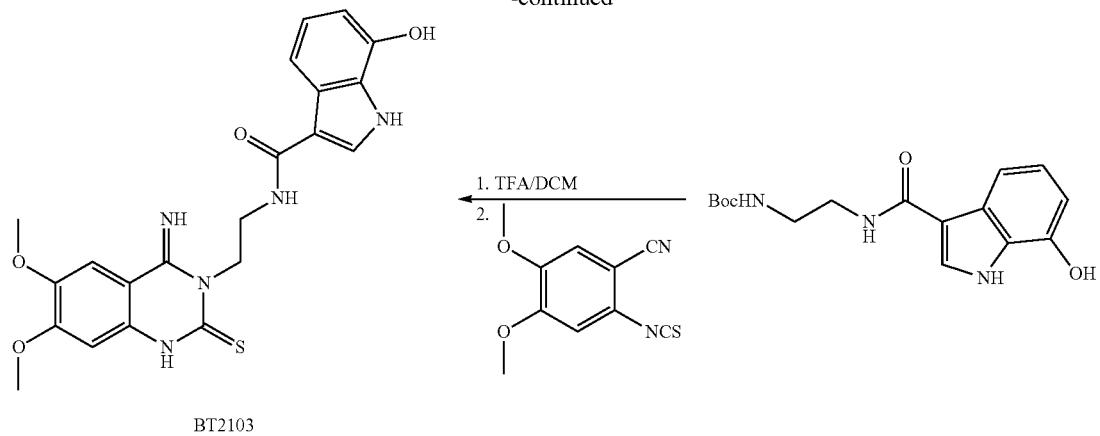

BT2103

7-(benzyloxy)-1H-indole-3-carboxylic acid

A magnetically stirred solution of 7-(benzyloxy)-1H-indole (2.0 g, 8.9 mmol) in anhydrous DMF (8 mL) maintained at 0° C. under an atmosphere of nitrogen was treated with trifluoroacetic acid anhydride (1.8 mL, 12.7 mmol) dropwise over 0.17 h. The mixture was then stirred for 2 h and poured into water (150 mL) and stirred vigorously for 0.17 h. The solid was collected by vacuum filtration and added to flask containing an aqueous solution of sodium hydroxide (50 mL, 4M) and refluxed for 2 h. The mixture was cooled over 18 h then diluted with water (150 mL) and extracted with ether (2×50 mL). The aqueous layer was then acidified to pH 0-1 with aqueous HCl (6M) and the precipitate collected by vacuum filtration and held under high vacuum for several hours to afford 7-(benzyloxy)-1H-indole-3-carboxylic acid as a brown powder (1.43 g, 60%) and used without further purification. $^1$H NMR (400 MHz, DMSO-$d_6$) δ 12.00 (s, 1H), 11.92 (s, 1H), 7.85 (d, J=3.1 Hz, 1H), 7.61-7.55 (m, 3H), 7.44-7.38 (m, 2H), 7.36-7.31 (m, 1H), 7.05 (t, J=7.8 Hz, 1H), 6.84 (d, J=7.8 Hz, 1H), 5.28 (s, 2H); $^{13}$C NMR (100 MHz, DMSO-$d_6$) δ 165.9, 145.3, 137.1, 131.5, 128.4 (2C), 127.8, 127.7, 127.6 (2C), 126.7, 121.6, 113.4, 108.0, 104.1, 69.3; (+)-LRESIMS m/z (rel. int.) 290 (100) [M+Na]$^+$, 557 (90) [2M+Na]$^+$; $v_{max}$ 3427, 1652, 1629, 1529, 1506, 1276, 1251, 1194, 1090, 1004, 759 cm$^{-1}$.

tert-butyl (2-(7-(benzyloxy)-1H-indole-3-carboxamido)ethyl)carbamate

Following a procedure analogous to General Procedure H, 7-(benzyloxy)-1H-indole-3-carboxylic acid (300 mg, 1.12 mmol) was converted to 7-(benzyloxy)-1H-indole-3-carbonyl chloride with oxalyl chloride (118 μL, 1.40 mmol) and reacted with tert-butyl (2-aminoethyl)carbamate (180 mg, 1.12 mmol) to afford tert-butyl (2-(7-(benzyloxy)-1H-indole-3-carboxamido)ethyl)carbamate (252 mg, 55%) as a tan solid. $^1$H NMR (400 MHz, DMSO-$d_6$) δ 11.65 (s, 1H), 7.91 (d, J=2.7 Hz, 1H), 7.87 (app. t, J=5.3 Hz, 1H), 7.71 (d, J=8.0 Hz, 1H), 7.57 (d, J=7.3 Hz, 2H), 7.41 (t, J=7.3 Hz, 2H), 7.37-7.32 (m, 1H), 6.99 (t, J=8.0 Hz, 1H), 6.89 (t, J=5.4 Hz, 1H), 6.80 (d, J=8.0 Hz, 1H), 5.26 (s, 2H), 3.27 (app. q, J=6.2 Hz, 2H), 3.09 (app. q, J=6.2 Hz, 2H), 1.38 (s, 9H); $^{13}$C NMR (100 MHz, DMSO-$d_6$) one $\underline{C}$H$_2$N obscured by DMSO-$d_6$ δ 164.7, 155.7, 145.1, 137.2, 128.4 (2C), 127.8, 127.8, 127.6 (2C), 127.3, 126.4, 120.8, 113.9, 111.1, 103.6, 77.6, 69.2, 38.8, 28.2 (3C). (+)-LRESIMS m/z (rel. int.) 432 (100) [M+Na]$^+$; $v_{max}$ 3296, 1695, 1614, 1537, 1437, 1284, 1215, 1170, 785, 723, 689 cm$^{-1}$.

tert-butyl (2-(7-hydroxy-1H-indole-3-carboxamido)ethyl)carbamate

A mixture of tert-butyl (2-(7-(benzyloxy)-1H-indole-3-carboxamido)ethyl)carbamate (200 mg, 0.49 mmol) and 10% palladium on carbon (10 mg), in a mixture of methanol (15 mL) and ethyl acetate (5 mL) was stirred under a balloon of hydrogen for 2 h. The mixture was treated with celite (5 mL) and then the reaction mixture filtered and the celite washed with EtOAc (10 mL). The filtrate was concentrated in vacuo to afford a residue that was purified by flash column chromatography [silica, 1:10 v/v MeOH/DCM elution] to give, after concentration of the appropriate fractions the debenzylated product as a tan powder (140 mg, 90%). $^1$H NMR (400 MHz, DMSO-$d_6$) δ 11.41 (s, 1H), 9.70 (s, 1H), 7.89-7.82 (m, 1H), 7.80 (t, J=5.6 Hz, 1H), 7.55 (d, J=8.0 Hz, 1H), 6.91-6.87 (m, 1H), 6.86 (dd, J=9.3, 6.6 Hz, 1H), 6.54 (d, J=7.5 Hz, 1H), 3.26 (app. q, J=6.5 Hz, 2H), 3.09 (app. q, J=6.5 Hz, 2H), 1.38 (s, 9H); (+)-LRESIMS m/z (rel. int.) 342 (100) [M+Na]$^+$; $v_{max}$ 3345, 3270, 1688, 1601, 1601, 1550, 1524, 1449, 1242, 1157, 630 cm$^{-1}$. The product formed directly above (140 mg, 0.44 mmol) was deprotected at 0° C. using a method analogous to General Procedure F to afford the deprotected, TFA-salt as a brown paste that was used without further purification. The TFA salt was then dissolved in ethanol (8 mL) and treated with triethylamine (244 μL, 1.76 mmol) and magnetically stirred for 5 min then treated with a solution of 2-isothiocyanato-4,5-dimethoxybenzonitrile (97 mg, 0.44 mmol) in DCM (3 mL). The mixture was then stirred for 1 h at rt and then heated to 72° C. and stirred for 1 h. The precipitate was collected by vacuum filtration which was washed with ether (5 mL) to afford BT2103 (102 mg, 53%) as a tan powder. (+)-LRESIMS m/z (rel. int.) 440 (100) [M+H]$^+$, 462 [M+Na]$^+$; $v_{max}$ 1614, 1583, 1505, 1440, 1293, 1233, 1175, 1073, 1046, 989, 736 cm$^{-1}$. $^1$H NMR analyses of BT2103 resulted in severe broadening. To overcome this, the trifluoroacetic acid salt of BT2103 was prepared. Accordingly, a portion of BT2103 (20 mg) suspended in CDCl$_3$ (1 mL) was treated with TFA (100 μL) and then after 1 min the solution was concentrated under a gentle stream of N$_2$ to furnish the TFA salt as a tan powder. $^1$H NMR (400 MHz, DMSO-$d_6$) δ 13.75 (s, 1H), 11.65 (d, J=3.1 Hz, 1H), 10.90 (s, 1H), 10.59 (s, 1H), 10.34-9.06 (br s, 1H), 8.74 (t, J=5.6 Hz, 1H), 7.94 (d, J=3.1

Hz, 1H), 7.77 (s, 1H), 7.51 (d, J=8.0 Hz, 1H), 6.96 (s, 1H), 6.90 (t, J=8.0 Hz, 1H), 6.58 (d, J=7.5 Hz, 1H), 5.74-4.95 (br m, 2H), 3.91 (s, 3H), 3.86 (s, 3H), 3.64 (app. q, J=7.1 Hz, 2H); $^{13}$C NMR (DMSO-d$_6$, 100 MHz) δ 171.3, 167.6, 158.4 (q, $^2J_{C-F}$=35.6 Hz), 157.2, 155.4, 147.7, 143.9, 135.2, 128.3, 127.7, 126.3, 121.6, 116.0 (q, $^1J_{C-F}$=292.8 Hz), 111.5, 109.3, 106.5, 105.1, 102.4, 97.8, 56.4, 56.4, 47.8, 34.7.

Synthesis Example 55—BT2104

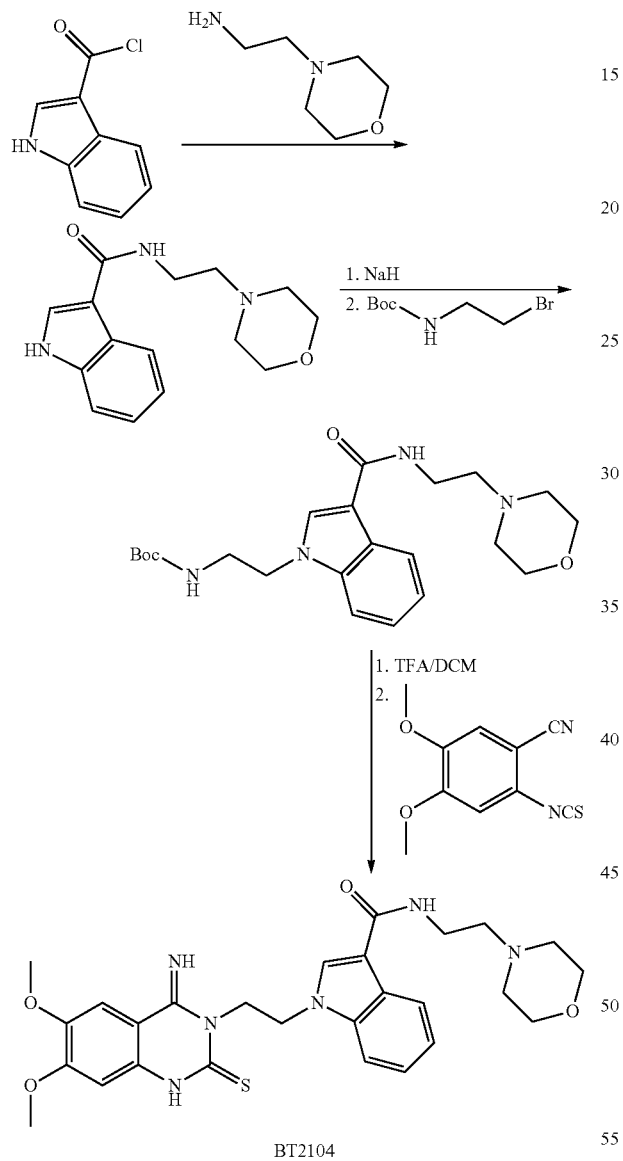

BT2104

N-(2-morpholinoethyl)-1H-indole-3-carboxamide

Following General Procedure H, 1H-indole-3-carbonyl chloride (499 mg, 2.78 mmol) was reacted with 2-morpholinoethan-1-amine (361 mg, 2.78 mmol) to afford N-(2-morpholinoethyl)-1H-indole-3-carboxamide (442 mg, 58%) as a cream solid and used without further purification. $^1$H NMR (400 MHz, DMSO-d$_6$) δ 11.51 (s, 1H), 8.14-8.09 (m, 1H), 7.97 (s, 1H), 7.78 (t, J=5.7 Hz, 1H), 7.43-7.39 (m, 1H), 7.16-7.06 (m, 2H), 3.60-3.56 (m, 4H), 3.38 (q, J=6.6 Hz, 2H), 2.49-2.40 (m, 6H); (+)-LRESIMS m/z (rel. int.) 274 (100) [M+H]$^+$, 296 (80) [M+Na]$^+$; v$_{max}$ 3379, 2818, 1635, 1546, 1525, 1212, 1114, 1005, 866, 800, 753 cm$^{-1}$.

tert-butyl (2-(3-((2-morpholinoethyl)carbamoyl)-1H-indol-1-yl)ethyl)carbamate

A magnetically stirred solution of N-(2-morpholinoethyl)-1H-indole-3-carboxamide (150 mg, 0.55 mmol) in DMF at 0° C. was treated in one portion with sodium hydride (26 mg, 0.66 mmol, 60% dispersion in mineral oil) and stirred for 1 h at rt. tert-Butyl (2-bromoethyl)carbamate (122 mg, 0.55 mmol) was added and the mixture stirred for 24 h at rt. The mixture was then quenched by the addition of methanol (1 mL) and concentrated in vacuo to afford a residue which was subjected to flash column chromatography [silica, 1:10 v/v MeOH/DCM elution] to give, after concentration of the appropriate fractions tert-butyl (2-(3-((2-morpholinoethyl)carbamoyl)-1H-indol-1-yl)ethyl)carbamate (65 mg, 28%) as a white foam. $^1$H NMR (400 MHz, Chloroform-d) δ 8.01-7.93 (m, 1H), 7.72 (s, 1H), 7.47-7.39 (m, 1H), 7.33-7.22 (m, 2H), 6.77 (t, J=4.8 Hz, 1H), 4.90 (t, J=6.2 Hz, 1H), 4.29 (t, J=6.1 Hz, 2H), 3.75 (t, J=4.6 Hz, 4H), 3.57 (q, J=5.6 Hz, 2H), 3.49 (q, J=6.1 Hz, 2H), 2.62 (t, J=6.0 Hz, 2H), 2.53 (t, J=4.6 Hz, 4H), 1.43 (s, 9H); (+)-LRESIMS m/z (rel. int.) 417 (100) [M+H]$^+$, 439 (80) [M+Na]$^+$; v$_{max}$ 3371, 1680, 1611, 1539, 1517, 1392, 1286, 1115, 984, 859, 751 cm$^{-1}$.

BT2104 tert-Butyl (2-(3-((2-morpholinoethyl)carbamoyl)-1H-indol-1-yl)ethyl)carbamate (60 mg, 0.14 mmol) was deprotected following General Procedure F to afford a pale-orange oil, and used directly without further purification. The powder so formed was reacted with triethylamine (174 μL, 1.73 mmol) and 2-isothiocyanato-4,5-dimethoxybenzonitrile (32 mg, 0.14 mmol) according to General Procedure C to afford BT2104 (32 mg, 43%) as a cream-coloured powder. $^1$H NMR (400 MHz, DMSO-d$_6$) δ 12.09 (s, 1H), 9.25 (s, 1H), 8.16 (d, J=7.8 Hz, 1H), 8.03 (s, 1H), 7.91 (t, J=5.6 Hz, 1H), 7.87 (d, J=8.2 Hz, 1H), 7.66 (s, 1H), 7.24-7.18 (m, 1H), 7.17-7.12 (m, 1H), 6.86 (s, 1H), 5.03-4.92 (m, 2H), 4.58-4.49 (m, 2H), 3.84 (s, 3H), 3.80 (s, 3H), 3.58 (app. t, J=4.7 Hz, 4H), 3.37 (app. q, J=6.5 Hz, 2H), 2.48-2.40 (m, 6H); (+)-LRESIMS m/z (rel. int.) 537 (100) [M+H]+, 559 (50) [M+Na]$^+$; v$_{max}$ 1615, 1537, 1514, 1438, 1437, 1230, 1113, 1010, 863, 728 cm$^{-1}$.

Synthesis Example 56—BT2105

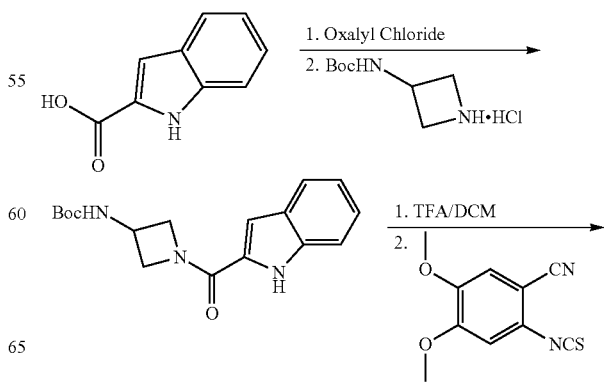

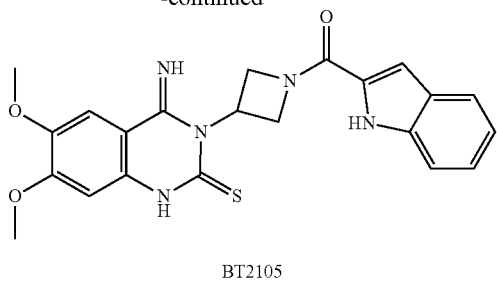

BT2105

Following a procedure analogous to General Procedure H, 1H-indole-2-carboxylic acid (500 mg, 3.10 mmol) was converted to 1H-indole-2-carbonyl chloride with oxalyl chloride (302 μL, 3.57 mmol) and reacted with tert-butyl azetidin-3-ylcarbamate hydrochloride (647 mg, 3.10 mmol) to afford tert-butyl (1-(1H-indole-2-carbonyl)azetidin-3-yl) carbamate (792 mg, 81%) as a white solid. $^1$H NMR (400 MHz, DMSO-d$_6$) δ 11.60 (s, 1H), 7.66 (d, J=7.3 Hz, 1H), 7.62 (d, J=8.0 Hz, 1H), 7.44 (d, J=8.2 Hz, 1H), 7.22-7.16 (m, 1H), 7.04 (t, J=7.3 Hz, 1H), 6.82-6.78 (m, 1H), 4.78-4.68 (m, 1H), 4.50-4.36 (m, 1H), 4.34-4.24 (m, 2H), 3.99-3.87 (m, 1H), 1.40 (s, 9H); $^{13}$C NMR (101 MHz, DMSO-d$_6$) δ 161.5, 154.8, 136.0, 129.2, 127.4, 123.6, 121.7, 119.8, 112.3, 104.4, 78.3, 59.6, 55.6, 40.7, 28.2 (3C). (+)-LRESIMS m/z (rel. int.) 338 (100) [M+Na]$^+$, 653 (80) [2M+Na]$^+$; $v_{max}$ 3229, 1686, 1607, 1530, 1458, 1415, 1345, 1172, 803, 741, 645 cm$^{-1}$. A portion of the Boc-protected compound formed directly above (200 mg, 0.63 mmol) was deprotected following General Procedure F with TFA (1.5 mL) and DCM (4.0 mL) to afford after trituration with ether (10 mL) TFA salt of (3-aminoazetidin-1-yl)(1H-indol-2-yl)methanone as a gum that was used directly in the next step without further purification. $^1$H NMR (400 MHz, DMSO-d$_6$) δ 11.68 (s, 1H), 8.61 (s, 3H), 7.64 (d, J=8.2 Hz, 1H), 7.45 (d, J=8.2 Hz, 1H), 7.21 (t, J=7.3 Hz, 1H), 7.06 (t, J=7.3 Hz, 1H), 6.84 (d, J=1.5 Hz, 1H), 4.87-4.70 (m, 1H), 4.54-4.41 (m, 1H), 4.39-4.25 (m, 1H), 4.22-4.04 (m 2H). A portion of the amine TFA-salt (150 mg, 0.46 mmol) was then suspended in ethanol (18 mL) and treated with triethylamine (380 μL, 2.73 mmol) and magnetically stirred for 5 min. The reaction mixture was then treated with a solution of 2-isothiocyanato-4,5-dimethoxybenzonitrile (100 mg, 0.46 mmol) in DCM (5 mL). The mixture was then stirred for 2 h followed by stirring at 70° C. for 1 h. The reaction mixture was cooled and then the precipitate was collected by vacuum filtration and washed with ether (5 mL) to afford BT2105 (168 mg, 85%) as a white solid. $^1$H NMR (400 MHz, DMSO-d$_6$) δ 11.85 (br s, 1H), 11.59 (s, 1H), 9.34 (s, 1H), 7.63 (d, J=8.0 Hz, 1H), 7.57 (s, 1H), 7.43 (d, J=8.3 Hz, 1H), 7.19 (t, J=7.6 Hz, 1H), 7.04 (t, J=7.6 Hz, 1H), 6.81 (s, 1H), 6.79 (d, J=1.6 Hz, 1H), 6.00-5.87 (m, 1H), 5.04-4.95 (m, 1H), 4.89-4.77 (m, 1H), 4.68-4.56 (m, 1H), 4.43-4.31 (m, 1H), 3.80 (m, 3H), 3.78 (s, 3H). (+)-LRESIMS m/z (rel. int.) 436 (100) [M+H]$^+$; $v_{max}$ 1625, 1596, 1537, 1510, 1434, 1229, 1006, 735 cm$^{-1}$.

Synthesis Example 57—BT2113

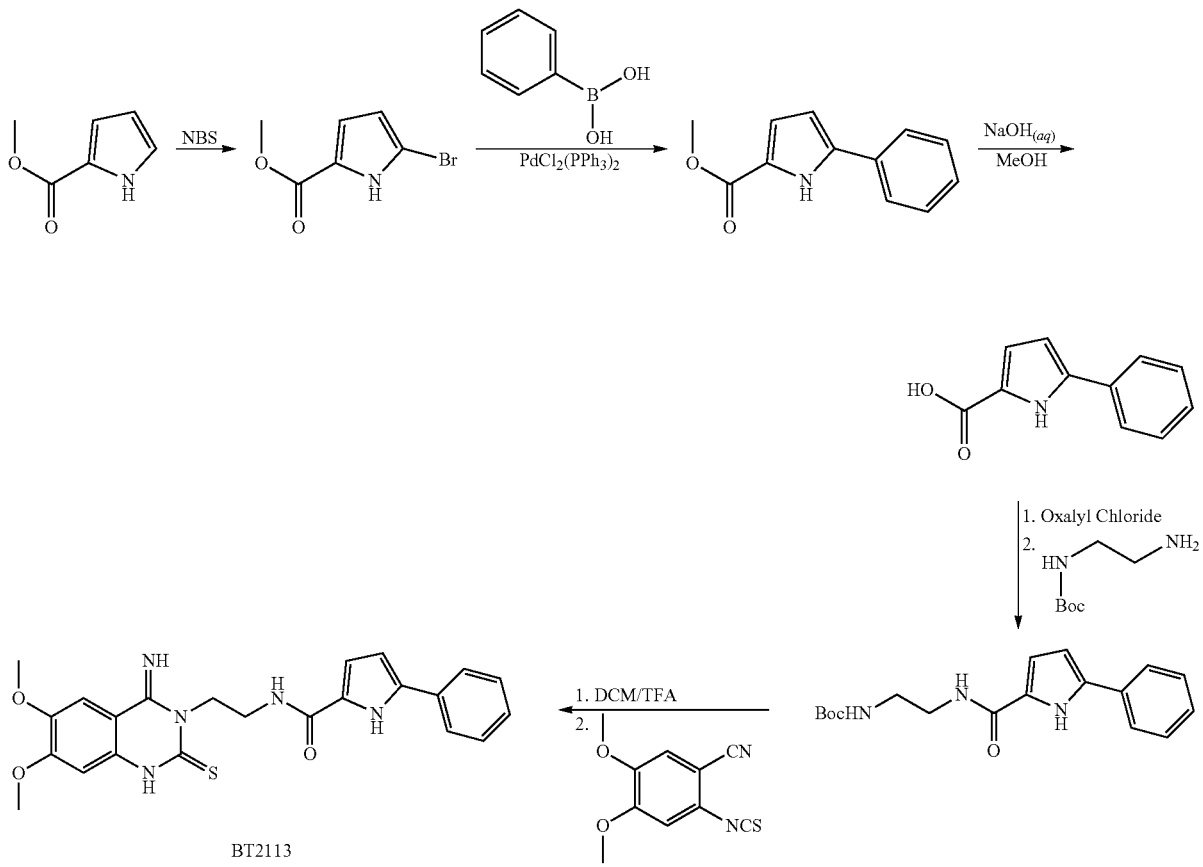

BT2113

Following a procedure analogous to that used by Trost et. al. (*Chem. Eur. J.* 2009, 15, 6910), magnetically stirred solution of methyl 1H-pyrrole-2-carboxylate (1.00 g, 7.99 mmol) in THF (80 mL) and methanol (40 mL) maintained at 0° C. was treated with N-bromosuccinimide (245 mg, 1.38 mmol) and followed by addition of portions of (315 mg, 1.77 mmol), (255 mg, 1.43 mmol), (635 mg, 3.57 mmoL) 0.5 h apart. The mixture was then and held at 2° C. without stirring for 18 h and then concentrated in vacuo and purified by gradient flash column chromatography [silica, 1:10→1:5 v/v EtOAc/pet spirit elution] to give, after concentration of the appropriate fractions, methyl 5-bromo-1H-pyrrole-2-carboxylate (562 mg, 34%) as a white powder. Spectral data were consistent with those reported by Trost et. al. $^1$H NMR (400 MHz, Chloroform-d) δ 9.20 (s, 1H), 6.82 (dd, J=3.9, 2.7 Hz, 1H), 6.22 (dd, J=3.9, 2.7 Hz, 1H), 3.86 (s, 3H).

Methyl 5-bromo-1H-pyrrole-2-carboxylate (147 mg, 0.72 mmol), was subjected to a palladium catalysed Suzuki-Miyaura reaction and reacted with phenylboronic acid (132 mg, 1.08 mmol) according to General Procedure D to afford a residue that was subjected to flash column chromatography [silica, 1:4 ether:pet. spirit elution] to give, after concentration of the appropriate fractions methyl 5-phenyl-1H-pyrrole-2-carboxylate (88 mg, 75%) as a white solid. Obtained spectral data were consistent with those reported by Laha et. al. (Chem. Commun. 2016, 52, 4329). $^1$H NMR (400 MHz, Chloroform-d) δ 9.28 (s, 1H), 7.60-7.54 (m, 2H), 7.46-7.38 (m, 2H), 7.34-7.28 (m, 1H), 6.96 (dd, J=3.9, 2.4 Hz, 1H), 6.55 (dd, J=3.9, 2.7 Hz, 1H), 3.88 (s, 3H); (+)-LRESIMS m/z (rel. int.) 224 (100) [M+Na]$^+$; $v_{max}$ 3291, 1675, 1466, 1441, 1339, 1268, 1152, 1005, 799, 757 cm$^{-1}$. A portion of the above compound, methyl 5-phenyl-1H-pyrrole-2-carboxylate (80 mg, 0.4 mmol) was dissolved in a mixture of methanol (8 mL) and aqueous sodium hydroxide (4 mL, 3M) and held at reflux for 4 h. The clear solution was then neutralised to pH 1 with aqueous HCl (1M) and the mixture extracted with EtOAc (2×15 mL) and DCM (2×15 mL). The EtOAc and DCM extracts were separately washed with brine (10 mL) then combined and dried (Na$_2$SO$_4$). Concentration in vacuo afforded a purple residue (68 mg, 91%) that was used without further purification. $^1$H NMR (400 MHz, DMSO-d$_6$) δ 12.29 (s, 1H), 11.96 (s, 1H), 7.84 (d, J=7.3 Hz, 2H), 7.37 (t, J=7.7 Hz, 2H), 7.27-7.22 (m, 1H), 6.81 (dd, J=3.8, 2.3 Hz, 1H), 6.62 (dd, J=3.8, 2.5 Hz, 1H); (+)-LRESIMS m/z (rel. int.) 186 (100) [M−H]$^-$; $v_{max}$ 3420, 1657, 1561, 1514, 1469, 1435, 1333, 1268, 1040, 910, 765, 749, 691 cm$^{-1}$. A portion of the acid, 5-phenyl-1H-pyrrole-2-carboxylic acid (60 mg, 0.18 mmol) was then converted to its acid chloride with oxalyl chloride (34 μL, 0.40 mmol) and reacted with tert-butyl(2-aminoethyl)carbamate (56 mg, 0.35 mmol according to General Procedure H. The residue obtained after workup, was subjected to flash column chromatography [silica, 1:5 ether:pet. spirit elution] to give, after concentration of the appropriate fractions tert-butyl (2-(5-phenyl-1H-pyrrole-2-carboxamido)ethyl)carbamate (70 mg, 61%) as a white solid. $^1$H NMR (400 MHz, DMSO-d$_6$) δ 11.69 (s, 1H), 8.13 (t, J=4.9 Hz, 1H), 7.79 (app. d, J=7.3 Hz, 2H), 7.41-7.30 (m, 2H), 7.26-7.16 (m, 1H), 6.96-6.88 (m, 1H), 6.80 (d, J=3.8 Hz, 1H), 6.56 (d, J=3.8 Hz, 1H), 3.27 (app. q, J=6.3 Hz, 2H), 3.09 (app. q, J=6.3 Hz, 2H), 1.38 (s, 9H); (+)-LRESIMS m/z (rel. int.) 352 (100) [M+Na]$^+$, 681 (10) [2M+Na]$^+$; $v_{max}$ 3302, 3224, 1695, 1606, 1562, 1537, 1269, 1155, 808, 773 cm$^{-1}$.

A portion of the Boc-protected compound formed directly above (60 mg, 0.18 mmol) was deprotected at rt following General Procedure F with TFA (1.5 mL) and DCM (4.0 mL) to afford after trituration with ether (3×5 mL) to afford the TFA salt of N-(2-aminoethyl)-5-phenyl-1H-pyrrole-2-carboxamide as a sticky gum that was used directly in the next step without further purification. The amine TFA-salt (0.18 mmol) was then suspended in ethanol (4 mL) and treated with triethylamine (304 μL, 2.22 mmol) and magnetically stirred for 5 min. The reaction mixture was then treated with a solution of 2-isothiocyanato-4,5-dimethoxybenzonitrile (40 mg, 0.18 mmol) in DCM (3 mL). The mixture was then maintained with stirring at 70-72° C. for 1 h, cooled to rt and then the precipitate was collected by vacuum filtration and washed with ether (5 mL) to afford BT2113 (62 mg, 77%) as a pale pink powder. $^1$H NMR (400 MHz, DMSO-d$_6$) δ 11.77 (s, 1H), 11.62 (s, 1H), 9.15 (s, 1H), 8.20 (s, 1H), 7.78 (d, J=7.5 Hz, 2H), 7.62 (s, 1H), 7.36 (t, J=7.5 Hz, 2H), 7.21 (t, J=7.2 Hz, 1H), 6.91-6.75 (m, 2H), 6.56 (s, 1H), 4.91-4.76 (m, 2H), 3.82 (s, 3H), 3.79 (s, 3H), 3.71-3.62 (m, 2H); (+)-LRESIMS m/z (rel. int.) 450 (100) [M+Na]$^+$; $v_{max}$ 1611, 1538, 1500, 1436, 1230, 1015, 857, 751 cm$^{-1}$.

Synthesis Example 58—BT2115

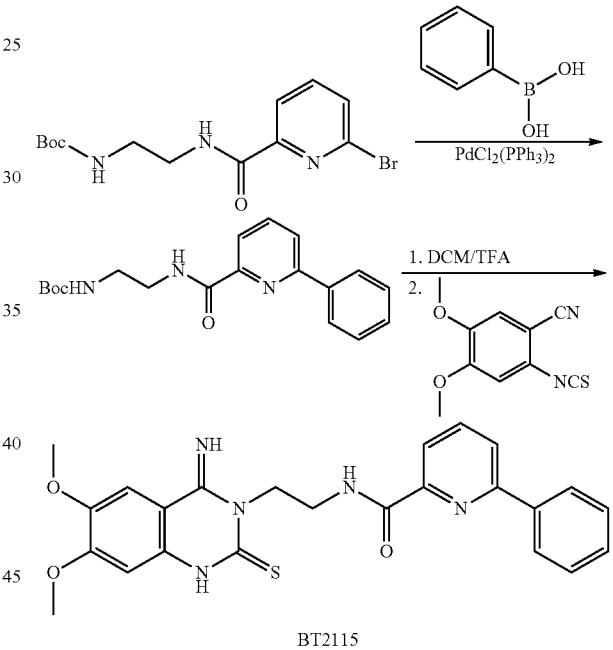

BT2115 tert-Butyl (2-(6-bromopicolinamido)ethyl)carbamate (102 mg, 0.30 mmol), was subjected to a palladium catalysed Suzuki-Miyaura reaction and reacted with phenylboronic acid (55 mg, 0.45 mmol) according to General Procedure D to afford a residue that was subjected to flash column chromatography [silica, 1:10 MeOH:DCM] to give, after concentration of the appropriate fractions tert-butyl (2-(6-phenylpicolinamido)ethyl)carbamate (76 mg, 75%) as a white solid. $^1$H NMR (400 MHz, Chloroform-d) δ 8.66-8.55 (m 1H), 8.14 (dd, J=7.6, 0.6 Hz, 1H), 8.11-8.04 (m, 2H), 7.92 (t, J=7.6 Hz, 1H), 7.87 (dd, J=7.9, 1.3 Hz, 1H), 7.56-7.41 (m, 3H), 5.04-4.95 (m, 1H), 3.64 (app. q, J=5.9 Hz, 2H), 3.43 (app. q, J=5.5 Hz, 2H), 1.41 (s, 9H); (+)-LRESIMS m/z (rel. int.) 364 (100) [M+Na]$^+$; $v_{max}$ 3384, 1676, 1513, 1249, 1162, 747 cm$^{-1}$. A portion of the Boc-protected compound formed directly above (41 mg, 0.12 mmol) was deprotected following General Procedure F with TFA (1.5 mL) and DCM (4.0 mL) to afford a clear glass that on trituration with ether afforded a white gum that was used directly without further purification. $^1$H NMR (400 MHz, DMSO-$d_6$) δ 9.08 (app. t, J=6.1 Hz, 1H), 8.34-8.29 (m, 2H), 8.21 (dd, J=7.8, 0.9 Hz, 1H), 8.09 (t, J=7.8 Hz, 1H), 8.01 (dd, J=7.8, 0.8 Hz, 1H), 7.84 (br s, 3H) 7.59-7.46 (m, 3H), 3.62 (app. q, J=6.2 Hz, 2H), 3.10-3.02 (m, 2H); LRESIMS m/z (rel. int.) 242 (100) [M+H]; The TFA-salt (0.12 mmol) was then suspended in ethanol (5 mL) and treated with triethylamine (244 μL, 1.20 mmol) and magnetically stirred for 5 min. The reaction was then treated with a solution of 2-isothiocyanato-4,5-dimethoxybenzonitrile (26 mg, 0.12 mmol) in DCM (2 mL). The mixture was then stirred for 1 h at rt then heated to 70° C. and stirred for 2 h. The precipitate was collected by vacuum filtration and then washed with ether (5 mL) to afford BT2115 (35 mg, 63%) as a white solid. $^1$H NMR (400 MHz, DMSO-$d_6$) δ 11.98 (br s, 1H), 9.10-9.02 (m, 2H), 8.34-8.22 (m, 2H), 8.16 (d, J=7.8 Hz, 1H), 8.04 (app. t, J=7.7 Hz, 1H), 7.94 (d, J=6.8 Hz, 1H), 7.58 (s, 1H), 7.56-7.46 (m, 3H), 6.82 (s, 1H), 5.05-4.93 (m, 2H), 3.86-3.80 (m, 2H), 3.80 (s, 3H), 3.78 (s, 3H). (+)-LRESIMS m/z (rel. int.) 462 (100) [M+H]$^+$; $v_{max}$ 1653, 1628, 1526, 1512, 1434, 1275, 1230 1014, 862, 756, 697 cm$^{-1}$.

Synthesis Example 59—BT2116 and BT2130 tert-Butyl (2-(6-bromopicolinamido)ethyl)carbamate (103 mg, 0.30 mmol), was subjected to a palladium catalysed Suzuki-Miyaura reaction and reacted with [4-(4-Methylpiperazine-1-carbonyl)phenyl]boronic acid pinacol ester (148 mg, 0.45 mmol) according to General Procedure D to afford a residue that was subjected to flash column chromatography [silica, 1:10 ammoniacal MeOH:DCM] to give, after concentration of the appropriate fractions the desired product (113 mg, 54%) as an amber glass. $^1$H NMR (400 MHz, DMSO-$d_6$) δ 9.01 (t, J=5.8 Hz, 1H), 8.40 (d, J=8.0 Hz, 2H), 8.22 (d, J=7.8 Hz, 1H), 8.09 (t, J=7.8 Hz, 1H), 8.01 (d, J=7.6 Hz, 1H), 7.51 (d, J=8.0 Hz, 2H), 7.02 (t, J=5.7 Hz, 1H), 3.70-3.57 (m, 2H), 3.40 (app. q, J=5.7 Hz, 2H), 3.38-3.33 (m, 2H), 3.18 (app. q, J=5.4 Hz, 2H), 2.45-2.23 (m, 4H), 2.20 (s, 3H), 1.35 (s, 9H). (+)-LRESIMS m/z (rel. int.) 468 (20) [M+H]$^+$, 490 (100) [M+Na]$^+$; $v_{max}$ 3373, 2806, 1707, 1682, 1627, 1517, 1448, 1422, 1268, 1169, 832 cm$^{-1}$. A portion of the Boc-protected compound formed directly above (67 mg, 0.14 mmol) was deprotected following General Procedure F with TFA (1.5 mL) and DCM (4.0 mL) to afford a white paste after trituration with ether (10 mL) that was used directly without further purification. LRESIMS m/z (rel. int.) 368 (100) [M+H]$^+$. The TFA-salt formed directly above (0.14 mmol) was then suspended in ethanol (5 mL) and treated with triethylamine (156 μL, 1.12 mmol)

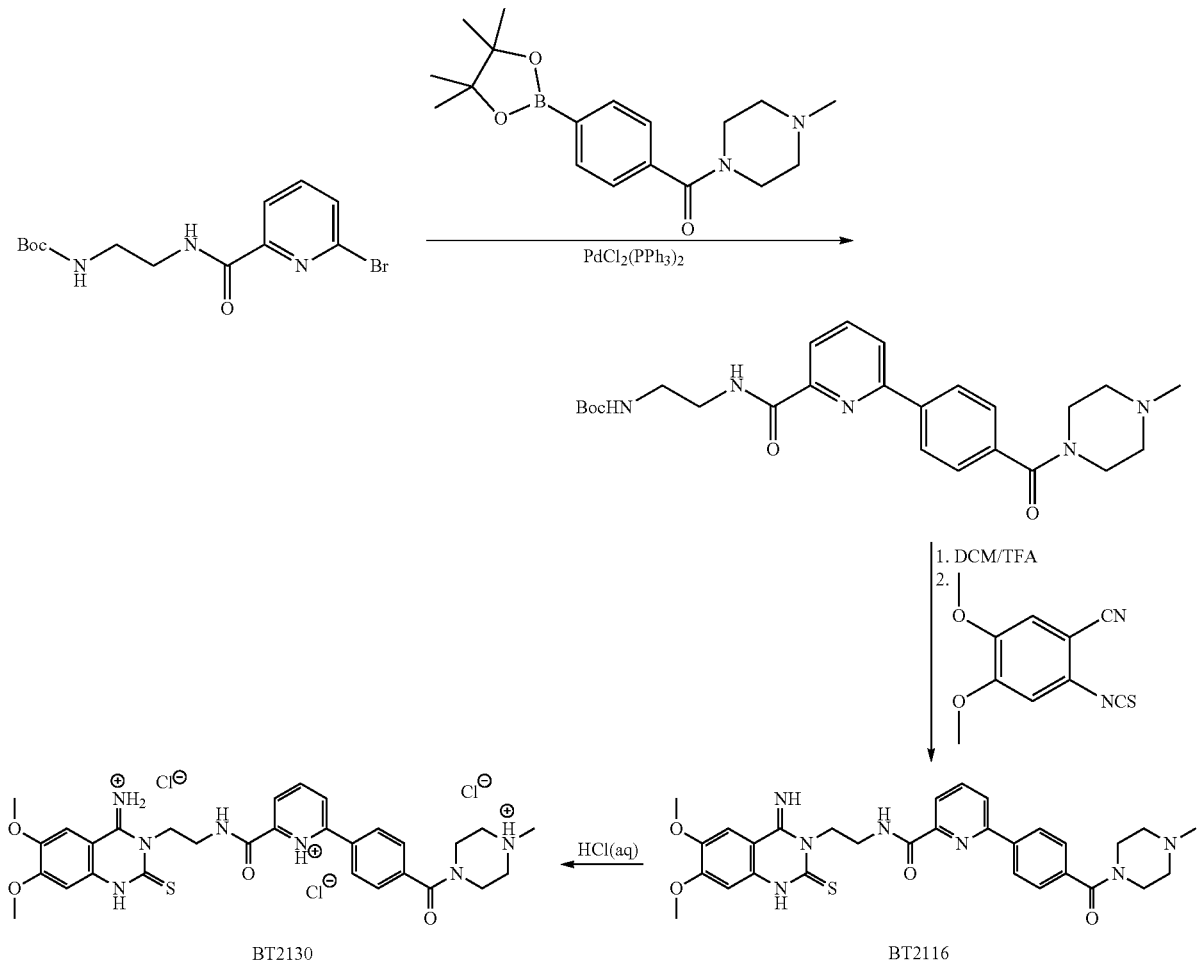

and magnetically stirred for 5 min. The reaction was then treated with a solution of 2-isothiocyanato-4,5-dimethoxybenzonitrile (32 mg, 0.14 mmol) in DCM (2 mL). The mixture was then stirred for 1 h at rt then heated to 70° C. and stirred for 2 h. The reaction was cooled and the precipitate was collected by vacuum filtration and washed with ether (5 mL) to afford BT2116 (47 mg, 56%) as a yellow solid. $^1$H NMR (400 MHz, DMSO-$d_6$) δ 11.99 (br s, 1H), 9.15 (m, 2H), 8.35 (d, J=7.9 Hz, 2H), 8.21 (d, J=7.8 Hz, 1H), 8.07 (t, J=7.8 Hz, 1H), 7.97 (d, J=7.6 Hz, 1H), 7.59 (s, 1H), 7.53 (d, J=8.3 Hz, 2H), 6.83 (s, 1H), 5.23-4.73 (m, 2H), 3.85-3.81 (m, 2H), 3.79 (s, 3H), 3.79 (s, 3H), 3.70-3.59 (m, 2H), 3.42-3.34 (m, 2H), 2.45-2.27 (m, 4H), 2.22 (s, 3H). (+)-LRESIMS m/z (rel. int.) 588 (100) [M+H]$^+$, 610 (50) [M+Na]$^+$; $v_{max}$ 1699, 1659, 1635, 1621, cm$^{-1}$. A portion of BT2116 (14 mg) was treated with aqueous HCl (3.5 mL, 2M), sonicated at rt for 5 min then stirred for 10 min before removal of water with a gentle stream of nitrogen to afford BT2130, the hydrochloride salt of BT2116. $^1$H NMR (400 MHz, DMSO-$d_6$) very broad —NCH$_2$— signals δ 13.75 (s, 1H), 11.16 (s, 1H), 10.82 (s, 1H), 10.32 (s, 1H), 9.42 (t, J=6.1 Hz, 1H), 8.44 (d, J=8.3 Hz, 2H), 8.28 (d, J=7.9 Hz, 1H), 8.11 (t, J=7.8 Hz, 1H), 8.05 (s, 1H), 7.99 (d, J=7.6 Hz, 1H), 7.58 (d, J=8.3 Hz, 2H), 7.03 (s, 1H), 5.45-4.30 (br m, 2H), 3.92 (s, 3H), 3.87 (s, 3H), 3.86-3.80 (m, 2H), 3.53-3.04 (m, 8H), 2.78 (s, 3H); (+)-LRESIMS m/z (rel. int.) 588 (100) [M+H]$^+$, 610 (10) [M+Na]$^+$; $v_{max}$ 2972, 1623, 1512, 1439, 1401, 1271, 1242, 1180, 1089, 1019, 975, 749 cm$^{-1}$ Synthesis Example 60—BT2117

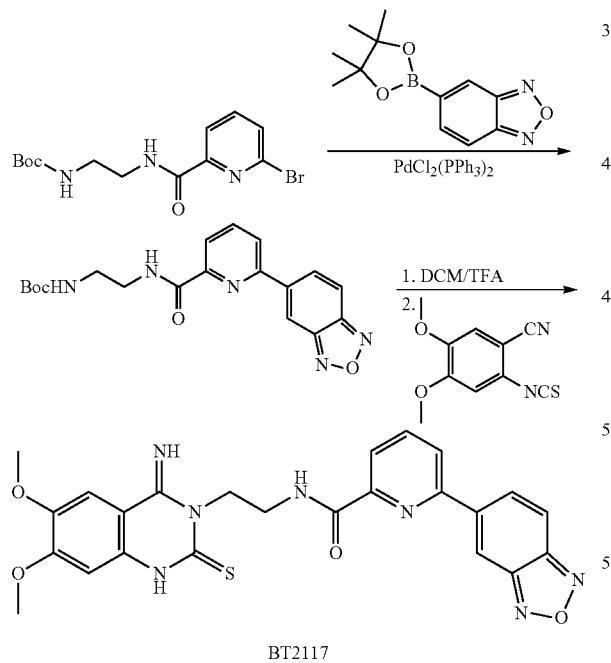

tert-Butyl (2-(6-bromopicolinamido)ethyl)carbamate (102 mg, 0.30 mmol), was subjected to a palladium catalysed Suzuki-Miyaura reaction and reacted with 5-(4,4,5,5-tetramethyl-1,3,2-dioxaborolan-2-yl)benzo[c][1,2,5]oxadiazole (55 mg, 0.45 mmol) according to General Procedure D to afford a residue that was subjected to flash column chromatography [silica, 1:10 MeOH:DCM] to give, after concentration of the appropriate fractions tert-butyl (2-(6-(benzo[c][1,2,5]oxadiazol-5-yl)picolinamido)ethyl)carbamate (84 mg, 74%) as a white solid. $^1$H NMR (400 MHz, DMSO-$d_6$) δ 9.14 (app. t, J=5.8 Hz, 1H), 9.08 (app. t, J=1.1 Hz, 1H), 8.69 (dd, J=9.5, 0.9 Hz, 1H), 8.46 (dd, J=7.8, 0.9 Hz, 1H), 8.20 (dd, J=9.5, 0.5 Hz, 1H), 8.17 (t, J=7.8 Hz, 1H), 8.11 (dd, J=7.6, 0.5 Hz, 1H), 7.02 (t, J=5.7 Hz, 1H), 3.42 (app. q, J=6.3 Hz, 2H), 3.19 (app. q, J=5.7, 2H), 1.35 (s, 9H); (+)-LRESIMS m/z (rel. int.) 406 (100) [M+Na]$^+$; $v_{max}$ 1668, 1511, 1449, 1253, 1167, 880 754 cm$^{-1}$. A portion of the Boc-protected compound formed directly above (43 mg, 0.11 mmol) was deprotected following General Procedure F with TFA (1.5 mL) and DCM (4.0 mL) to afford a clear glass that was used directly without further purification. LRESIMS m/z (rel. int.) 284 (90) [M+H]$^+$, 306 (100) [M+Na]$^+$, 589 (30) [2M+Na]$^+$; The TFA-salt formed directly above (0.11 mmol) was then suspended in ethanol (5 mL) and treated with triethylamine (156 μL, 1.12 mmol) and magnetically stirred for 5 min. The reaction was then treated with a solution of 2-isothiocyanato-4,5-dimethoxybenzonitrile (25 mg, 0.11 mmol) in DCM (2 mL). The mixture was then stirred for 1 h at rt then heated to 70° C. and stirred for 2 h. The reaction was cooled and the precipitate was collected by vacuum filtration and washed with ether (5 mL) to afford BT2117 (42 mg, 75%) as a white solid. $^1$H NMR (400 MHz, DMSO-$d_6$) δ 11.88 (br s, 1H), 9.19 (br s, 1H), 9.09-8.97 (m, 2H), 8.64 (d, J=8.1 Hz, 1H), 8.44 (d, J=7.3 Hz, 1H), 8.19 (dd, J=9.5, 0.5 Hz, 1H), 8.15 (d, J=7.8 Hz, 1H), 8.06 (d, J=7.8 Hz, 1H), 7.53 (s, 1H), 6.81 (s, 1H), 5.07-4.92 (m, 2H), 3.87-3.79 (m, 2H), 3.77 (s, 3H), 3.76 (s, 3H); LRESIMS m/z (rel. int.) 504 (100) [M+H]$^+$; $v_{max}$ 1652, 1626, 1588, 1528, 1514, 1434, 1231, 1176, 1022, 857, 761 cm$^{-1}$.

Synthesis Example 61—BT2125

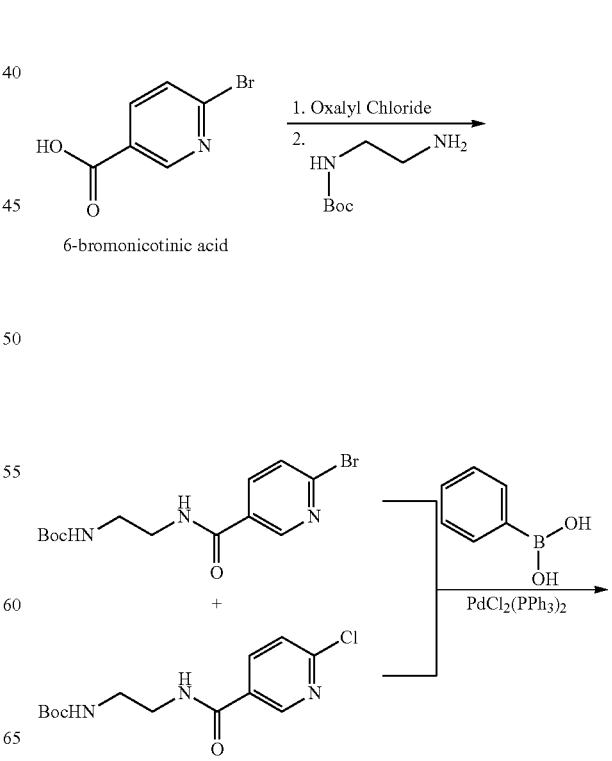

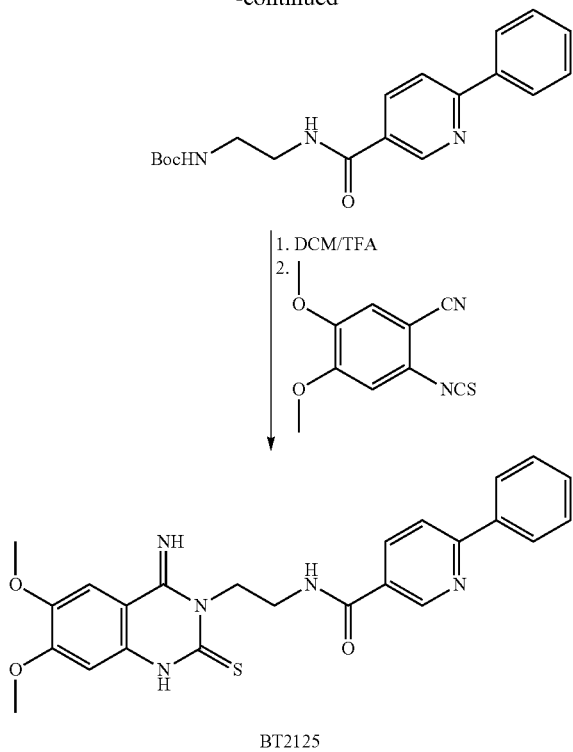

BT2125

Following a procedure analogous to General Procedure H, 6-bromonicotinic acid (2.00 g, 9.90 mmol) was converted to 6-bromonicotinoyl chloride with oxalyl chloride (0.88 mL, 10.40 mmol) and reacted with tert-butyl(2-aminoethyl)carbamate (1.59 g, 9.90 mmol) to afford 1.03 g of tert-butyl (2-(6-chloropicolinamido)ethyl)carbamate (major) and tert-butyl (2-(6-bromopicolinamido)ethyl)carbamate (minor) (10:3.8 mixture) as a white powder that was used without further purification. (+)-LRESIMS m/z (rel. int.) 322 (100) $C_{13}H_{18}{}^{35}ClN_3NaO_3$ $[M+Na]^+$, 324 (40) $C_{13}H_{18}{}^{37}ClN_3NaO_3$ $[M+Na]^+$, 366 (30) $C_{13}H_{18}{}^{79}BrN_3NaO_3$ $[M+Na]^+$, 368 (30) $C_{13}H_{18}{}^{81}BrN_3NaO_3$ $[M+Na]^+$; $v_{max}$ 3359, 2978, 1704, 1640, 1543, 1517, 1448, 1340, 1272, 1160, 1103, 970, 853, 764, 606 cm$^{-1}$.

tert-butyl (2-(6-chloropicolinamido)ethyl)carbamate $^1$H NMR (400 MHz, DMSO-d$_6$) δ 8.81 (d, J=2.1 Hz, 1H), 8.72 (t, J=5.3 Hz, 1H), 8.21 (dd, J=8.3, 2.4 Hz, 1H), 7.64 (d, J=8.3 Hz, 1H), 6.92 (t, J=5.9 Hz, 1H), 3.28 (app. q, J=6.1 Hz, 2H), 3.11 (app. q, J=6.2 Hz, 2H), 1.36 (s, 9H).

tert-butyl (2-(6-bromopicolinamido)ethyl)carbamate $^1$H NMR (400 MHz, DMSO-d$_6$) δ 8.78 (d, J=2.2 Hz, 1H), 8.72 (t, J=5.3 Hz, 1H), 8.10 (dd, J=8.3, 2.6 Hz, 1H), 7.78 (d, J=8.3 Hz, 1H), 6.92 (t, J=5.9 Hz, 1H), 3.28 (app. q, J=6.1 Hz, 2H), 3.11 (q, J=6.2 Hz, 2H), 1.36 (s, 9H).

A portion of the mixture formed above (103 mg, 0.33 mmol), was subjected to a palladium catalysed Suzuki-Miyaura reaction with the addition of sodium bromide (61 mg, 0.60 mmol) and reacted with phenylboronic acid (73 mg, 0.60 mmol) according to General Procedure D, to afford tert-butyl (2-(6-phenylnicotinamido)ethyl)carbamate as a white solid (87 mg, 77%) that was used without further purification. $^1$H NMR (400 MHz, DMSO-d$_6$) δ 9.07 (s, 1H), 8.68 (app. t, J=5.2 Hz, 1H), 8.26 (dd, J=8.5, 1.5 Hz, 1H), 8.17-8.13 (m, 2H), 8.08 (d, J=8.3 Hz, 1H), 7.58-7.43 (m, 3H), 6.94 (app. t, J=5.5 Hz, 1H), 3.37-3.28 (m, 2H), 3.13 (app. q, J=6.0 Hz, 2H), 1.37 (s, 9H). A portion of the Boc-protected compound formed directly above (80 mg, 0.23 mmol) was deprotected following General Procedure F with TFA (1.5 mL) and DCM (4.0 mL) to afford a gum after trituration with ether (10 mL) to afford the TFA salt of tert-butyl (2-(6-phenylnicotinamido)ethyl)carbamate that was used directly in the next step without further purification. The amine TFA-salt (0.23 mmol) was then suspended in ethanol (4 mL) and treated with triethylamine (156 μL, 1.12 mmol) and magnetically stirred for 5 min. The reaction mixture was then treated with a solution of 2-isothiocyanato-4,5-dimethoxybenzonitrile (52 mg, 0.23 mmol) in DCM (2 mL). The mixture was then stirred for 2 h at rt then the precipitate was collected by vacuum filtration and washed with ether (5 mL) to afford BT2125 (83 mg, 78%) as a yellow solid. $^1$H NMR (400 MHz, DMSO-d$_6$) δ 11.93 (br s, 1H), 9.13 (br s, 1H), 9.02 (s, 1H), 8.82 (br s, 1H), 8.21 (d, J=7.6 Hz, 1H), 8.14 (d, J=7.1 Hz, 2H), 8.05 (d, J=8.1 Hz, 1H), 7.61 (s, 1H), 7.57-7.44 (m, 3H), 6.84 (s, 1H), 4.93-4.84 (m, 2H), 3.82 (s, 3H), 3.79 (s, 3H), 3.77-3.70 (m, 2H); (+)-LRESIMS m/z (rel. int.) 462 (100) $[M+H]^+$; $v_{max}$ 1666, 1625, 1561, 1501, 1438, 1327, 1290, 1233, 1157, 1061, 987, 856, 747, cm$^{-1}$.

Synthesis Example 62—BT2132 and BT2144

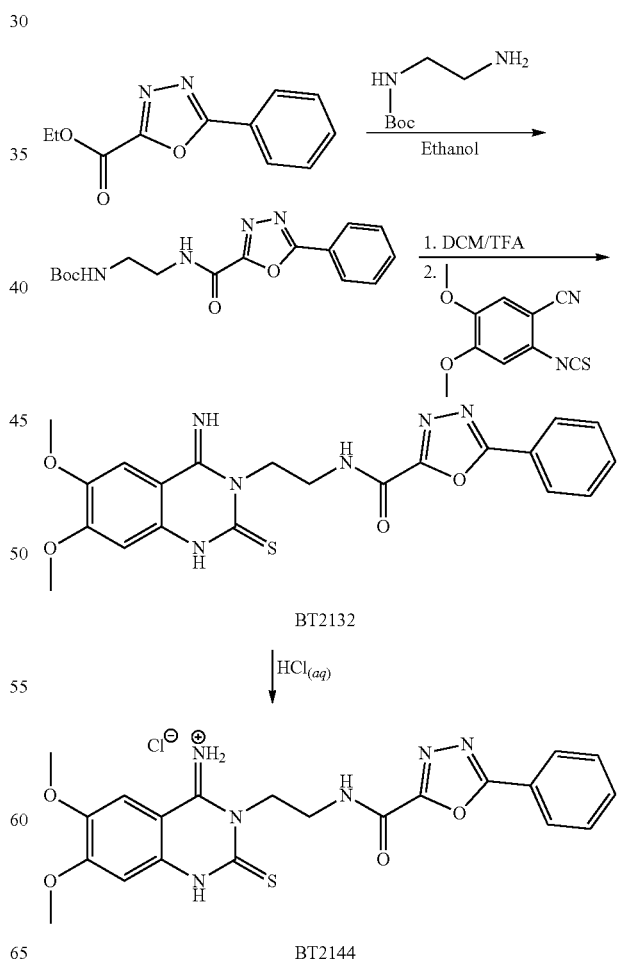

BT2132

BT2144

A mixture of ethyl 5-phenyl-1,3,4-oxadiazole-2-carboxylate (500 mg, 2.29 mmol) prepared according to the procedure of Dost et. al. (*J. Prakt. Chem.* 1985, 327, 109) and tert-butyl (2-aminoethyl)carbamate (1.50 mL) in ethanol (15 mL) was stirred for 18 h The mixture was then concentrated in vacuo and purified by flash column chromatography [silica, 1:10 v/v ether/DCM elution] to give, after concentration of the appropriate fractions, tert-butyl (2-(5-phenyl-1,3,4-oxadiazole-2-carboxamido)ethyl)carbamate as a white powder (401 mg, 52%). $^1$H NMR (400 MHz, Chloroform-d) δ 8.19-8.11 (m, 2H), 7.94 (s, 1H), 7.63-7.48 (m, 3H), 5.06 (s, 1H), 3.64 (app. q, J=5.7 Hz, 2H), 3.43 (app. q, J=5.8 Hz, 2H), 1.43 (s, 9H); 13C NMR (101 MHz, CDCl$_3$) δ 166.4, 158.4, 156.6, 153.9, 132.6, 129.2 (2C), 127.5 (2C), 122.8, 80.0, 40.9, 40.0, 28.3 (3C). (+)-LRESIMS m/z (rel. int.) 355 (100) [M+Na]$^+$; v$_{max}$ 3350, 1683, 1535, 1450, 1276, 1169, 985, 849, 710 cm$^{-1}$. A portion of the Boc-protected compound formed directly above (72 mg, 0.22 mmol) was deprotected at 0° C. following General Procedure F with TFA (1.5 mL) and DCM (5.0 mL) to afford after trituration with ether (3×5 mL) to afford the TFA salt of N-(2-aminoethyl)-5-phenyl-1,3,4-oxadiazole-2-carboxamide as a sticky gum that was used directly in the next step without further purification. The amine TFA-salt (0.22 mmol) was then suspended in ethanol (5 mL) and treated with triethylamine (181 μL, 1.30 mmol) and magnetically stirred for 5 min. The reaction mixture was then treated with a solution of 2-isothiocyanato-4,5-dimethoxybenzonitrile (48 mg, 0.22 mmol) in DCM (2 mL). The mixture was then maintained at rt with stirring for 2 h and further at 70° C. for 1 h. The mixture was cooled to rt and the precipitate collected by vacuum filtration and washed with ether (5 mL) to afford BT2132 (79 mg, 80%) as a white powder. $^1$H NMR (400 MHz, DMSO-d$_6$) δ 11.95 (s, 1H), 9.49 (s, 1H), 9.12 (s, 1H), 8.10-8.03 (m, 2H), 7.73-7.59 (m, 4H), 6.84 (s, 1H), 4.95-4.87 (m, 2H), 3.80 (s, 3H), 3.79 (s, 3H), 3.78-3.70 (m, 2H). (+)-LRESIMS m/z (rel. int.) 453 (100) [M+H]$^+$; v$_{max}$ 3310, 1678, 1634, 1549, 1520, 1508, 1456, 1442, 1284, 1240, 1205, 1082, 1016, 867, 710 cm$^{-1}$.

BT2144

A portion of BT2132 (15 mg) at rt was treated with aqueous HCl (1.5 mL, 1.5 M), sonicated for 5 min then stirred for 10 min before removal of water with a gentle stream of nitrogen to afford BT2144 (16 mg, 99%) as a white solid, the hydrochloride salt of BT2132. $^1$H NMR (400 MHz, DMSO-d$_6$) δ 13.75 (s, 1H), 10.73 (s, 1H), 9.95 (s, 1H), 9.50 (t, J=6.2 Hz, 1H), 8.08 (dt, J=9.0, 1.6 Hz, 3H), 7.76-7.60 (m, 3H), 7.03 (s, 1H), 5.00 (s, 2H), 3.93 (s, 3H), 3.90 (s, 3H), 3.77 (q, J=6.3 Hz, 2H). (+)-LRESIMS m/z (rel. int.) 453 (100) [M+H]f; v$_{max}$ 1686, 1665, 1626, 1545, 1513, 1402, 1281, 1239, 1210, 1175, 1084, 847, 685 cm$^{-1}$.

Synthesis Example 63—BT2133

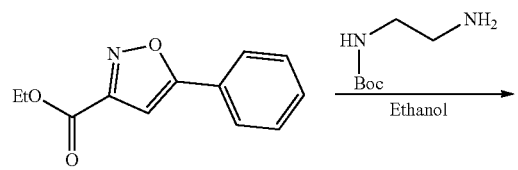

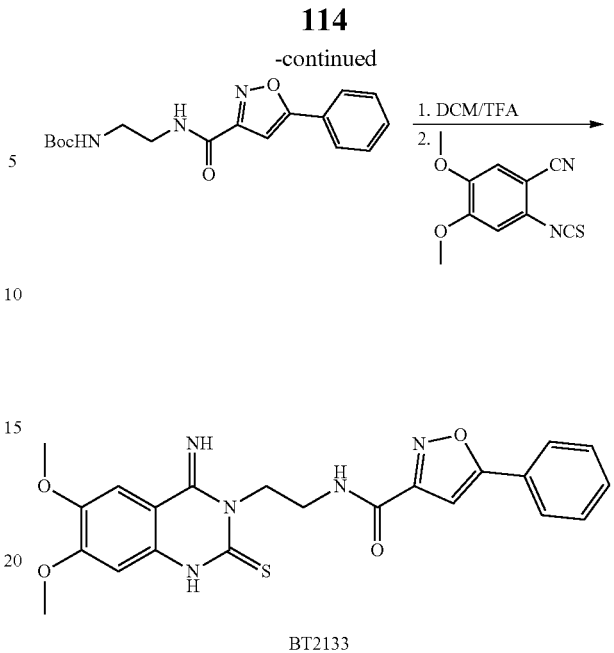

BT2133

A mixture of ethyl 5-phenylisoxazole-3-carboxylate (100 mg, 0.46 mmol) prepared according to the procedure of Watterson et. al. (*J. Med. Chem.* 2016, 59, 2820) and tert-butyl (2-aminoethyl)carbamate (100 mg, 0.62 mmol) in ethanol (2 mL) was stirred for 72 h at rt. The mixture was then concentrated in vacuo and purified by flash column chromatography [silica, 1:10 v/v ether/DCM elution] to give, after concentration of the appropriate fractions, tert-butyl (2-(5-phenylisoxazole-3-carboxamido)ethyl)carbamate as a white powder (32 mg, 21%). $^1$H NMR (400 MHz, Chloroform-d) δ 7.84-7.76 (m, 2H), 7.54-7.44 (m, 3H), 7.33-7.25 (m, 1H), 6.96 (s, 1H), 4.89 (s, 1H), 3.59 (app. q, J=5.8 Hz, 2H), 3.39 (app. q, J=5.9 Hz, 2H), 1.44 (s, 9H). $^{13}$C NMR (100 MHz, CDCl$_3$) δ 171.6, 159.5, 159.0, 156.4, 130.7, 129.1, 126.8, 125.9, 99.0, 79.8, 40.2, 40.2, 28.3; (+)-LRESIMS m/z (rel. int.) 354 (100) [M+Na]$^+$; v$_{max}$ 3382, 3343, 1685, 1665, 1548, 1524, 1446, 1274, 1262, 1154, 1174, 969, 766 cm$^{-1}$. The Boc-protected compound tert-butyl (2-(5-phenylisoxazole-3-carboxamido)ethyl)carbamate (62 mg, 0.19 mmol) was deprotected at 0° C. following General Procedure F with TFA (1.5 mL) and DCM (6.0 mL) to afford after trituration with ether (3×5 mL) to afford the TFA salt of N-(2-aminoethyl)-5-phenylisoxazole-3-carboxamide as a sticky gum that was used directly in the next step without further purification. The amine TFA-salt (0.19 mmol) was then suspended in ethanol (4 mL) and treated with triethylamine (156 μL, 1.12 mmol) and magnetically stirred for 5 min. The reaction mixture was then treated with a solution of 2-isothiocyanato-4,5-dimethoxybenzonitrile (41 mg, 0.19 mmol) in DCM (2 mL). The mixture was then maintained at rt with stirring for 2 h and further at 70° C. for 1 h. The mixture was cooled to rt and the precipitate collected by vacuum filtration and washed with ether (5 mL) to afford BT2133 (38 mg, 47%) as a white powder. $^1$H NMR (400 MHz, DMSO-d$_6$) δ 11.93 (s, 1H), 9.13 (s, 1H), 8.99 (s, 1H), 7.96-7.88 (m, 2H), 7.63 (s, 1H), 7.60-7.50 (m, 3H), 7.32 (s, 1H), 6.83 (s, 1H), 4.96-4.82 (m, 2H), 3.82 (s, 3H), 3.79 (s, 3H), 3.75-3.68 (m, 2H); (+)-LRESIMS m/z (rel. int.) 452 (100) [M+H]$^+$; v$_{max}$ 1653, 1553, 1535, 1512, 1434, 1228, 1193, 1020, 859, 761, 592 cm$^{-1}$.

Synthesis Example 64—BT2134

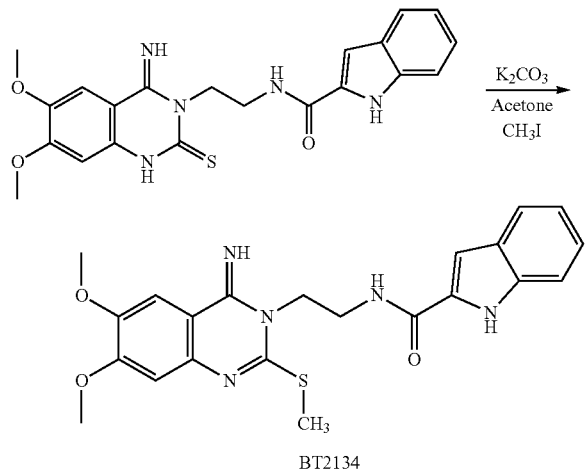

BT2134

A mixture of BT2058 (50 mg, 0.12 mmol), potassium carbonate (32 mg, 0.23 mmol) in acetone at rt was treated with methyl iodide (29 µL, 0.47 mmol) in one portion. The mixture was stirred for 48 h and then water (4 mL) was added and the mixture stirred for 1 min. The mixture was filtered by vacuum filtration to afford a solid that was washed with acetone (3 mL) to afford a BT2134 as a white powder (23 mg, 45%). $^1$H NMR (DMSO-$d_6$, 400 MHz) δ 11.56 (s, 1H), 8.81 (app. t, J=5.6 Hz, 1H), 8.46 (s, 1H), 7.64 (s, 1H), 7.60 (d, J=8.0 Hz, 1H), 7.41 (d, J=8.0 Hz, 1H), 7.17 (t, J=7.6 Hz, 1H), 7.04 (s, 1H), 7.01 (d, J=7.6 Hz, 1H), 6.83 (s, 1H), 4.39-4.32 (m, 2H), 3.85 (s, 3H), 3.84 (s, 3H), 3.72-3.64 (m, 2H), 2.48 (s, 3H). $^{13}$C NMR (DMSO-$d_6$, 100 MHz) δ 161.4, 155.2, 152.8, 147.5, 139.3, 136.4, 131.8, 127.1, 123.2, 121.4, 119.6, 112.3, 111.0 (br), 107.5, 106.1, 102.3, 56.1, 55.7, 44.7, 39.5, 36.6, 14.6. (+)-LRESIMS m/z (rel. int.) 438 (100) [M+H]$^+$; $v_{max}$ 3409, 3250, 1708, 1636, 1607, 1549, 1503, 1230, 1015, 744 cm$^{-1}$.

Synthesis Example 65—BT2135

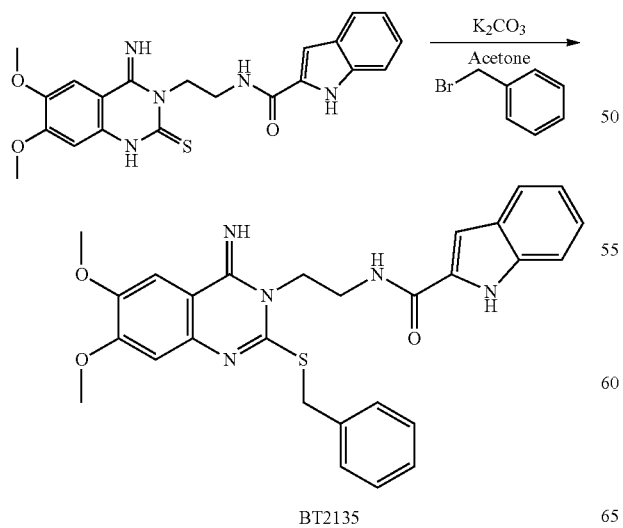

BT2135

A mixture of BT2058 (50 mg, 0.12 mmol), potassium carbonate (32 mg, 0.23 mmol) in acetone at rt was treated with benzyl bromide (56 µL, 0.47 mmol) in one portion. The mixture was stirred for 18 h and then water (5 mL) was added and the mixture stirred for 1 min. The mixture was filtered by vacuum filtration to afford a solid that was washed with acetone (5 mL) to provide BT2135 as a white powder (36 mg, 59%). $^1$H NMR (400 MHz, DMSO-$d_6$) δ 11.57 (s, 1H), 8.78 (s, 1H), 8.46 (s, 1H), 7.65 (s, 1H), 7.61 (d, J=7.8 Hz, 1H), 7.43 (d, J=8.2 Hz, 1H), 7.27-7.00 (m, 8H), 6.88 (s, 1H), 4.32 (d, J=9.0 Hz, 4H), 3.86 (s, 3H), 3.85 (s, 3H), 3.72-3.62 (m, 2H); (+)-LRESIMS m/z (rel. int.) 514 (100) [M+H]$^+$; $v_{max}$ 3419, 3264, 1711, 1637, 1609, 1547, 1501, 1439, 1339, 1228, 1015, 771, 743 cm$^{-1}$.

Synthesis Example 66—BT2136

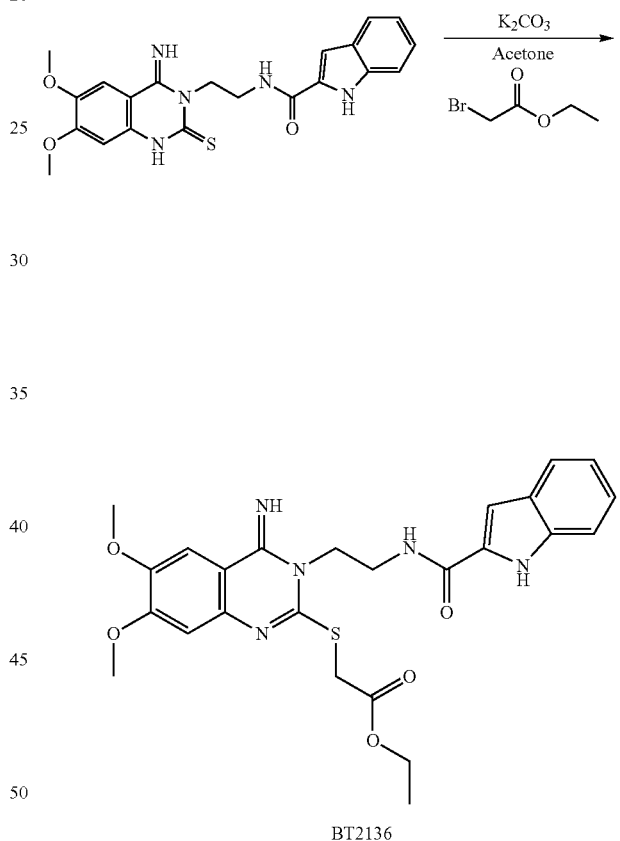

BT2136

BT2136 was prepared and purified using General Procedure J from BT2058 (50 mg, 0.12 mmol), potassium carbonate (32 mg, 0.23 mmol) and ethyl 2-bromoacetate (53 µL, 0.47 mmol) in acetone (2.0 mL) to afford BT2136 as a white powder (23 mg, 39%). $^1$H NMR (DMSO-$d_6$, 400 MHz) δ 11.55 (s, 1H), 8.81 (t, J=5.4 Hz, 1H), 8.53 (s, 1H), 7.65 (s, 1H), 7.60 (d, J=8.0 Hz, 1H), 7.41 (d, J=8.0 Hz, 1H), 7.17 (t, J=7.5 Hz, 1H), 7.06 (d, J=1.2 Hz, 1H), 7.02 (t, J=7.5 Hz, 1H), 6.67 (s, 1H), 4.35 (app. t, J=6.0 Hz, 2H), 4.09 (q, J=7.1 Hz, 2H), 3.96 (s, 2H), 3.85 (s, 3H), 3.82 (s, 3H), 3.74-3.65 (app. q, J=6.0 Hz, 2H), 1.17 (t, J=7.1 Hz, 3H). (+)-LRESIMS m/z (rel. int.) 510 (100) [M+H]$^+$; $v_{max}$ 3295, 1739, 1631, 1600, 1543, 1501, 1232, 1152, 1017, 744 cm$^{-1}$.

Synthesis Example 67—BT2137

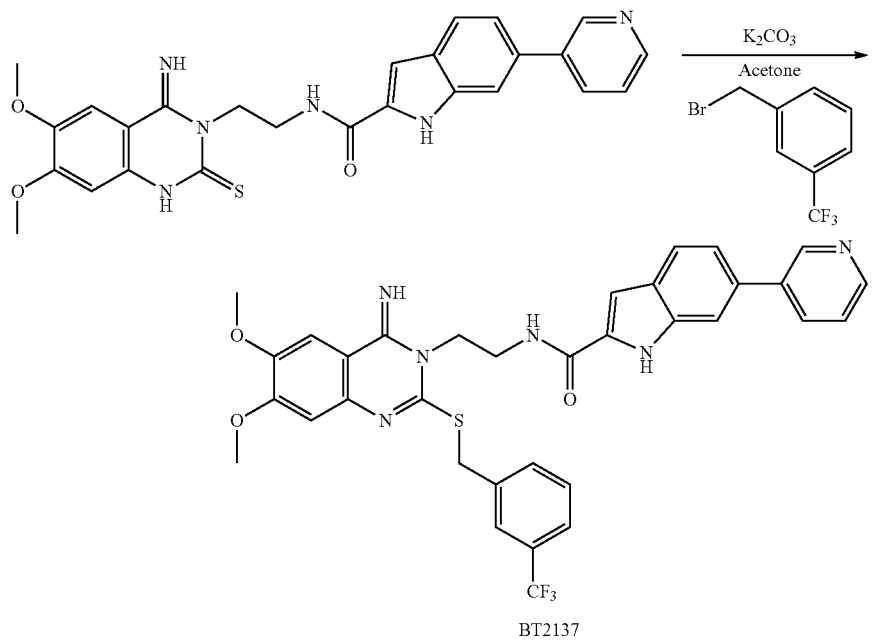

Prepared and purified using a method analogous to General Procedure J from BT2072 (50 mg, 0.10 mmol), potassium carbonate (28 mg, 0.20 mmol) and 1-(bromomethyl)-3-(trifluoromethyl)benzene (48 mg, 0.20 mmol) in acetone (1.5 mL) to afford BT2137 as a white powder (13 mg, 20%). $^1$H NMR (400 MHz, DMSO-$d_6$) δ 11.74 (s, 1H), 8.89 (d, J=1.6 Hz, 1H), 8.83 (t, J=5.8 Hz, 1H), 8.55 (dd, J=4.6, 0.9 Hz, 1H), 8.49 (br s, 1H), 8.06 (dt, J=8.0, 2.0 Hz, 1H), 7.88 (s, 1H), 7.74 (d, J=8.3 Hz, 1H), 7.69 (s, 1H), 7.64 (s, 1H), 7.53-7.45 (m, 3H), 7.41 (dd, J=8.3, 1.6 Hz, 1H), 7.25 (t, J=7.8 Hz, 1H), 7.07 (d, J=0.8 Hz, 1H), 6.89 (s, 1H), 4.43 (s, 2H), 4.34-4.26 (m, 2H), 3.86 (s, 3H), 3.85 (s, 3H), 3.69-3.63 (m, 2H); (+)-LRESIMS m/z (rel. int.) 659 (100) [M+H]$^+$; $v_{max}$ 1603, 1547, 1501, 1439, 1329 1231, 1161, 1114, 1070, 1017, 803, 698 cm$^{-1}$.

Synthesis Example 68—BT2138

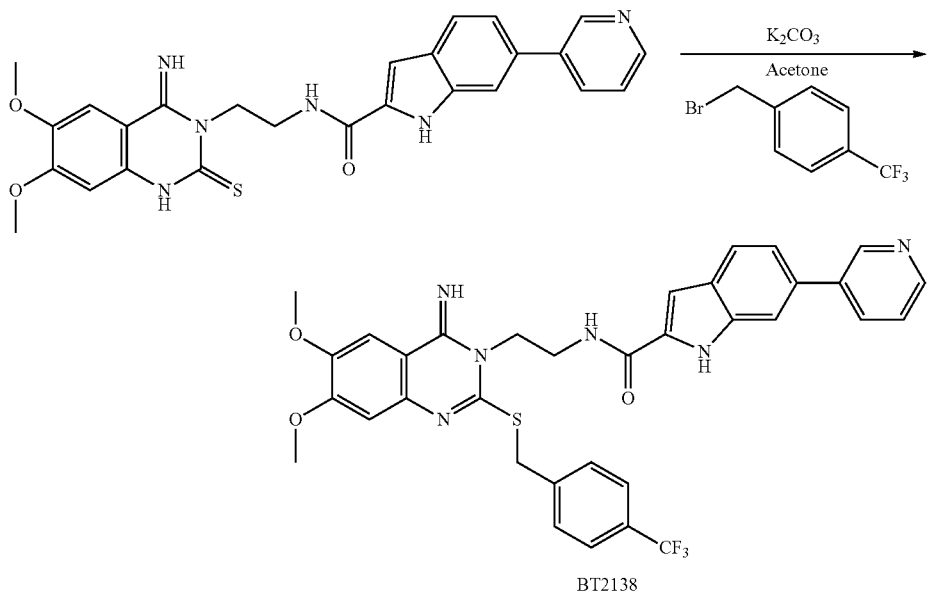

Prepared and purified using a method analogous to General Procedure J from BT2072 (50 mg, 0.10 mmol), potassium carbonate (28 mg, 0.20 mmol) and 1-(bromomethyl)-

4-(trifluoromethyl)benzene (48 mg, 0.20 mmol) in acetone (1.5 mL) to afford, after flash column chromatography [silica, 1:10 v/v ammoniacal MeOH/DCM elution] BT2138 as a white powder (11 mg, 17%). $^1$H NMR (DMSO-d6, 400 MHz) δ 11.75 (s, 1H), 8.88 (d, J=1.5 Hz, 1H), 8.83 (app. t, J=5.8 Hz, 1H), 8.55 (d, J=4.7 Hz, 1H), 8.48 (br s, 1H), 8.05 (dt, J=8.0, 1.5 Hz, 1H), 7.75 (d, J=8.4 Hz, 1H), 7.69 (s, 1H), 7.65 (s, 1H), 7.50 (dd, J=7.8, 4.8 Hz, 1H), 7.42 (dd, J=8.4, 1.5 Hz, 1H), 7.38 (d, J=7.8 Hz, 2H), 7.28 (d, J=7.9 Hz, 2H), 7.10 (br s, 1H), 6.86 (s, 1H), 4.42 (s, 2H), 4.37-4.25 (m, 2H), 3.86 (s, 3H), 3.85 (s, 3H), 3.74-3.63 (m, 2H); $v_{max}$ 1644, 1601, 1545, 1500, 1438, 1325, 1229, 1156, 1110, 1066, 1017, 810 cm$^{-1}$.

Synthesis Example 69—BT2139 and BT2140

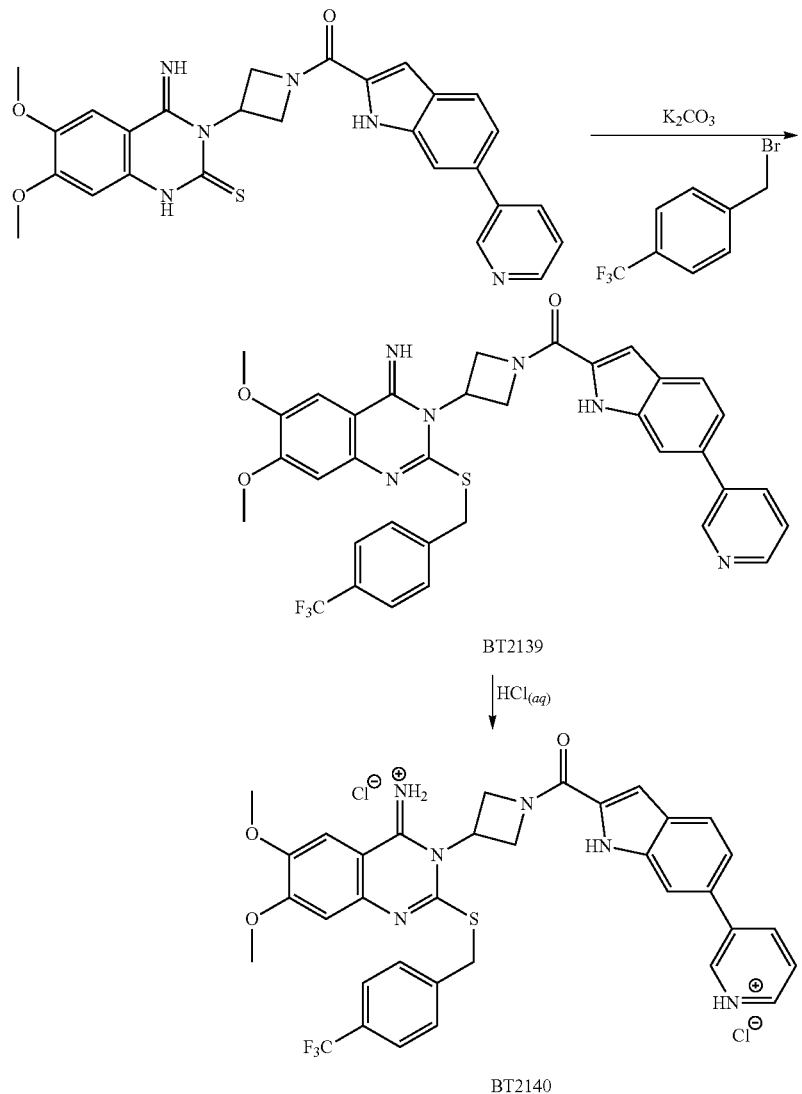

Hz, 1H), 8.79 (s, 1H), 8.55 (dd, J=4.7, 1.5 Hz, 2H), 8.05 (dt, J=8.0, 1.8 Hz, 2H), 7.78-7.73 (m, 2H), 7.72-7.69 (m, 2H), 7.58 (s, 1H), 7.49 (dd, J=7.7, 4.7 Hz, 1H), 7.40 (dd, J=8.4, 1.7 Hz, 1H), 6.92 (s, 1H), 6.87-6.80 (d, J=1.4 Hz, 1H), 5.41-5.32 (m, 1H), 5.32-5.24 (m, 1H), 4.95-4.85 (m, 1H), 4.84-4.75 (m, 1H), 4.59 (s, 2H), 4.39-4.28 (m, 1H), 3.87 (s, 3H), 3.81 (s, 3H). (+)-LRESIMS m/z (rel. int.) 336 (100) [M+2H]$^{2+}$; 671 (40) [M+H]$^+$; $v_{max}$ 3239, 1604, 1553, 1507, 1454, 1322, 1220, 1114, 1065, 1011, 796 cm$^{-1}$.

BT2140

A portion of BT2139 (7.3 mg) in methanol (300 µL) at rt was treated with aqueous HCl (1.5 mL, 1.5 M), sonicated for 5 min then stirred for 10 min before removal of water with a gentle stream of nitrogen to afford BT2140 (7.5 mg), the hydrochloride salt of BT2139. $^1$H NMR (400 MHz, DMSO-d$_6$) δ 12.05 (s, 1H), 10.69 (br s, 1H), 9.64 (br s, 1H), 9.15

Prepared and purified using a method analogous to General Procedure J from BT2154 (40 mg, 78 µmol), potassium carbonate (22 mg, 0.16 mmol) and 1-(bromomethyl)-4-(trifluoromethyl)benzene (19 mg, 86 µmol) in acetone (1.5 mL) to afford BT2139 as a white powder (38 mg, 73%). $^1$H NMR (400 MHz, DMSO-d$_6$) δ 11.79 (s, 1H), 8.88 (d, J=2.0

(s, 1H), 8.79 (d, J=5.2 Hz, 1H), 8.65 (d, J=8.2 Hz, 1H), 8.14 (s, 1H), 7.96 (dd, J=7.9, 5.5 Hz, 1H), 7.89 (d, J=8.4 Hz, 1H), 7.82 (d, J=8.2 Hz, 2H), 7.80 (s, 1H), 7.69 (d, J=8.2 Hz, 2H), 7.54 (dd, J=8.4, 1.5 Hz, 1H), 7.29 (s, 1H), 6.89-6.87 (m, 1H), 5.49-5.37 (m, 1H), 5.27-5.15 (m, 1H), 4.87-4.77 (m, 2H), 4.76 (s, 2H), 4.49-4.38 (m, 1H), 4.01 (s, 3H), 3.94 (s, 3H);

(+)-LRESIMS m/z (rel. int.) 671 (100) [M+H]$^+$; $v_{max}$ 1601, 1503, 1440, 1392, 1326, 1299, 1169, 1100, 1066, cm$^{-1}$.

Synthesis Example 70—BT2141 and BT2143

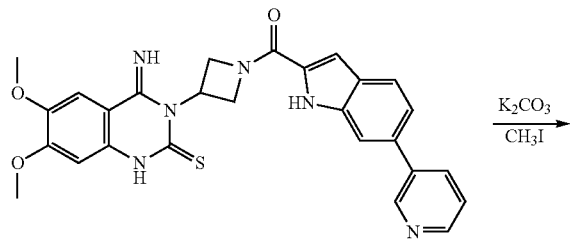

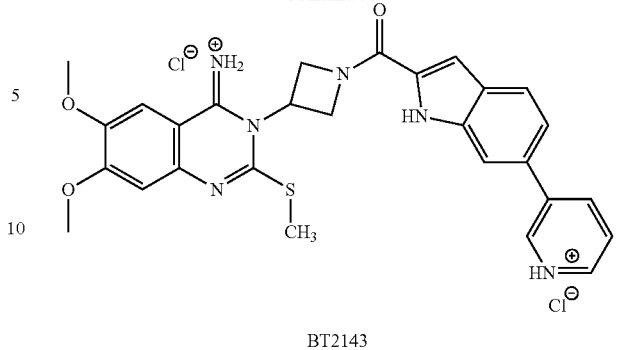

BT2143

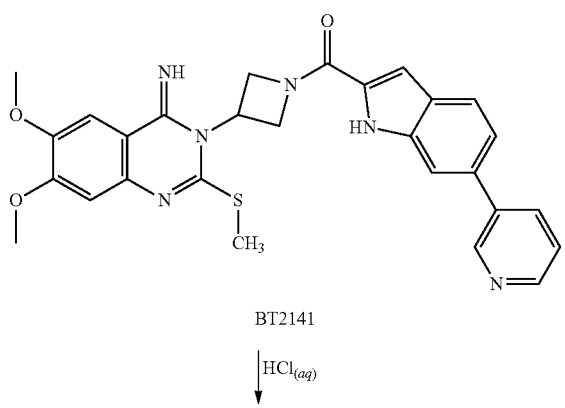

BT2141

Prepared and purified using a method analogous to General Procedure J from BT2154 (80 mg, 0.16 mmol), potassium carbonate (43 mg, 0.32 mmol) and methyl iodide (11 μL, 17 mmol) in acetone (2.0 mL) to afford BT2141 as a white powder (20 mg, 24%). $^1$H NMR (400 MHz, DMSO-d$_6$) δ 11.80 (s, 1H), 8.88 (d, J=2.0 Hz, 1H), 8.74 (s, 1H), 8.55 (dd, J=4.7, 1.3 Hz, 1H), 8.06 (ddd, J=7.9, 1.8 Hz, 1H), 7.76 (d, J=8.4 Hz, 1H), 7.71 (s, 1H), 7.57 (s, 1H), 7.49 (dd, J=7.8, 4.8 Hz, 1H), 7.41 (dd, J=8.3, 1.8 Hz, 1H), 6.86 (d, J=1.3 Hz, 1H), 6.84 (s, 1H), 5.48-5.36 (m, 1H), 5.38-5.27 (m, 1H), 4.98-4.86 (m, 1H), 4.88-4.78 (m, 1H), 4.37 (t, J=8.9 Hz, 1H), 3.84 (s, 3H), 3.81 (s, 3H), 2.58 (s, 3H); (+)-LRESIMS m/z (rel. int.) 527 (100) [M+H]$^+$; $v_{max}$ 3266, 1597, 1506, 1439, 1374, 1231, 1014, 798, 622 cm$^{-1}$.

BT2143

A portion of BT2141 (5.0 mg) at rt was treated with aqueous HCl (1.5 mL, 1.5 M), sonicated for 5 min then stirred for 10 min before removal of water with a gentle stream of nitrogen to afford BT2143 (4 mg, 70%), the hydrochloride salt of BT2141. H NMR (400 MHz, DMSO-d$_6$) δ 12.03 (s, 1H), 10.55 (br s, 1H), 9.54 (br s, 1H), 9.11 (d, J=1.7 Hz, 1H), 8.75 (d, J=4.7 Hz, 1H), 8.57 (d, J=7.8 Hz, 1H), 8.09 (s, 1H), 7.91-7.88 (m, 1H), 7.86 (d, J=8.3 Hz, 1H), 7.78 (s, 1H), 7.51 (dd, J=8.4, 1.4 Hz, 1H), 7.19 (s, 1H), 6.94-6.93 (m, 1H), 5.48-5.40 (m, 1H), 5.28-5.16 (m, 1H), 5.00-4.87 (m, 1H), 4.85-4.75 (m, 1H), 4.56-4.42 (m, 1H), 3.98 (s, 3H), 3.94 (s, 3H), 2.75 (s, 3H); (+)-LRESIMS m/z (rel. int.) 527 (100) [M+H]$^+$; $v_{max}$ 3258, 1678, 1592, 1531, 1507, 1468, 1441, 1393, 1300, 1251, 1119, 998, 861 cm$^{-1}$.

Synthesis Example 71—BT2142 and BT2145

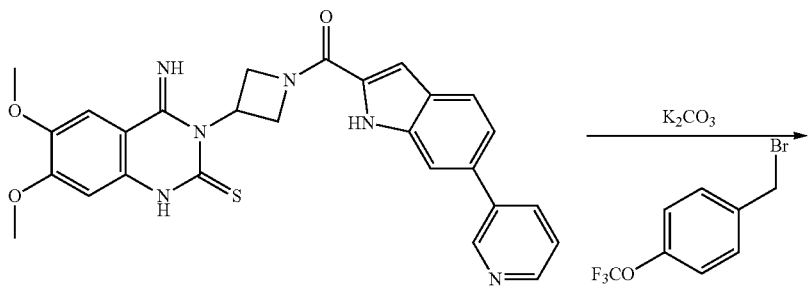

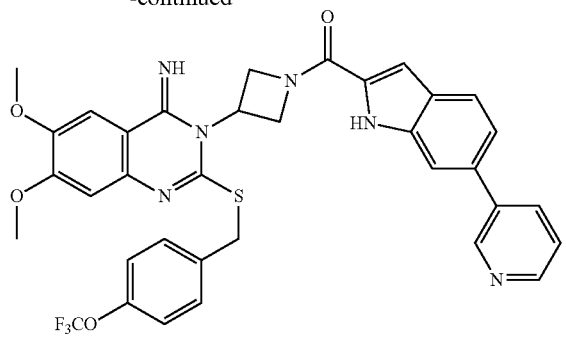

BT2142

↓ HCl(aq)

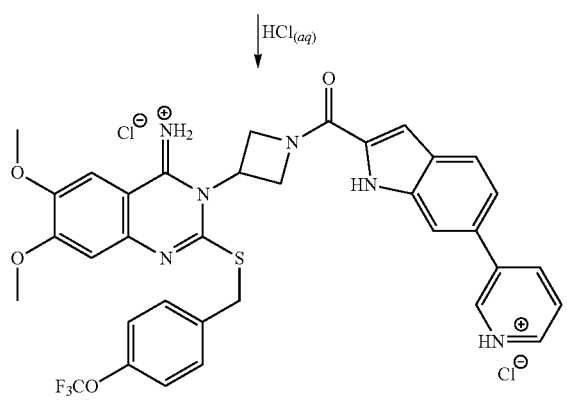

BT2145

Prepared using a method analogous to General Procedure J from BT2154 (40 mg, 78 μmol), potassium carbonate (22 mg, 0.16 mmol) and 1-(bromomethyl)-4-(trifluoromethoxy)benzene (14 μL, 86 μmol) in acetone (1.0 mL) and purified by flash column chromatography [silica, 1:20 v/v ammoniacal MeOH/DCM elution] to give, after concentration of the appropriate fractions, BT2142 as a white powder (35 mg, 65%). $^1$H NMR (400 MHz, DMSO-d$_6$) δ 11.79 (s, 1H), 8.88 (d, J=1.9 Hz, 1H), 8.78 (s, 1H), 8.55 (dd, J=4.7, 1.5 Hz, 1H), 8.05 (ddd, J=8.0, 2.2, 1.7 Hz, 1H), 7.75 (d, J=8.4 Hz, 1H), 7.70 (s, 1H), 7.65 (d, J=8.7 Hz, 2H), 7.58 (s, 1H), 7.49 (ddd, J=8.0, 4.8, 0.5 Hz, 1H), 7.40 (dd, J=8.4, 1.6 Hz, 1H), 7.34 (d, J=8.0 Hz, 2H), 6.83 (d, J=1.4 Hz, 1H), 5.41-5.33 (m, 1H), 5.33-5.27 (m, 1H), 4.95-4.87 (m, 1H), 4.84-4.74 (m, 1H), 4.54 (s, 2H), 4.37-4.28 (m, 1H), 3.87 (s, 6H), 3.81 (s, 6H); (+)-LRESIMS m/z (rel. int.) 687 (100) [M+H]$^+$; ν$_{max}$ 3242, 1607, 1550, 1506, 1454, 1269, 1220, 1165, 1010, 797 cm$^{-1}$.

BT2145

A portion of BT2142 (5.0 mg) at rt was treated with aqueous HCl (1.5 mL, 1.5 M), sonicated for 5 min then stirred for 10 min before removal of water with a gentle stream of nitrogen to afford BT2145 (5 mg), the hydrochloride salt of BT2142. H NMR (400 MHz, DMSO-d$_6$) δ 12.01 (s, 1H), 10.60 (br s, 1H), 9.55 (br s, 1H), 9.10 (s, 1H), 8.75 (d, J=5.1 Hz, 1H), 8.56 (d, J=8.1 Hz, 1H), 8.11 (s, 1H), 7.91-7.84 (m, 2H), 7.78 (s, 1H), 7.71 (d, J=8.6 Hz, 2H), 7.51 (dd, J=8.4, 1.5 Hz, 1H), 7.32 (d, J=8.1 Hz, 2H), 7.29 (s, 1H), 6.88-6.85 (m, 1H), 5.47-5.35 (m, 1H), 5.20 (s, 1H), 4.76 (s, 2H), 4.70 (s, 2H), 4.43 (s, 1H), 4.00 (s, 3H), 3.94 (s, 3H). (+)-LRESIMS m/z (rel. int.) 687 (100) [M+H]$^+$; ν$_{max}$ 1600, 1502, 1441, 1300, 1237, 1219, 1167, 999, 739 cm$^{-1}$.

Synthesis Example 72—BT2153

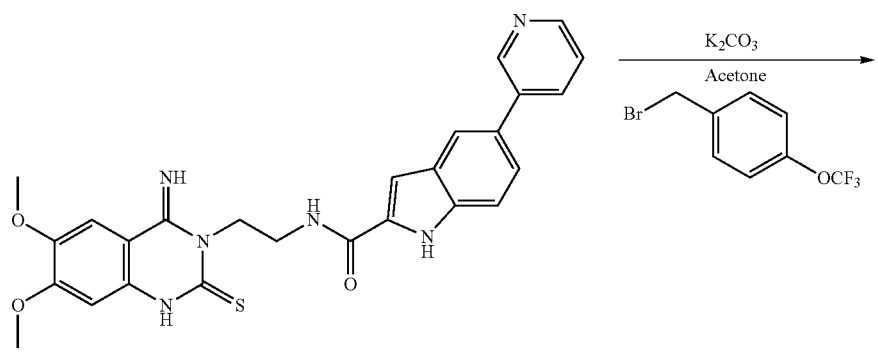

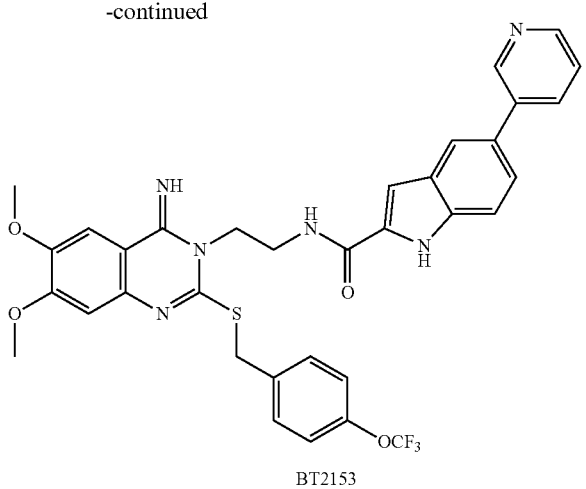

BT2153

Prepared and purified using a method analogous to General Procedure J from BT2070 (50 mg, 0.10 mmol), potassium carbonate (28 mg, 0.20 mmol) and 1-(bromomethyl)-4-(trifluoromethoxy)benzene (26 mg, 0.10 mmol) in acetone (1.5 mL) to afford BT2153 as a white powder (36 mg, 53%). $^1$H NMR (DMSO-d$_6$, 400 MHz) δ 11.73 (s, 1H), 8.92 (d, J=1.9 Hz, 1H), 8.84 (t, J=5.8 Hz, 1H), 8.52 (dd, J=4.9, 1.9 Hz, 1H), 8.47 (s, 1H), 8.07 (ddd, J=7.9, 1.7 Hz, 1H), 7.98 (s, 1H), 7.65 (s, 1H), 7.57 (dd, J=8.7, 1.7 Hz, 1H), 7.54 (d, J=8.7 Hz, 1H), 7.46 (dd, J=7.9, 4.9, 1H), 7.30 (d, J=8.3 Hz, 2H), 7.13 (d, J=1.5 Hz, 1H), 6.96 (d, J=8.3 Hz, 2H), 6.87 (s, 1H), 4.36 (s, 2H), 4.34-4.29 (m, 2H), 3.86 (s, 3H), 3.85 (s, 3H), 3.72-3.65 (m, 2H). $^{13}$C NMR (100 MHz, DMSO-d$_6$) δ 161.4, 155.3, 154.1, 152.8, 147.6, 147.5, 147.2, 139.1, 136.8, 136.5, 136.2, 133.9, 132.8, 130.9, 128.9, 127.8, 123.7 (2C), 122.6, 120.6 (2C), 119.9 (q, J$_{C-F}$=256.2 Hz), 119.9, 113.0, 111.2, 107.4, 106.1, 102.9, 56.2, 55.7, 45.2, 36.3, 34.5. (+)-LRESIMS m/z (rel. int.) 675 (100) [M+H]$^+$; ν$_{max}$ 1623, 1601, 1547, 1502, 1436, 1266, 1214, 1159, 1019, 794 cm$^{-1}$.

Synthesis Example 73—BT2154

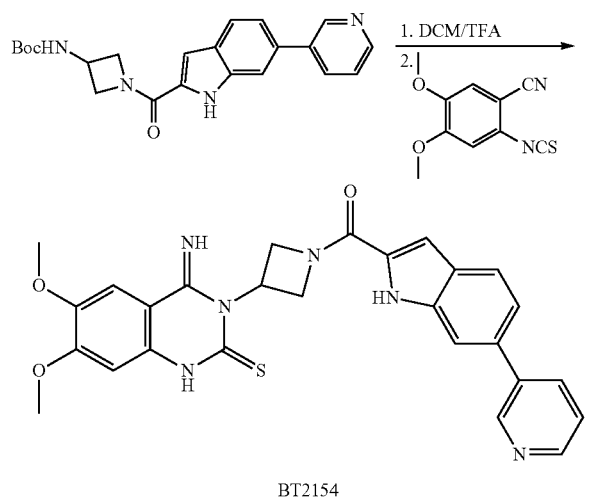

BT2154

Four 10 mL snap-cap microwave vessels, each fitted with a magnetic stirring bar, were charged with a mixture of 3-(4,4,5,5-tetramethyl-1,3,2-dioxaborolan-2-yl)pyridine (160 mg, 0.78 mmol), tert-butyl (1-(6-bromo-1H-indole-2-carbonyl)azetidin-3-yl)carbamate (205 mg, 0.52 mmol) and potassium carbonate (380 mg, 2.74 mmol) then treated with a degassed mixture of dimethoxyethane, water and ethanol (7:3:2, 7 mL). Bis(triphenylphosphine)palladium(II) dichloride (10 mg) was added and the mixture was sparged with nitrogen for 0.05 hr, sealed then separately subjected to microwave irradiation (120° C./0.33 h, ramp time 1 minute, maximum power 200 W). All vessels were poured into one conical flask containing water (35 mL) and the resulting precipitate collected via vacuum filtration. The residue obtained was then washed with ether (30 mL) to afford the desired indole derivative substituted at C-6 as a tan solid (740 mg, 91% combined yield) and used without further purification. $^1$H NMR (400 MHz, DMSO-d$_6$) δ 11.78 (s, 1H), 8.87 (d, J=1.5 Hz, 1H), 8.55 (dd, J=4.4, 0.8 Hz, 1H), 8.09-8.01 (m, 1H), 7.76 (d, J=8.4 Hz, 1H), 7.69 (s, 1H), 7.67 (d, J=7.3 Hz, 1H), 7.49 (dd, J=8.0, 4.8 Hz, 1H), 7.41 (dd, J=8.4, 1.7 Hz, 1H), 7.22 (br s, 1H), 4.79-4.72 (m, 1H), 4.48-4.39 (m, 1H), 4.36-4.25 (m, 2H), 3.99-3.90 (m, 1H), 1.40 (s, 9H); (+)-LRESIMS m/z (rel. int.) 393 (100) [M+H]$^+$; ν$_{max}$ 3260, 1700, 1594, 1532, 1506, 1456, 1365, 1161, 799 cm$^{-1}$. The product formed directly above (324 mg, 0.83 mmol) was deprotected at 0° C. using a method analogous to that described in General Procedure F to afford the di-TFA-salt of the compound formed directly above as a tan solid (310 mg) that was dissolved in ethanol (10 mL), magnetically stirred and treated with triethylamine (663 μL, 4.77 mmol). The resulting solution was then treated with a solution of 2-isothiocyanato-4,5-dimethoxybenzonitrile (131 mg, 0.60 mmol) in DCM (3 mL) dropwise and stirred for 2 hours at rt. The mixture was diluted with ethanol (20 mL) then heated at 70° C. for 30 mins, cooled to rt, and the solid collected and washed with ether (10 mL) to afford BT2154 (239 mg, 78%) as a brown solid. $^1$H NMR (400 MHz, DMSO-d$_6$) δ 12.09 (s, 1H), 11.76 (s, 1H), 9.34 (s, 1H), 8.88 (s, 1H), 8.55 (d, J=4.6 Hz, 1H), 8.06 (d, J=7.9 Hz, 1H), 7.77 (d, J=8.4 Hz, 1H), 7.70 (s, 1H), 7.57 (s, 1H), 7.49 (dd, J=7.5, 5.2 Hz, 1H), 7.40 (d, J=8.3 Hz, 1H), 6.85 (s, 1H), 6.81 (s, 1H), 6.01-5.89 (m, 1H), 5.08-4.96 (m, 1H), 4.90-4.79 (m, 1H), 4.71-4.57 (m, 1H), 4.44-4.33 (m, 1H), 3.80 (s, 3H), 3.78 (s, 3H). (+)-LRESIMS m/z (rel. int.) 513 (100)

[M+H]+; $v_{max}$ 3213, 1625, 1599, 1534, 1508, 1432, 1387, 1281, 1245, 1232, 1008, 797 cm$^{-1}$.

II. BIOLOGICAL EXAMPLES

Figure 2:
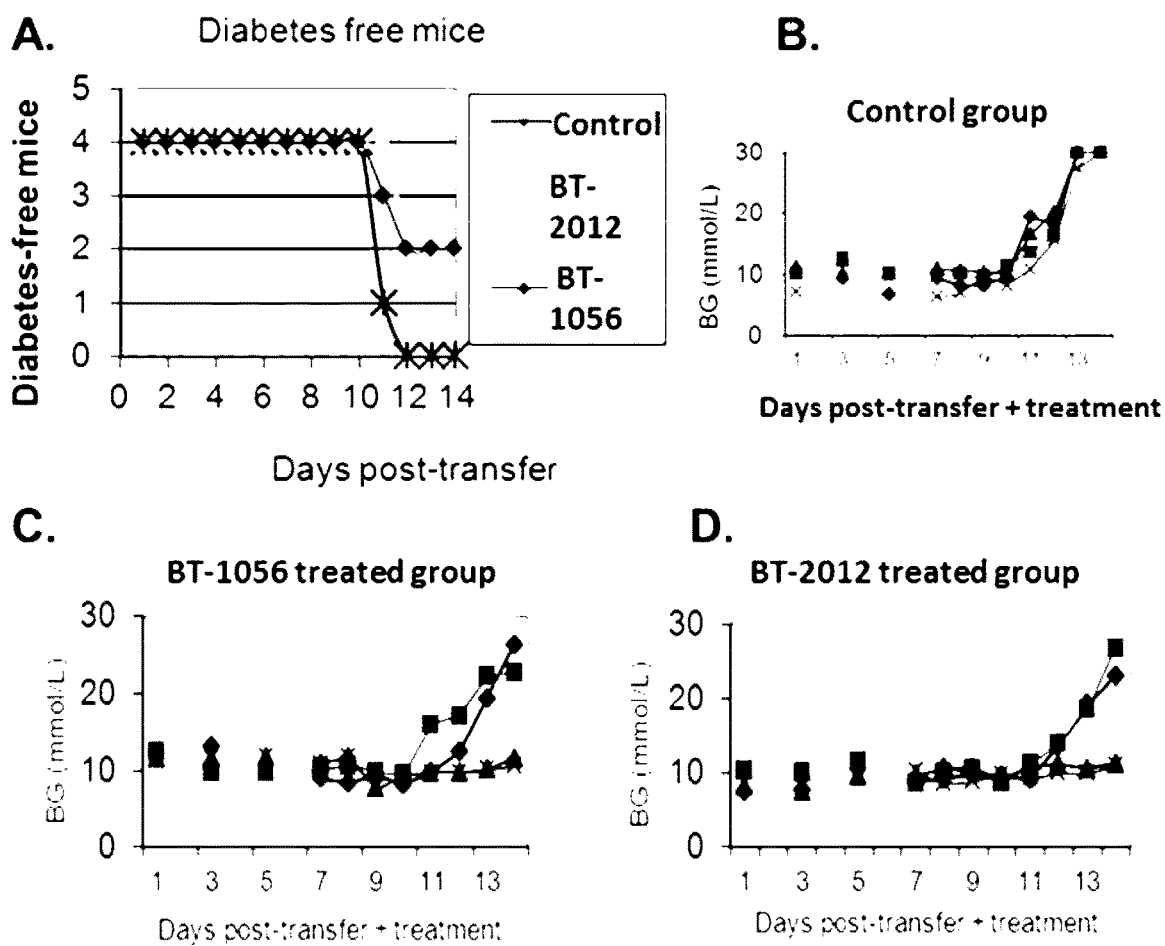
FIG. 2. Treatment of RIP-OVA$^{hi}$ mice from the time of adoptive transfer of OVA-specific OT-1 and activated OT-III tg T cells with the small molecule heparanase inhibitor BT-2012 (10 mg/kg QD, IP in saline/50% DMSO). (A) Incidence of diabetes (blood glucose >12 mmol) was significantly reduced (50%) following treatment with BT-2012. Daily blood glucose levels of individual control (saline/50% DMSO treated) mice (B) were significantly higher in all controls compared to the treatment groups (C & D) where blood glucose remained normal in 50% of the individual treated mice or did not reach the same high levels as untreated in the 14 day assay period when treated with small molecule heparanase inhibitors BT-2012 or a comparator heparanase inhibitor (denoted "BT-1056").
Figure 3:
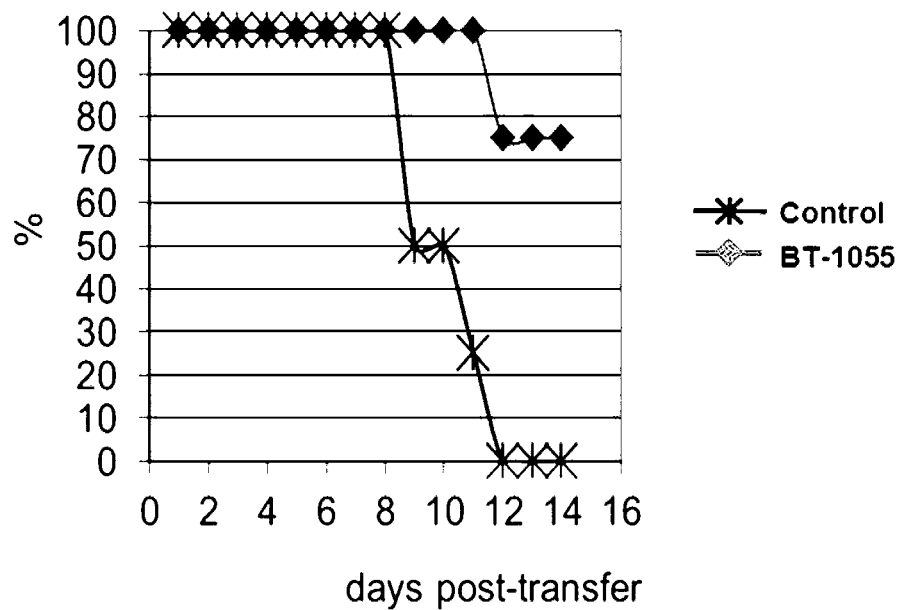
FIG. 3. Treatment of RIP-OVA$^{hi}$ mice from the time of adoptive transfer of OVA-specific OT-1 and activated OT-II tg T cells with a control heparanase inhibitor, (denoted "BT-1055") (10 mg/kg QD, IP in saline/20% DMSO). (A) Incidence of diabetes (blood glucose >12 mmol) was significantly reduced (75%) following treatment with BT-1055. Daily blood glucose levels of individual control (saline/20% DMSO treated) mice (B) were significantly higher in all controls compared to mice treated with comparator heparanase inhibitor (C) where blood glucose remained normal in 75% of the individual treated mice or did not reach the same high levels as untreated in the 14 day assay period.
Figure 3:
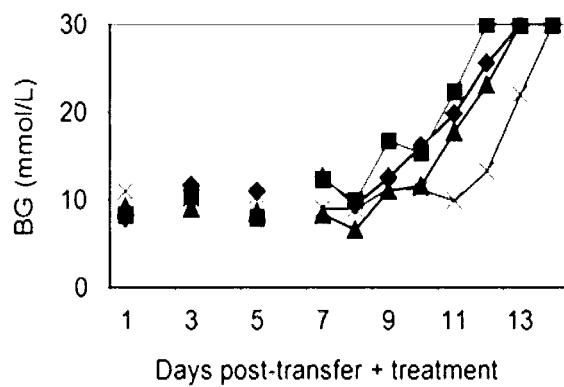
Figure 3:
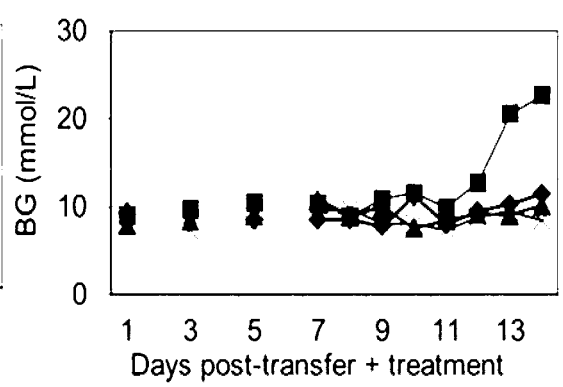
Figure 4:
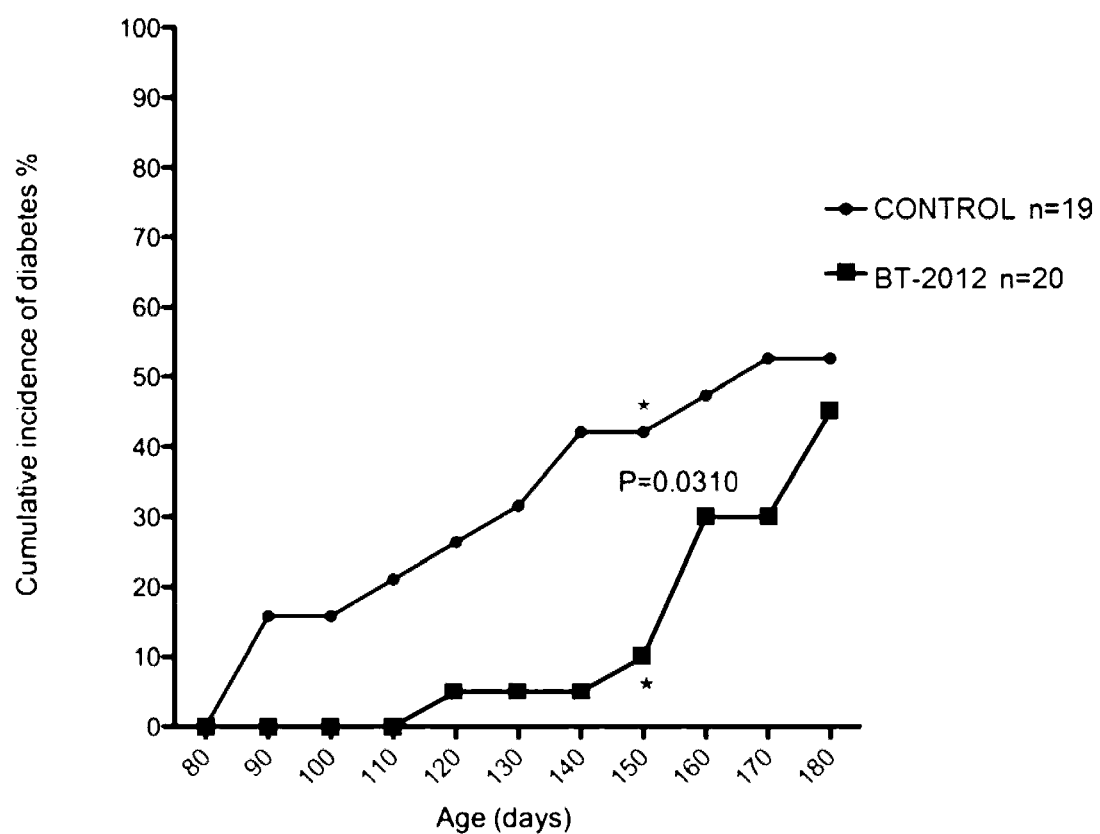
FIG. 4. Treatment of NOD/Lt mice with the small molecule heparanase inhibitor BT-2012. All mice were dosed daily at 10 mg/kg, IP in saline/50% DMSO from 80-180 days of age. Onset of clinical diabetes was determined by measuring urine glucose twice weekly with Multistix reagent strips and confirmed by measuring non-fasting blood glucose levels in tail vein blood using a MediSense glucometer with hyperglycemia defined as 2 consecutive blood glucose readings of 16 mmol/I or greater.

Example I—Establishment of the Adoptive Transfer of Type 1 Diabetes in Transgenic RIP-OVAhi Mice: An Acute Experimental Type 1 Diabetes Model for Rapid Drug Efficacy Profiling In NOD mice, the autoimmune disease process develops slowly because of the asynchronous destruction of the beta cells in different islets. Indeed Type 1 diabetes develops only after >90% of the total islet beta cell mass has been destroyed. The slow course of the disease in NOD mice offers realistic potential for immune intervention but, unfortunately, high throughput screening of test drugs is not feasible. A more acute model of diabetes can be induced experimentally using RIP-OVAhi transgenic mice which express a foreign ovalbumin (OVA) peptide, under the control of the rat insulin promoter (RIP), only in islet beta cells. Following adoptive transfer of naïve OVA specific CD8+ (OT-I) and activated OVA-specific CD4+ (OT-II) transgenic T cells, the transgenic T cells traffic to the host lymph nodes where the OT-I T cells become activated and then to the OVA-expressing pancreatic islets where they rapidly induce islet beta cell destruction and diabetes, all mice succumbing to rapid onset of high blood glucose levels (hyperglycaemia) in the second week after cell transfer. Using heparanase knockout donor and recipient mouse strains, it has been demonstrated that this acute model of Type 1 diabetes is heparanase-dependent (FIG. 1). Compared to the development of Type 1 diabetes within 14 days in heparanase normal mice, lack of heparanase completely prevented Type 1 diabetes and the mice remained normoglycaemic for the duration of the experiment (FIG. 1). These findings together with the acute clinical manifestation of this highly aggressive 'pseudoautoimmune' disease allows rapid initial screening of compounds to identify a suitable clinically relevant lead to replace PI-88 (see Example 2, Table 1). Using the RIP-OVAhi acute model of Type 1 diabetes to test the drug candidates, the inventors demonstrate that 10 mg/kg BT-2012, BT-1056 and BT-1055 (a comparator small molecule heparanase inhibitor) protected RIPOVAhi mice from Type 1 diabetes induction following adoptive transfer of diabetogenic tg T cells, with significant numbers of mice remaining Type 1 diabetes disease-free by 14 days after transfer (FIGS. 2 and 3).

Comparative Example II—Control of Blood Glucose Levels

Using the RIP-OVAhi transgenic mice the effect of a heparanase inhibitor compound (denoted "BT-1055") was tested for its effect on blood glucose levels. Following adoptive transfer of naïve OVA specific CD8+ (OT-I) and activated OVA-specific CD4+ (OT-II) transgenic T cells into a number of RIP-OVAhi mice blood glucose was monitored regularly over two weeks in populations of mice treated with BT-1055 and a control group administered saline (FIG. 3).

Figure 5:
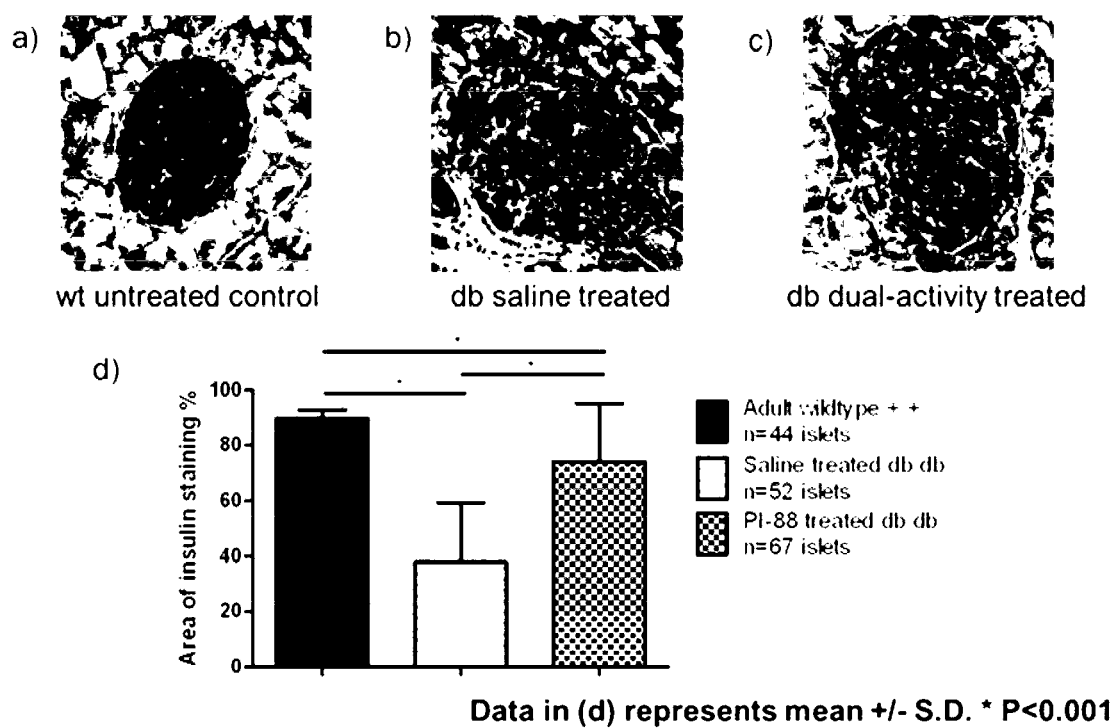
FIG. 5. Insulin content in pancreas sections in db/db mice a model of Type 2 diabetes. Mice were treated daily with 50 mg/kg PI-88 IP from 4 weeks of age. Onset of clinical diabetes was determined by measuring urine glucose twice weekly with Multistix reagent strips and confirmed by measuring non-fasting blood glucose levels in tail vein blood using a MediSense glucometer with hyperglycemia defined as 2 consecutive blood glucose readings of 16 mmol/I or greater. Insulin was detected by anti-insulin antibody staining.

Comparative Example III—Effect of Treatment with a Sulfated Oligosaccharide (PI-88) on Insulin Production The db/db mouse has defective leptin signalling resulting from a point mutation in the leptin receptor gene. Plasma insulin levels become elevated very early in life (10-14 days of age), and the affected animals are obese by the time they are 3-4 weeks old. The animals are insulin resistant, hypertriglyceridemic, and have impaired glucose tolerance.

db/db mice were treated with saline or 50 mg/kg of PI-88 by daily intraperitoneal injection. At the cessation of treatment pancreatic islets were isolated and stained for insulin and the level of insulin expression assessed by quantitative morphometric analyses. FIG. 5 shows that compared to islets from untreated wild-type mice a significant reduction in insulin expression occurs in db/db mice treated with saline. However treatment of the db/db mice with PI-88 results in expression of insulin in islets that is increased compared to the saline treated db/db mice and is near to the level of insulin expression in the wild-type mice.

Figure 6:
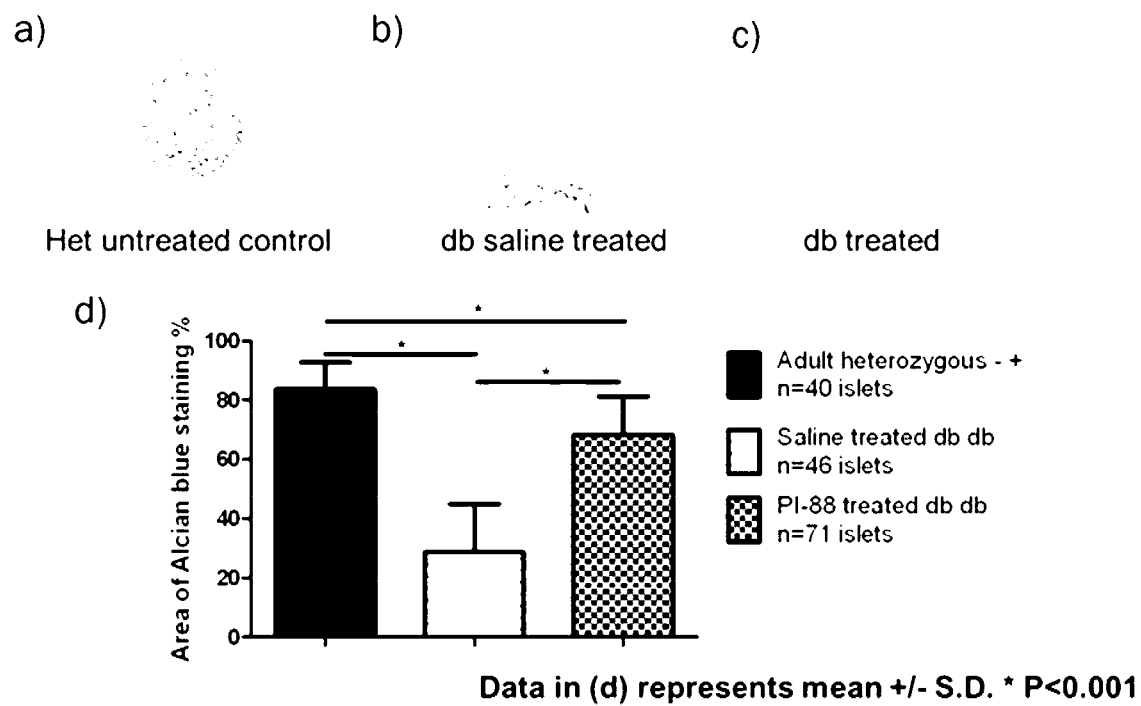
FIG. 6. Intra-islet HS content in pancreas sections in treated db/db mice. Mice were treated daily with 50 mg/kg PI-88 IP from 4 weeks of age. Onset of clinical diabetes was determined by measuring urine glucose twice weekly with Multistix reagent strips and confirmed by measuring non-fasting blood glucose levels in tail vein blood using a MediSense glucometer with hyperglycemia defined as 2 consecutive blood glucose readings of 16 mmol/l or greater. Islet HS was detected by Alcian blue staining.

Comparative Example IV—Effect of Treatment with a Sulfated Oligosaccharide (PI-88) on Heparan Sulfate Levels db/db mice were treated with saline or 50 mg/kg of PI-88 daily by intraperitoneal injection. At the cessation of treatment pancreatic islets were isolated and stained with alcian blue to visualise heparan sulfate and the heparan sulfate content of the islets was assessed by quantitative morphometric analyses. FIG. 6 shows that compared to islets from untreated wild-type mice a significant reduction in heparan sulfate content occurs in the islets of db/db mice treated with saline. However treatment of the db/db mice with the sulfated polysaccharide results in islet heparan sulfate levels that are increased compared to the saline treated db/db mice and are near to the levels of heparan sulfate in the islets of wild-type mice.

Example V—General Screening Protocol for Compounds

1. Heparanase Inhibition:

Heparanase inhibitor compounds of the invention may be tested for inhibition of heparanase at 10 µM using a standardised enzymatic assay (Hammond E, et al. Development of a colorimetric assay for heparanase activity suitable for kinetic analysis and inhibitor screening. *Anal Biochem.* 2010; 396:112-116). Molecules exhibiting 50% or greater heparanase inhibition may be further assessed to determine the specific half-maximal inhibitor concentrations of heparanase (IC$_{50}$). Molecules with heparanase inhibition IC$_{50}$ within a desired range (e.g., 100 µM and below, 50 µM and below, 10 µM and below, 5 µM and below, 2 µM and below, etc) may be prioritised for further in vitro and in vivo screening as appropriate.

2. Establish Off-Target Activity Counter-Screens:

A first category of counter-screens may be used to determine whether heparanase inhibition by compounds of the invention occurs via competitive inhibition and not protein aggregation. A second category of counter-screens forms part of a larger suite of biochemical characterization to identify areas that might be improved as part of lead optimisation. For example, the second category of counter-screens may be used to assess off-target activity against the following:

heparanase-related glycosidases including (α,β)-glucosidase and β-glucuronidase;
heparan sulfate binding proteins including VEGF, FGF-1 and FGF-2; and
kinase inhibition panels to establish the ratio of on-target to off-target activity.

3. In Vitro Toxicity:

Heparanase inhibitor compounds of the invention may be tested for dose dependent in vitro toxicity using the Jurkat cell line and the MTT assay which provides a measure of mitochondrial function as a surrogate for cell viability. Data may be represented as Tox50 as drug concentration at which only 50% of cells remain viable. Typically, compounds that have a Tox50 of 200 μM or greater may be prioritised for further evaluation.

4. In Vitro ADME (Absorption, Distribution, Metabolism, and Excretion):

Compounds of the invention can undergo an initial assessment of ADMET (absorption, distribution, metabolism, excretion and toxicology) properties using standard methods.

Initial in vitro assays may include the following:
- A. Solubility: Compounds may be tested for solubility in a standard kinetic solubility assay at different pH levels (pH 2.1, 4.0 and 7.4) with a typical target solubility of 100 μg/ml.
- B. PAMPA assays (membrane permeability/adsorption): The PAMPA assay is a well validated surrogate measure of membrane permeability which uses an artificial lipid bilayer, and is used increasingly in place of the Caco2 cell. Compounds may be compared with known standards drug compounds including Verapamil (high permeability) and Theophyline (low permeability). High permeability may be a criterion for prioritising compounds for further testing.
- C. Liver microsome assay: The liver microsome assay is a well-established method for determining the oxidative metabolic stability of drug candidates. Mouse and human microsomes may be used to support decision making when selecting candidate compounds for in vivo studies in mouse models. The percentage of compound remaining at multiple time points (0, 5, 15, 30, 45 min) may be determined in comparison with standard drug compounds including Propranolol (highly stable), Ketoprofen (intermediate stability) and Verapamil (rapid clearance).
- D. Protein binding: The plasma clearance of drug candidates is determined by a combination of metabolic and renal clearance. The renal clearance of drug candidates which have high protein binding is lowered, since renal clearance is size dependent and proteins exceed the upper cut-off. Excessive protein binding can however limit the availability of the drug towards the biological target. Acceptable values may typically be in the range 90-98%. Measurement of free drug concentration in plasma using equilibrium dialysis in comparison to drug standards including Propranolol (low binding), Paroxetine (intermediate binding) and Losartan (high binding). Compounds with intermediate protein binding may be prioritised.

Example VI—Heparanase Inhibition

Compounds of the invention were tested over a range of concentrations in a beta cell protection assay to evaluate their capacity to protect beta cells from dying in culture, compared to untreated controls. In addition to measuring uptake of Sytox green by flow cytometry, as a measure of cell death, a beta cell survival assay using Calcein, a dye taken up only by viable cells, in combination with the DNA-binding dye propidium iodide (PI) that identifies dead and dying cells. Mouse islets were isolated from BALB/c pancreas dispersed into beta cell suspensions using a modified method of Josefsen et al (*J. Endocrinol* 1996 149:145-154) and the beta cells cultured for 2 days in the presence or absence of compounds of the invention (0.5-50 μg/ml). Heparin and PI-88 (Muparfostat, Progen Pharmaceuticals) were included in the assays as positive controls for protection.

Heparanase inhibition was determined using standard methods and the results expressed as the half maximal inhibitory concentration ($IC_{50}$) being the concentration of the compound of the invention required to achieve 50% inhibition of heparanase. The results are shown in Table 1:

TABLE 1

Heparanase inhibition ($IC_{50}$)

| Compound Code | Structure | $IC_{50}$ |
|---|---|---|
| BT2012 | 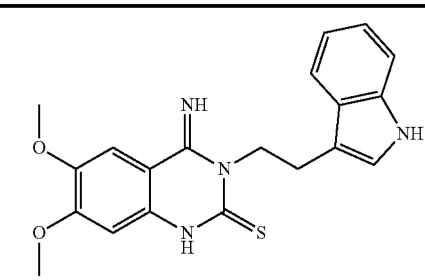 | 14.8 μM |
| BT2014 | 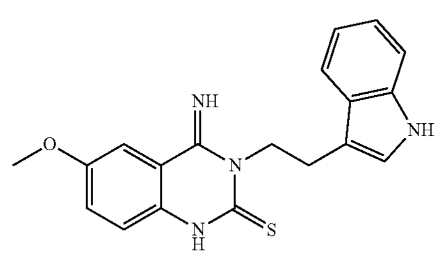 [SMILES: COc1ccc2[nH]c(=S)n(CCc3c[nH]c4ccccc34)c(=N)c2c1] | 49.3 μM |

TABLE 1-continued

Heparanase inhibition (IC$_{50}$)

| Compound Code | Structure | IC$_{50}$ |
|---|---|---|
| BT2022 | 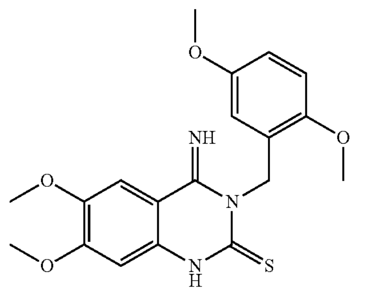 | 37.2 μM |
| BT2024 | 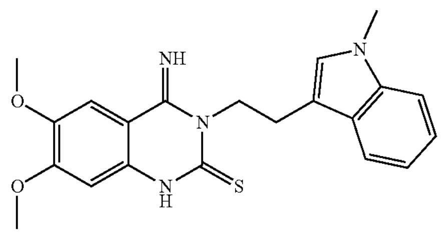 [SMILES: COc1cc2[nH]c(=S)n(CCc3cn(C)c4ccccc34)c(=N)c2cc1OC] | 27.4 μM |
| BT2027 | 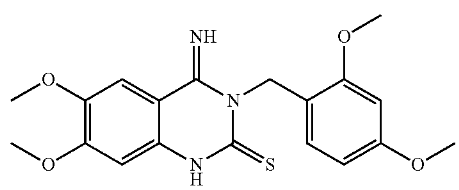 | 40.1 μM |
| BT2044 (BT2012•HCl) | 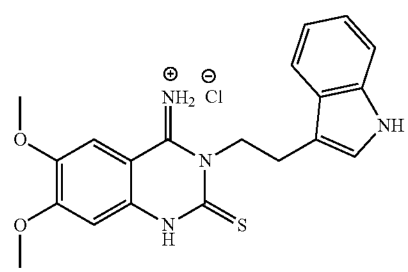 [SMILES: COc1cc2[nH]c(=S)n(CCc3c[nH]c4ccccc34)c(=[NH2+])c2cc1OC ; [Cl-]] | 30 μM |
| BT2046 | 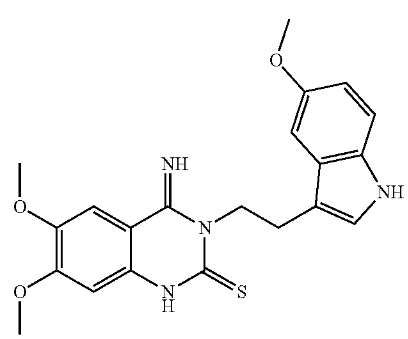 [SMILES: COc1ccc2[nH]cc(CCn3c(=S)[nH]c4cc(OC)c(OC)cc4c3=N)c2c1] | 9.4 μM |

TABLE 1-continued

Heparanase inhibition (IC$_{50}$)

| Compound Code | Structure | IC$_{50}$ |
|---|---|---|
| BT2055 | 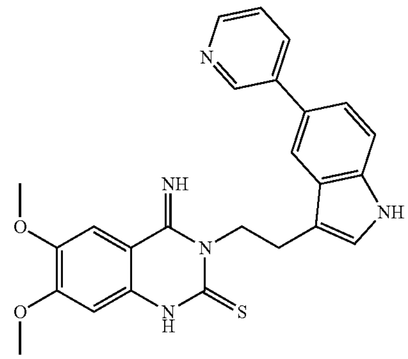 [SMILES: COc1cc2[nH]c(=S)n(CCc3c[nH]c4ccc(-c5cccnc5)cc34)c(=N)c2cc1OC] | 19.1 μM |
| BT2058 | 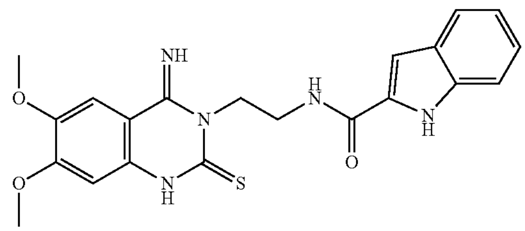 [SMILES: COc1cc2[nH]c(=S)n(CCNC(=O)c3cc4ccccc4[nH]3)c(=N)c2cc1OC] | 9 μM |
| BT2066 | 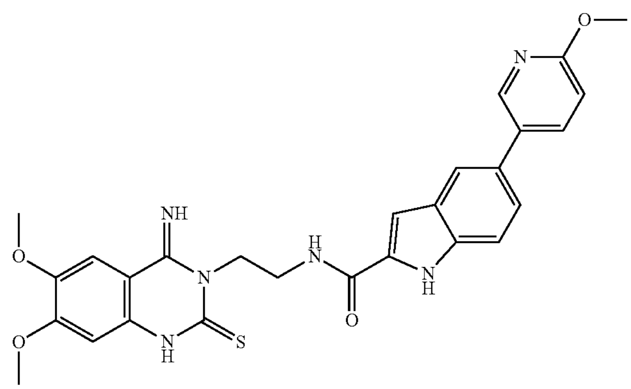 [SMILES: COc1ccc(-c2ccc3[nH]c(C(=O)NCCn4c(=S)[nH]c5cc(OC)c(OC)cc5c4=N)cc3c2)cn1] | 4.2 μM |
| BT2068 | 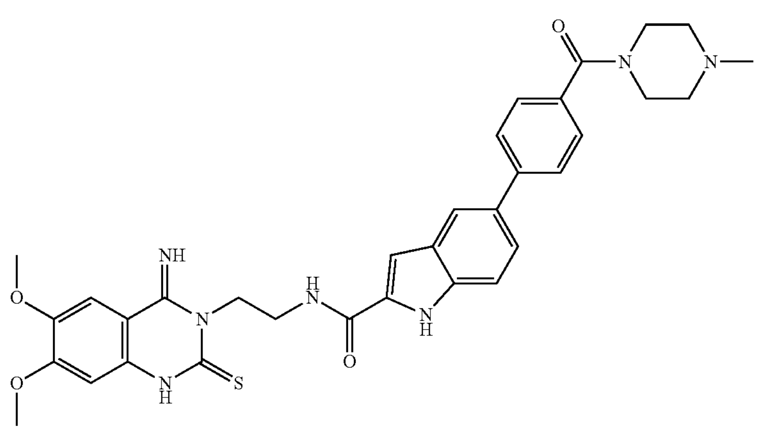 [SMILES: COc1cc2[nH]c(=S)n(CCNC(=O)c3cc4cc(-c5ccc(C(=O)N6CCN(C)CC6)cc5)ccc4[nH]3)c(=N)c2cc1OC] | 2.8 μM |

TABLE 1-continued

Heparanase inhibition (IC$_{50}$)

| Compound Code | Structure | IC$_{50}$ |
|---|---|---|
| BT2070 | 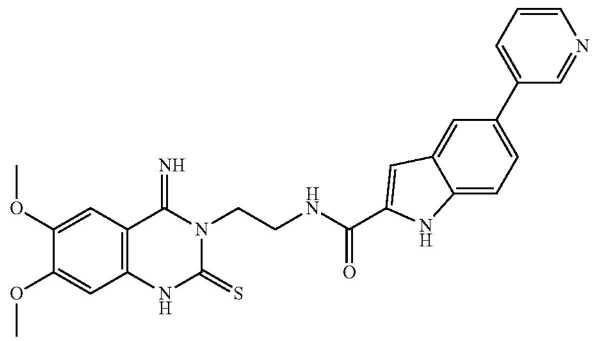 [SMILES: COc1cc2[nH]c(=S)n(CCNC(=O)c3cc4cc(-c5cccnc5)ccc4[nH]3)c(=N)c2cc1OC] | 1.0 μM |
| BT2071 | 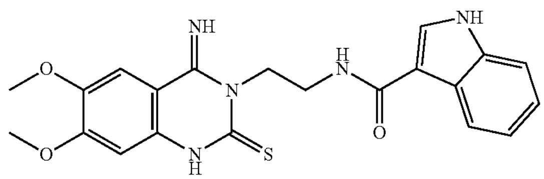 [SMILES: COc1cc2[nH]c(=S)n(CCNC(=O)c3c[nH]c4ccccc34)c(=N)c2cc1OC] | 7 μM |
| BT2072 | 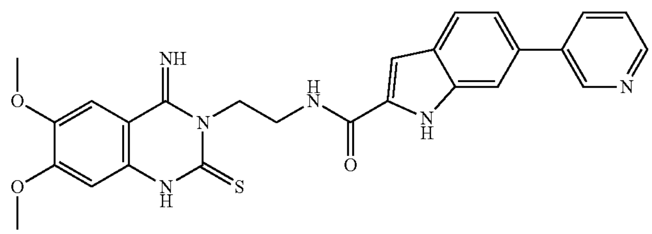 [SMILES: COc1cc2[nH]c(=S)n(CCNC(=O)c3cc4ccc(-c5cccnc5)cc4[nH]3)c(=N)c2cc1OC] | 3.1 μM |
| BT2073 | 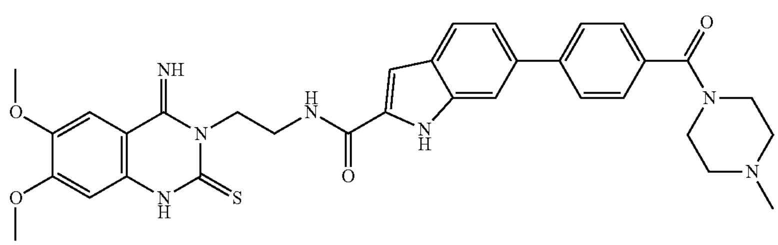 [SMILES: COc1cc2[nH]c(=S)n(CCNC(=O)c3cc4ccc(-c5ccc(C(=O)N6CCN(C)CC6)cc5)cc4[nH]3)c(=N)c2cc1OC] | 51 μM |
| BT2075 | 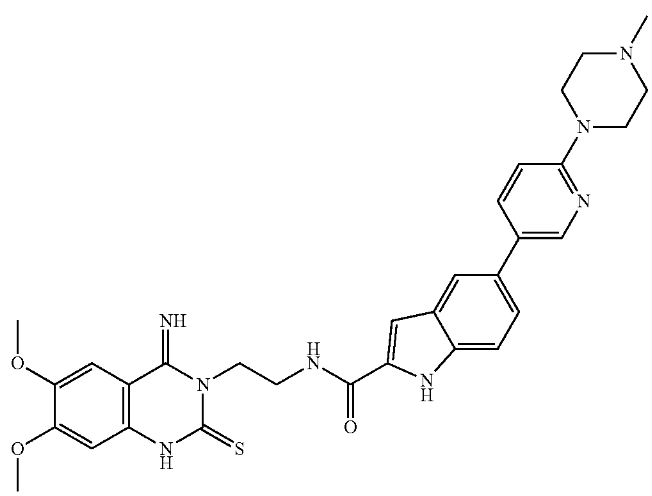 [SMILES: COc1cc2[nH]c(=S)n(CCNC(=O)c3cc4cc(-c5ccc(N6CCN(C)CC6)nc5)ccc4[nH]3)c(=N)c2cc1OC] | 20.6 μM |

TABLE 1-continued

Heparanase inhibition (IC$_{50}$)

| Compound Code | Structure | IC$_{50}$ |
|---|---|---|
| BT2076 | 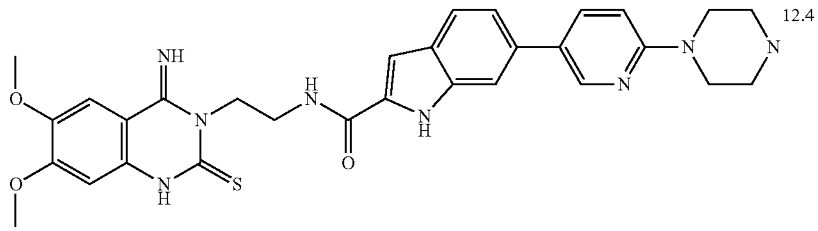 | 12.4 μM |
| BT2078 | 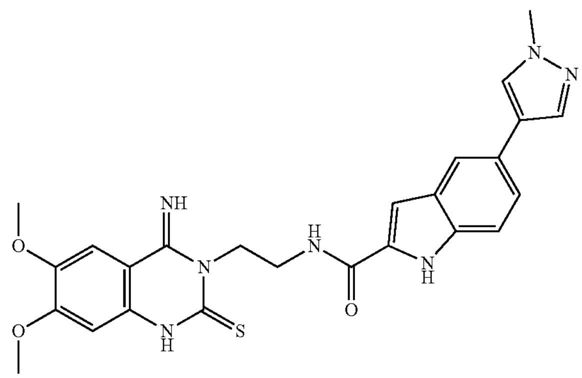 [SMILES: COc1cc2[nH]c(=S)n(CCNC(=O)c3cc4cc(-c5cnn(C)c5)ccc4[nH]3)c(=N)c2cc1OC] | 34.8 μM |
| BT2079 | 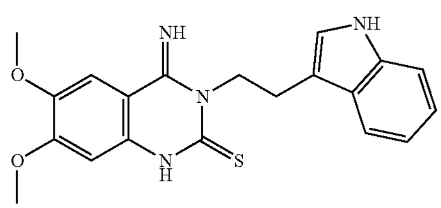 [SMILES: COc1cc2[nH]c(=S)n(CCc3c[nH]c4ccccc34)c(=N)c2cc1OC] | 103.4 μM |
| BT2080 | 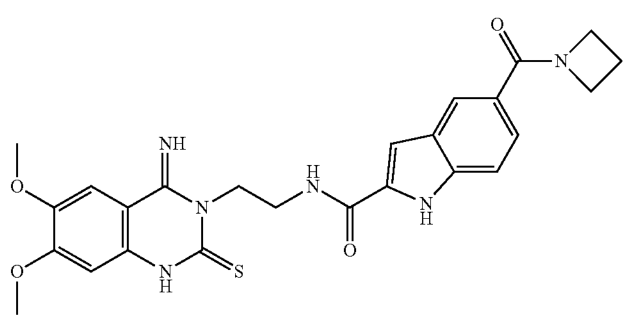 [SMILES: COc1cc2[nH]c(=S)n(CCNC(=O)c3cc4cc(C(=O)N5CCC5)ccc4[nH]3)c(=N)c2cc1OC] | 90.4 μM |
| BT2081 | 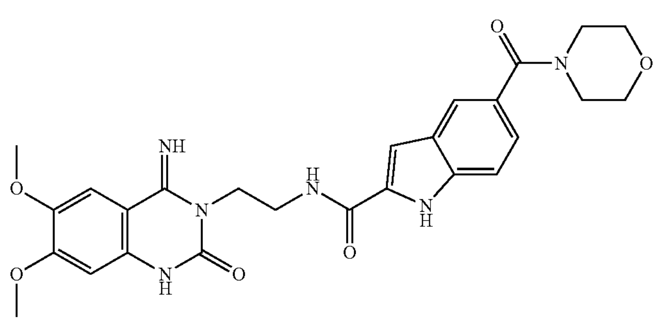 | 90.4 μM |

TABLE 1-continued

Heparanase inhibition (IC$_{50}$)

| Compound Code | Structure | IC$_{50}$ |
|---|---|---|
| BT2082 | 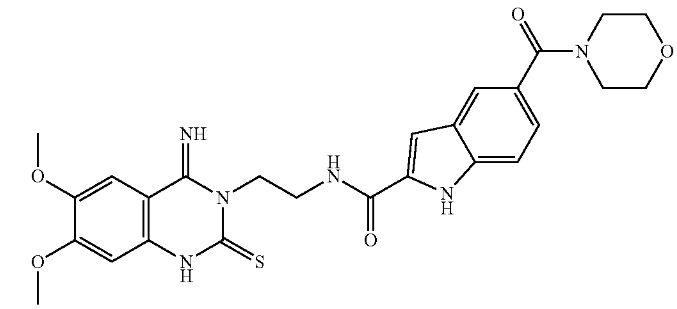 [SMILES: COc1cc2[nH]c(=O)n(CCNC(=O)c3cc4cc(C(=O)N5CCOCC5)ccc4[nH]3)c(=N)c2cc1OC] | 35 μM |
| BT2083 | 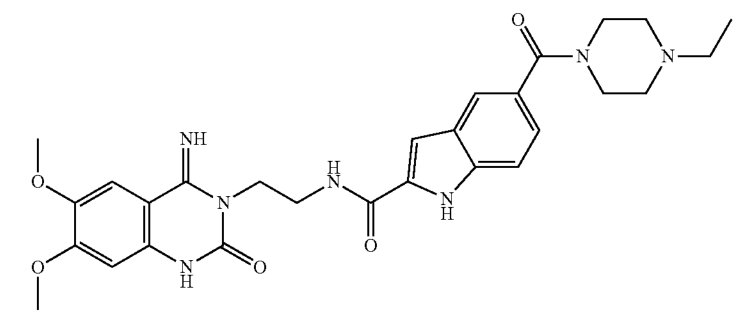 [SMILES: CCN1CCN(C(=O)c2ccc3[nH]c(C(=O)NCCn4c(=O)[nH]c5cc(OC)c(OC)cc5c4=N)cc3c2)CC1] | 10.1 μM |
| BT2085 | 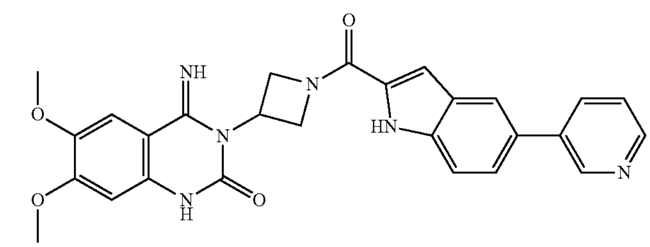 [SMILES: COc1cc2[nH]c(=O)n(C3CN(C(=O)c4cc5cc(-c6cccnc6)ccc5[nH]4)C3)c(=N)c2cc1OC] | 1.3 μM |
| BT2100 | 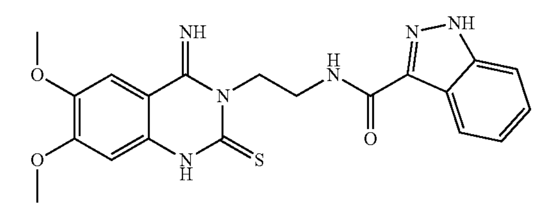 [SMILES: COc1cc2[nH]c(=S)n(CCNC(=O)c3n[nH]c4ccccc34)c(=N)c2cc1OC] | 37.0 μM |
| BT2103 | 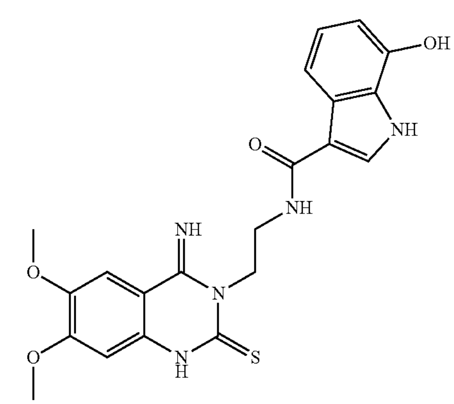 [SMILES: COc1cc2[nH]c(=S)n(CCNC(=O)c3c[nH]c4c(O)cccc34)c(=N)c2cc1OC] | 10.7 μM |

TABLE 1-continued

Heparanase inhibition (IC$_{50}$)

| Compound Code | Structure | IC$_{50}$ |
|---|---|---|
| BT2104 | 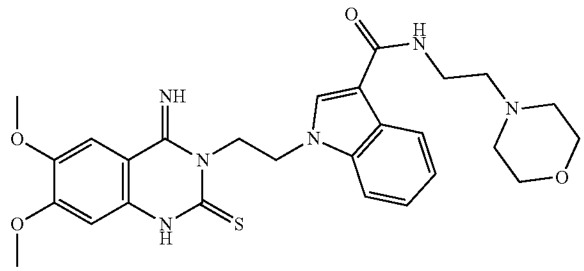 [SMILES: COc1cc2[nH]c(=S)n(CCn3cc(C(=O)NCCN4CCOCC4)c4ccccc43)c(=N)c2cc1OC] | 44.8 μM |
| BT2113 | 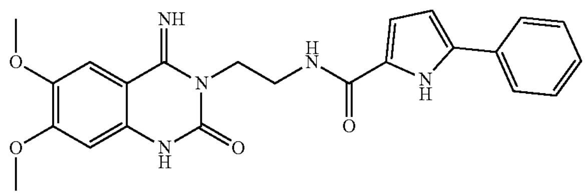 [SMILES: COc1cc2[nH]c(=O)n(CCNC(=O)c3ccc(-c4ccccc4)[nH]3)c(=N)c2cc1OC] | 10.6 μM |
| BT2115 | 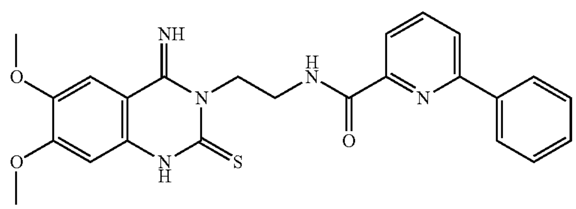 [SMILES: COc1cc2[nH]c(=S)n(CCNC(=O)c3cccc(-c4ccccc4)n3)c(=N)c2cc1OC] | 19.7 μM |
| BT2116 | 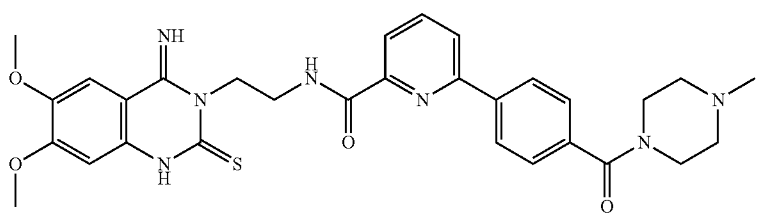 [SMILES: COc1cc2[nH]c(=S)n(CCNC(=O)c3cccc(-c4ccc(C(=O)N5CCN(C)CC5)cc4)n3)c(=N)c2cc1OC] | 12.8 μM |
| BT2117 | 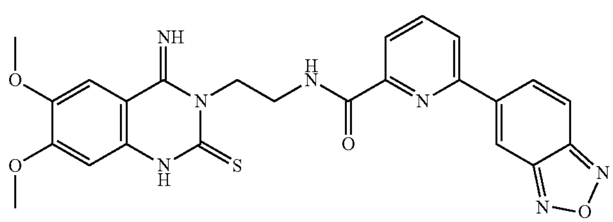 [SMILES: COc1cc2[nH]c(=S)n(CCNC(=O)c3cccc(-c4ccc5nonc5c4)n3)c(=N)c2cc1OC] | 12.5 μM |
| BT2125 | 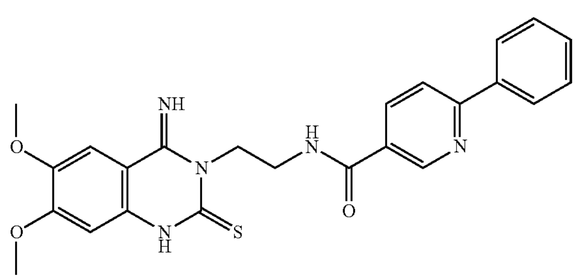 [SMILES: COc1cc2[nH]c(=S)n(CCNC(=O)c3ccc(-c4ccccc4)nc3)c(=N)c2cc1OC] | 15.6 μM |

TABLE 1-continued
Heparanase inhibition (IC$_{50}$)
| Compound Code | Structure | IC$_{50}$ |
|---|---|---|
| BT2130 (BT2116 HCl) | 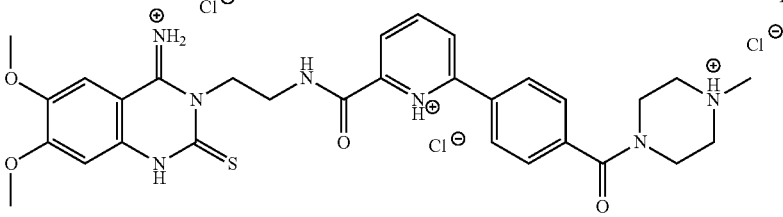 | 12.8 μM |
| BT2132 | 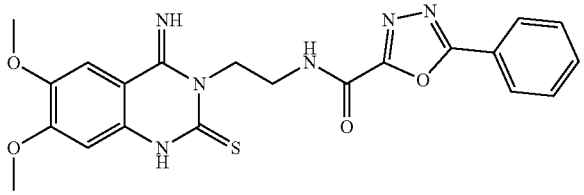 [SMILES: COc1cc2[nH]c(=S)n(CCNC(=O)c3nnc(-c4ccccc4)o3)c(=N)c2cc1OC] | 58.6 μM |
| BT2133 | 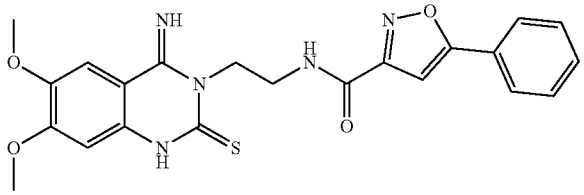 [SMILES: COc1cc2[nH]c(=S)n(CCNC(=O)c3cc(-c4ccccc4)on3)c(=N)c2cc1OC] | 31.7 μM |
| BT2134 | 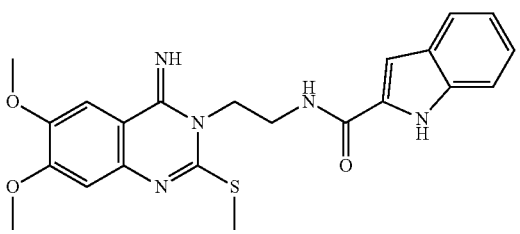 [SMILES: COc1cc2nc(SC)n(CCNC(=O)c3cc4ccccc4[nH]3)c(=N)c2cc1OC] | 24.9 μM |
| BT2135 | 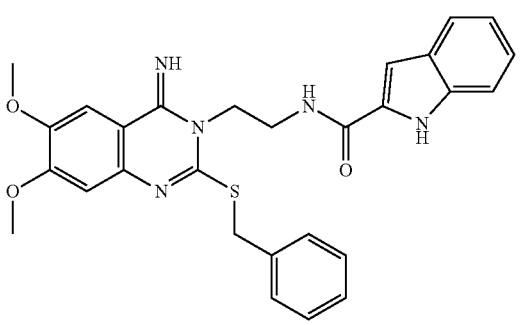 [SMILES: COc1cc2nc(SCc3ccccc3)n(CCNC(=O)c3cc4ccccc4[nH]3)c(=N)c2cc1OC] | 64.0 μM |
| BT2136 | 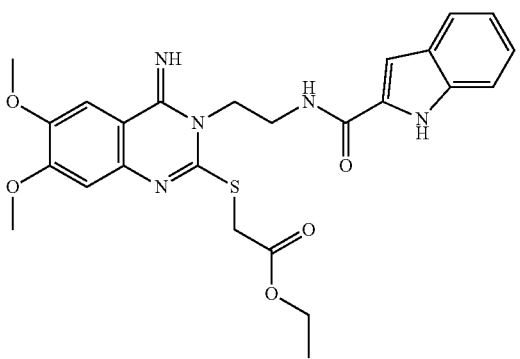 [SMILES: CCOC(=O)CSc1nc2cc(OC)c(OC)cc2c(=N)n1CCNC(=O)c1cc2ccccc2[nH]1] | 26.8 μM |

TABLE 1-continued
Heparanase inhibition (IC$_{50}$)
| Compound Code | Structure | IC$_{50}$ |
| --- | --- | --- |
| BT2137 | 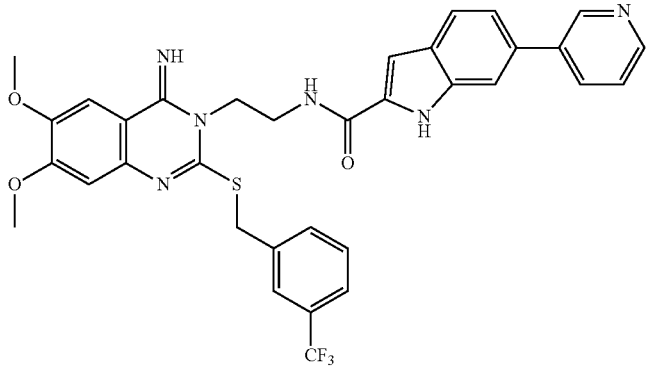 [SMILES: COc1cc2nc(SCc3cccc(C(F)(F)F)c3)n(CCNC(=O)c3cc4ccc(-c5cccnc5)cc4[nH]3)c(=N)c2cc1OC] | 28.0 μM |
| BT2138 | 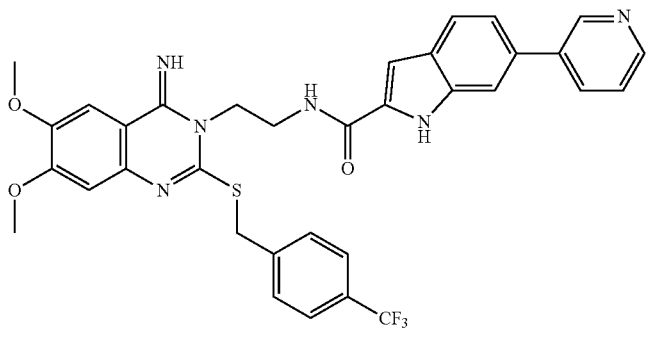 [SMILES: COc1cc2nc(SCc3ccc(C(F)(F)F)cc3)n(CCNC(=O)c3cc4ccc(-c5cccnc5)cc4[nH]3)c(=N)c2cc1OC] | 5.9 μM |
| BT2139 | 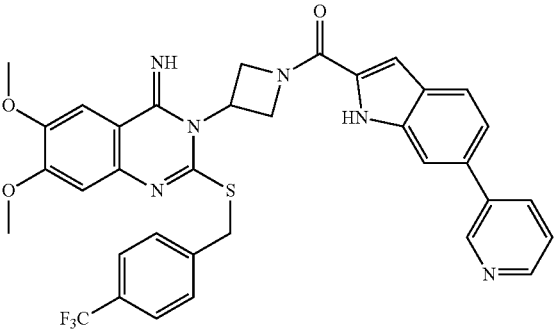 [SMILES: COc1cc2nc(SCc3ccc(C(F)(F)F)cc3)n(C3CN(C(=O)c4cc5ccc(-c6cccnc6)cc5[nH]4)C3)c(=N)c2cc1OC] | 13.0 μM |
| BT2140 (BT2139 HCl) | 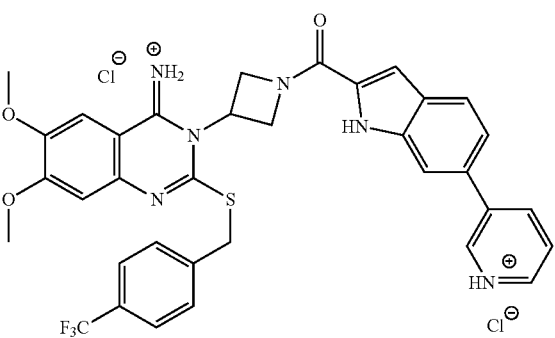 [SMILES: COc1cc2nc(SCc3ccc(C(F)(F)F)cc3)n(C3CN(C(=O)c4cc5ccc(-c6ccc[nH+]c6)cc5[nH]4)C3)c(=[NH2+])c2cc1OC ; [Cl-] ; [Cl-]] | 37.5 μM |

TABLE 1-continued

Heparanase inhibition (IC$_{50}$)

| Compound Code | Structure | IC$_{50}$ |
|---|---|---|
| BT2141 | 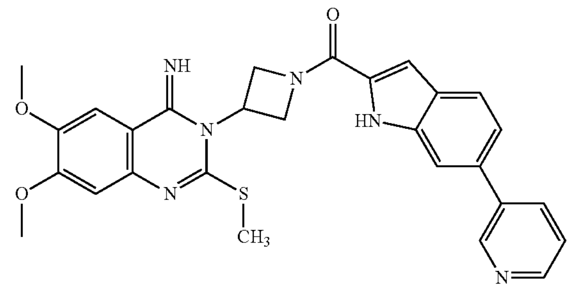 [SMILES: COc1cc2nc(SC)n(C3CN(C(=O)c4cc5ccc(-c6cccnc6)cc5[nH]4)C3)c(=N)c2cc1OC] | 23.6 μM |
| BT2142 | 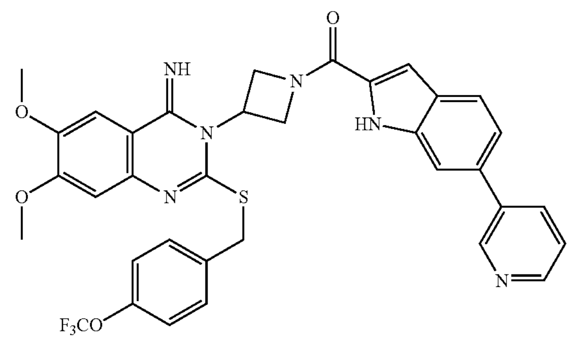 [SMILES: COc1cc2nc(SCc3ccc(OC(F)(F)F)cc3)n(C3CN(C(=O)c4cc5ccc(-c6cccnc6)cc5[nH]4)C3)c(=N)c2cc1OC] | 7.0 μM |
| BT2143 (BT2141 HCl) | 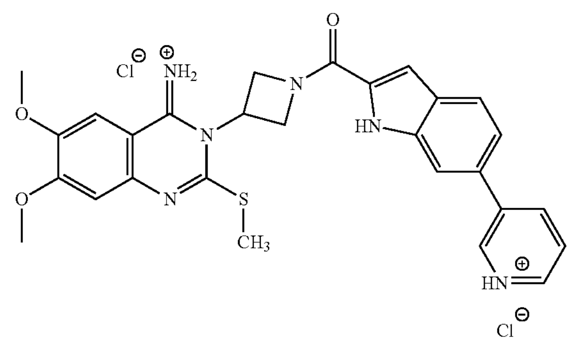 [SMILES: COc1cc2nc(SC)n(C3CN(C(=O)c4cc5ccc(-c6ccc[nH+]c6)cc5[nH]4)C3)c(=[NH2+])c2cc1OC ; [Cl-] ; [Cl-]] | 33.0 μM |
| BT2144 (BT2132 HCl) | 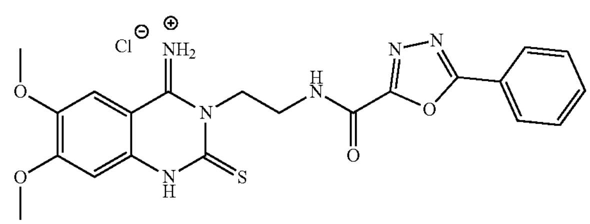 [SMILES: COc1cc2[nH]c(=S)n(CCNC(=O)c3nnc(-c4ccccc4)o3)c(=[NH2+])c2cc1OC ; [Cl-]] | 59.9 μM |
| BT2145 (BT2142 HCl) | 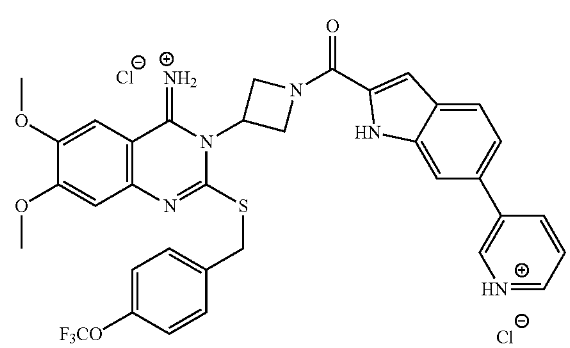 [SMILES: COc1cc2nc(SCc3ccc(OC(F)(F)F)cc3)n(C3CN(C(=O)c4cc5ccc(-c6ccc[nH+]c6)cc5[nH]4)C3)c(=[NH2+])c2cc1OC ; [Cl-] ; [Cl-]] | 22.0 μM |

TABLE 1-continued

Heparanase inhibition (IC$_{50}$)

| Compound Code | Structure | IC$_{50}$ |
|---|---|---|
| BT2152 | 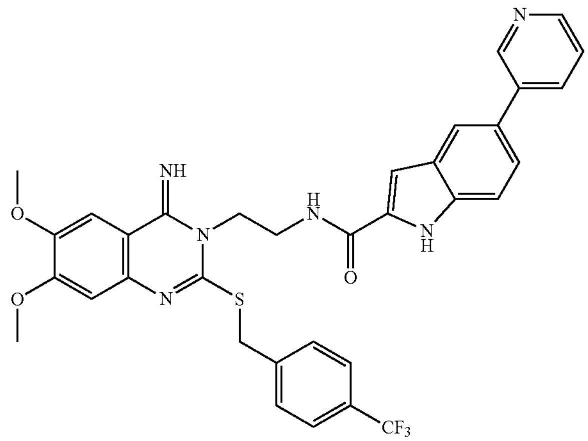 [SMILES: COc1cc2nc(SCc3ccc(C(F)(F)F)cc3)n(CCNC(=O)c3cc4cc(-c5cccnc5)ccc4[nH]3)c(=N)c2cc1OC] | 2.89 µM |
| BT2153 | 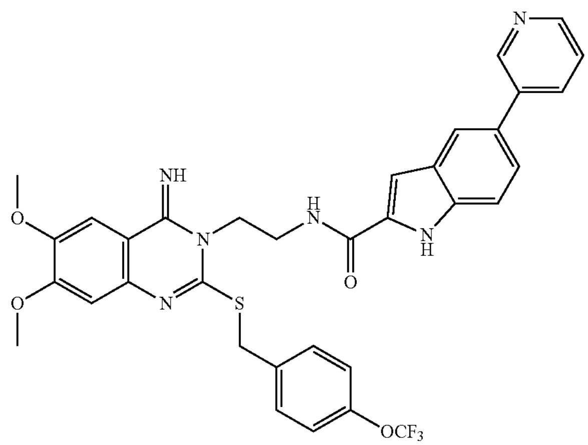 [SMILES: COc1cc2nc(SCc3ccc(OC(F)(F)F)cc3)n(CCNC(=O)c3cc4cc(-c5cccnc5)ccc4[nH]3)c(=N)c2cc1OC] | 5.7 µM |

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A compound of formula

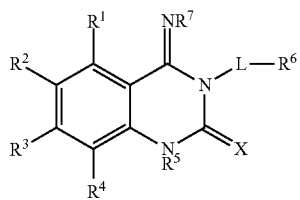

or a pharmaceutically acceptable salt, tautomer or stereoisomer thereof,
wherein:
X is S or O;
R$^1$ is selected from H, hydroxyl, halo, C$_{1-6}$alkyl, C$_{1-4}$alkoxy, O-CH$_2$phenyl, O-phenyl;
R$^2$ is selected from H, hydroxyl, halo, C$_{1-6}$alkyl, C$_{1-4}$alkoxy, O-CH$_2$phenyl, O-phenyl;
R$^3$ is selected from H, hydroxyl, halo, C$_{1-6}$alkyl, C$_{1-4}$alkoxy, O-CH$_2$phenyl, O-phenyl;
R$^4$ is selected from H, hydroxyl, halo, C$_{1-6}$alkyl, C$_{1-4}$alkoxy, O-CH$_2$phenyl, O-phenyl;
or R$^1$ and R$^2$, or R$^2$ and R$^3$, or R$^3$ and R$^4$ together form C$_{1-3}$alkylenedioxy;
R$^5$ is selected from H and C$_{1-6}$ alkyl;
L is selected from C$_{1-6}$ alkylene-indolyl, C$_{1-6}$alkylene-NHC(O)—, azetidinyl-C(O)—, C$_{1-6}$alkylene-NHC(O)-indolyl, and C$_{1-6}$alkylene-NHSO$_2$—;
R$^6$ is selected from H, halo, hydroxyl, C$_{1-6}$alkyl, C$_{2-6}$alkenyl, C$_{2-6}$alkynyl, C$_{6-10}$aryl optionally substituted with 1 or 2 R$^X$ groups, C$_{1-9}$heteroaryl optionally substituted with 1 or 2 R$^X$ groups, C$_{2-5}$heterocycloalkyl optionally substituted with 1 or 2 R$^X$ groups, or is absent;
each R$^X$ is independently selected from hydroxyl, halo, nitro, NR'R''; C$_{1-4}$alkyl, C$_{3-6}$cycloalkyl, haloC$_{1-4}$alkyl, C$_{1-4}$alkoxy, C$_{6-10}$aryl optionally substituted with 1 or 2 R$^Y$ groups, C$_{1-9}$heteroaryl, C$_{1-4}$alkyl-(C$_{1-9}$heteroaryl), C(O)OC$_{1-4}$alkyl, C(O)NHR$^Y$, C$_{2-5}$heterocycloalkyl optionally substituted with 1 or 2 C$_{1-4}$alkyl groups, C(O)—(C$_{2-5}$heterocycloalkyl)

optionally substituted with 1 or 2 $C_{1-4}$alkyl groups, or two adjacent $R^X$ groups together form $C_{1-3}$alkylenedioxy;

$R^Y$ is selected from H, hydroxyl, halo, $C_{1-4}$ alkyl, halo$C_{1-4}$ alkyl, $C_{1-4}$ alkoxy, $C_{1-4}$ alkylheterocycloalkyl, C(O)—($C_{1-4}$ alkyl$C_{2-5}$heterocycloalkyl), $C_{1-4}$alkylNR'R";

R' and R" are independently selected from H, $C_{1-4}$alkyl, $C_{1-4}$ alkyl$C_{2-5}$heterocycloalkyl;

$R^7$ is selected from H, $C_{1-4}$alkyl, $C_{1-6}$alkyl$C_{1-9}$heteroaryl, wherein the term heterocycloalkyl refers to a cycloalkyl ring in which one or more carbon atoms has been replaced by one or more heteroatoms.

2. A compound of formula

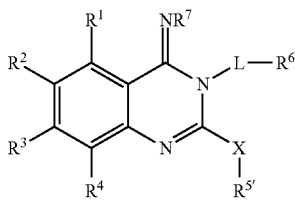

or a pharmaceutically acceptable salt, tautomer or stereoisomer thereof,
wherein:
X is S or O;
$R^1$ is selected from H, hydroxyl, halo, $C_{1-6}$alkyl, $C_{1-4}$alkoxy, O-CH$_2$phenyl, O-phenyl;
$R^2$ is selected from H, hydroxyl, halo, $C_{1-6}$alkyl, $C_{1-4}$alkoxy, O-CH$_2$phenyl, O-phenyl;
$R^3$ is selected from H, hydroxyl, halo, $C_{1-6}$alkyl, $C_{1-4}$alkoxy, O-CH$_2$phenyl, O-phenyl;
$R^4$ is selected from H, hydroxyl, halo, $C_{1-6}$alkyl, $C_{1-4}$alkoxy, O-CH$_2$phenyl, O-phenyl;
or $R^1$ and $R^2$, or $R^2$ and $R^3$, or $R^3$ and $R^4$ together form $C_{1-3}$alkylenedioxy;
$R^{5'}$ is selected from $C_{1-6}$ alkyl, $C_{1-3}$alkylC(O)OC$_{1-4}$alkyl and $C_{1-3}$alkyl$C_{6-10}$aryl optionally substituted with 1 or 2 groups independently selected from halo$C_{1-3}$alkyl and halo$C_{1-3}$alkoxy;
L is selected from $C_{1-6}$ alkylene-indolyl, $C_{1-6}$alkylene-NHC(O)—, azetidinyl-C(O)—, $C_{1-6}$alkylene-NHC(O)-indolyl, and $C_{1-6}$alkylene-NHSO$_2$—;
$R^6$ is selected from H, halo, hydroxyl, $C_{2-6}$alkyl, $C_{2-6}$alkenyl, $C_{2-6}$alkynyl, $C_{6-10}$aryl optionally substituted with 1 or 2 $R^X$ groups, $C_{1-9}$heteroaryl optionally substituted with 1 or 2 $R^X$ groups, $C_{2-5}$heterocycloalkyl optionally substituted with 1 or 2 $R^X$ groups, or is absent;
each $R^X$ is independently selected from hydroxyl, halo, nitro, NR'R"; $C_{1-4}$alkyl, $C_{3-6}$cycloalkyl, $C_{1-4}$alkoxy, $C_{6-10}$aryl optionally substituted with 1 or 2 $R^Y$ groups, $C_{1-9}$heteroaryl, $C_{1-4}$alkyl-($C_{1-9}$heteroaryl), C(O)OC$_{1-4}$alkyl, C(O)NHR$^Y$, $C_{2-5}$heterocycloalkyl optionally substituted with 1 or 2 $C_{1-4}$alkyl groups, C(O)—($C_{2-5}$heterocycloalkyl) optionally substituted with 1 or 2 $C_{1-4}$alkyl groups, or two adjacent $R^X$ groups together form $C_{1-3}$alkylenedioxy;
$R^Y$ is selected from H, hydroxyl, halo, $C_{1-4}$ alkyl, halo$C_{1-4}$ alkyl, $C_{1-4}$ alkoxy, $C_{1-4}$ alkylheterocycloalkyl, C(O)—($C_{1-4}$ alkyl$C_{2-5}$heterocycloalkyl), $C_{1-4}$alkylNR'R";

R' and R" are independently selected from H, $C_{1-4}$alkyl, $C_{1-4}$ alkyl$C_{2-5}$heterocycloalkyl;

$R^7$ is selected from H, $C_{1-6}$alkyl$C_{1-9}$heteroaryl, wherein the term heterocycloalkyl refers to a cycloalkyl ring in which one or more carbon atoms has been replaced by one or more heteroatoms.

3. The compound according to claim 1, wherein each heteroaryl and each heterocycloalkyl group has at least one nitrogen heteroatom.

4. The compound according to claim 1, wherein X is S.

5. The compound according to claim 1, wherein $R^1$ and $R^4$ are hydrogen.

6. The compound according to claim 1, wherein $R^2$ and $R^3$ are independently selected from hydroxyl, halo, and $C_{1-3}$ alkoxy.

7. The compound according to claim 1, wherein $R^2$ and $R^3$ are both methoxy, or $R^2$ and $R^3$ together are methylenedioxy.

8. The compound according to claim 2, wherein $R^{5'}$ is a benzyl group optionally substituted with 1 or 2 groups selected from CF$_3$ and OCF$_3$.

9. The compound according to claim 1, wherein each heteroaryl is independently selected from indolyl, pyridyl, pyrazolyl, pyrrolyl, oxazolyl, ozadiazolyl, benzoxadiazolyl and triazolyl, each of which is optionally substituted with 1 or 2 $R^X$ groups.

10. The compound according to claim 1, wherein each heterocycloalkyl is independently selected from aziridinyl, morpholinyl, piperidinyl, piperazinyl, each of which is optionally substituted with 1 or 2 $R^X$ groups.

11. The compound according to claim 1, wherein $R^6$ is a group selected from indolyl, phenyl, pyridyl, N-morpholinyl, N-piperidinyl, N-piperazinyl, triazolyl, pyrrolyl, pyrazolyl, oxazolyl, ozadiazolyl, benzodiazolyl and pyrrolopyridinyl, wherein each group is optionally substituted with 1 or 2 $R^X$ groups.

12. The compound according to claim 1, wherein L is $C_{1-2}$alkylene-NHC(O)— and $R^6$ is 2-indolyl, pyridyl, oxazolyl or oxadiazolyl, each of which is optionally substituted with 1 or 2 groups.

13. The compound according to claim 1, wherein L is $C_{1-2}$alkylene-NHC(O)-indolyl and $R^6$ is selected from phenyl optionally substituted with 1 or 2 $R^X$ groups, $C_{3-8}$heteroaryl optionally substituted with 1 or 2 $R^X$ groups, C(O)($C_{3-8}$heteroaryl) optionally substituted with 1 or 2 $R^X$ groups, C(O)($C_{2-5}$heterocycloalkyl) optionally substituted with 1 or 2 $R^X$ groups, C(O)NH$^Y$.

14. The compound according to claim 1, wherein each $R^X$ is independently selected from hydroxyl, halo, $C_{1-3}$alkyl, $C_{1-4}$alkoxy, C(O)OC$_{1-4}$alkyl, phenyl, NR'R" wherein R' and R" are independently selected from H, $C_{1-3}$alkyl, morpholinyl optionally substituted with 1 or 2 $C_{1-3}$alkyl groups, piperazinyl optionally substituted with 1 or 2 $C_{1-3}$alkyl groups, C(O)morpholinyl optionally substituted with 1 or 2 $C_{1-3}$alkyl groups, C(O)piperazinyl optionally substituted with 1 or 2 $C_{1-3}$alkyl groups, $C_{6-10}$aryl optionally substituted with 1 or 2 C(O)—($C_{1-4}$alkyl$C_{2-5}$heterocycloalkyl), or two adjacent $R^X$ groups together form methylenedioxy, pyridyl.

15. The compound according to claim 1 having formula (IA), formula (IB), formula (IC), or a pharmaceutically acceptable salt, tautomer or stereoisomer thereof:

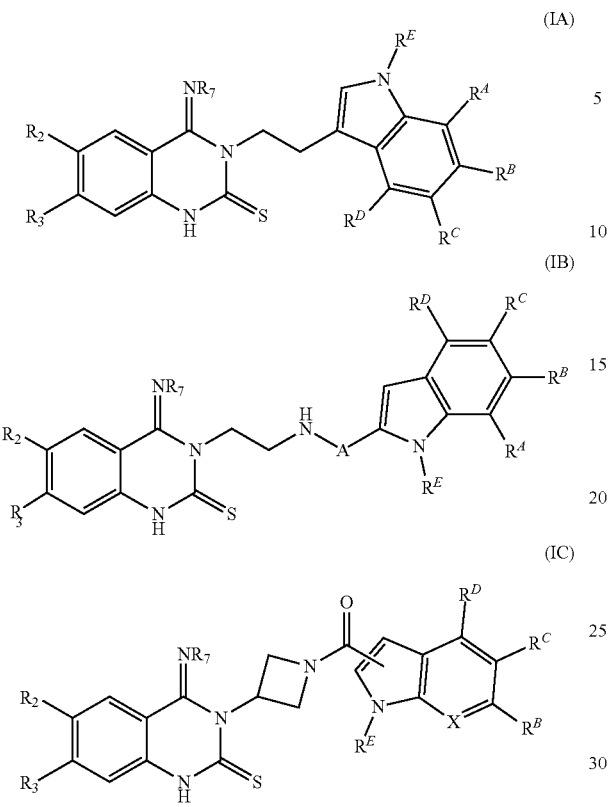
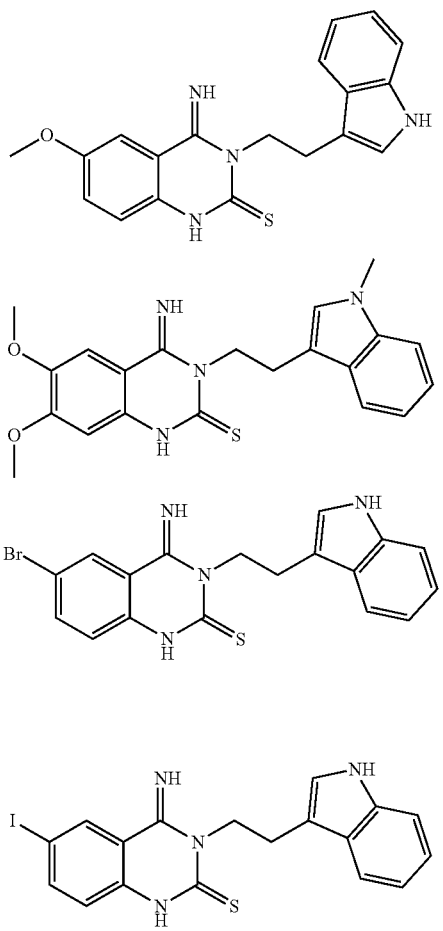

wherein:
R² is H, halo, C₁₋₃alkoxy, O-CH₂phenyl, O-phenyl;
R³ is H, halo, C₁₋₃alkoxy, O-CH₂phenyl, O-phenyl;
R⁷ is H;
A is C=O or SO₂;
X is C or N;
R^E is H, C₁₋₃alkyl, C(O)—C₂₋₅heterocycloalkyl (e.g., C(O)—(N-morpholinyl));
R^A, R^B, R^C and R^D are independently selected from H, OH, C₁₋₃ alkyl, OC₁₋₃ alkyl, C(O)—(N-heterocycloalkyl) optionally substituted with 1 or 2 C₁₋₃alkyl groups; N-heteroaryl optionally substituted with 1 or 2 groups selected from OH, halo, C₁₋₃alkyl, C₁₋₃alkoxy; phenyl optionally substituted with 1 or 2 groups selected from OH, halo, C₁₋₃alkyl, C₁₋₃alkoxy, C(O)NHC₁₋₃alkyl-[N(C₁₋₃alkyl)₂], C(O)—C₂₋₅heterocycloalkyl optionally substituted with 1 or 2 C₁₋₃alkyl groups.

16. The compound according to claim 1 selected from:

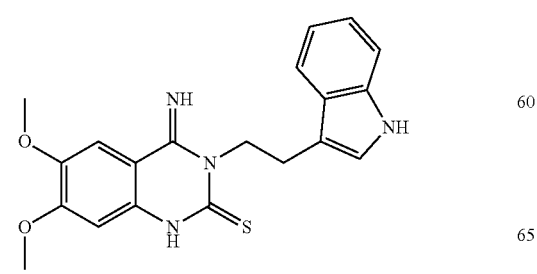
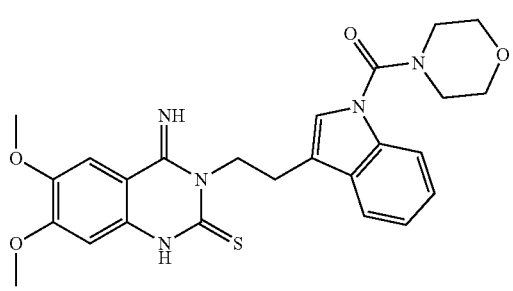
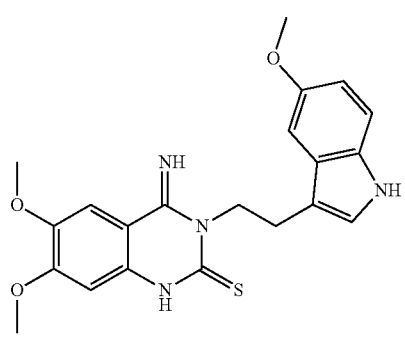

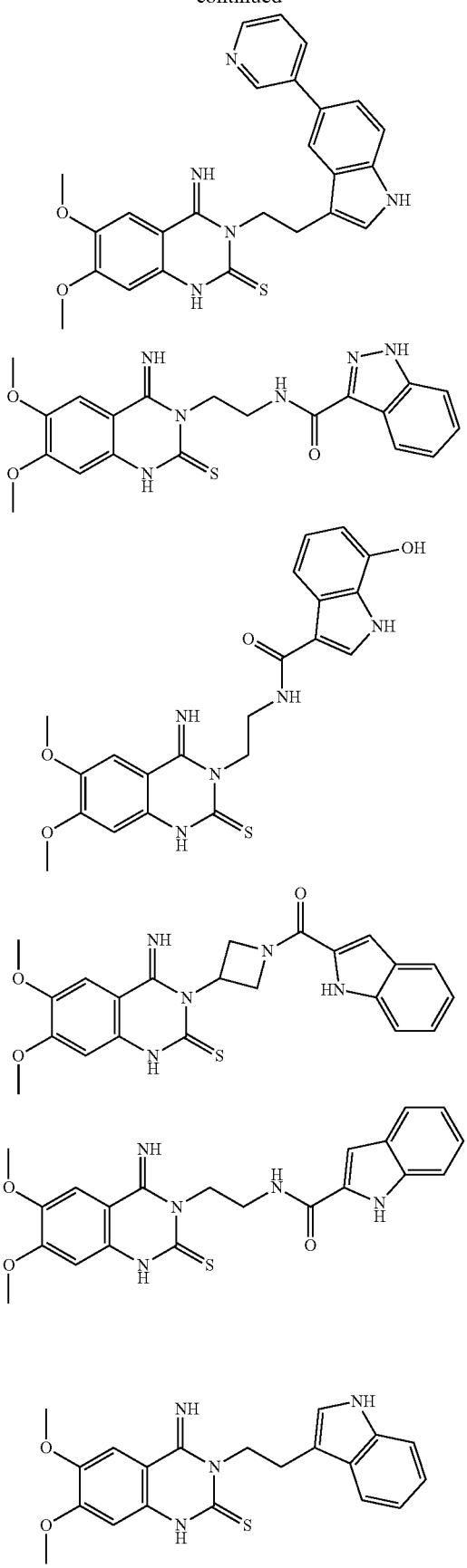
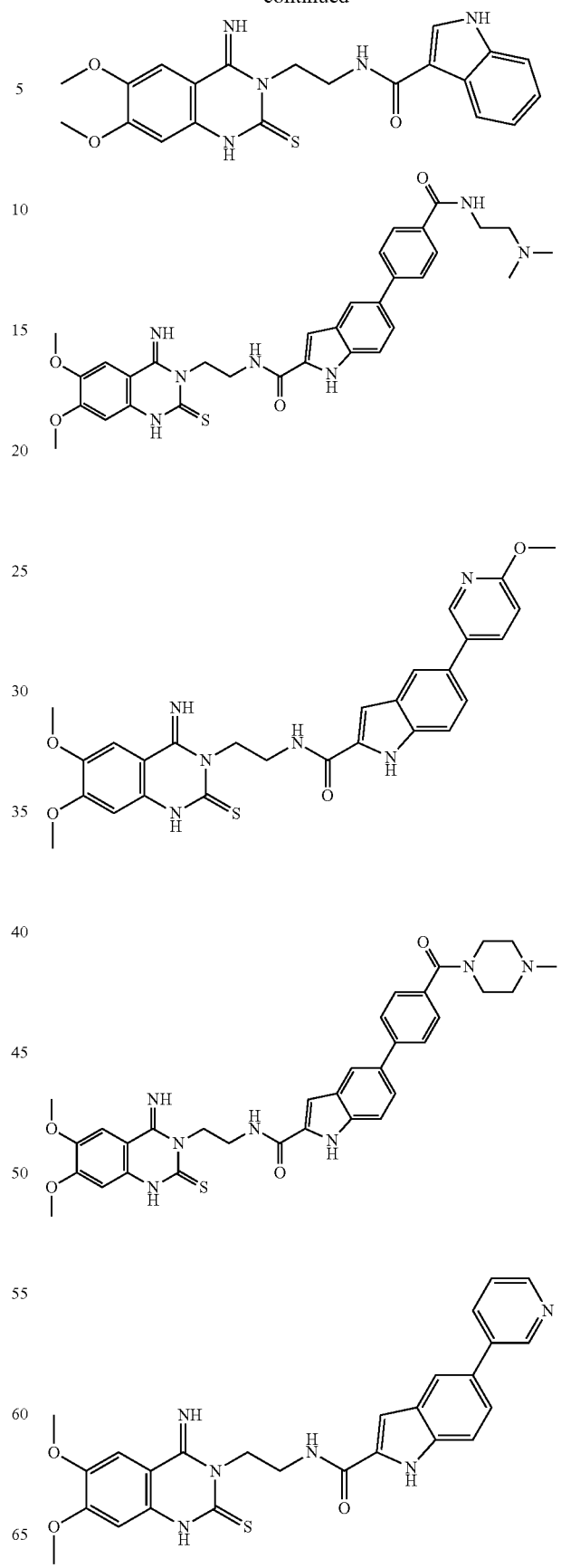

157
-continued
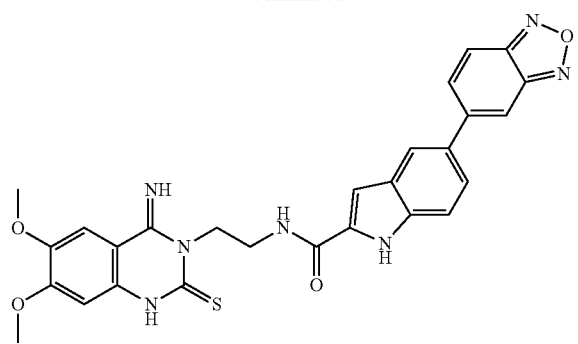
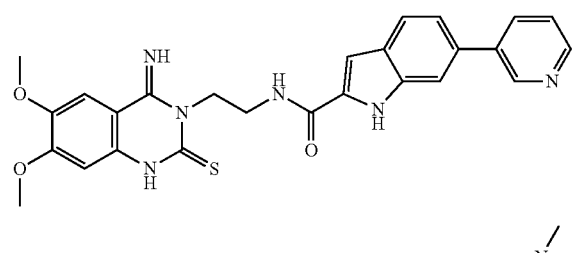
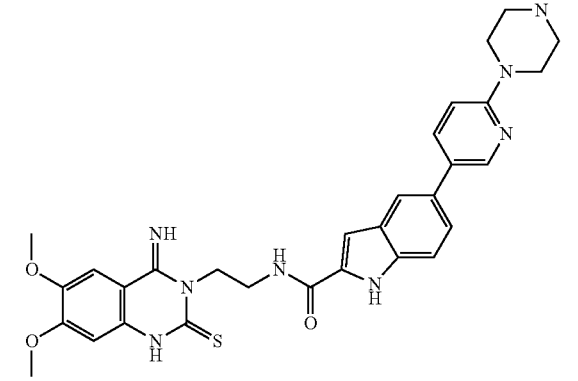
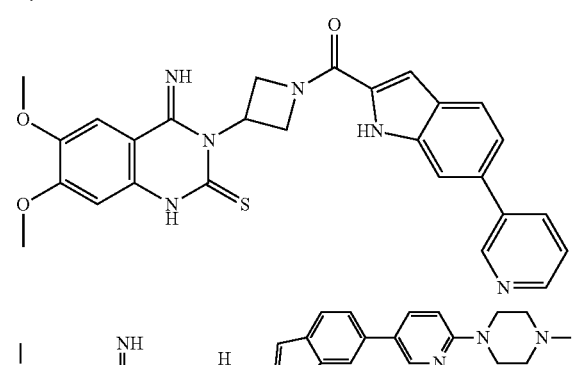
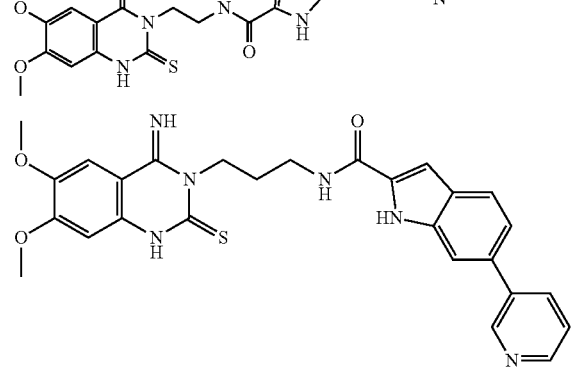
158
-continued
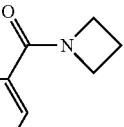
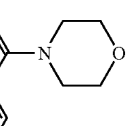
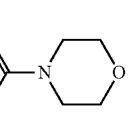
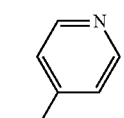

159
-continued
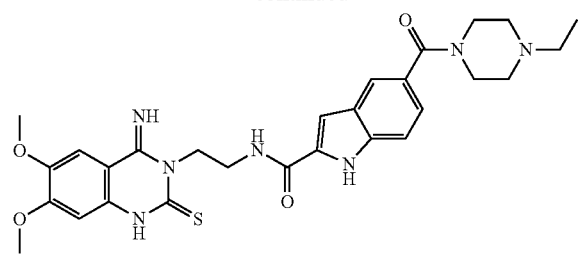
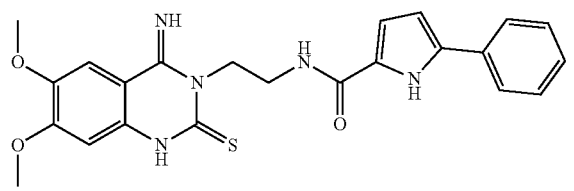
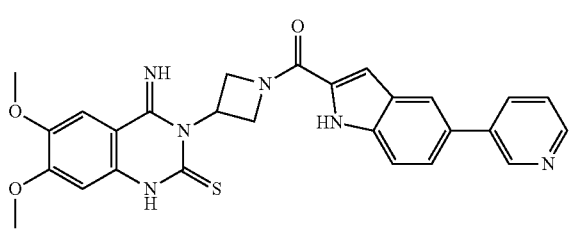
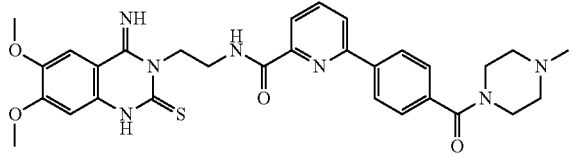
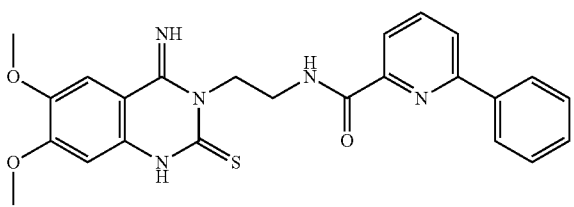
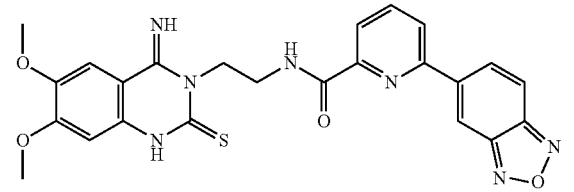
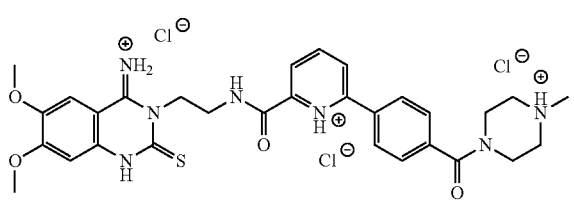
160
-continued
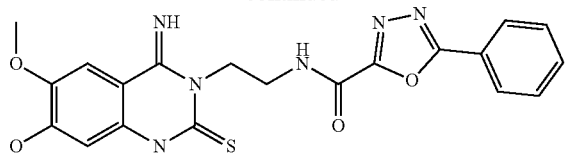
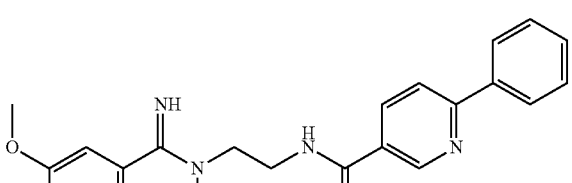
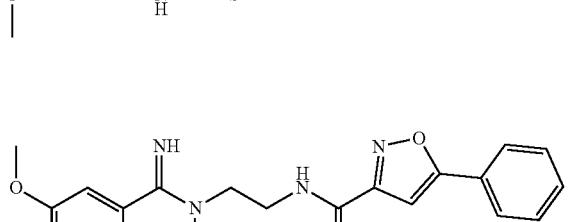
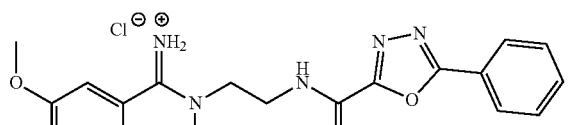
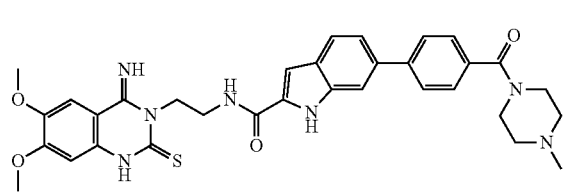
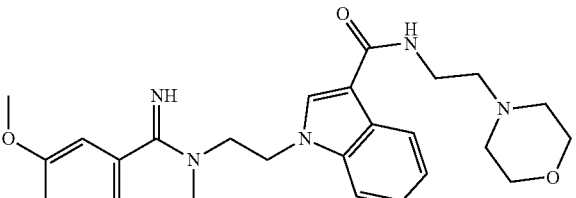
or a pharmaceutically acceptable salt, tautomer or stereoisomer thereof.

17. The compound according to claim 1 selected from
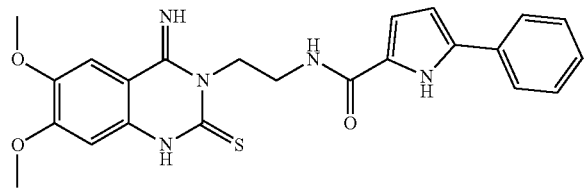
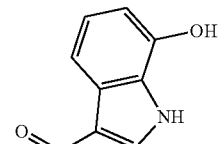
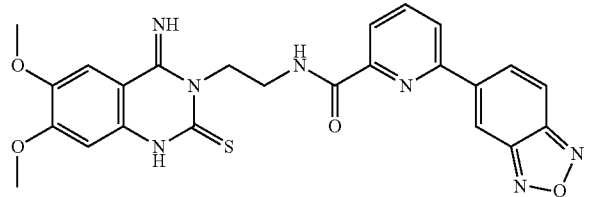
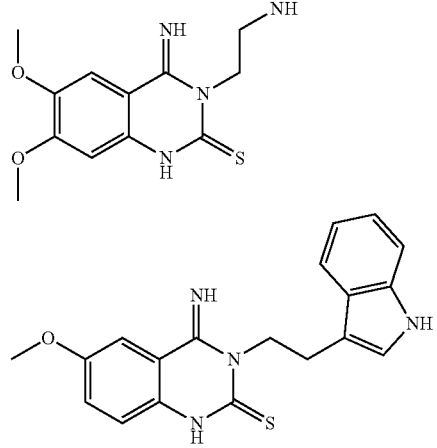
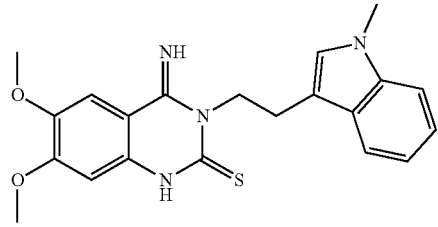
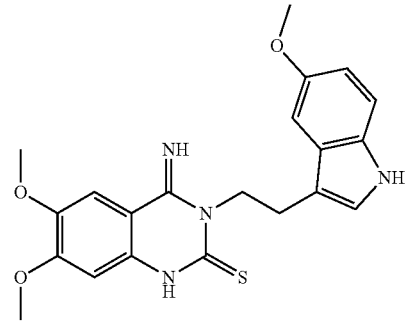
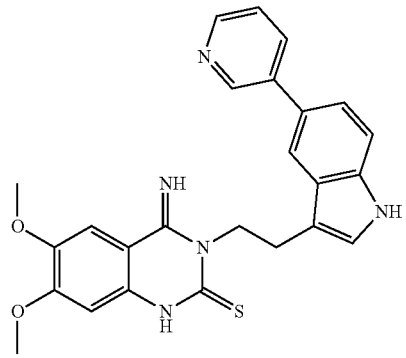
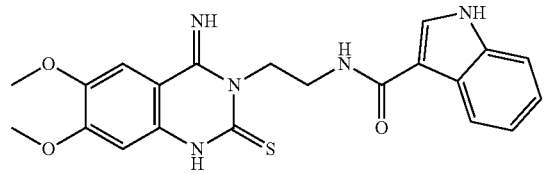
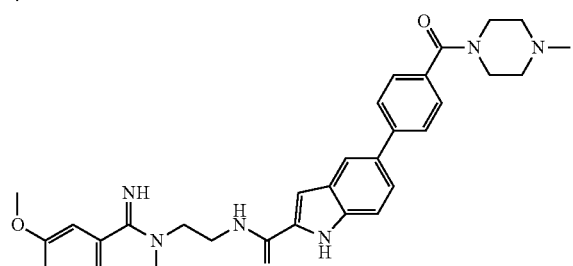
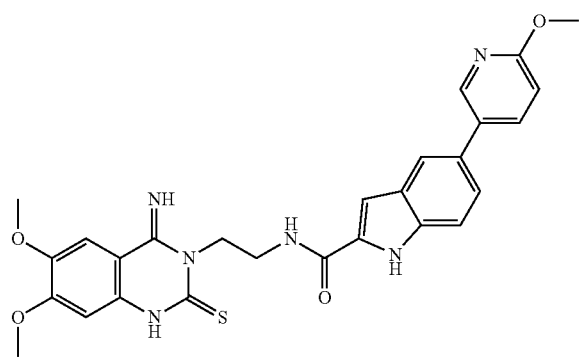

163
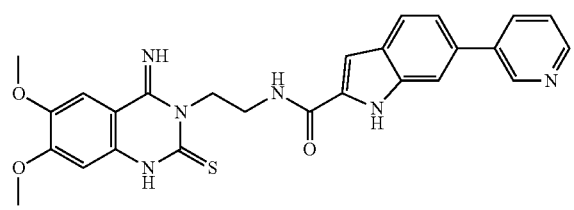
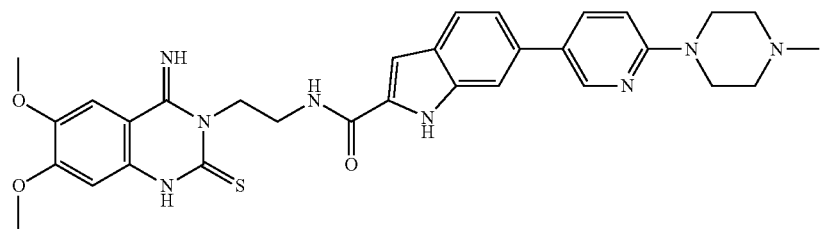
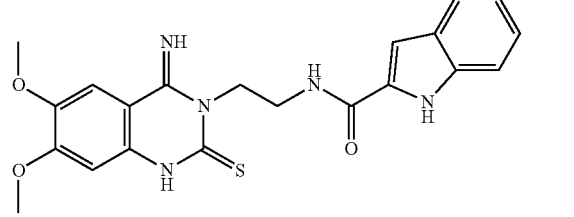
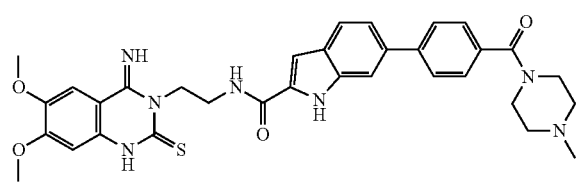
164
-continued
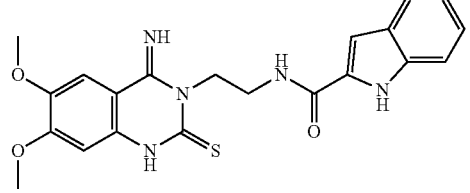
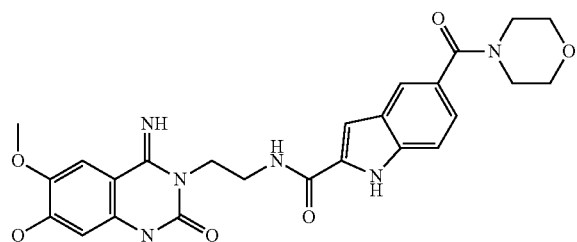
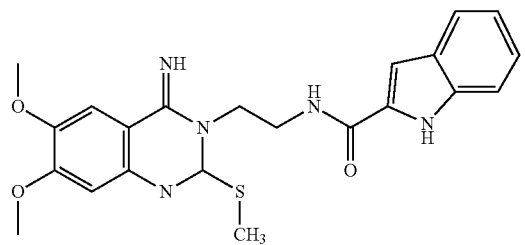
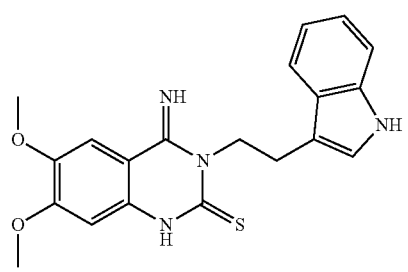

-continued

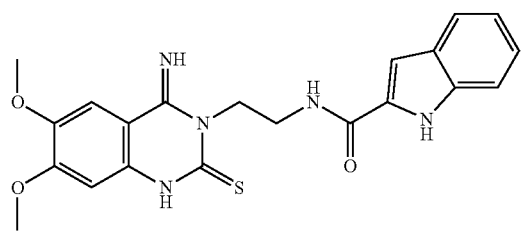 [SMILES: COc1cc2[nH]c(=S)n(CCNC(=O)c3cc4ccccc4[nH]3)c(=N)c2cc1OC]

or a pharmaceutically acceptable salt, tautomer or stereoisomer thereof.

18. A pharmaceutical composition comprising a compound of claim 1, or a pharmaceutically acceptable salt thereof, together with one or more pharmaceutically acceptable carriers, diluents or excipients.

19. A pharmaceutical composition comprising a compound of claim 2, or a pharmaceutically acceptable salt thereof, together with one or more pharmaceutically acceptable carriers, diluents or excipients.

20. The compound according to claim 2 having formula (IIA) or formula (IIB), or a pharmaceutically acceptable salt, tautomer or stereoisomer thereof:

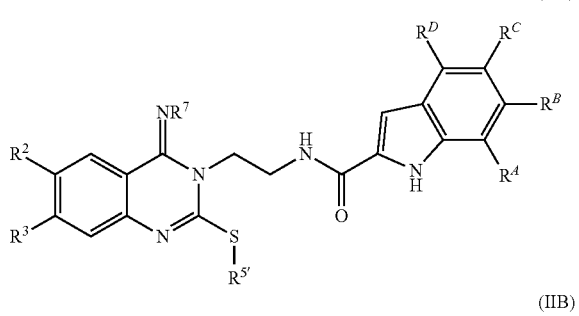

(IIA)

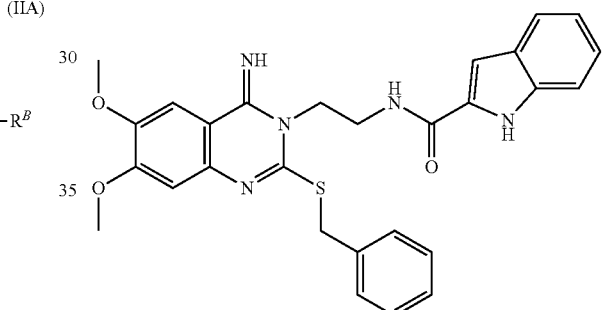

(IIB)

wherein:
$R^2$ is H, halo, $C_{1-3}$alkoxy, O-$CH_2$phenyl, O-phenyl;
$R^3$ is H, halo, $C_{1-3}$alkoxy, O-$CH_2$phenyl, O-phenyl;
$R^{5'}$ is selected from H, $C_{1-6}$ alkyl, $C_{1-3}$alkylC(O)O$C_{1-4}$ alkyl and $C_{1-3}$alkyl$C_{6-10}$aryl optionally substituted with 1 or 2 groups independently selected from halo$C_{1-3}$ alkyl and halo$C_{1-3}$alkoxy;
$R^7$ is H;
A is C=O or $SO_2$;
X is C or N;
$R^A$, $R^B$, $R^C$ and $R^D$ are independently selected from H, OH, $C_{1-3}$ alkyl, O$C_{1-3}$ alkyl, C(O)—(N-heterocycloalkyl) optionally substituted with 1 or 2 $C_{1-3}$alkyl groups; N-heteroaryl optionally substituted with 1 or 2 groups selected from OH, halo, $C_{1-3}$alkyl, $C_{1-3}$alkoxy; phenyl optionally substituted with 1 or 2 groups selected from OH, halo, $C_{1-3}$alkyl, $C_{1-3}$alkoxy, C(O)NH$C_{1-3}$alkyl-[N($C_{1-3}$alkyl)$_2$], C(O)—$C_{2-5}$heterocycloalkyl optionally substituted with 1 or 2 $C_{1-3}$alkyl groups.

21. The compound according to claim 2 selected from:

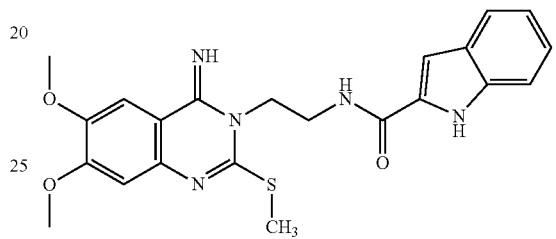

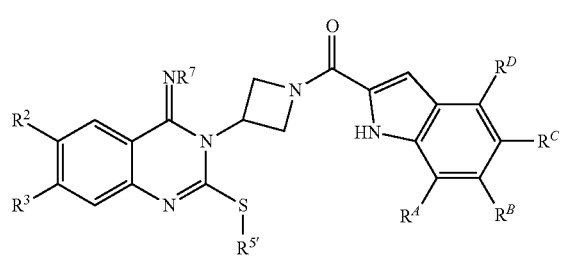

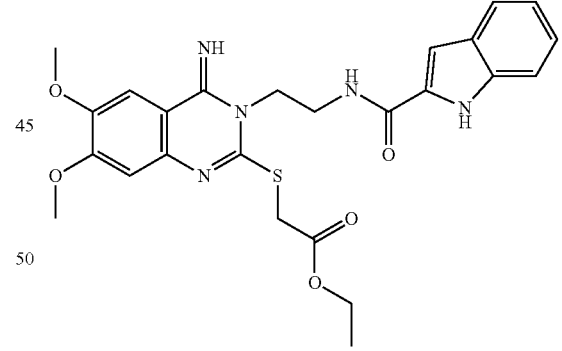

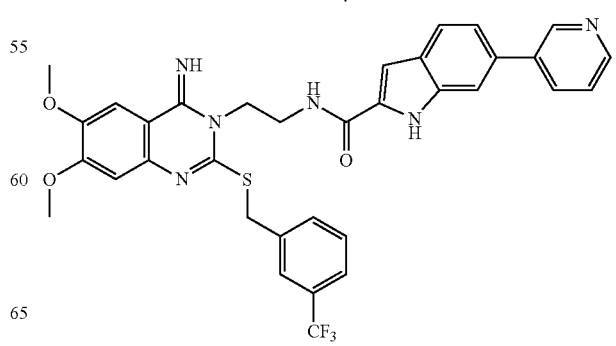

167
-continued
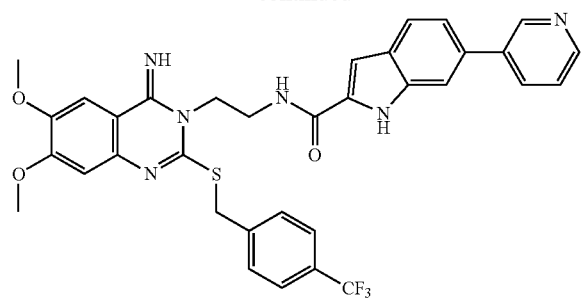
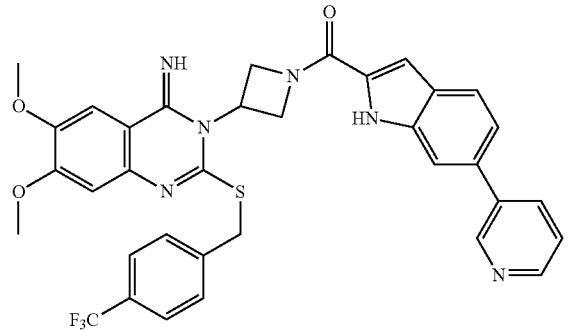
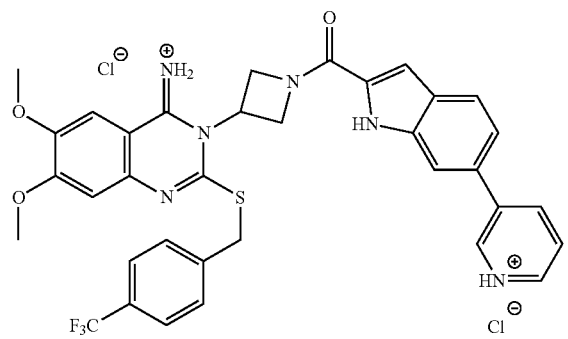
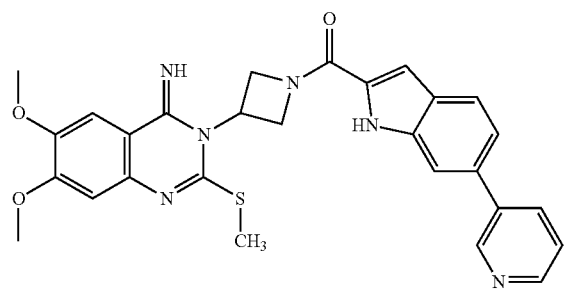
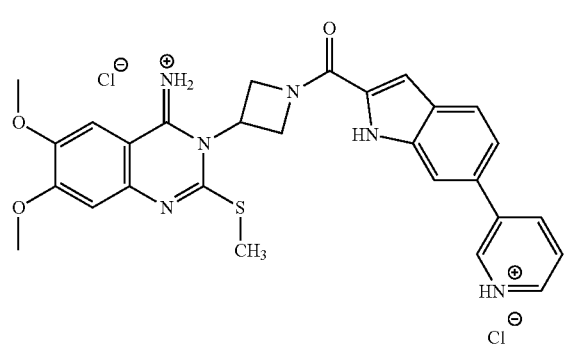
168
-continued
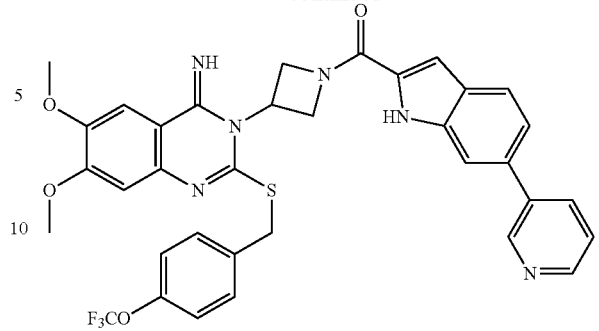
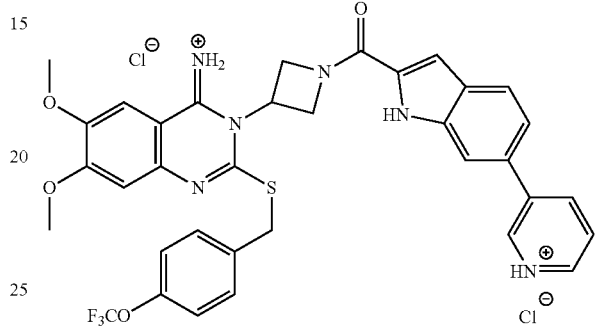
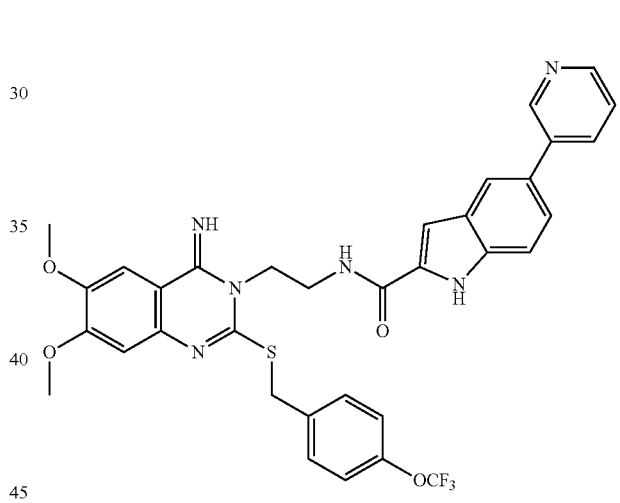
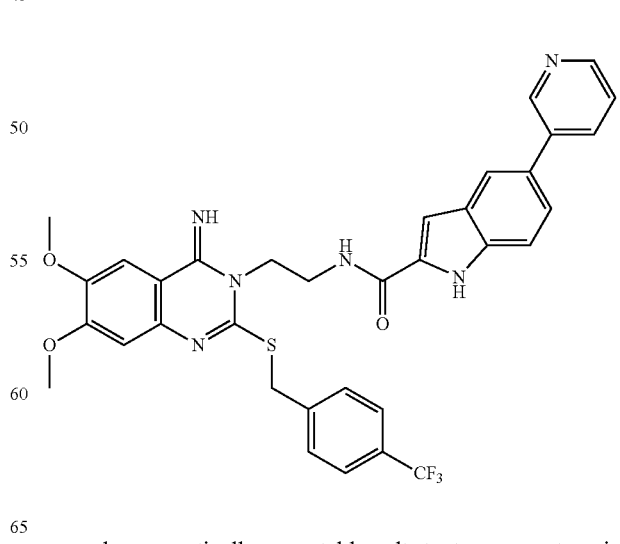
or a pharmaceutically acceptable salt, tautomer or stereoisomer thereof.

22. The compound according to claim 2 selected from
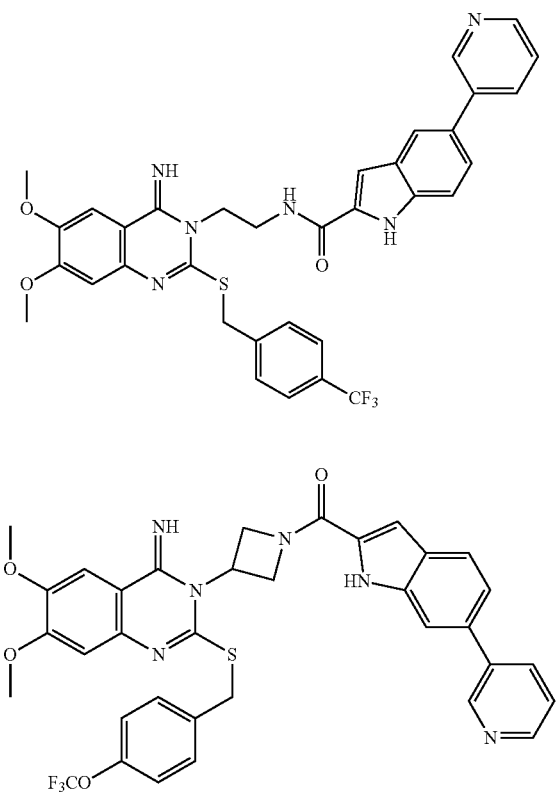
-continued
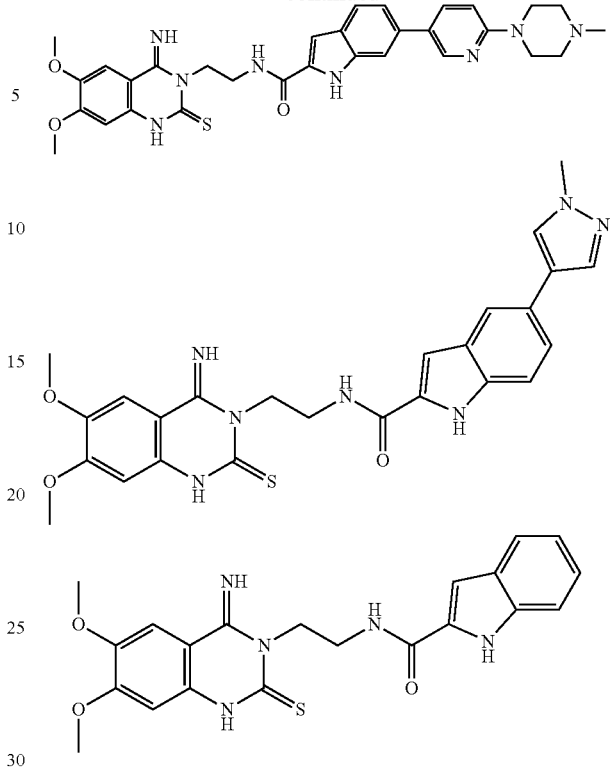
or a pharmaceutically acceptable salt, tautomer or stereoisomer thereof.
* * * * *